US010697975B2

(12) United States Patent
Staudt et al.

(10) Patent No.: US 10,697,975 B2
(45) Date of Patent: Jun. 30, 2020

(54) METHODS FOR IDENTIFYING, DIAGNOSING, AND PREDICTING SURVIVAL OF LYMPHOMAS

(71) Applicants: The United States of America, as represented by the Secretary, Department of Health and Human Services, Bethesda, MD (US); Board of Regents of the University of Nebraska, Lincoln, NE (US); University of Rochester, Rochester, NY (US); Arizona Board of Regents on Behalf of the University of Arizona, Tucson, AZ (US); Universitat de Barcelona, Barcelona (ES); Fundacio Clinic, Barcelona (ES); Hospital Clinic de Barcelona, Barcelona (ES); Julius-Maximilians-University of Wurzburg, Wurzburg (DE); British Columbia Cancer Agency Branch, Vancouver (CA); Oslo University Hospital HF, Oslo (NO); Queen Mary and Westfield College, University of London, London (GB)

(72) Inventors: Louis M. Staudt, Bethesda, MD (US); George Wright, Rockville, MD (US); Sandeep Dave, Chapel Hill, NC (US); Bruce Tan, Chicago, IL (US); John I. Powell, Ijamsville, MD (US); Wyndham Wilson, Washington, DC (US); Elaine S. Jaffe, Great Falls, VA (US); Wing C. Chan, Pasadena, CA (US); Timothy C. Greiner, Council Bluffs, IA (US); Dennis Weisenburger, Glendora, CA (US); James Armitage, Omaha, NE (US); Kai Fu, Omaha, NE (US); Richard I. Fisher, Pittsford, NY (US); Lisa M. Rimsza, Scottsdale, AZ (US); Thomas Miller, Tucson, AZ (US); Thomas Grogan, Tucson, AZ (US); Elias Campo Guerri, Barcelona (ES); Silvia M. Bea, Sabadell (ES); Itziar Salaverria, Barcelona (ES);

(Continued)

(73) Assignees: The United States of America, as represented by the Secretary, Department of Health and Human Services, Bethesda, MD (US); Board of Regents of the University of Nebraska, Lincoln, NE (US); University of Rochester, Rochester, NY (US); Arizona Board of Regents on behalf of the University of Arizona, Tuscon, AZ (US); Universitat de Barcelona, Barcelona (ES); Fundacio Clinic, Barcelona (ES); Hospital Clinic de Barcelona, Barcelona (ES); Julius-Maximilians-University of Würzburg, Würzburg (DE); British Columbia Cancer Agency Branch, Vancouver (CA); Oslo University Hospital HF, Oslo (NO); Queen Mary and Westfield College, University of London, London (GB)

( * ) Notice: Subject to any disclaimer, the term of this patent is extended or adjusted under 35 U.S.C. 154(b) by 281 days.

(21) Appl. No.: 15/630,751

(22) Filed: Jun. 22, 2017

(65) Prior Publication Data
US 2018/0011106 A1 Jan. 11, 2018

Related U.S. Application Data

(60) Continuation of application No. 13/409,416, filed on Mar. 1, 2012, now abandoned, which is a division of
(Continued)

(51) Int. Cl.
*G01N 33/48* (2006.01)
*G01N 33/68* (2006.01)
(Continued)

(52) U.S. Cl.
CPC ....... *G01N 33/6842* (2013.01); *C12Q 1/6886* (2013.01); *G16B 25/00* (2019.02);
(Continued)

(58) Field of Classification Search
None
See application file for complete search history.

(56) References Cited

U.S. PATENT DOCUMENTS

2004/0152651 A1  8/2004 Rana
2005/0112630 A1  5/2005 Shaughnessy et al.
(Continued)

FOREIGN PATENT DOCUMENTS

WO   WO 02/024956 A2   3/2002
WO   WO 03/021229 A2   3/2003

OTHER PUBLICATIONS

Alizadeh et al., "The Lymphochip: a specialized cDNA microarray for the genomic-scale analysis of gene expression in normal and malignant lymphocytes," *Cold Spring Harbor Symp. Quant. Biol.*, 64, 71-78 (1999).

(Continued)

*Primary Examiner* — Anna Skibinsky
(74) *Attorney, Agent, or Firm* — Leydig, Voit & Mayer, Ltd.

(57) ABSTRACT

Gene expression data provides a basis for more accurate identification and diagnosis of lymphoproliferative disorders. In addition, gene expression data can be used to
(Continued)

develop more accurate predictors of survival. The present invention discloses methods for identifying, diagnosing, and predicting survival in a lymphoma or lymphoproliferative disorder on the basis of gene expression patterns. The invention discloses a novel microarray, the Lymph Dx microarray, for obtaining gene expression data from a lymphoma sample. The invention also discloses a variety of methods for utilizing lymphoma gene expression data to determine the identity of a particular lymphoma and to predict survival in a subject diagnosed with a particular lymphoma. This information will be useful in developing the therapeutic approach to be used with a particular subject.

5 Claims, 45 Drawing Sheets

(72) Inventors: Armando Lopez-Guillermo, Barcelona (ES); Emilio Montserrat, Barcelona (ES); Victor Moreno, Barcelona (ES); Andreas Zettl, Wurzburg (DE); German Ott, Bietigheim-Bissingen (DE); Hans-Konrad Muller-Hermelink, Wurzburg (DE); Andreas Rosenwald, Wurzburg (DE); Julie Vose, Omaha, NE (US); Randy Gascoyne, North Vancouver (CA); Joseph Connors, Vancouver (CA); Erlend B. Smeland, Oslo (NO); Stein Kvaloy, Oslo (NO); Harald Holte, Oslo (NO); Jan Delabie, Toronto (CA); T. Andrew Lister, London (GB)

Related U.S. Application Data application No. 11/493,387, filed on Jul. 25, 2006, now Pat. No. 8,131,475, which is a continuation-in-part of application No. 10/934,930, filed on Sep. 3, 2004, now Pat. No. 7,711,492.

(60) Provisional application No. 60/500,377, filed on Sep. 3, 2003.

(51) Int. Cl.
  *G16B 25/00* (2019.01)
  *C12Q 1/6886* (2018.01)
  *G16B 40/00* (2019.01)

(52) U.S. Cl.
  CPC .. *C12Q 2600/112* (2013.01); *C12Q 2600/118* (2013.01); *C12Q 2600/158* (2013.01); *G01N 2333/51* (2013.01); *G16B 40/00* (2019.02); *Y02A 90/26* (2018.01)

(56) References Cited

U.S. PATENT DOCUMENTS

2007/0248659 A1   10/2007   Shanahan et al.
2008/0132504 A1   6/2008    Garcia-Echeverria et al.
2008/0193462 A1   8/2008    Kung et al.

OTHER PUBLICATIONS

Alizadeh et al., "Distinct types of diffuse large B-cell lymphoma identified by gene expression profiling," *Nature*, 403, 503-511 (Feb. 2000).
Alon et al., "Broad patterns of gene expression revealed by clustering analysis of tumor and normal colon tissues probed by oligonucleotide arrays," *Proc. Natl. Acad. Sci. USA*, 96, 6745-6750 (1999).
Ando et al., "Fuzzy Neural Network Applied to Gene Expression Profiling for Predicting the Prognosis of Diffuse Large B-cll Lymphoma," *Jpn. J. Cancer Res.*, 93, 1207-1212 (Nov. 2002).
Andreasson et al., "Genomic amplifications of CCDN2 is rare in non-Hodgkin lymphomas," *Cancer Genet. Cytogenet.*, 102, 81-82 (1998).
Basso et al., "Tracking CD40 signaling during germinal center development," *Blood*, 104, 4088-4096 (2004).
Bea et al., "Diffuse large B-cell lymphoma subgroups have distinct genetic profiles that influence tumor biology and improve gene expression-based survival prediction," *Blood*, 106(9), 3183-3190 (Nov. 1, 2005).
Bea et al., "Increased number of chromosomal imbalances and high-level DNA amplifications in mantle cell lymphoma are associated with blastoid variants," *Blood*, 93, 4365-4374 (1999).
Bea et al., "Clinicopathologic significance and prognostic value of chromosomal imbalances in diffuse large B-cell lymphomas," *J. Clin. Oncol.*, 22, 3498-3506 (2004).
Berglund et al., "Chromosomal imbalances in diffuse large B-cell lymphoma detected by comparative genomic hybridization," *Mod. Pathol.*, 15, 807-816 (2002).
Bergsagel et al., "Critical roles for immunoglobulin translocations and cyclin D dysregulation in multiple myeloma," *Immunol. Rev.*, 194, 96-104 (2003).
Bishop et al., "Burkitt's lymphoma: molecular pathogenesis and treatment," *Cancer Invest.*, 18, 574-583 (2000).
Boxer et al., "Translocations involving c-myc and c-myc function," *Oncogene*, 20, 5595-5610 (2001).
Chiarle et al., "Increased proteasome degradation of cyclin-dependent kinase inhibitor p27 is associated with a decreased overall survival in mantle cell lymphoma," *Blood*, 95, 619-626 (2000).
Cigudosa et al., "Cytogenetic analysis of 363 consecutively ascertained diffuse large B-cell lymphomas," *Genes Chromosomes Cancer*, 25, 123-133 (1999).
Copie-Bergman et al., "Interleukin 4-induced gene 1 is activated in primary mediastinal large B-cell lymphoma *Blood*," 101, 2756-2761 (2003).
Copie-Bergman et al., "MAL expression in lymphoid cells: further evidence for MAL as a distinct molecular marker of primary mediastinal large B-cell lymphomas." *Mod. Pathol.*, 15, 1172-1180 (2002).
Dave et al., "Cytogenetic characterization adiffuse large cell lymphoma using multi-color fluorescence in situ hybridization," *Cancer Genet. Cytogenet.*, 132, 125-132 (2002).
Dave et al. "Molecular Diagnosis of Burkitt's Lymphoma,"*N. England J. Med.*, 354(23): 2431-2442 (Jun. 8, 2006).
Delmer et al., "Overexpression of cyclin D2 in chronic B-cell malignancies," *Blood*, 85, 2870-2876 (1995).
Derisi et al., "Use of a cDNA microarray to analyze gene expression patterns in human cancer," *Nat. Genet.*, 14, 457-460 (1996).
Doglioni et al., "Cyclin D3 expression in normal, reactive and neoplastic tissues." *J. Pathol.*, 185, 159-166 (1998).
Dudoit et al., "Comparison of discrimination methods for the classification of tumors using gene expression data." *J. Am. Stat. Assoc.*, 97, 77-87 (2002).
Dybkaer et al.,"Molecular Diagnosis and Outcome Prediction in Diffuse Large B-Cell Lymphoma and Other Subtypes of Lymphoma," *Clinical Lymphoma*, 5(1), 19-28 (Jun. 2004).
Eisen et al., "Cluster analysis and display of genome-wide expression patterns," *Proc. Natl. Acad. Ci. USA*, 95, 14863-14868 (Dec. 1998).
European Patent Office: Partial European Search Report in European Patent Application No. 09170243.1 (dated Jun. 24, 2010).
European Patent Office, European Search Report in European Patent Application No. 10014565.5 (dated Feb. 16, 2011).
Feuerhake et al., "NFkappaB activity, function, and target-gene signatures in primary mediastinal large B-cell lymphoma and diffuse large B-cell lymphoma subtypes," *Blood*, 106, 1392-1399 (2005).

(56) References Cited

OTHER PUBLICATIONS

Fu et al., "Cyclin D1-negative mantle cell lymphoma: a clinicopatholigic study based on gene expression profiling," *Blood*, 106(13): 4315-4321 (Dec. 15, 2005).
Gerbitz et al., "Deregulation of the proto-oncogene c-myc through t(8;22) translocation in Burkitt's lymphoma," *Oncogene*, 18, 1745-1753 (1999).
Goff et al., "The use of real-time quantitative polymerase chain reaction and comparative genomic hybridizations to identify amplification of the REL gene in follicular lymphoma," *Br. J. Haematol.*, 111, 618-625 (2000).
Golub et al., "Molecular classification of cancer: class discovery and class prediction by gene expression monitoring," *Science*, 286, 531-537 (1999).
Gress et al., "A pancreatic cancer-specific expression profile," *Oncogene*, 13, 819-1830 (1996).
Hans et al., "Expression of PKC-beta or cyclin D2 predicts for inferior survival in diffuse large B-cell lymphoma" Modern Pathology, 18, 1377-1384 (2005).
Haralambieva et al., "Clinical, immunophenotypic, and genetic analysis of adult lymphomas with morphologic features of Burkitt lymphoma," *Am. J. Surg. Pathol.*, 29, 1086-1094 (2005).
Harpole et al., "A Prognostic Model of Recurrence and Death in Stage I Non-Small Cell Lung Cancer Utilizing Presentation, Histopathology, and Oncoprotein Expression," *Cancer Research*, 55, 51-56 (Jan. 1, 1995).
Huang et al., "The t(14;18) defines a unique subset of diffuse large B-cell lymphoma with a germinal center B-cell gene expression profile," *Blood*, 99, 2285-2290 (2002).
Hummel et al., "A biologic Definition of Burkitt's Lymphoma from Transcriptional and Genomic Profiling," *New England Journal of Medicine*, 354(23), 2419-2430 (Jun. 2006).
Huvale et al., "The gene for human thioredoxin maps on the short arm of chromosome 3 at bands 3pl 1-p12" FEBS Letters, 255, 89-91 (1989).
Hyman et al., "Impact of DNA amplification on gene expression patterns in breast cancer." *Cancer Res.*, 62, 6240-6245 (2002).
Iqbal et al., "BCL2 translocation defines a unique tumor subset within the germinal center B-cell-like diffuse large B-cell lymphoma," *Am. J. Pathol.*, 165, 159-166 (2004).
Jares et al., "Expression of retinoblastoma gene product (pRb) in mantle cell lymphomas. Correlation with cyclin D1 (PRAD1/CCND1) mRNA levels and proliferative activity," *Am. J. Pathol.*, 148, 1591-1600 (1996).
Khan et al., "Classification and Diagnostic Prediction of Cancers Using Gene Expression Profiling and Artificial Neural Networks," *Nature Medicine*, 7, 673-679 (Jun. 2001).
Kovacs et al., "Consistent chromosome 3p deletion and icss of heterozygosity in renal cell carcinoma" Proc. Natl. Acad. Sci. USA, 85, 1571-1575 (1988).
Kramer et al., "Clinical relevance of BCL2, BCL6, and MYC rearrangements in diffuse large B-cell lymphoma," *Blood*, 92, 3152-3162 (1998).
Kusumoto et al., "Diffuse Large B-Cell Lymphoma with extra Bcl-2 Gene Signals Detected by FISH Analysis is Associate with a "Non-Germinal Center Pehnotype"" *Am. J. Surg.Pathol.*, 29, 1-7 (2005).
Li, "Survival prediction of diffuse large-B-cell lymphoma based on both clinical and gene expression information," *Bioinformatics*, 22: 466-471 (2006).
Martinez et al., "The Molecular Signature of Mantle Cell Lymphoma Reveals Multiple Signals Favoring Cell Survival," *Cancer Research*, 63, 8226-8232 (Dec. 1, 2003).
Monni et al., "DNA copy number changes in diffuse large B-cell lymphoma-comparative genomic hybridization study," *Blood*, 87, 5269-5278 (1996).
Mounier et al., "Rituximab plus CHOP (R-CHOP) overcomes bcl-2—associated resistance to chemotherapy in elderly patients with diffuse large B-cell lymphoma (DLBCL)" *Blood*, 101, 4279-4284 (2003).

Neri et al., "Different regions of the immunoglobulin heavy-chain locus are involved in chromosomal translocations in distinct pathogenetic forms of Burkitt lymphoma," *Proc. Natl. Acad. Sci. USA*, 85, 2748-2752 (1988).
Orsetti et al., "Genomic and expression profiling of chromosome 17 in breast cancer reveals complex patterns of alterations and novel candidate genes," *Cancer Res.*, 64, 6453-6460 (2004).
Ott et al., "Cyclin D1 expression in mantle cell lymphoma is accompanied by downregulation of cyclin D3 and is not related to the proliferative activity," *Blood*, 90, 3154-3159 (1997).
Pruneri et al., "Immunoreactivity for cyclin D3 is frequently detectable in high-grade primary gastric lymphomas in the absence of the t(6;14)(p21.1;q32.3) chromosomal translocation," *J. Pathol.*, 200, 596-601 (2003).
Quintanilla-Martinez et al., "Mantle cell lymphomas lack expression of p27Kipl, a cyclin-dependent kinase inhibitor," *Am. J. Pathol.*, 153, 175-182 (1998).
Radmacher et al., "A paradigm for class prediction using gene expression profiles," *J. Comput. Biol.*, 9, 505-511 (2002).
Ramaswamy et al., "Multiclass cancer diagnosis using tumor gene expression signatures," *Proc. Natl. Acad Sci. USA*, 98, 15149-15154 (2001).
Ransohoff, "Rules of evidence for cancer molecular-marker discovery and validation," *Nat. Rev. Cancer*, 4, 309-314 (2004).
Rao et al., "Chromosomal and gene amplification in diffuse large B-cell lymphoma," *Blood*, 92, 234-240 (1998).
Rosenwald et al., "Gene Expression Profiling of Diffuse Large B-Cell Lymphoma" *Leukemia and Lymphoma*, 44, s41-s47 (2003).
Rosenwald et al., "The proliferation gene expression signature is a quantitative integrator of oncogenic events that predicts survival in mantle cell lymphoma," *Cancer Cell*, 3, 185-197 (2003).
Rosenwald et al., "Molecular diagnosis of primary rnediastinal B cell lymphoma identifies a clinically favorable subgroup of diffuse large B cell lymphoma related to Hodgkin lymphoma," *J. Exp. Med.*, 198, 851-862 (2003).
Rosenwald et al., "The use of molecular profiling to predict survival after chemotherapy for diffuse large-B-cell lymphoma," *New Engl. J. Med.*, 346, 1937-1947 (2002).
Savage et al., "The molecular signature of mediastinal large B-cell lymphoma differs from that of other diffuse large B-cell lymphomas and shares features with classical Hodgkin lymphoma," *Blood*, 102, 3871-3879 (2003).
Shipp et al., "Diffuse large B-cell lymphoma outcome prediction by gene-expression profiling and supervised machine learning," *Nature Medicine*, 8, 68-74 (Jan. 2002).
Sonoki et al., "Cyclin D3 is a target gene of t(6;14)(p21.1;q32.3) of mature B-cell malignancies." *Blood*, 98, 2837-2844 (2001).
European Patent Office: European Supplementary European Search Report in European Patent Application No. 04783330.6 (dated Jul. 10, 2008).
Tagawa et al., "Comparison of genome profiles for identification of distinct subgroups of diffuse large B-cell lymphoma," *Blood*, 106, 1770-1777 (2005).
Tibshirani et al., "Diagnosis of multiple cancer types by shrunken centroids of gene expression," *Proc. Natl. Acad. Sci. USA*, 99, 6567-6572 (2002).
Winter et al., "Prognostic significance of Bcl-6 protein expression in DLBCL treated with CHOP or R-CHOP: a prospective correlative study," *Blood* 107, 4207-4213 (Jun. 2006).
Wright et al., "A gene expression-based method to diagnose clinically distinct subgroups of diffuse large B cell lymphoma," *Proc. Natl. Acad. Sci. USA*, 100, 9991-9996 (2003).
Wuthrich et al., "MHC class II, antigen presentation and tumor necrosis factor in renal tubular epithelial cells" *Kidney International*, 37, 783-792 (1990).
Yatabe et al., "Significance of cyclin D1 overexpression for the diagnosis of mantle cell lymphoma: a clinicopathologic comparison of cyclin DI-positive MCL and cyclin D1-negative MCL-like B-cell lymphoma," *Blood*, 95, 2253-2261 (2000).
Ye et al., "Variable frequencies of t(11 ; 18)(q21;q21) in Malt lymphomas of different sites: significant association with CagA strains of H pylori in gastric MALT lymphoma," *Blood*, 102, 1012-1018 (2003).

(56) References Cited

OTHER PUBLICATIONS

Zeller et al., "An integrated database of genes responsive to the Myc oncogenic transcription factor: identification of direct genomic targets," *Genome Biol.*, 4, R69 (2003).
European Patent Office: Extended European Search Report in European Patent Application No. 09170243.1 (dated Nov. 10, 2010).
U.S. Appl. No. 10/934,930, filed Sep. 3, 2004.
U.S. Appl. No. 11/493,387, filed Jul. 25, 2006.
U.S. Appl. No. 13/008,403, filed Jan. 18, 2011.
U.S. Appl. No. 13/409,416, filed Mar. 1, 2012.

| | ABC | GCB | Other |
|---|---|---|---|
| ABC | 37 | 1 | 4 |
| GCB | 1 | 58 | 0 |

Training Set

| | ABC | GCB | Other |
|---|---|---|---|
| ABC | 38 | 1 | 2 |
| GCB | 2 | 57 | 6 |
| Type 3 | 14 | 19 | 25 |

Validation Set

| | ABC | GCB | Other |
|---|---|---|---|
| ABC | 75 | 2 | 6 |
| GCB | 3 | 115 | 10 |
| Type 3 | 14 | 19 | 25 |

All Samples

DLBCL Subgroup by Hierarchical Clustering

Model Prediction

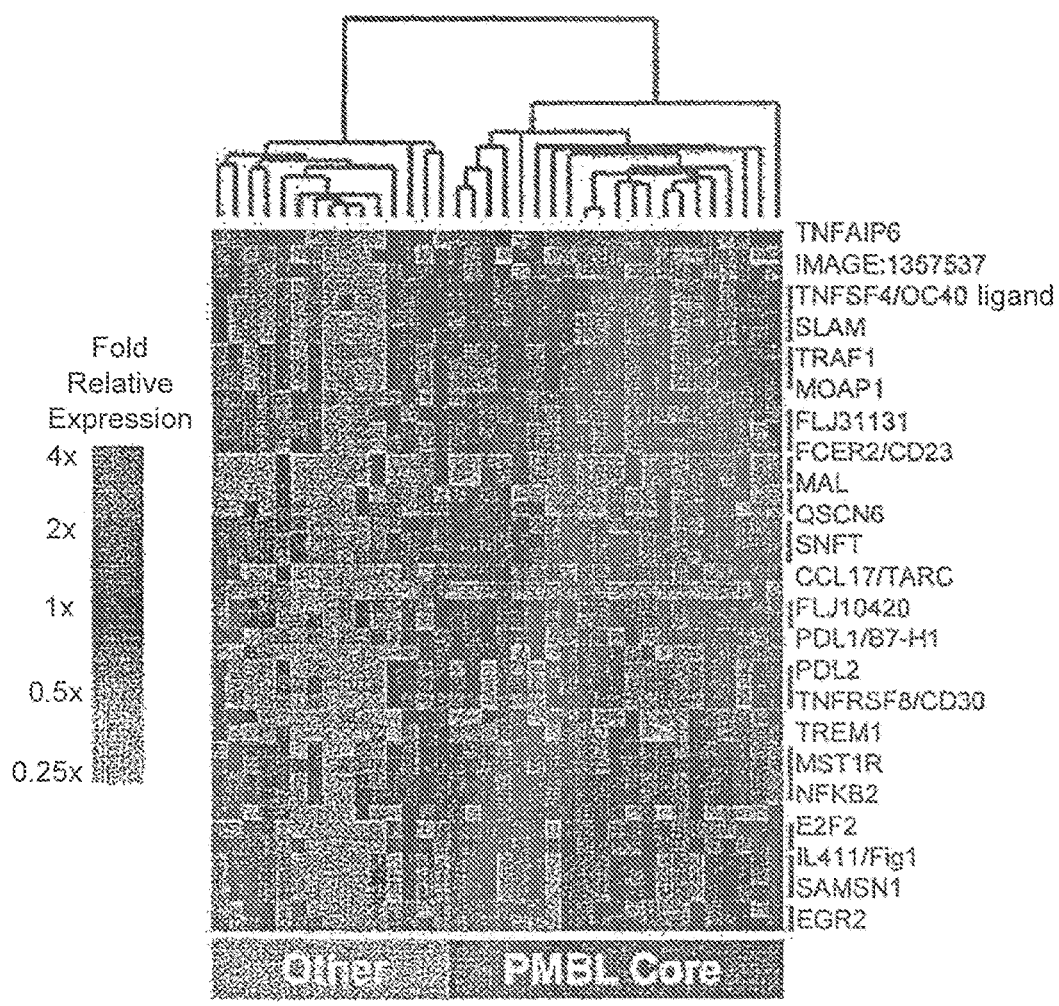

GCB DLBCL (n=87)

ABC DLBCL (n=77)

PMBL (n=19)

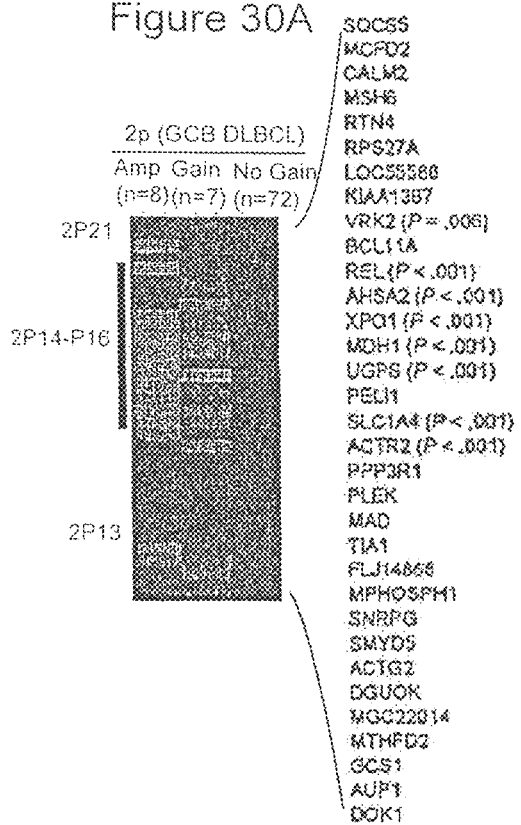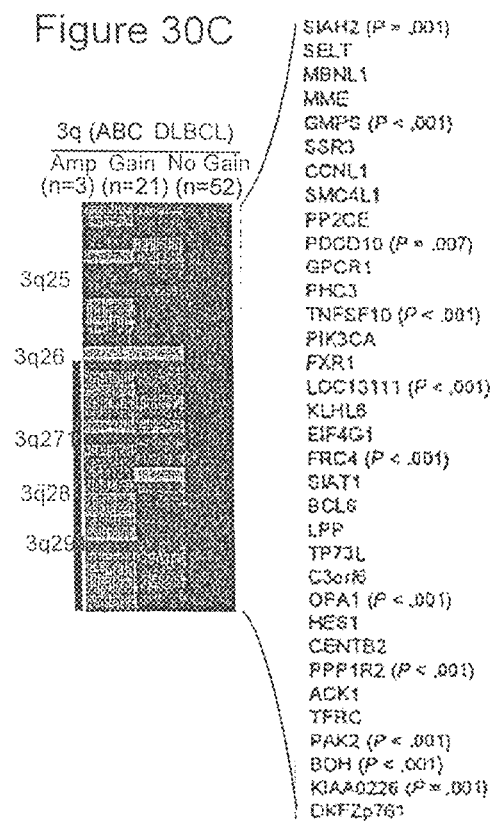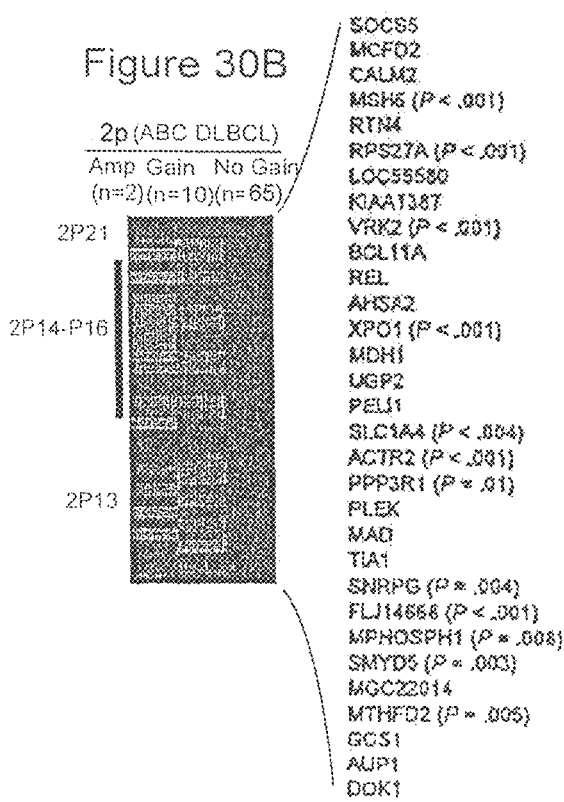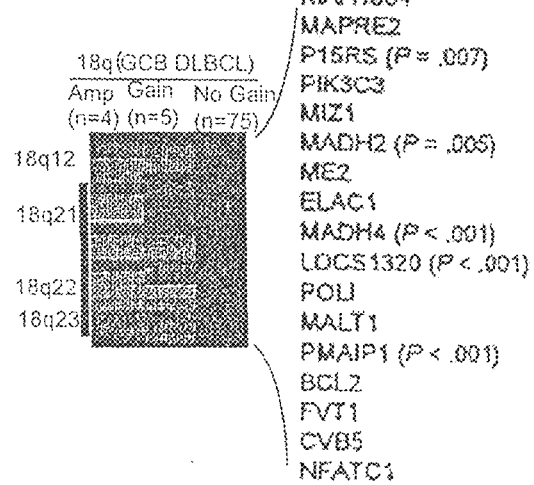

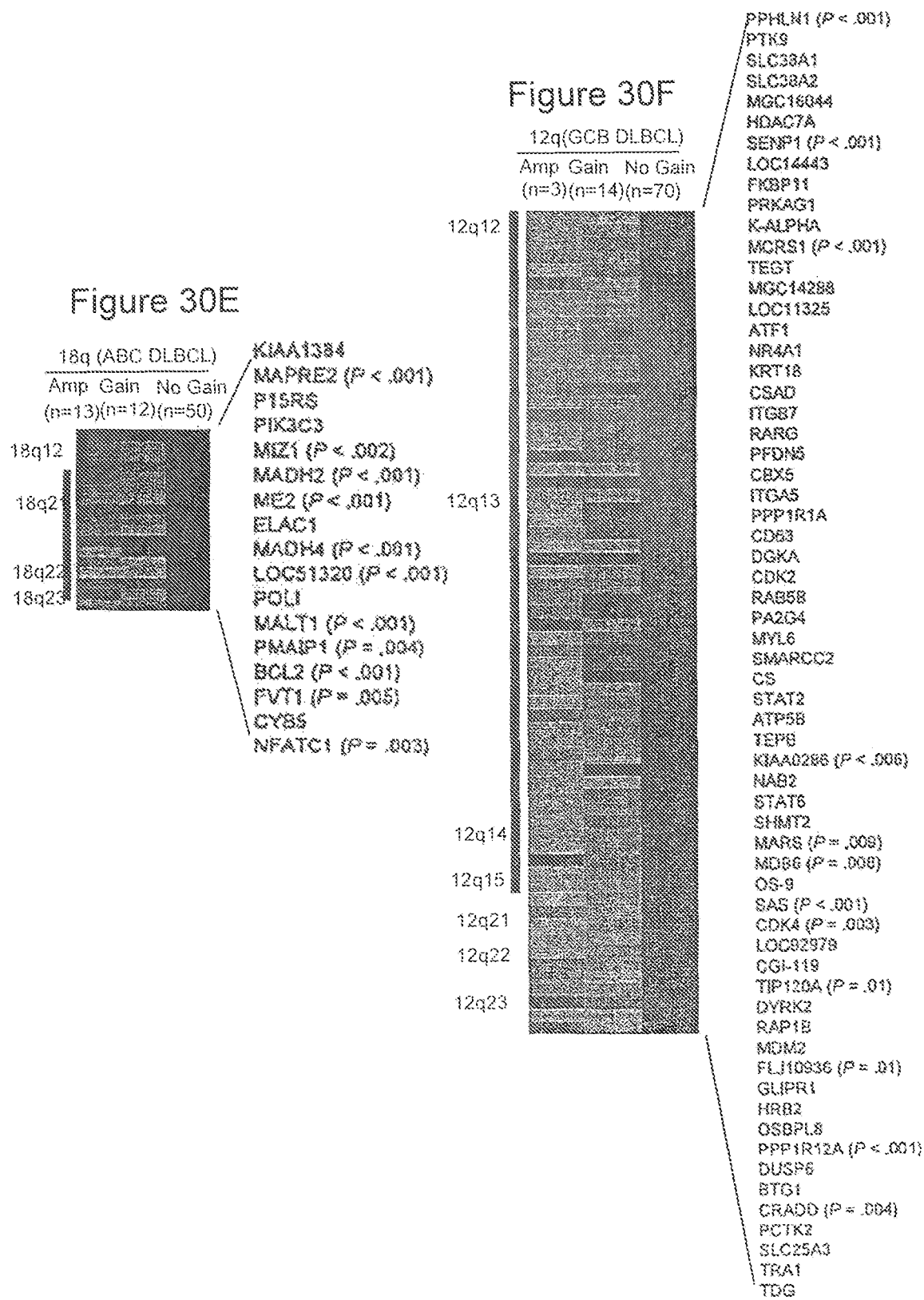

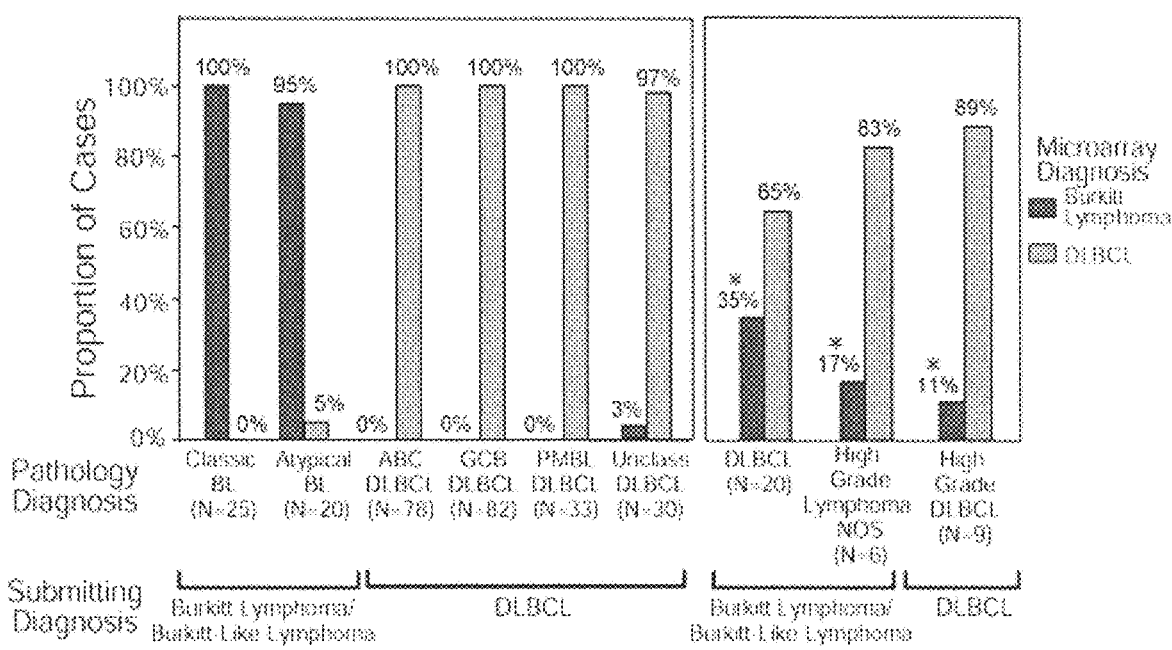

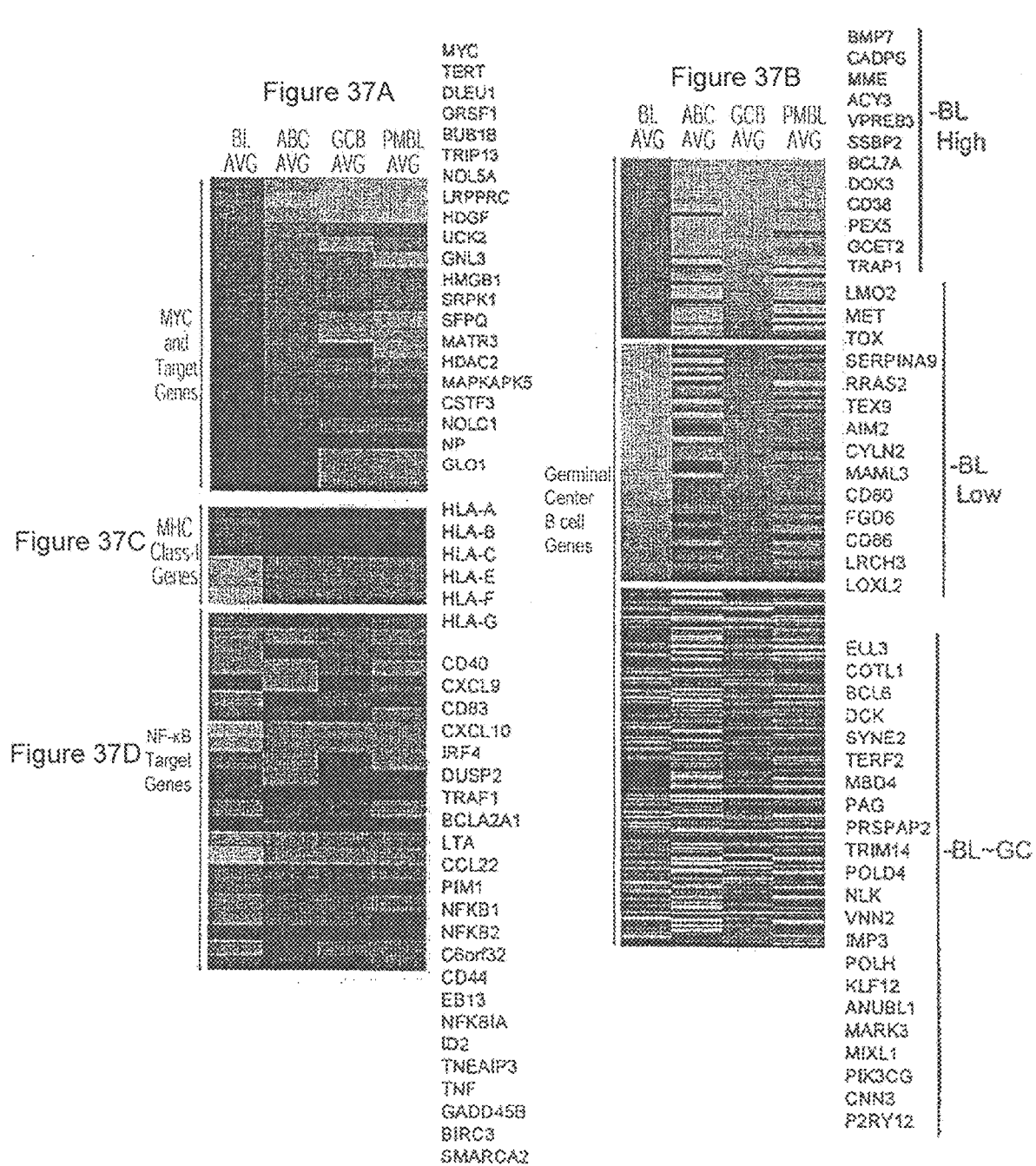

METHODS FOR IDENTIFYING, DIAGNOSING, AND PREDICTING SURVIVAL OF LYMPHOMAS

RELATED APPLICATIONS

The present utility application is a continuation of U.S. patent application Ser. No. 13/409,416, filed Mar. 1, 2012, which is a divisional of U.S. patent application Ser. No. 11/493,387, filed Jul. 25, 2006 (now U.S. Pat. No. 8,131,475), which is a continuation-in-part of U.S. application Ser. No. 10/934,930 (Staudt et al.), filed Sep. 3, 2004 (now U.S. Pat. No. 7,711,492), which claims priority to provisional patent application U.S. Ser. No. 60/500,377, filed Sep. 3, 2003, the disclosures of which are both incorporated by reference herein in their entirety, including but not limited to the electronic data submitted on 21 CD-ROMs accompanying the provisional application.

STATEMENT REGARDING FEDERALLY SPONSORED RESEARCH AND DEVELOPMENT

This invention was made with government support under Grant No. U01 CA084967, awarded by NIH. This invention was made with Government support under project number ZIA BC 011006 by the National Institutes of Health, National Cancer Institute. The government has certain rights in the invention.

REFERENCE TO TABLES SUBMITTED ON COMPACT DISC

Tables 2-1723 and 1725-2358 are contained on 21 CD-ROMs provided herewith. These CD-ROMs are numbered 1-21 of 22. Each CD-ROM is provided in two copies, for a total of 44 CD-ROMs. The name, size, and date of creation for each file is presented in the file entitled "Table_of_contents.txt," located on CD number 21 of 22. The name of each file incorporates the number of the corresponding table. Any reference to a table or file should be considered an incorporation by reference of the contents of the table and/or file at that particular place in the specification.

REFERENCE TO COMPUTER PROGRAM LISTING APPENDIX SUBMITTED ON COMPACT DISC

A computer program listing appendix is contained on one CD-ROM provided herewith. Three copies of this CD-ROM, numbered 22 of 22, are provided. The computer program listing appendix contains files related to the implementation of an algorithm for determining lymphoma type. The name, size, and date of creation for each file in the computer program listing appendix is presented in the file entitled "Table_of_contents.txt," located on CD-ROM 22. Any reference to a file contained in the computer program listing appendix should be considered an incorporation by reference of the contents of that file at that particular place in the specification.

BACKGROUND

A variety of systems for identifying and classifying lymphomas have been proposed over the last 20 years. In the 1980's, the Working Formulation was introduced as a method of classifying lymphomas based on morphological and clinical characteristics. In the 1990's, the Revised European-American Lymphoma (REAL) system was introduced in an attempt to take into account immunophenotypic and genetic characteristics in classifying lymphomas (Harris 1994). The most recent standard, set forth by the World Health Organization (WHO), attempts to build on these previous systems (Jaffe 2001). The WHO classification of lymphomas is based on several factors, including tumor morphology, immunophenotype, recurrent genetic abnormalities, and clinical features. Table 1, below, contains a list of the B and T cell neoplasms that have been recognized by the WHO classification. Each malignancy is listed according to its WHO classification nomenclature, followed by a WHO classification number.

TABLE 1

| Category | Name | WHO ID # |
|---|---|---|
| B-cell neoplasms | | |
| Precursor B-cell neoplasms | Precursor B-cell lymphoblastic leukemia | 9835/3 |
| | Precursor B-cell lymphoblastic lymphoma | 9728/3 |
| Mature B-cell neoplasms | Chronic lymphocytic leukemia | 9823/3 |
| | Small lymphocytic lymphoma | 9670/3 |
| | B-cell prolymphocytic leukemia | 9833/3 |
| | Lymphoplasmacytic lymphoma | 9671/3 |
| | Splenic marginal zone lymphoma | 9689/3 |
| | Hairy cell leukemia | 9940/3 |
| | Plasma cell myeloma | 9732/3 |
| | Solitary plasmacytoma of bone | 9731/3 |
| | Extraosseous plasmacytoma | 9734/3 |
| | Extranodal marginal zone B-cell lymphoma of mucosa-associated lymphoid tissue (MALT lymphoma) | 9699/3 |
| | Nodal marginal zone B-cell lymphoma | 9699/3 |
| | Follicular lymphoma (Grade 1, 2, 3a, 3b) | 9690/3 |
| | Mantle cell lymphoma | 9673/3 |
| | Diffuse large B-cell lymphoma | 9680/3 |
| | Mediastinal (thymio) large B-cell lymphoma | 9679/3 |
| | Intravascular large B-cell lymphoma | 9680/3 |
| | Primary effusion lymphoma | 9678/3 |
| | Burkitt lymphoma | 9687/3 |
| | Burkitt leukemia | 9826/3 |
| B-cell proliferations of uncertain malignant potential | Lymphomatoid granulomatosis | 9766/1 |
| | Post-transplant lymphoproliferative disorder, polymorphic | 9970/1 |
| T-cell and NK-cell neoplasms | | |
| Precursor T-cell and NK-cell neoplasms | Precursor T lymphoblastic leukemia | 9837/3 |
| | Precursor T lymphoblastic lymphoma | 9729/3 |
| | Blastic NK-cell lymphoma | 9727/3 |
| Mature T-cell and NK-cell neoplasms | T-cell prolymphocytic leukemia | 9834/3 |
| | T-cell large granular lymphocytic leukemia | 9831/3 |
| | Aggressive NK-cell leukemia | 9948/3 |
| | Adult T-cell leukemia/lymphoma | 9827/3 |
| | Extranodal NK-/T-cell lymphoma, nasal type | 9719/3 |
| | Enteropathy-type T-cell lymphoma | 9717/3 |
| | Hepatosplenic T-cell lymphoma | 9716/3 |
| | Subcutaneous panniculitis-like T-cell lymphoma | 9708/3 |

TABLE 1-continued

| Category | Name | WHO ID # |
|---|---|---|
| | Mycosis fungoides | 9700/3 |
| | Sezary syndrome (9701/3) | 9701/3 |
| | Primary cutaneous anaplastic large cell lymphoma (C-ALCL) | 9718/3 |
| | Peripheral T-cell lymphoma, unspecified | 9702/3 |
| | Angioimmunoblastic T-cell lymphoma | 9705/3 |
| | Anaplastic large cell lymphoma | 9714/3 |
| T-cell proliferation of uncertain malignant potential | Lymphomatoid papulosis | 9718/3 |
| Hodgkin lymphoma | Nodular lymphocyte predominant Hodgkin lymphoma | 9659/3 |
| | Classical Hodgkin lymphoma | 9650/3 |
| | Classical Hodgkin lymphoma, nodular sclerosis | 9663/3 |
| | Classical Hodgkin lymphoma, lymphocyte-rich | 9651/3 |
| | Classical Hodgkin lymphoma, mixed cellularity | 9652/3 |
| | Classical Hodgkin lymphoma, lymphocyte depleted | 9653/3 |

Other diagnoses that have not been given WHO diagnostic numbers include HIV-associated lymphoma, germinal center B cell-like subtype of diffuse large B cell lymphoma, activated B cell-like subtype of diffuse large B-cell lymphoma, follicular hyperplasia (non-malignant), and infectious mononucleosis (non-malignant).

Although the WHO classification has proven useful in patient management and treatment, patients assigned to the same WHO diagnostic category often have noticeably different clinical outcomes. In many cases, these different outcomes appear to be due to molecular differences between tumors that cannot be readily observed by analyzing tumor morphology. More precise methods are needed for identifying and classifying lymphomas based on their molecular characteristics.

SUMMARY

In certain embodiments, a composition is provided comprising the set of probes listed in Table 2, which is contained in the file entitled "Table_0002_LymphDx_Probe_List.txt." Preferably, this composition comprises a microarray.

In certain embodiments, a method is provided for generating a survival predictor for a particular lymphoma type. In this method, one or more biopsy samples that have been diagnosed as belonging to a particular lymphoma type are obtained. Gene expression data is obtained for these samples, and genes with expression patterns associated with longer or shorter survival are identified. Hierarchical clustering is performed to group these genes into gene expression signatures, and the expression of all genes within each signature are averaged to obtain a gene expression signature value for each signature. Those gene expression signature values are then used to generate a multivariate survival predictor.

In certain embodiments, a method is provided for predicting survival in a follicular lymphoma (FL) subject. In this method, a biopsy sample is obtained from the subject and gene expression data is obtained from the biopsy sample. The expression level of those genes belonging to an immune response-1 or immune response-2 gene expression signature are averaged to generate gene expression signature values for each signature. A survival predictor score is then calculated using an equation:

[2.71*(immune response-2 gene expression signature value)]−[2.36*(immune response-1 gene expression signature value)].

A higher survival predictor score is associated with a less favorable outcome. In one embodiment, the gene expression data used in this method is obtained using a microarray.

In certain embodiments, another method is provided for predicting survival in a follicular lymphoma (FL) subject. In the method, a biopsy sample is obtained from the subject and gene expression data is obtained from the biopsy sample. The expression level of those genes belonging to a B cell differentiation, T-cell, or macrophage gene expression signature are averaged to generate gene expression signature values for each signature. A survival predictor score is then calculated using an equation:

[2.053*(macrophage gene expression signature value)]−[2.344*(T-cell gene expression signature value)]−[0.729*(B-cell gene expression signature value)].

A higher survival predictor score is associated with a less favorable outcome. In one embodiment, the gene expression data used in this method is obtained using a microarray.

In certain embodiments, yet another method is provided for predicting survival in a follicular lymphoma (FL) subject. In this method, a biopsy sample is obtained from the subject and gene expression data is obtained from the biopsy sample. The expression level of those genes belonging to a macrophage, T-cell, or B-cell differentiation gene expression signature are averaged to generate gene expression signature values for each signature. A survival predictor score is then calculated using an equation:

[1.51*(macrophage gene expression signature value)]−[2.11*(T-cell gene expression signature value)]−[0.505*(B-cell differentiation gene expression signature value)].

A higher survival predictor score is associated with a less favorable outcome. In one embodiment, the gene expression data used in this method is obtained using a microarray.

In certain embodiments, a method is provided for predicting survival in a diffuse large B cell lymphoma (DLBCL) subject. In this method, a biopsy sample is obtained from the subject and gene expression data is obtained from the biopsy sample. The expression level of those genes belonging to an ABC DLBCL high, lymph node, or MHC class II gene expression signature are averaged to generate gene expression signature values for each signature. A survival predictor score is then calculated using an equation:

[0.586*(ABC DLBCL high gene expression signature value)]−[0.468*(lymph node gene expression signature value)]−[0.338*(MHC class II gene expression signature value)].

A higher survival predictor score is associated with a less favorable outcome. In the embodiment, the pane expression data used in this method is obtained using a microarray.

In certain embodiments, another method is provided for predicting survival in a diffuse large B cell lymphoma (DLBCL) subject. In this method, a biopsy sample is obtained from the subject and gene expression data is obtained from the biopsy sample. The expression level of those genes belonging to a lymph node, germinal B cell, proliferation, or MHC class II gene expression signature are averaged to generate gene expression signature values for each signature. A survival predictor score is then calculated using an equation:

[−0.4337*(lymph node gene expression signature)]+ [0.09*(proliferation gene expression signature)]−[0.4144*(germinal center B-cell gene expression signature)]−[0.2006*(MHC class II gene expression signature)].

A higher survival predictor score is associated with a less favorable outcome. In one embodiment, the gene expression data used in this method is obtained using a microarray.

In certain embodiments, yet another method is provided for predicting survival in a diffuse large B cell lymphoma (DLBCL) subject. In this method, a biopsy sample is obtained from the subject and gene expression data is obtained from the biopsy sample. The expression level of those genes belonging to a lymph node, germinal B cell, or MHC class II gene expression signature are averaged to generate gene expression signature values for each signature. A survival predictor score is then calculated using an equation:

[−0.32*(lymph node gene expression signature)]− [0.176*(germinal B cell gene expression signature)]−[0.20*(MHC class II gene expression signature)].

A higher survival predictor score is associated with a less favorable outcome. In one embodiment, the gene expression data used in this method is obtained using a microarray. In another embodiment, the gene expression data is obtained using RT-PCR.

In certain embodiments, a method is provided for refining a method for predicting survival in a diffuse large B cell lymphoma (DLBCL). In this method, gains or amplifications of the 3p11-p12 region in chromosome 3 are identified, wherein gains or amplifications of this region are associated with a less favorable outcome. This information can be integrated into an existing method for predicting DLBCL survival. For example, a survival predictor score may be calculated using an equation such as:

Survival predictor score=[0.241*(proliferation gene expression signature value)]+[0.310*(BMP6 expression value)]−[0.290*(germinal center B cell gene expression signature value)]−[0.311* (MHC class II gene expression signature value)]−[0.249*(lymph node gene expression signature value)].

wherein a higher survival predictor score is associated with a less favorable outcome. The DLBCL sample may then be assayed for gains or amplifications in the 3p11-p12 using any available method, including for example CGH. The identification of gains or amplifications in this region indicate a decrease in survival. This information can be used to adjust the survival predictor score accordingly. Alternatively, identification of a gain or amplification of 3p11-p12 may be used as a stand-alone indicator of less favorable outcome for a DLBCL patient in the absence of additional gene expression data.

In certain embodiments, a method is provided for predicting survival in a mantle cell lymphoma (MCL) subject. In this method, a biopsy sample is obtained from the subject and gene expression data is obtained from the biopsy sample. The expression level of those genes belonging to a proliferation gene expression signature are averaged to generate a gene expression signature value. A survival predictor score is then calculated using an equation:

[1.66*(proliferation gene expression signature value)].

A higher survival predictor score is associated with a less favorable outcome. In one embodiment, the gene expression data used in this method is obtained using a microarray.

In certain embodiments, a method is provided for determining the probability that a sample X belongs to a first lymphoma type or a second lymphoma type. In this method, a set of genes is identified that is differentially expressed between the two lymphoma types in question, and a set of scale factors representing the difference in expression between the lymphoma types for each of these genes are calculated. A series of linear predictor scores are generated for samples belonging to either of the two lymphoma types based on expression of these genes. Gene expression data is then obtained for sample X, and a linear predictor score is calculated for this sample. The probability that sample X belongs to the first lymphoma type is calculated using an equation that incorporates the linear predictor score of sample X and the mean and variance of the linear predictor scores for the known samples of either lymphoma type.

In certain embodiments, a method is provided for determining the lymphoma type of a sample X. In this method, a set of genes is identified that is differentially expressed between a first lymphoma type and a second lymphoma type, and a set of scale factors representing the difference in expression of each of these genes between the two lymphoma types are calculated. A series of linear predictor scores are generated for samples belonging to either of the two lymphoma types based on expression of these genes. Gene expression data is then obtained for sample X, and a linear predictor score is calculated for this sample. The probability that sample X belongs to the first lymphoma type is calculated using an equation that incorporates the linear predictor score of sample X and the mean and variance of the linear predictor scores for the known samples of either lymphoma type. This entire process is then repeated with various lymphoma types being substituted for the first lymphoma type, the second lymphoma type, or both.

In certain embodiments, a method is provided for determining the lymphoma type of a sample X. In this method, a series of lymphoma type pairs are created, with each pair consisting of a first lymphoma type and a second lymphoma type. For each type pair, gene expression data is obtained for a set of genes, and a series of scale factors representing the difference in expression of each of these genes between the two lymphoma types are calculated. A subset of z genes with the largest scale factors are identified, and a series of linear predictor scores are generated for samples belonging to either of the two lymphoma types. Linear predictor scores are calculated for anywhere from 1 to z of these genes. The number of genes from 1 to z that results in the largest difference in linear predictor scores between the two lymphoma types is selected, and gene expression data for these genes is obtained for sample X. A linear predictor score is generated for sample XT and the probability that the sample belongs to the first lymphoma type is calculated using an equation that incorporates the linear predictor score for sample X and the mean and variance of the linear predictor scores for the known samples of either lymphoma type.

In certain embodiments, another method is provided for determining the lymphoma type of a sample X. In this method, a series of lymphoma type pairs are created, with each pair consisting of a first lymphoma type and a second lymphoma type. For each type pair, gene expression data is obtained for a set of genes, and a series of scale factors representing the difference in expression of each of these genes between the two lymphoma types are calculated. The set of genes is divided into gene-list categories indicating correlation with a gene expression signature. Within each gene-list category, a subset of z genes with the largest scale factors are identified, and a series of linear predictor scores are generated for samples belonging to either of the two lymphoma types. Linear predictor scores are calculated for anywhere from 1 to z of these genes. The number of genes from 1 to z that results in the largest difference in linear predictor scores between the two lymphoma types is selected, and gene expression data for these genes is obtained for sample X. A linear predictor score is generated for sample X, and the probability q that the sample belongs to the first lymphoma type is calculated using an equation that incorporates the linear predictor score for sample X and the mean and variance of the linear predictor scores for the known samples of either lymphoma type. A high probability q indicates that sample X belongs to the first lymphoma type, a low probability q indicates that sample X belongs to the second lymphoma type, and a "middle probability" indicates that sample X belongs to neither lymphoma type. The cut-off point between high, middle, and low probability values is determined by ranking samples of known lymphoma type according to their probability values, then analyzing every possible cut-off point between adjacent samples by: 3.99*[(% of first lymphoma type misidentified as second lymphoma type)+(% of second lymphoma type misidentified as a first lymphoma type)]+[(% of first lymphoma type identified as belonging to neither lymphoma type)+(% of second lymphoma type identified as belonging to neither lymphoma type)]. The final cut-off points are those that minimize the value of this equation.

In certain embodiments, a method is provided for classifying a sample as BL. In this method, a series of lymphoma type pairs are created, with each pair consisting of a first lymphoma type (BL) and a second lymphoma type. In certain embodiments, the second lymphoma type is DLBCL, and in certain of these embodiments, the DLBCL is ABC, GCB, or PMBL. For each type pair, gene expression data is obtained for a set of genes, and a series of scale factors representing the difference in expression of each of these genes between the two lymphoma types are calculated. The set of genes is divided into two subsets. The first subset includes c-myc and c-myc target genes, while the second subset includes z genes from the gene set that exhibit the largest scale factors and do not fall into the first subset. In certain embodiments, z is 100. A first and second series of linear predictor scores are generated for samples belonging to either of the two lymphoma types, with the first series based on expression of the first gene subset and the second series based on expression of the second gene subset. Expression of the first and second gene subsets is measured for sample X, and a first and second linear predictor score is generated for sample X based on the expression of the first and second gene subsets, respectively. Two probabilities, $q_1$ and $q_2$, are calculated using equations that incorporate the first and second linear predictor scores for sample X, respectively, and the mean and variance of the linear predictor scores for the known samples of either lymphoma type. Sample X is classified as BL if both $q_1$ and $q_2$ are greater than 90%.

In certain embodiments, a method is provided for identifying a lymphoma sample as cyclin D1-negative MCL. In this method, a candidate sample X is identified based on a lack of cyclin D1 expression. A series of lymphoma type pairs are created, with each pair consisting of MCL and a second lymphoma type. For each type pair, gene expression data is obtained for a set of genes G, and a series of scale factors representing the difference in expression of each of these genes between the two lymphoma types are calculated. A subset of genes g with the largest scale factors are identified, and a series of linear predictor scores are generated for samples belonging to either of the two lymphoma types. Gene expression data for the subset of genes g is obtained for sample X. A linear predictor score is generated for sample X, and the probability that the sample belongs to the first lymphoma type is calculated using an equation that incorporates the linear predictor score for sample X and the mean and variance of the linear predictor scores for the known samples of either lymphoma type. A probability greater than 90% indicates that the sample X is cyclin D1-negative MCL.

BRIEF DESCRIPTION OF THE DRAWINGS

FIG. 5: Kaplan-Meier plot of survival in FL samples based on survival predictor scores. 191 FL samples were divided into quartiles based on their survival predictor scores. The survival predictor scores were calculated by:

[(2.71*immune*response-2 gene expression signature value)]−[(2.36×immune response-1 gene expression signature value)].

Figure 6:
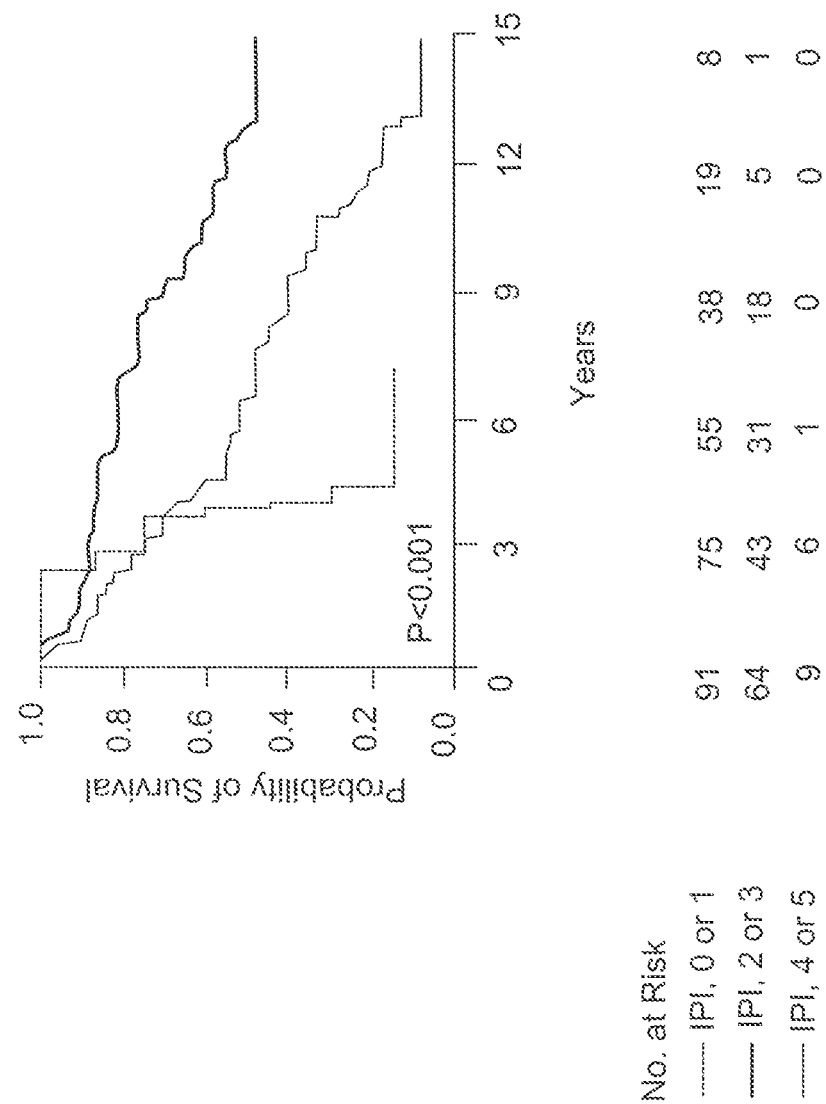

FIG. 6: Kaplan-Meier plot of aurvlvalln FL samples based on IPI score. 96 FL samples were divided into three groups based on their IPI scores.

Figure 7:
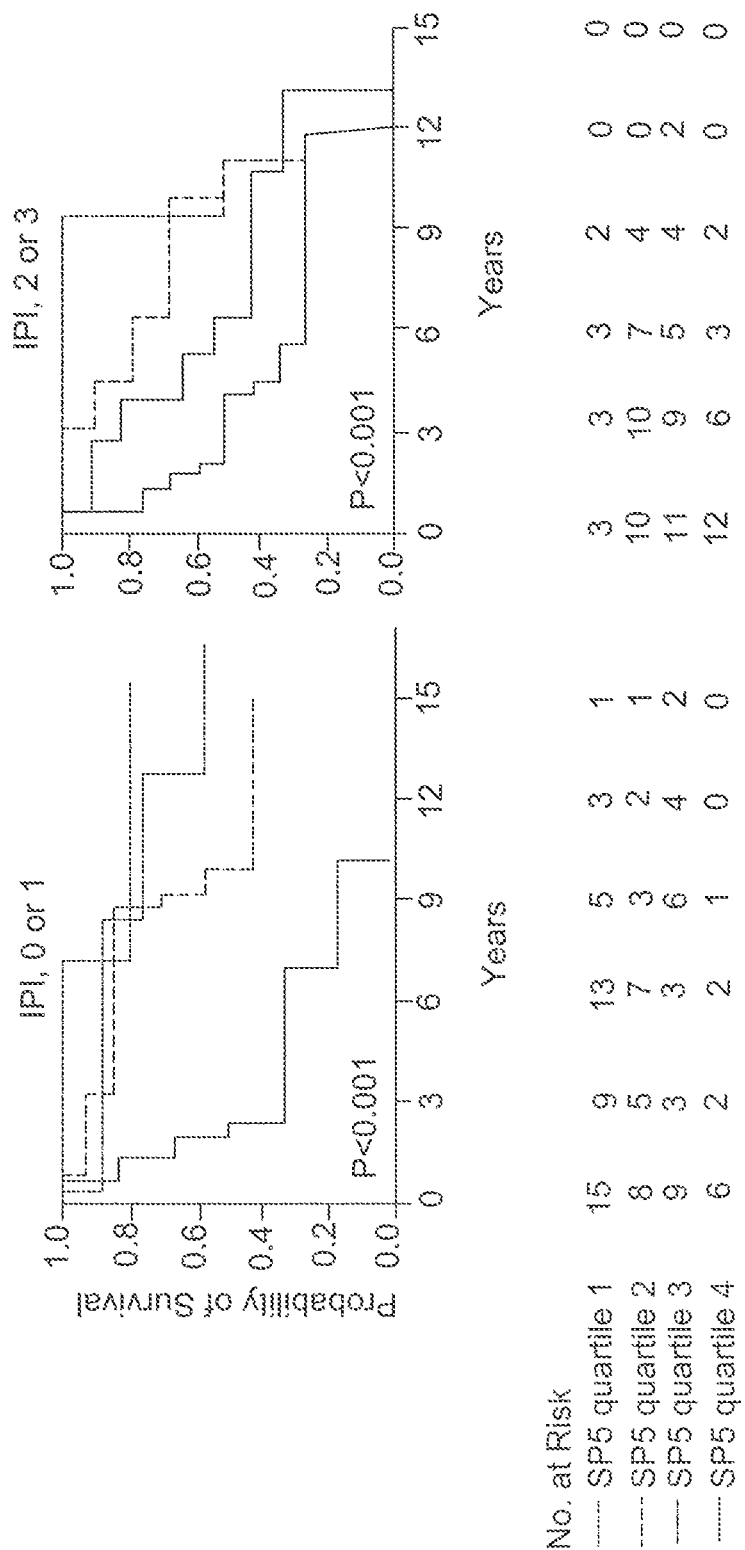

FIG. 7: Kaplan-Meier plot of survival in FL samples with low or high risk IPI scores based on survival predictor scares. 96 FL samples with low risk (left panel) or intermediate risk (right panel) IPI scores were divided into quartiles based on their survival predictor scores. The survival predictor scores were calculated by:

[(2.71*immune response-2 gene expression signature value)]−[(2.36×immune response-1 gene expression signature value)].

Figure 8:
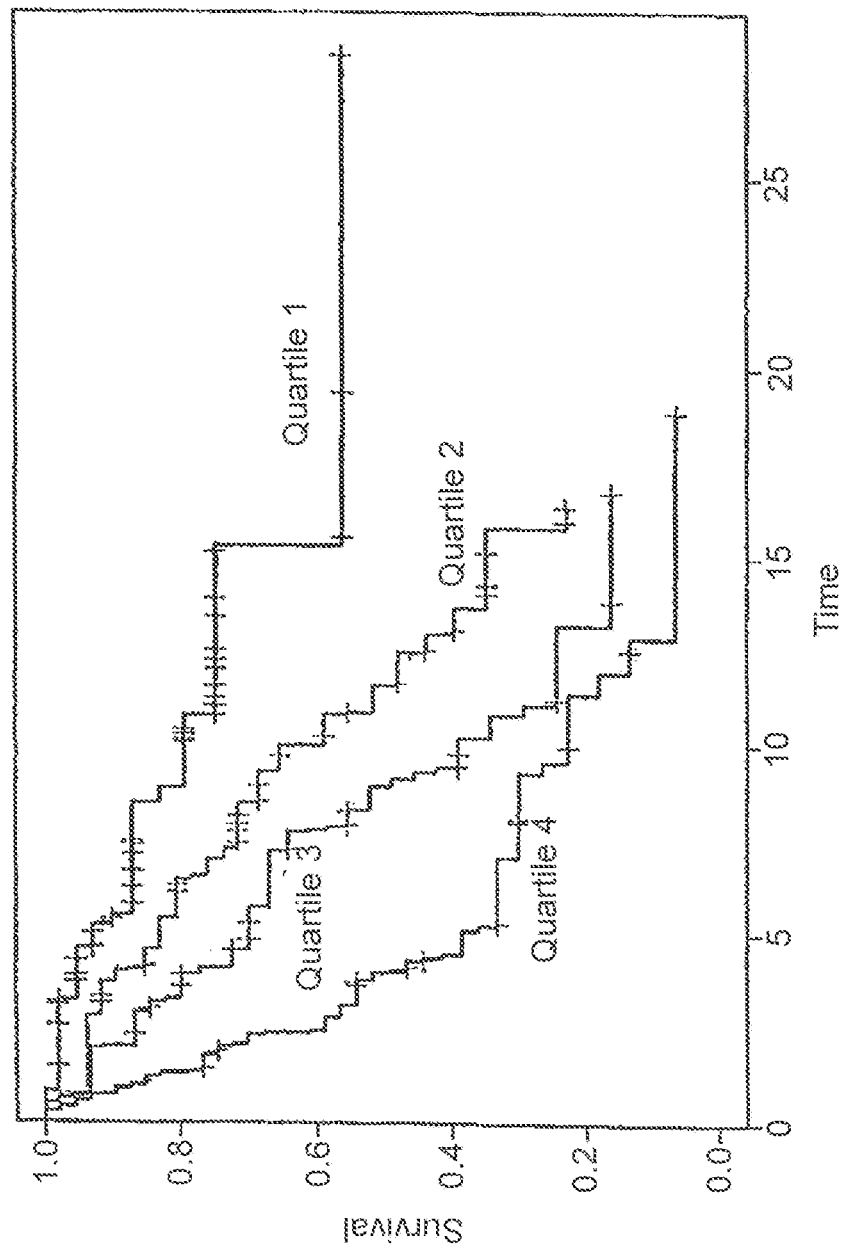

FIG. 8: Kaplan-Meier plot of survival in FL samples based on survival predictor scores. 191 FL samples were divided into quartiles based on their survival predictor scores. The survival predictor scores were calculated by:

[2.053*(macrophage gene expression signature value)]−[2.344*(T-cell gene expression signature value)]−[0.729*(B-cell differentiation gene expression signature value)].

Figure 9:
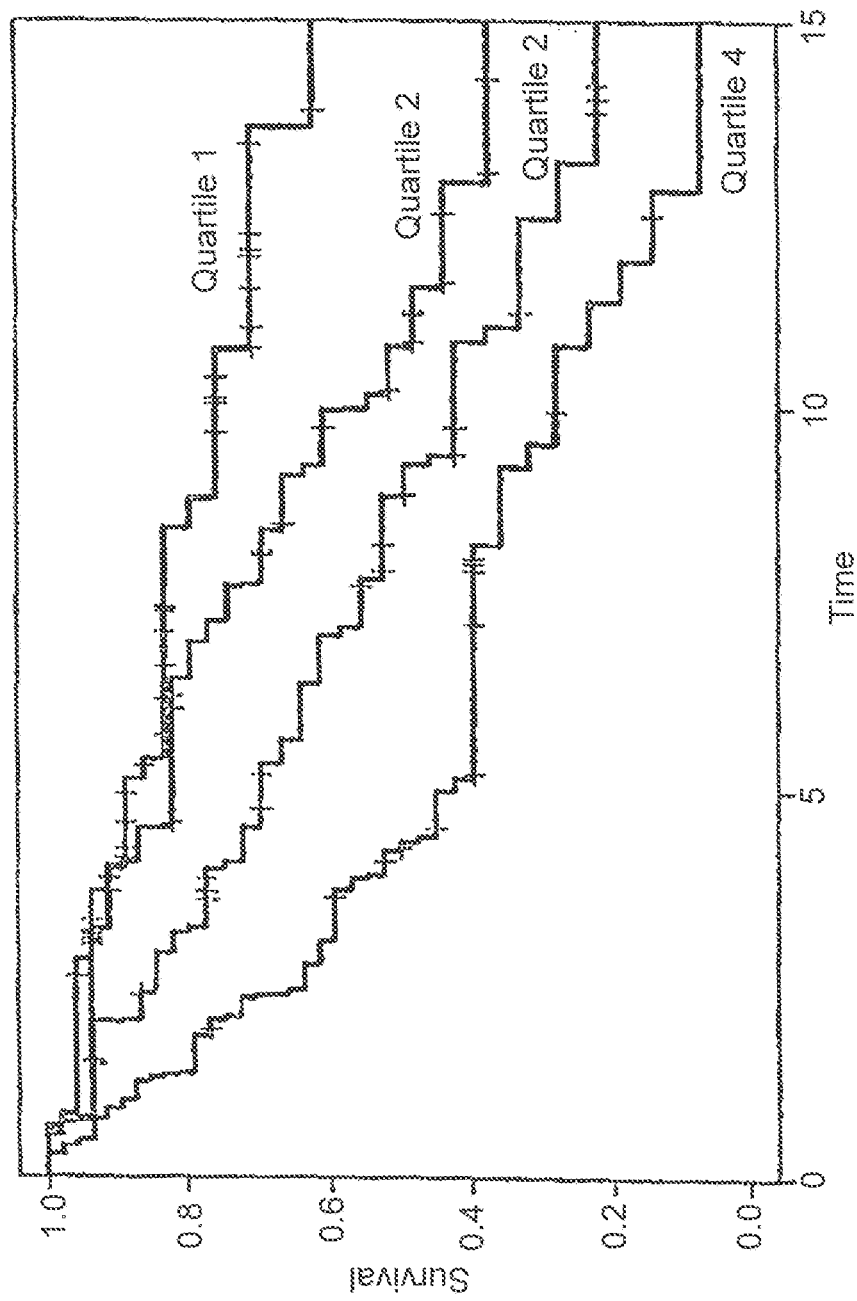

FIG. 9: Kaplan-Meier plot of survival in FL samples based on survival predictor scores. 191 FL samples were divided into quartiles based on their survival predictor scores. The survival predictor scores were calculated by:

[1.51*(macrophage gene expression signature value)]−[2.11*(T-cell gene expression signature value)]−[0.505*(B-cell differentiation gene expression signature value)].

Figure 10:
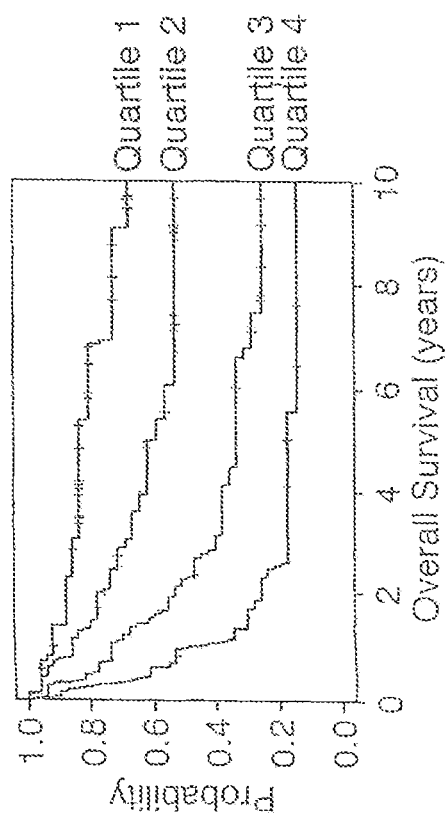

FIG. 10: Kaplan-Meier plot of survival in DLBCL samples based on survival predictor scores. 231 DLBCL samples were divided into quartiles based on their survival predictor scores. The survival predictor scores were calculated by:

[0.586*(ABC DLBCL high gene expression signature value)]−[0.468*(lymph node gene expression signature value)]−[(0.336*MHC Class II gene expression signature value)].

Figure 11:
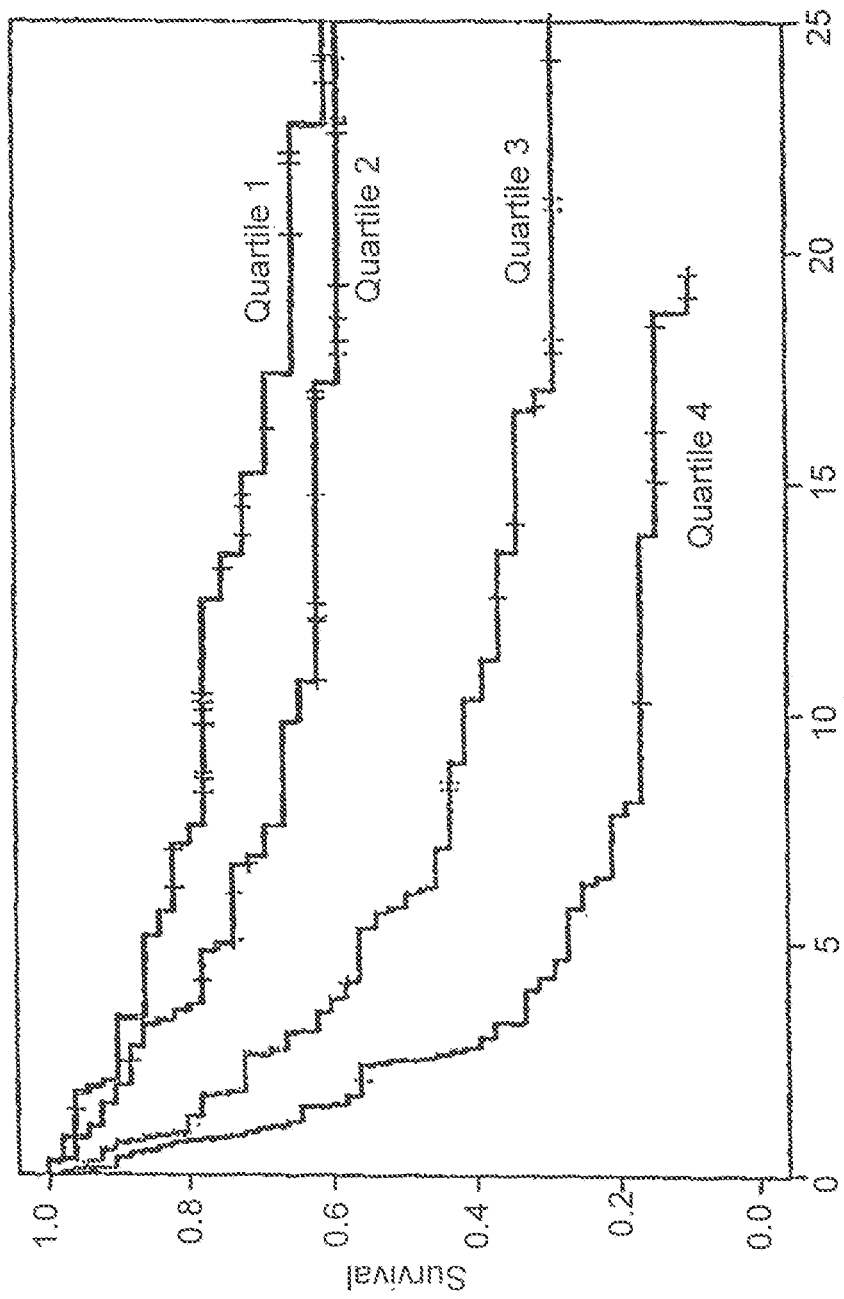

FIG. 11: Kaplan-Meier plot of survival in DLBCL samples based on survival predictor scores. 200 DLBCL samples were divided into quartiles based on their survival predictor scores. The survival predictor scores were calculated by:

[−0.4337*(lymph node gene expression signature value)]+[0.09*(proliferation gene expression, signature value)]−[0.4144*(germinal center B-cell gene expression signature value)]−[0.2006*(MHC class II gene expression signature value)].

Figure 12:
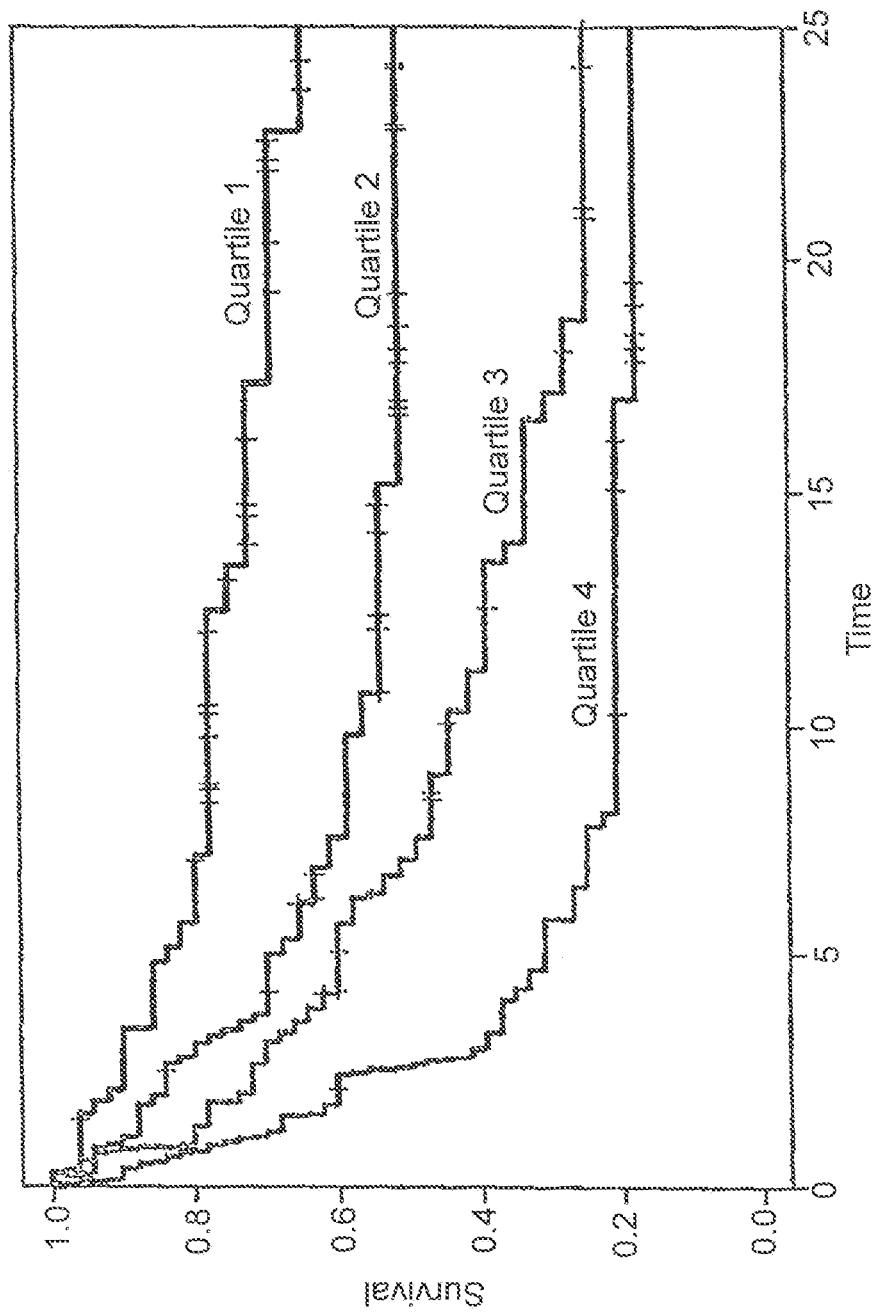

FIG. 12: Kaplan-Meier plot of survival in DLBCL samples based on survival predictor scores. 200 DLBCL samples were divided into quartiles based on their survival predictor scores. The survival predictor scores were calculated by:

[−0.32*(lymph node gene expression signature value)]−[0.176*(germinal center B-cell gene expression signature value)]−[0.206*(MHC class II gene expression signature value)].

Figure 13:
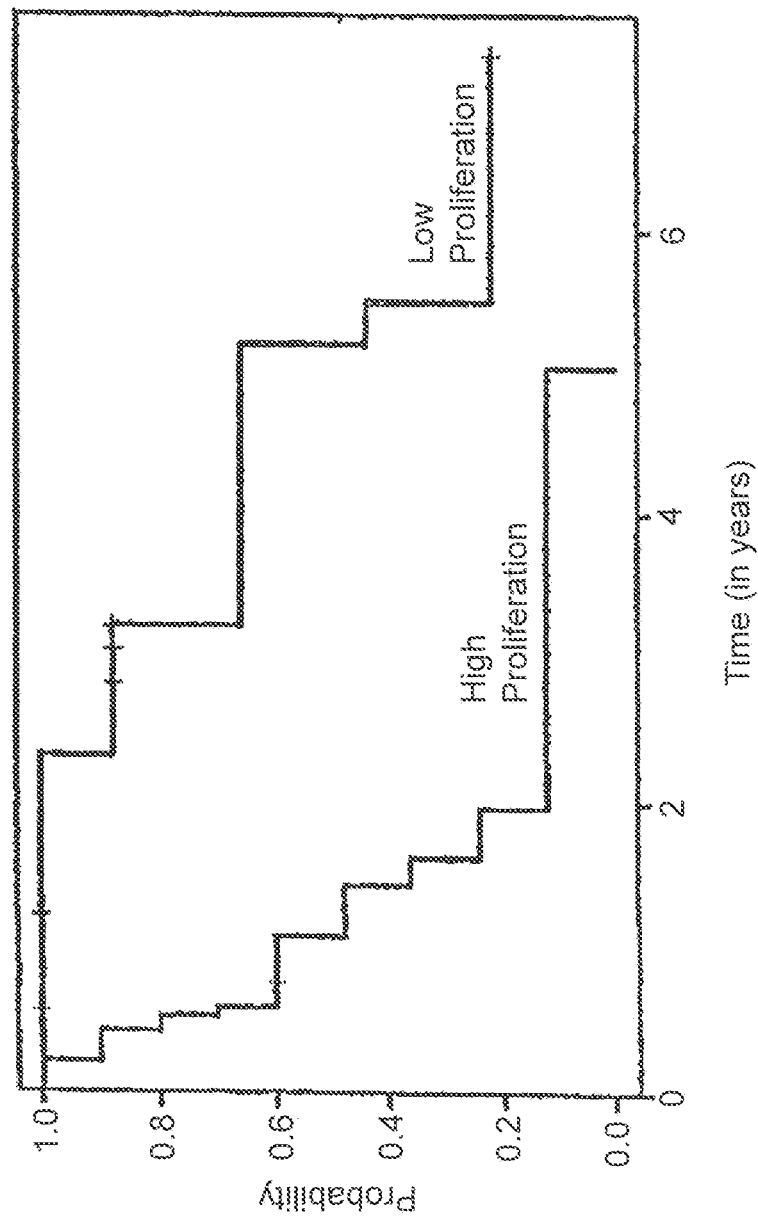

FIG. 13: Kaplan-Meier plot of survival in MCL samples based on survival predictor scores. 21 MCL samples were divided into two equivalent groups based on their survival predictor scores. The survival predictor scores were calculated by:

1.66*(proliferation gene expression signature value).

Figure 14:
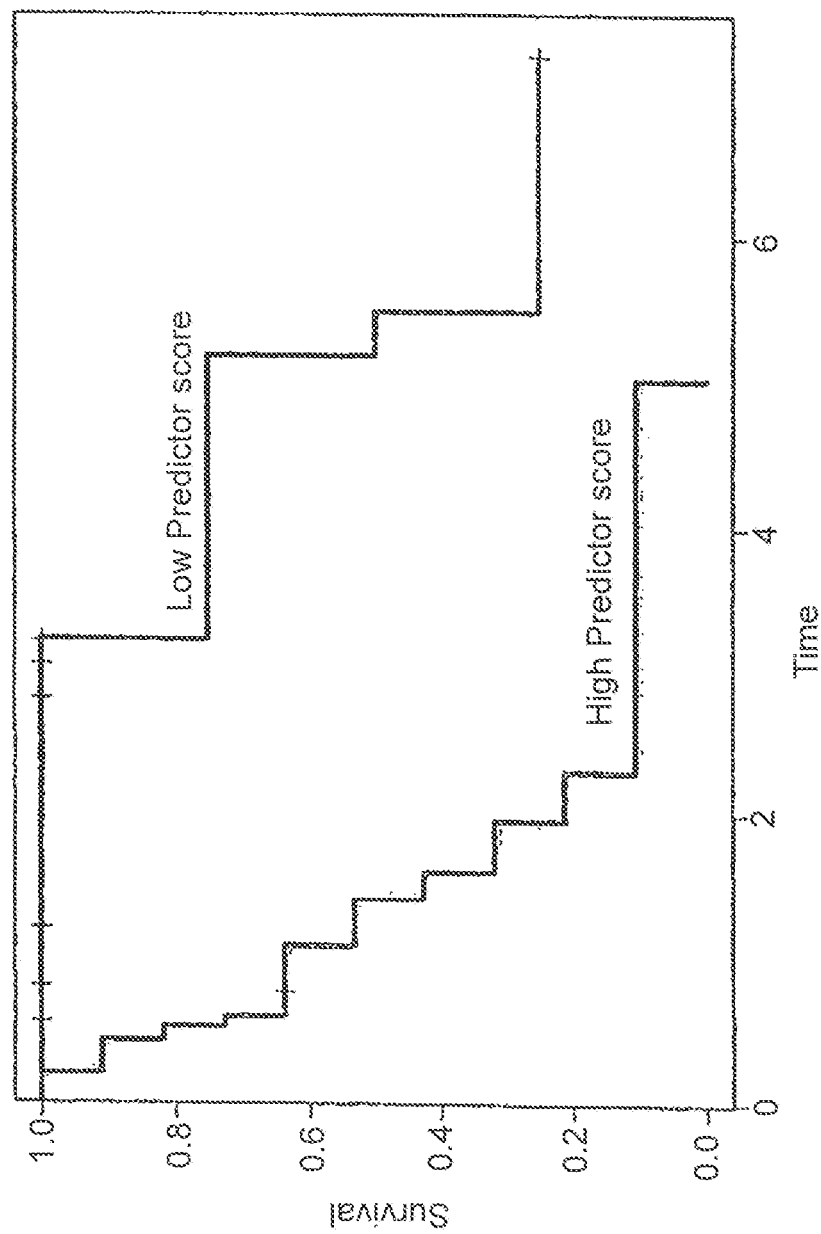

FIG. 14: Kaplan-Meier plot of survival in MCL samples based on survival predictor scores. 21 MCL samples were divided into two equivalent groups based on their survival predictor scores. The survival predictor scores were calculated by:

1.66*(proliferation gene expression signature value).

Figure 15:
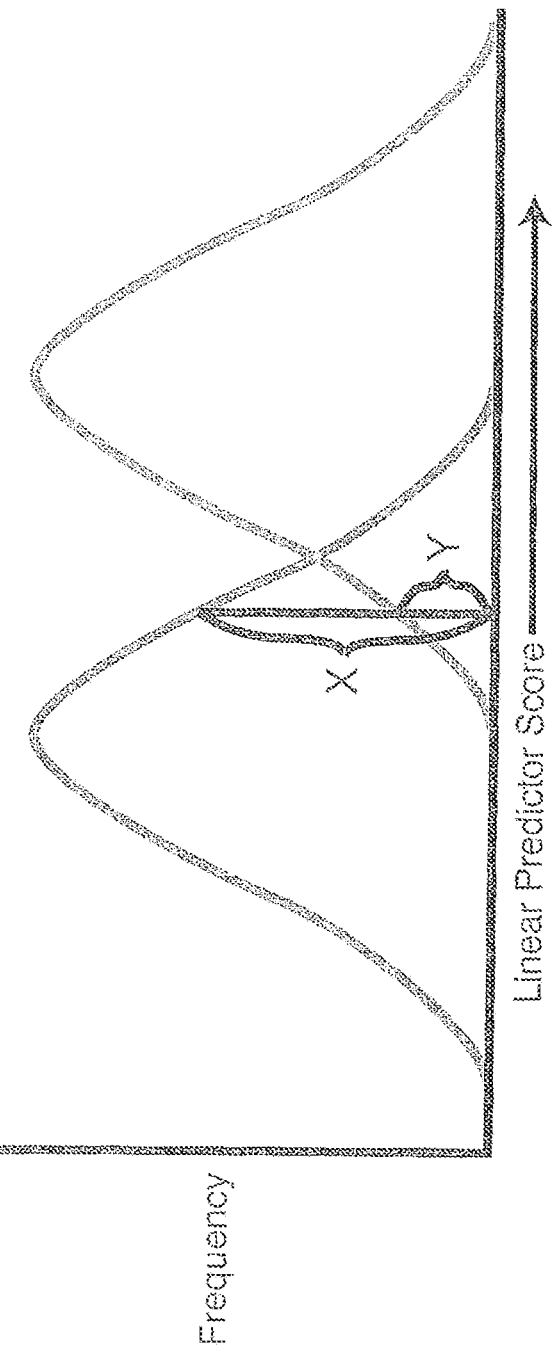

FIG. 15: Predicting lymphoma type using Bayesian analysis. Bayes' rule can be used to determine the probability that an unknown sample belongs to a first lymphoma type rather than a second lymphoma type. A linear predictor score is generated for the sample, and the probability that the sample belongs to the first lymphoma type is determined based on the distribution of linear predictor scores within the first and second lymphoma type.

Figure 16:
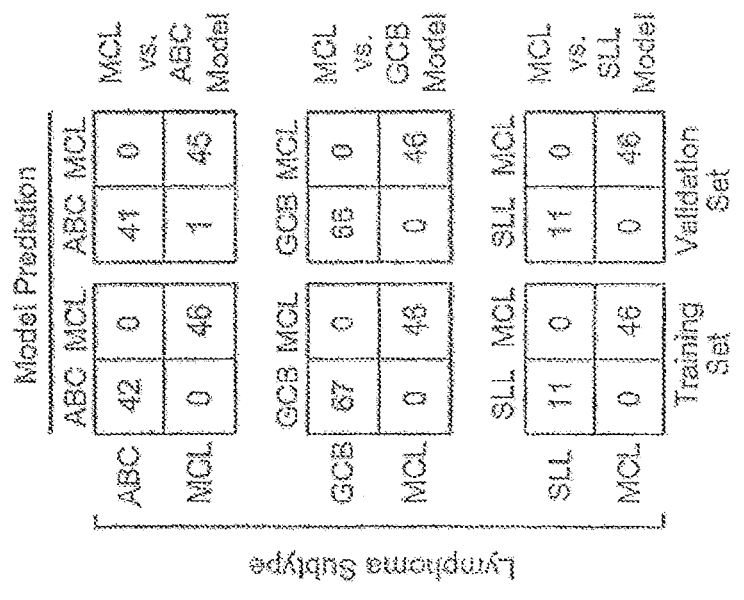

FIG. 16: Performance of MCL predictor model. Results of the gene-expression based predictor model for MCL are shown for three models (MCL vs. ABC, MCL vs. GCB, MCL vs. SLL). Performance is shown for both the training set and the validation set.

Figure 17:
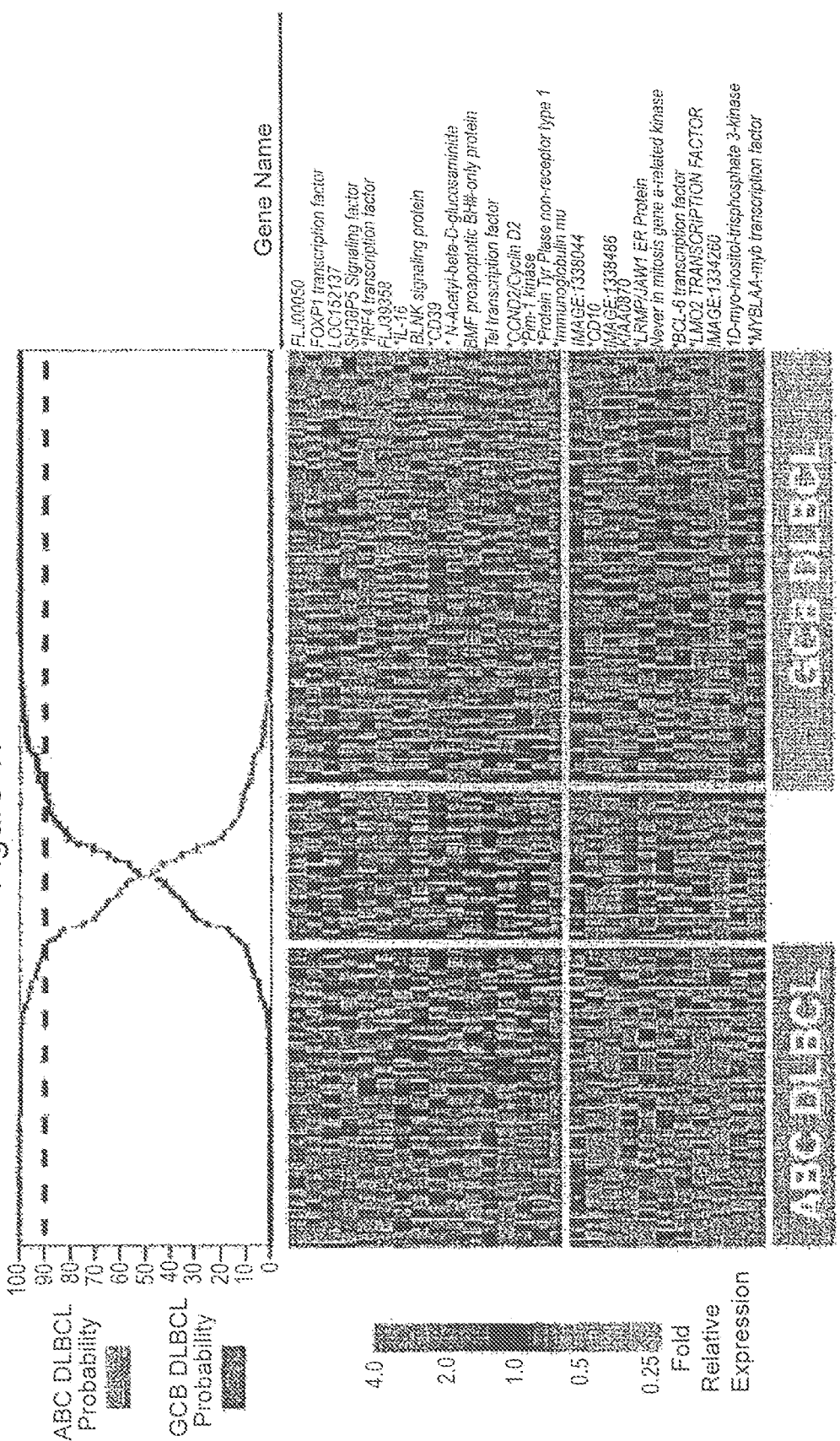

FIG. 17: Gene expression-based identification of DLBCL. Expression levels for 27 genes in a subgroup predictor are shown for 274 DLBCL samples. Expression levels are depicted according to the color scale shown at the left. The 14 genes used to predict the DLBCL subgroups in the Affymetrix data set are indicated with asterisks. The probabilities that the DLBCL samples belong to the ABC or GCB subtypes are graphed at the top, and the DLBCL cases are arranged accordingly. Cases belonging to either ABC or GCB with 90% or greater probability are indicated.

FIG. 18: Performance of DLBCL subtype predictor model. Assignments of DLBCL samples to the ABC or GCB subtypes based on hierarchical clustering vs. the predictor model disclosed herein are compared within the training, validation, and total set of samples.

Figure 19A:
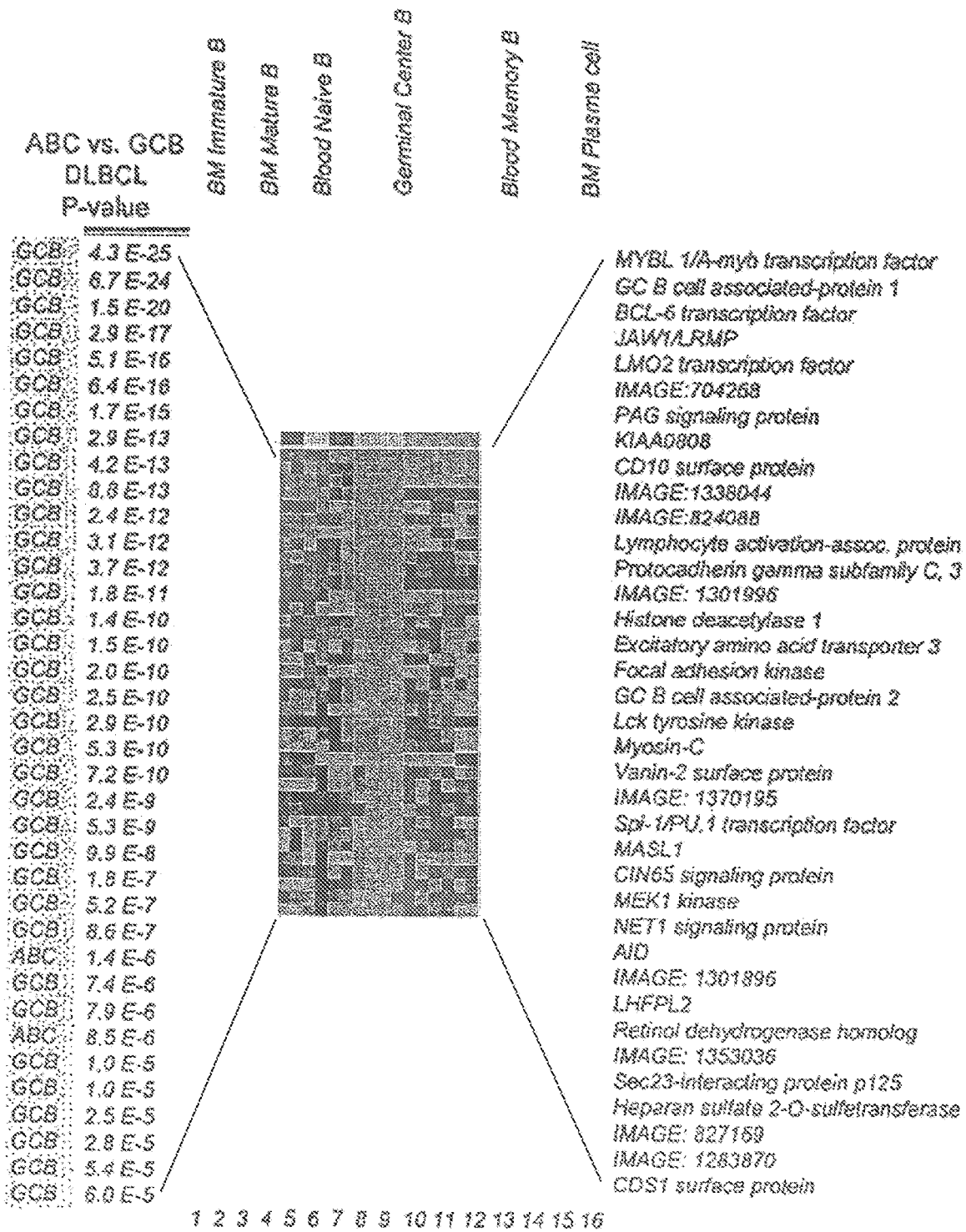
Figure 19B:
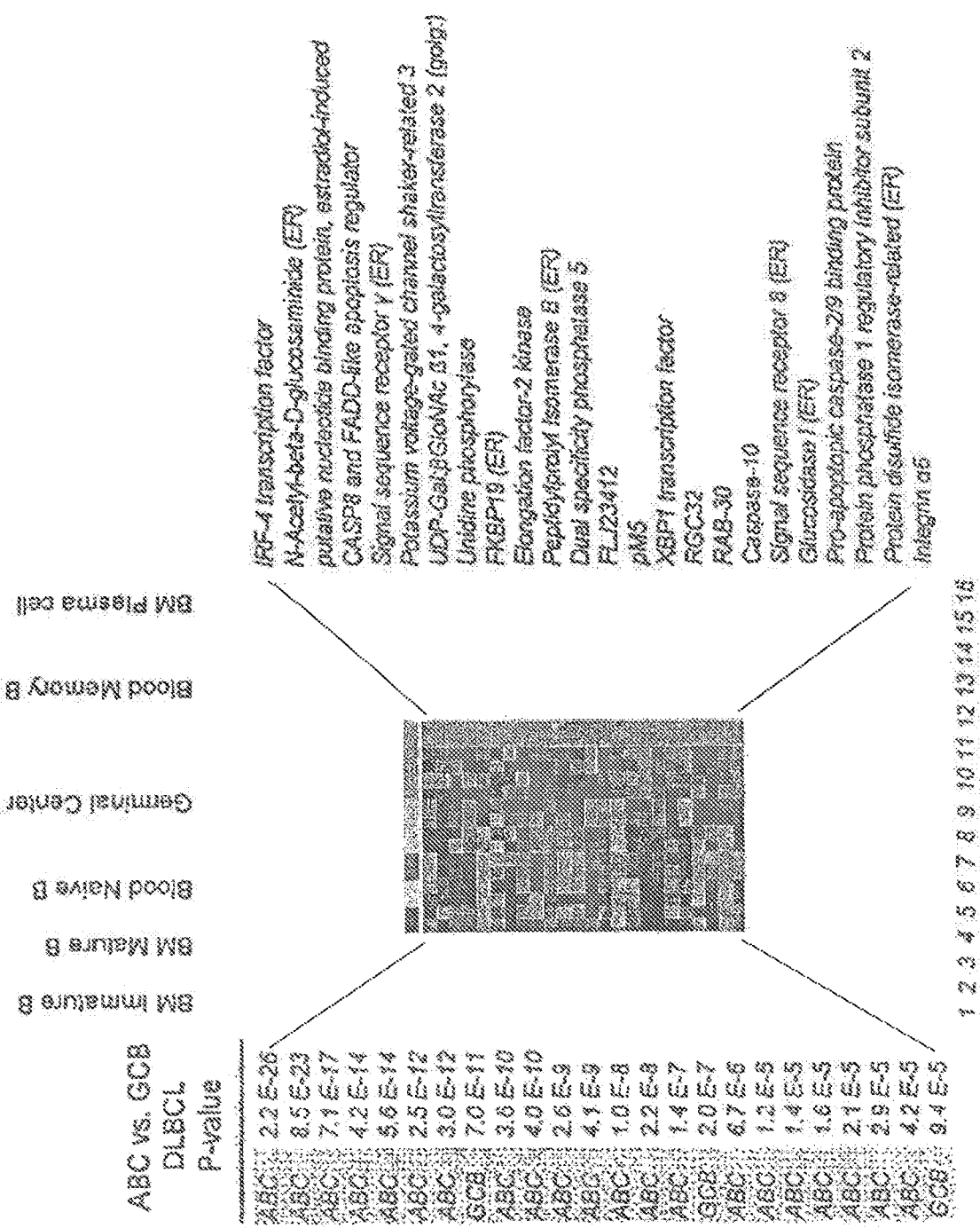

FIGS. 19A and 19B: Relationship of gene expression in normal B cell subpopulations to DLBCL subtypes. Relative gene expression in the indicated purified B cell populations is depicted according to the color scale in FIG. 17. The P value of the difference in expression of these genes between the GCB and ABC DLBCL subtypes is shown, and the subtype with the higher expression is shown is indicated (blue, ABC; orange, GCB). FIG. 19A. DLBCL subtype distinction genes that are more highly expressed in germinal center B cells than at other B cell differentiation stages. FIG. 19B. DLBCL subtype distinction genes that are more highly expressed in plasma cells than at other B cell differentiation stages.

Figure 20A:
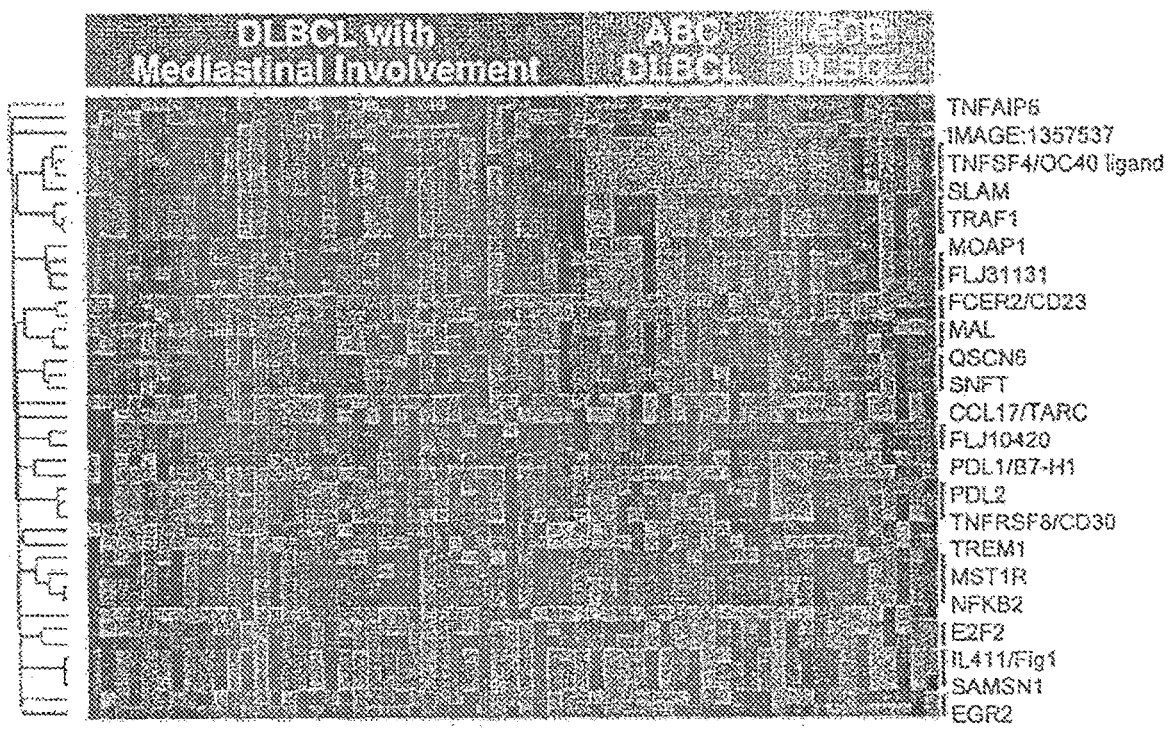

FIGS. 20A and 20B: Identification of a PMBL gene expression signature. FIG. 20A. Hierarchical clustering identified a set of 23 PMBL signature genes that were more highly expressed in most lymphomas with a clinical diagnosis of PMBL than in lymphomas assigned to the GCB or ABC subtypes. Each row presents gene expression measurements from a single Lymphochip microarray feature representing the genes indicated. Each column represents a single lymphoma biopsy sample. Relative gene expression is depicted according to the color scale shown. FIG. 20B. Hierarchical clustering of the lymphoma biopsy samples based on expression of the PMBL signature genes identified in (A). A "core" cluster of lymphoma cases was identified that highly expressed the PMBL signature genes.

Figure 21A:
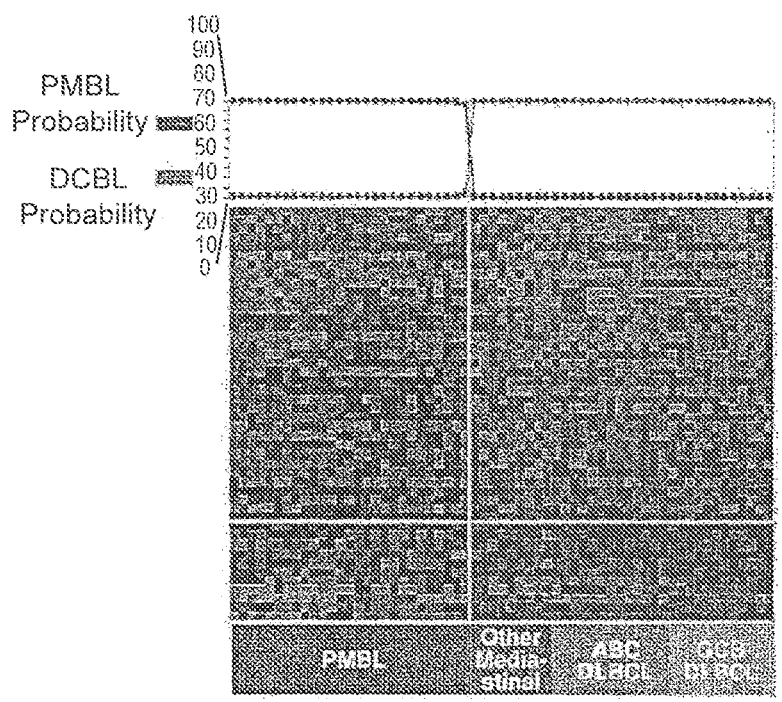
Figure 21B:
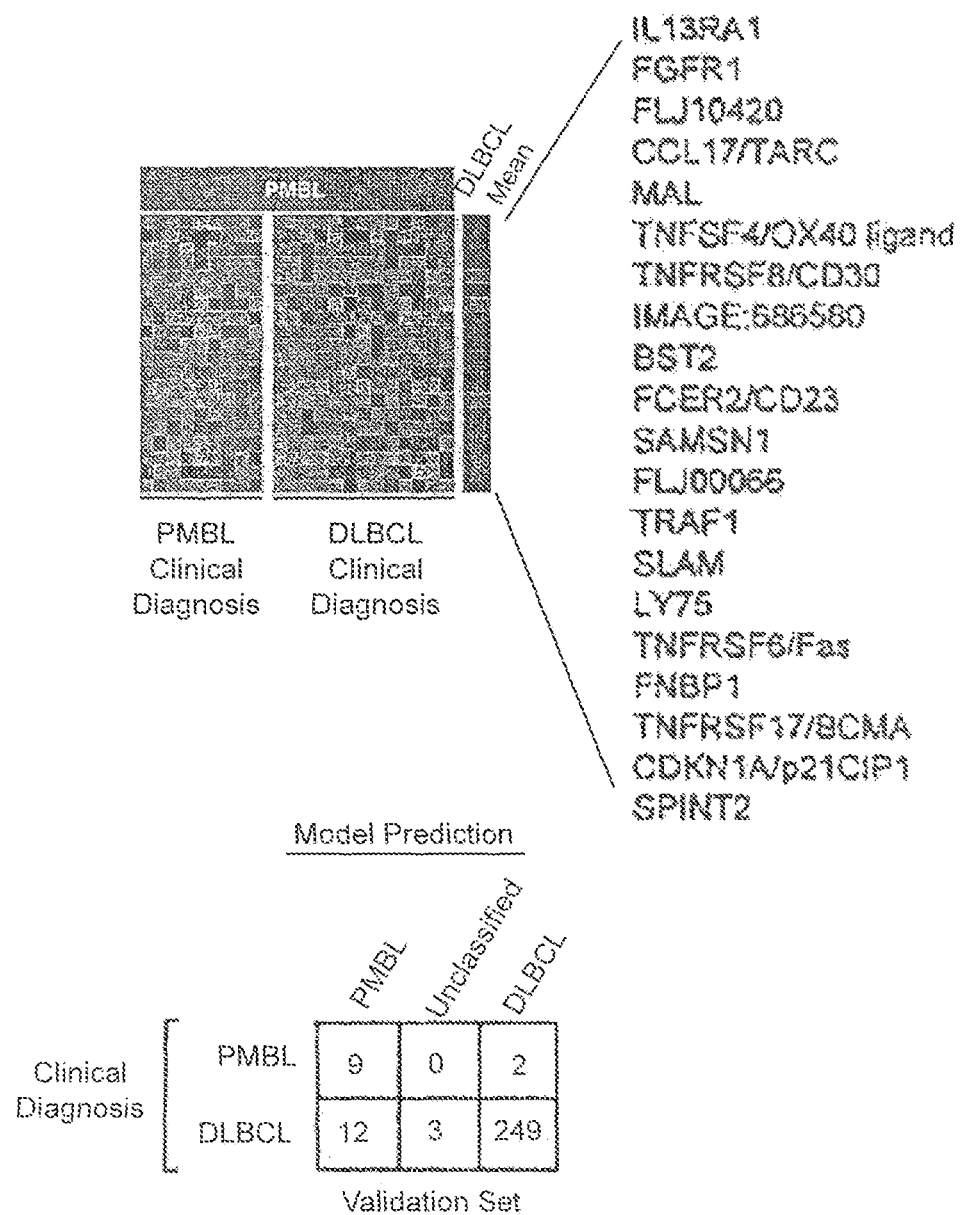

FIGS. 21A and 21B: Development of a gene expression-based molecular diagnosis of PMBL. FIG. 21A. A PMBL predictor was created based on expression of the 46 genes shown. Relative gene expression for each lymphoma biopsy sample is presented according to the color scale shown in FIG. 20. The probability that each sample is PMBL or DLBCL based on gene expression is shown at the top. FIG. 21B. The PMBL predictor was used to classify 274 lymphoma samples as PMBL or DLBCL. Prediction results are summarized on the right, and the relative gene expression for each case that was classified by the predictor as PMBL is shown on the left. Average expression of each gene in samples classified as DLBCL is also shown. The 20 genes listed are those represented on the Lymphochip that were more highly expressed in PMBL than in DLBCL. Not shown are eight genes from the PMBL predictor that were more highly expressed in DLBCL than in PMBL.

Figure 22:
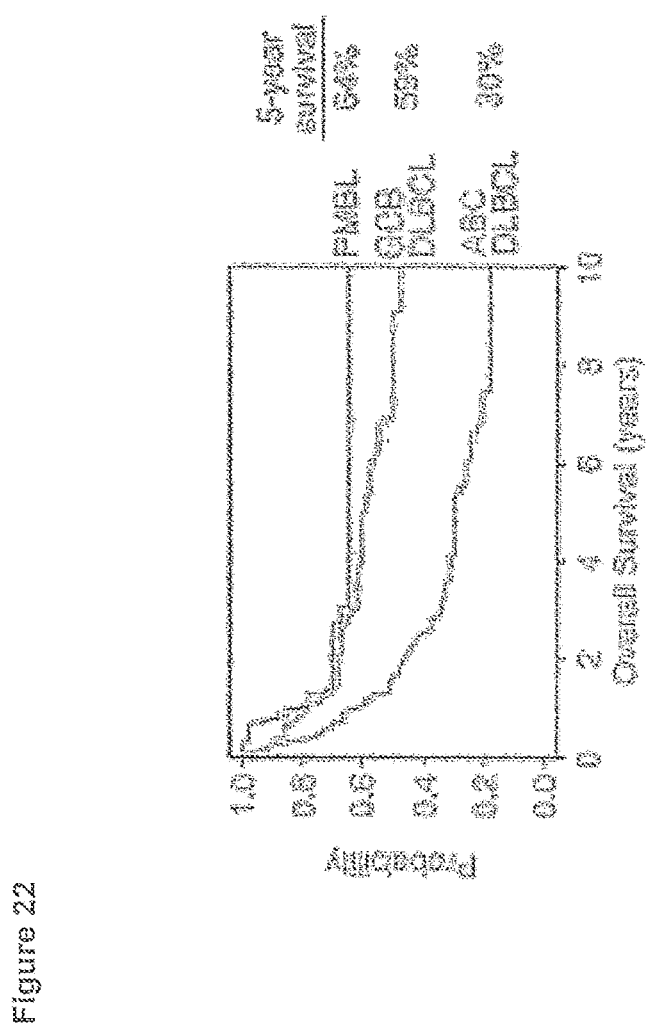

FIG. 22: Clinical characteristics of PMBL patients. Kaplan-Meier plot of overall survival in PMBL, GCB, and ABC patients after chemotherapy.

Figure 23:
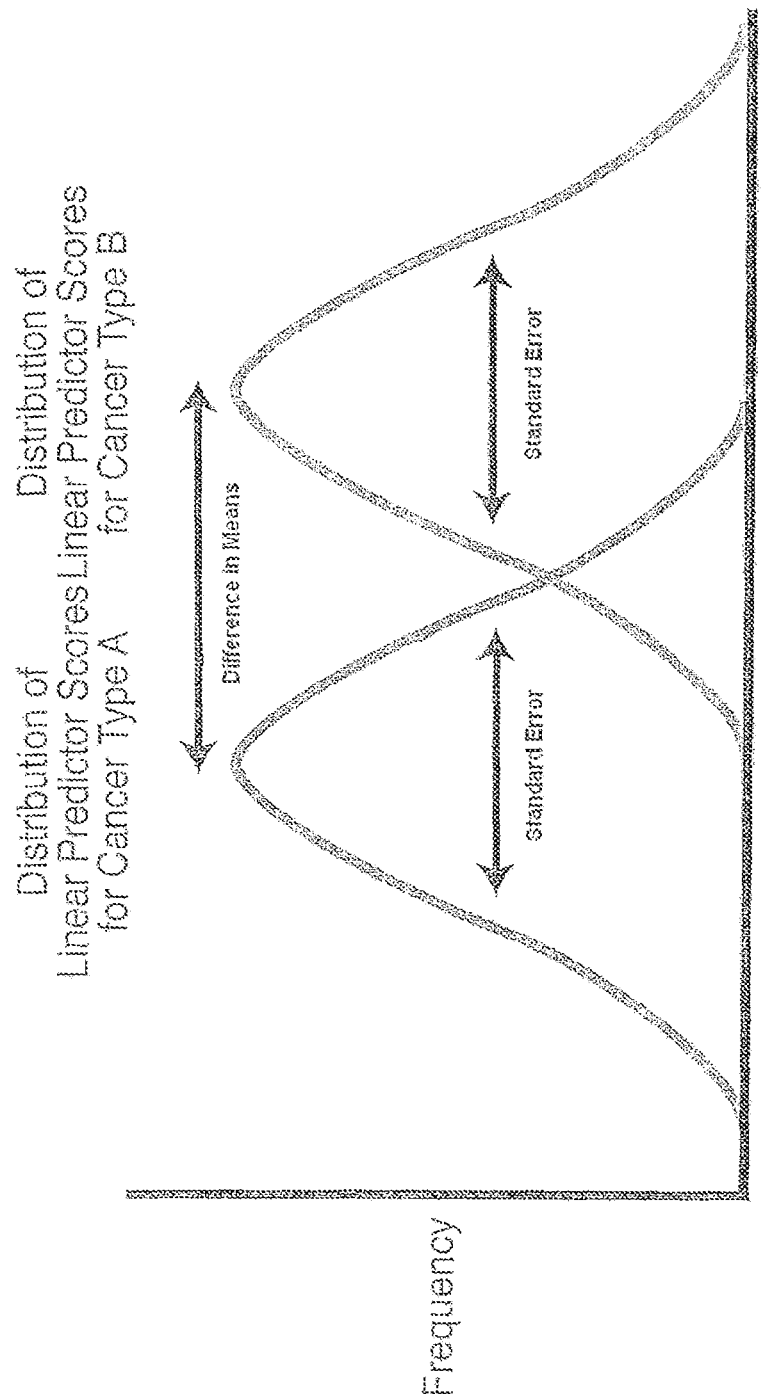

FIG. 23: Optimization of gene number in lymphoma predictor. The optimal number of genes for inclusion in the lymphoma type predictor model is that number which generates a maximum t-statistic when comparing the LPS of two samples from different lymphoma types.

Figure 24:
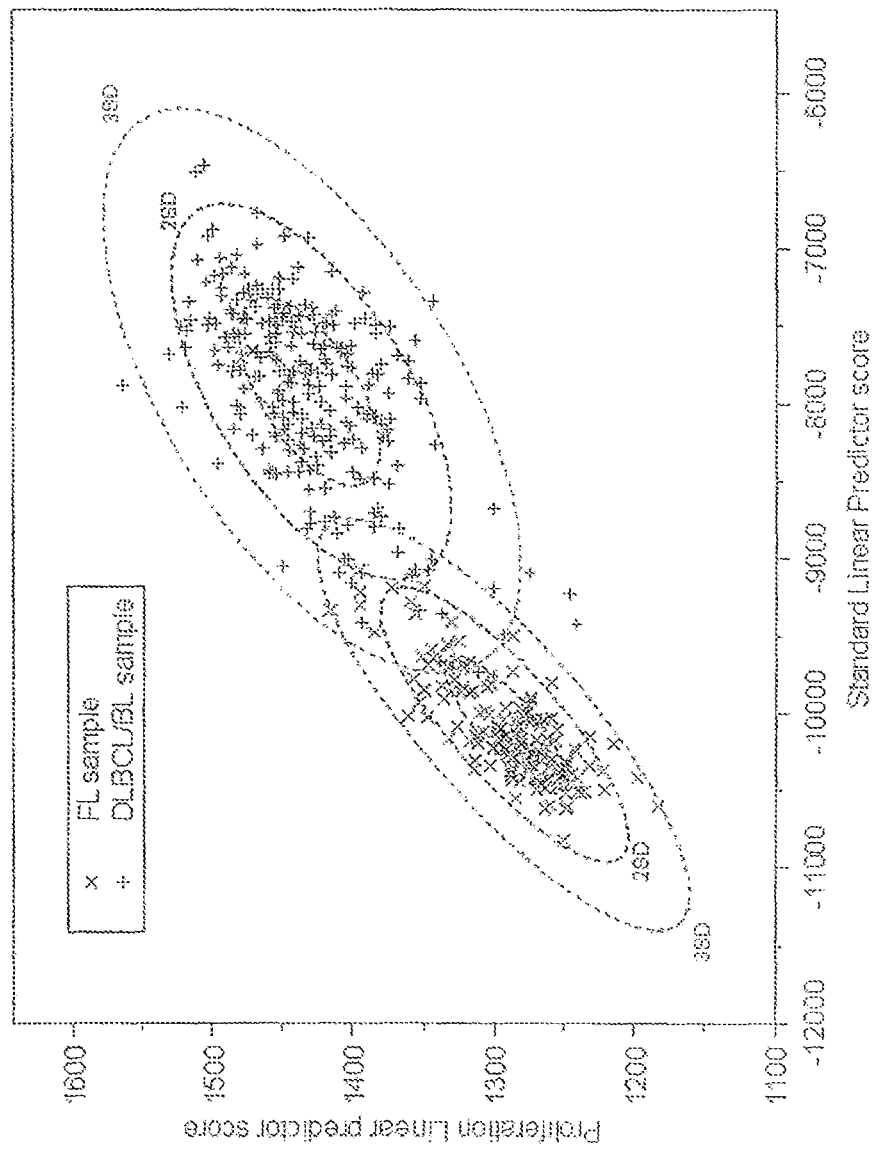

FIG. 24: LPS distribution among FL and DLBCL/BL samples. Standard and proliferation LPSs for FL (×) and DLBCL/BL (+) samples. Dotted lines indicate standard deviations from the fitted multivariate normal distributions.

Figure 25:
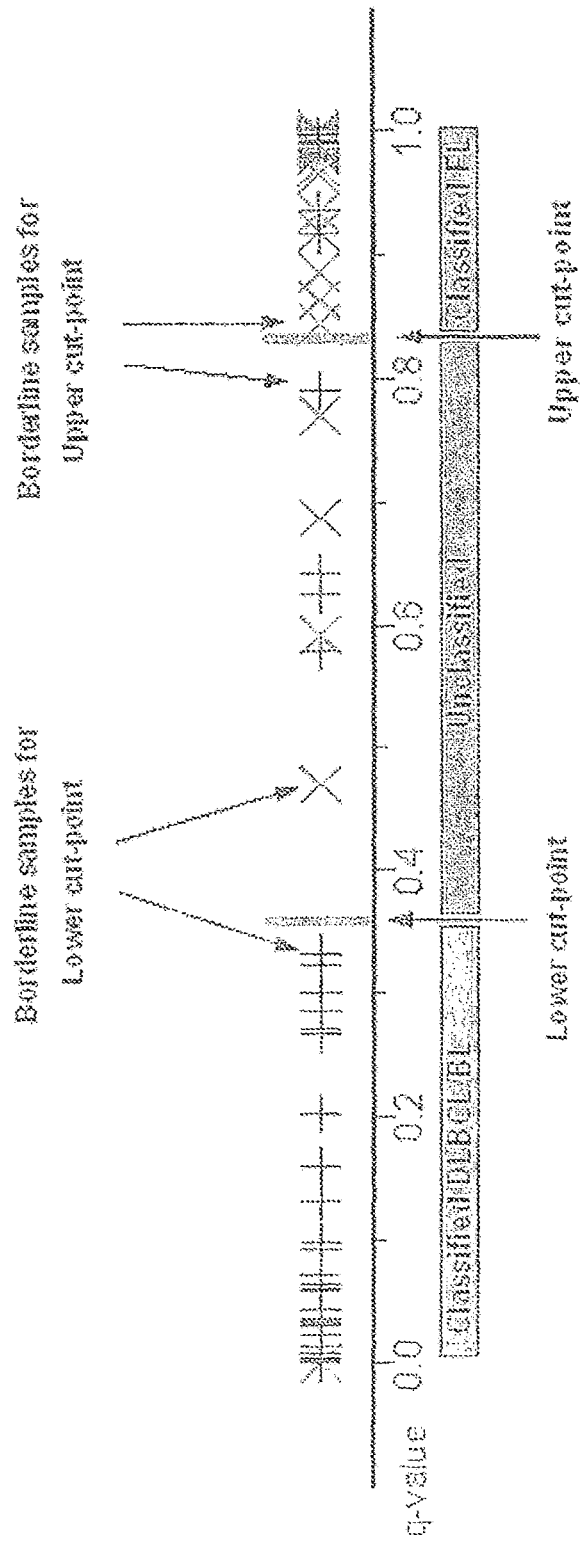

FIG. 25: Determination of cut-off points for lymphoma classification. The cut-off points between samples classified as DLBCL/BL, FL, or unclassified were optimized to minimize the number of samples classified as the wrong lymphoma type. The optimal lower cut-off point was at q=0.49, while the optimal upper cut-off point was at q=0.84.

Figure 26:
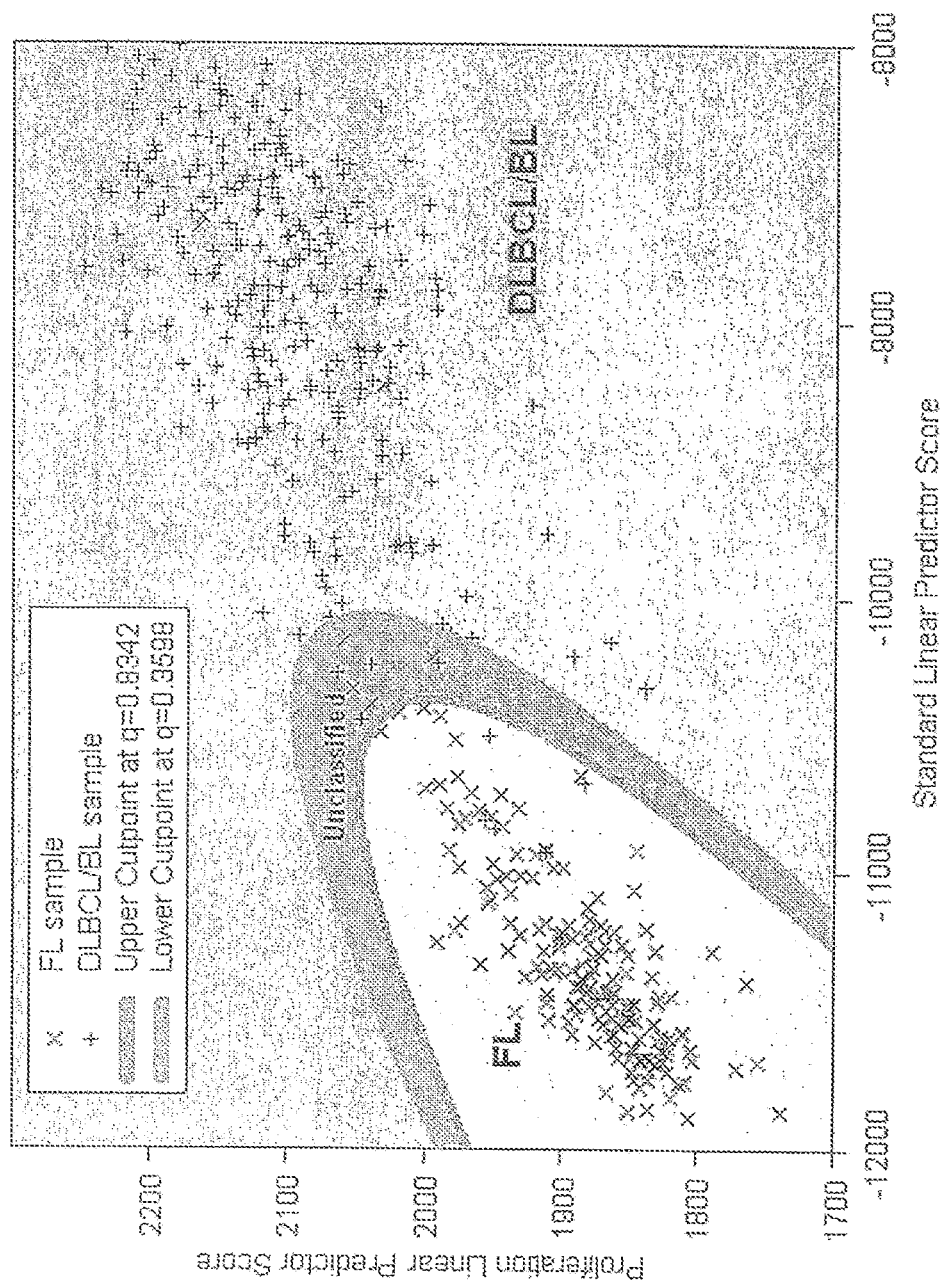

FIG. 26: Division of LPSs among FL and DLBCL/FL samples. Illustrations of how the cut-off points described in FIG. 25 divided the space between the LPSs of FL (×) and DLBCL/BL (+) samples.

Figure 27:
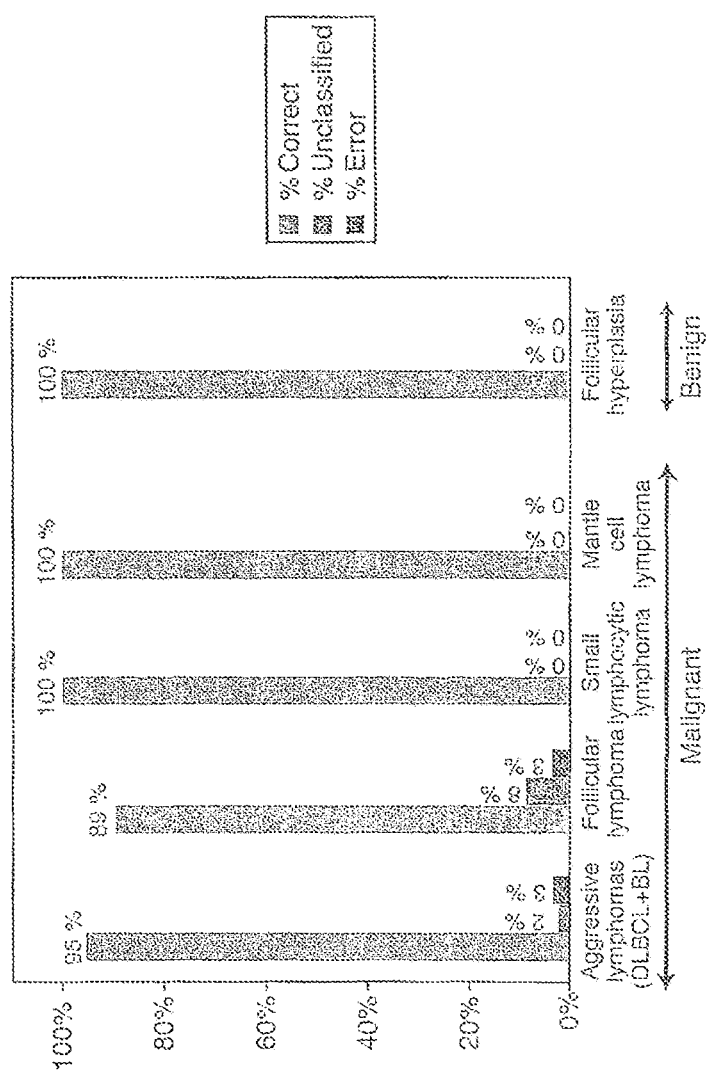

FIG. 27: Lymphoma classification results. Results of lymphoma classification based on gene expression. 100% of SLL, MCL, and FH samples were classified correctly, and only 3% of DLBCL/BL and FL samples were classified incorrectly.

Figure 28:
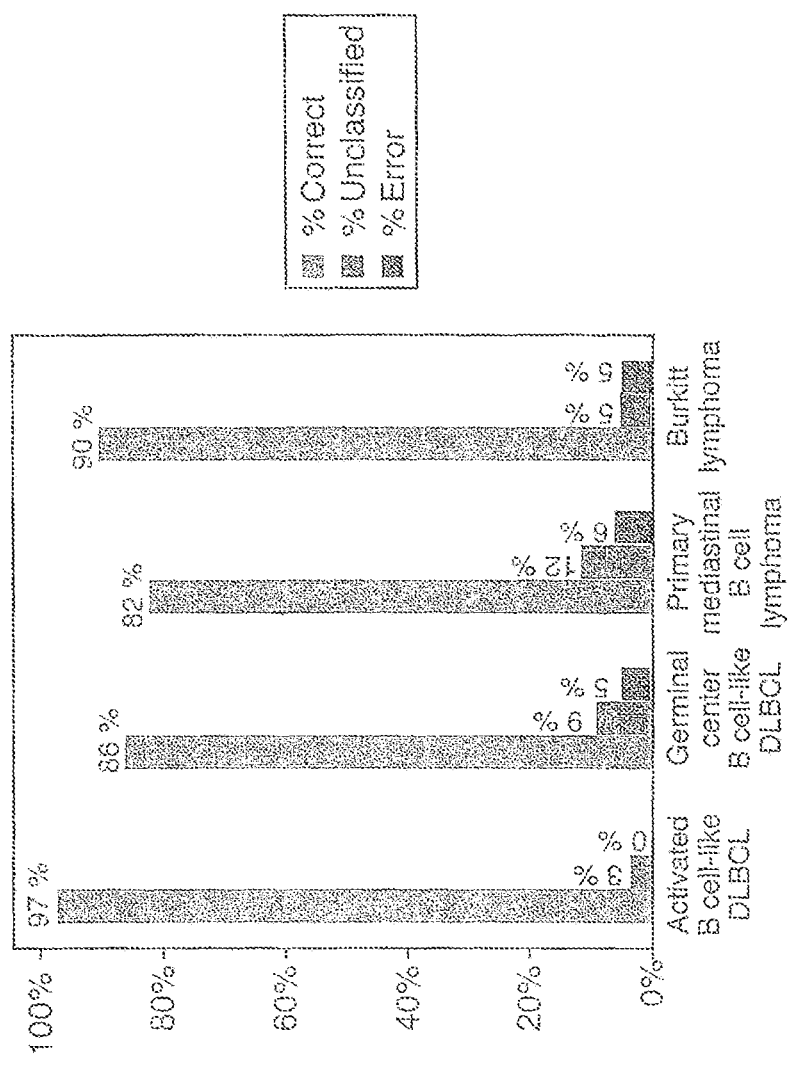

FIG. 28: DLBCL subtype classification based on gene expression. None of the ABC samples were classified as the wrong subtype, while only one of the BL samples was classified incorrectly. Of the GCB and PMBL samples, only 5% and 6%, respectively, were classified incorrectly.

Figure 29A:
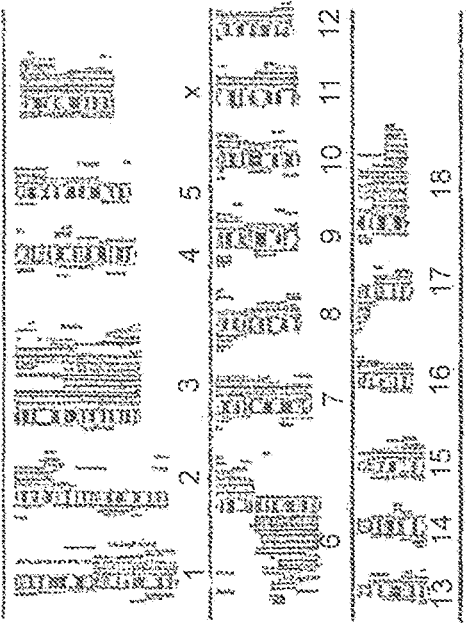

FIGS. 29A-29D: Summary of chromosomal imbalances in DLBCL samples. Chromosomal alterations in 224 untreated DLBCL samples were classified by gene expression profiling. Each bar represents a chromosomal region gained or lost in a single sample. Red bars on left side of ideogram represent losses of chromosomal material. Green bars on the right side of the ideogram represent gains of chromosomal material. Thick green bars represent chromosomal gains exceeding the cut-off value of 1.5 in a large chromosomal region, and solid dots represent high-level DNA amplifications. FIG. 29A. Chromosomal alterations in GCB samples (n=87).

Figure 29B:
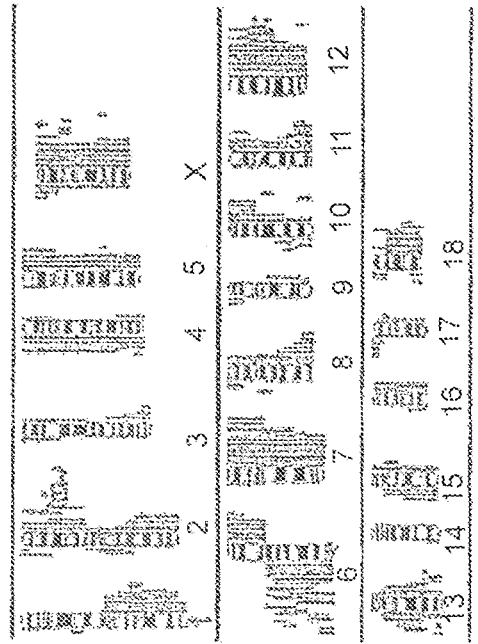
Figure 29C:
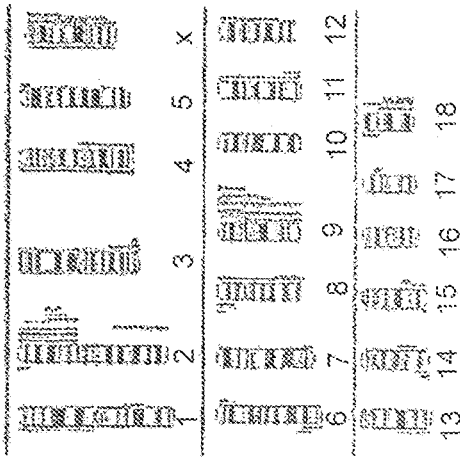
Figure 29D:
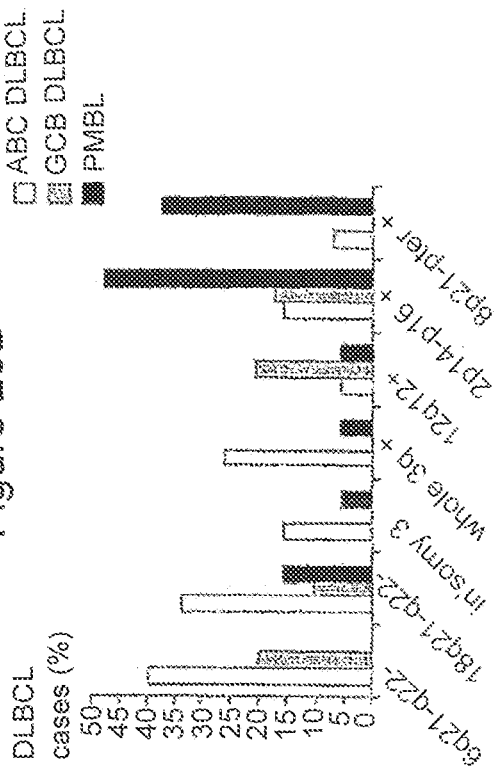

FIG. 29B. Chromosomal alterations in ABC samples (n=77). FIG. 29C. Chromosomal alterations in PMBL samples (n=19). FIG. 29D. Diagram indicating frequencies of chromosomal imbalances that distinguish between ABC, GCB, and PMBL. All differences were statistically significant at p<0.05, with the exception of 12q12 gains (P=0.059).

FIGS. 30A-30F: Influence of chromosomal gains and amplifications on locus-specific gene expression levels. Changes in gene expression levels are depicted for each gene (averaged in each cohort) with regard to locus-specific genetic status (wild-type vs. gain vs. amplification). Genes are ordered according to their chromosomal position. Gene locus information was obtained from the web site for Genes On Sequence Map (*Homo sapiens* built 33). For genes represented by more than one element on the Lymphochip, the average expression of different clones was calculated. The black bar on the left indicates the minimally gained region in all cases. Expression level comparisons were performed using the ANOVA test. Genes with significant differences (P<0.01) are highlighted in red.

Figure 31:
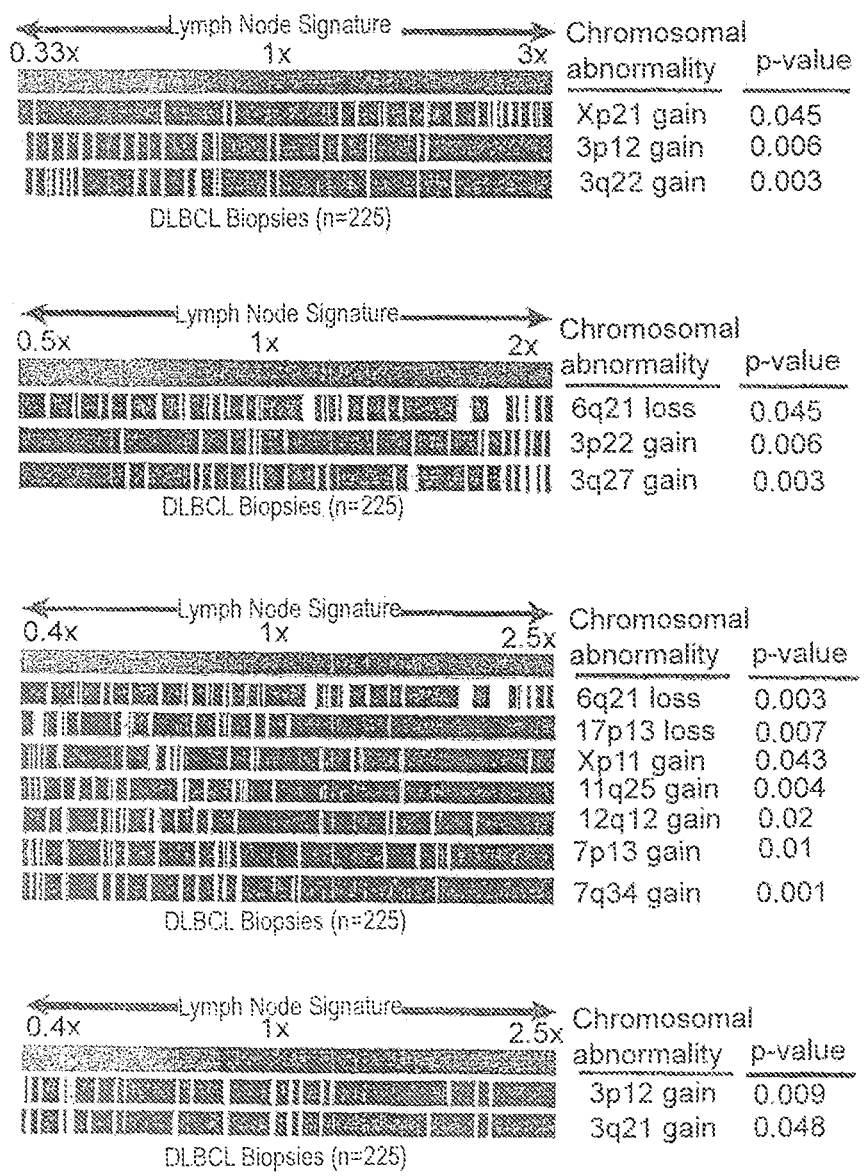

FIG. 31: Effect of chromosomal imbalances on gene expression signatures, in each of the 4 panels, DLBCL cases are ordered according to their average expression of the following gene expression signatures: lymph node, proliferation, T cell, and MHC class II. Samples with the chromosomal abnormalities shown on the right are marked with a yellow bar. Correlations with a P-value<0.05 are shown. If more than one cytoband in one chromosomal arm showed a P-value<0.05, the cytoband with the lowest p-value is displayed.

Figure 32:
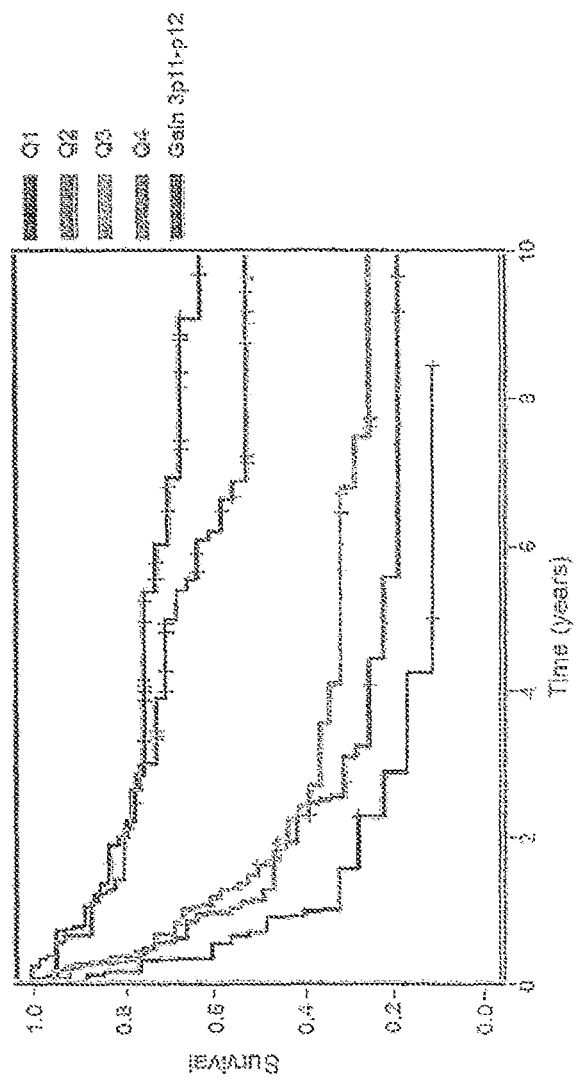

FIG. 32: Impact of genomic gains of 3p11-p12 on survival of DLBCL patients. Kaplan-Meier survival estimates of DLBCL patients with genomic gains of 3p11-p12 in comparison to their stratification into survival quartiles based on the gene expression based outcome predictor model alone 3 (Q=Quartile) (P=0.029).

FIG. 32: Kaplan-Meier plot of survival on DLBCL samples based on survival predictor scores. The survival predictor was calculated by:

$$[0.241*(\text{proliferation gene expression signature value})]+[0.310*(\text{BMP6})]-[0.290*(\text{germinal center B cell gene expression signature value})]-[0.311*(\text{MHC class II gene expression signature value})]-[0.249*(\text{lymph node gene expression signature value})],$$

with chromosome 3 gains involving the 3p11-p12 region considered as an independent prognostic indicator.

Figure 33:
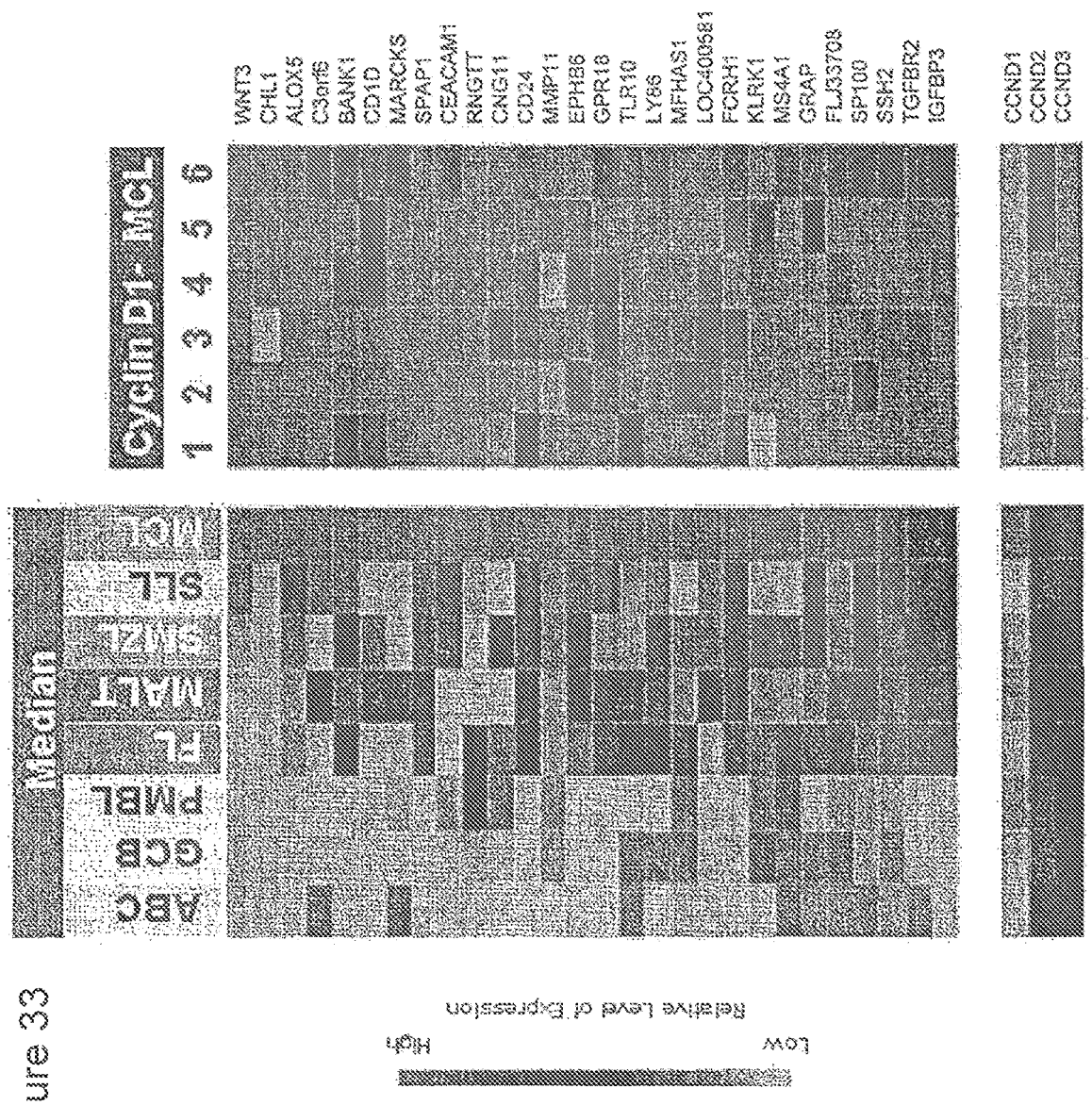

FIG. 33: Gene expression profiles of MCL signature genes in cyclin D1-negative MCL cases. Expression profiles for cyclin D1-negative MCL cases were compared to those of ABC, GCB, PMBL, FL, MALT, SMZL, SLL, and MCL. Median expression levels of the MCL signature genes are shown. For the cyclin-D1 MCL cases, each column represents a single lymphoma specimen and each row represents the level of expression of a single gene in the MCL signature. Red squares indicate increased expression. Green squares indicate decreased expression relative to the median expression level according to the color scale shown over a four-fold range. The lower panel shows expression levels of the D-type cyclins according to the color scale over a sixteen-fold range.

Figure 34B:
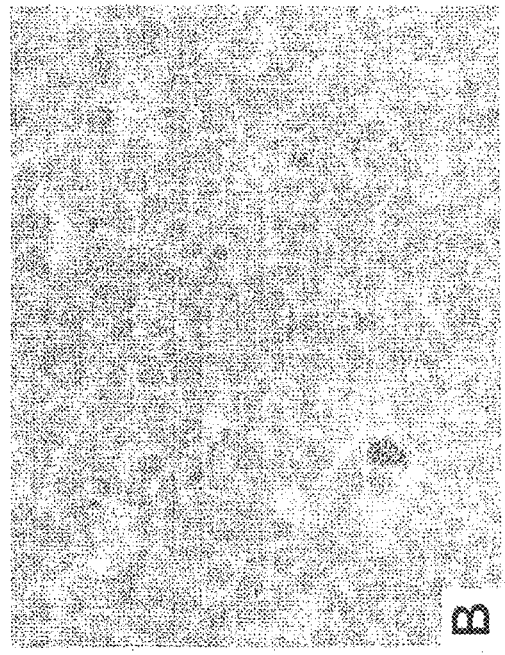
Figure 34D:
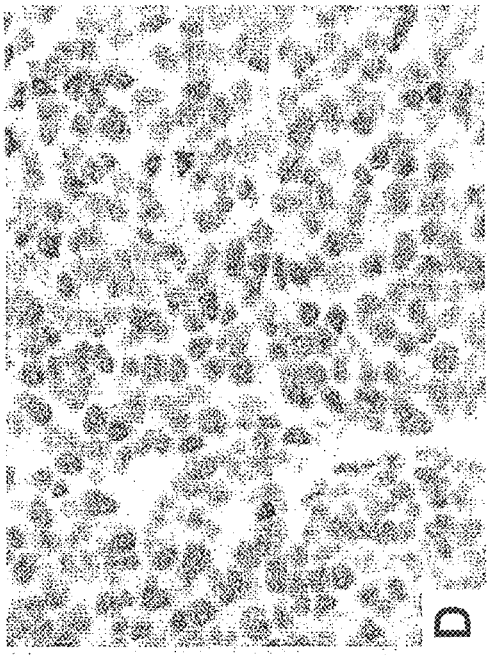
Figure 34A:
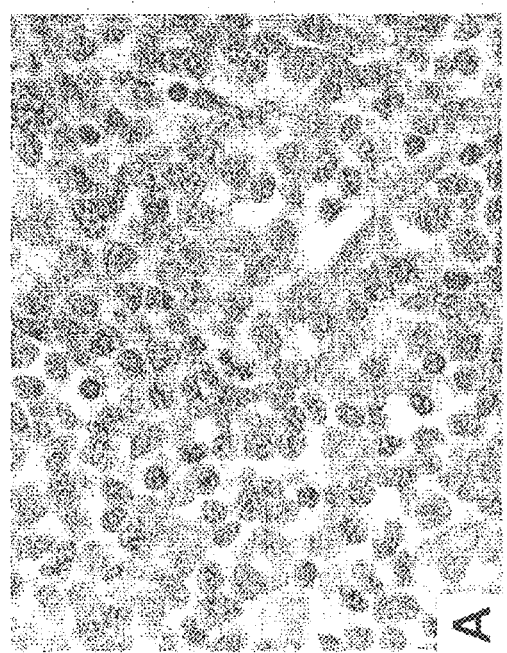
Figure 34C:
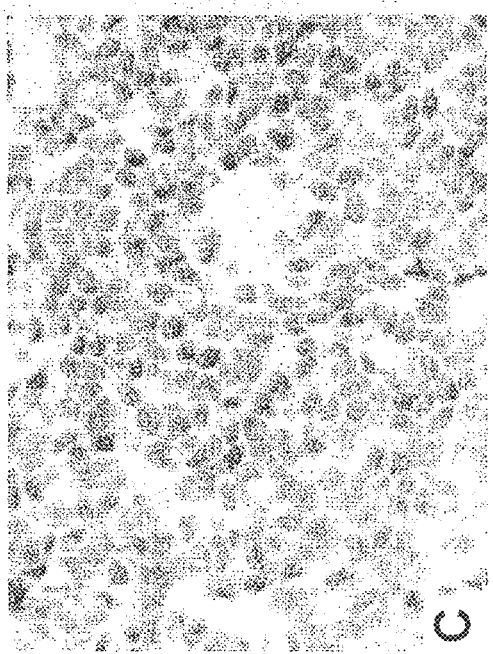

FIGS. 34A-34D: Cytologic features and expression of D-type cyclins in cyclin D1-negative MCL. FIG. 34A. Typical MCL cytology (case 1) (hematoxylin and eosin stain, original magnification ×500). FIG. 34B. Cyclin D1 protein, showing only a rare non-tumor cell with nuclear staining (case 1). FIG. 34C. Cyclin D2 protein, showing strong nuclear staining of the tumor cells (case 2). FIG. 34D. Cyclin D3 protein, showing strong nuclear staining of the tumor cells (case 4) (immunoperoxidase stains, original magnification ×400).

Figure 35A:
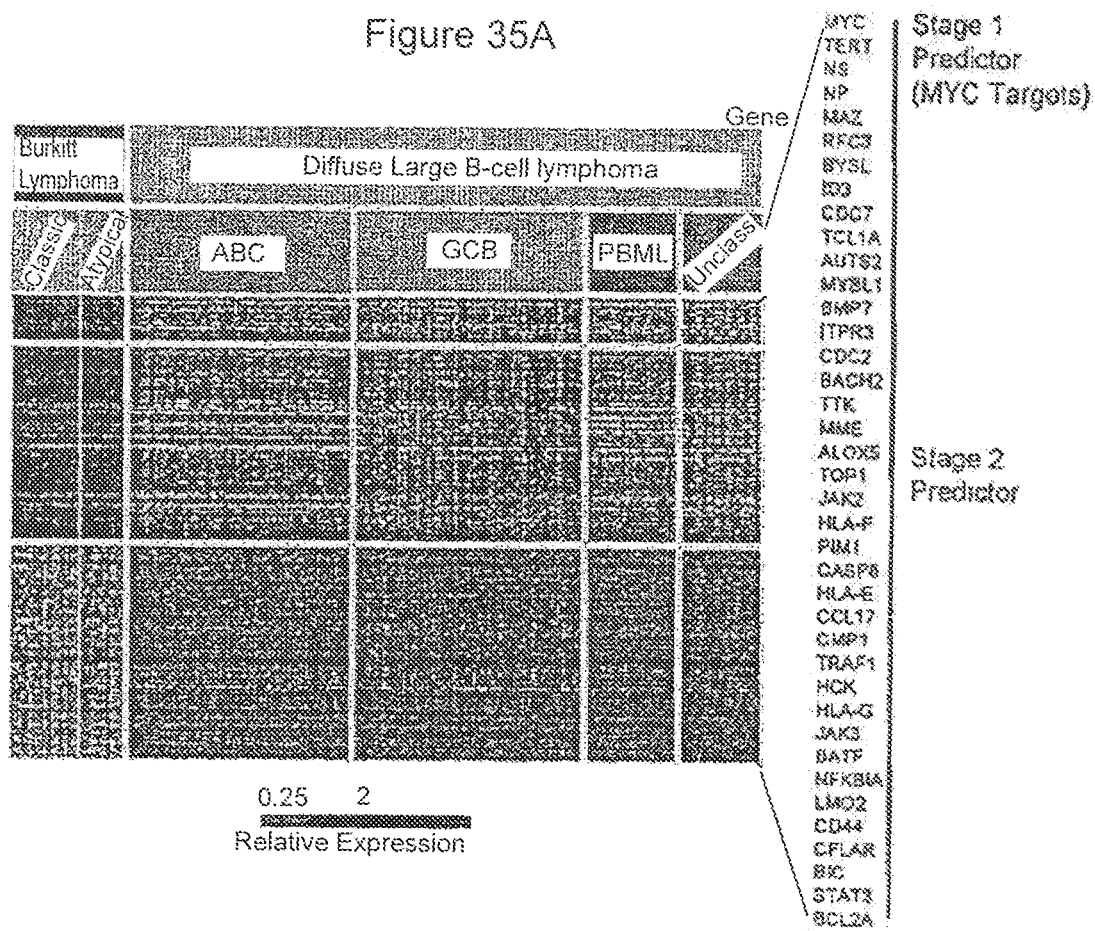
Figure 35B:
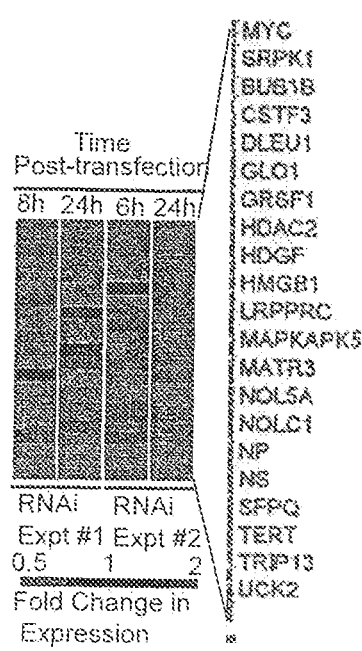

FIGS. 35A-35D: Molecular predictor of BL. FIG. 35A. Distinction between BL and DLBCL using gene expression. Each row represents the expression level of a gene and each column represents a lymphoma sample. Relative gene expression levels are depicted according to the color scale shown. Stage one utilized c-myc and its target genes. Stage two utilized 100 additional genes that distinguish BL from ABC, GCB, or PMBL. The panel includes only those cases for which the pathology-based diagnosis and the gene expression-based diagnosis agreed. FIG. 35B. Creation of an unbiased list of c-myc target genes using RNA-interference experiments. The OCl-Ly10 DLBCL cell line was transfected by electroporation with small interfering RNAs targeting the c-myc gene, and gene expression was compared to that of control-transfected cells by DNA microarray at the indicated times post-transfection. Downregulation of c-myc and its targets is depicted in green according to the color scale shown. FIG. 35C. Performance of the gene expression-based predictor according to leave-one-out cross-validation analysis. Samples submitted as BL or Burkitt-like lymphoma were classified upon pathology review as classic and atypical BL. Samples submitted as DLBCL were further classified by gene expression as ABC, GCB, PMBL, or unclassified. FIG. 35D. Classification of samples submitted as BL or Burkitt-like lymphoma that were reclassified as either DLBCL or high grade lymphoma not otherwise specified. Also shown are samples submitted and verified as high grade DLBCL. Those cases for which the pathology-based diagnosis and the gene expression-based diagnosis disagreed (BL-discrepant cases) are marked with an asterisk.

Figure 36A:
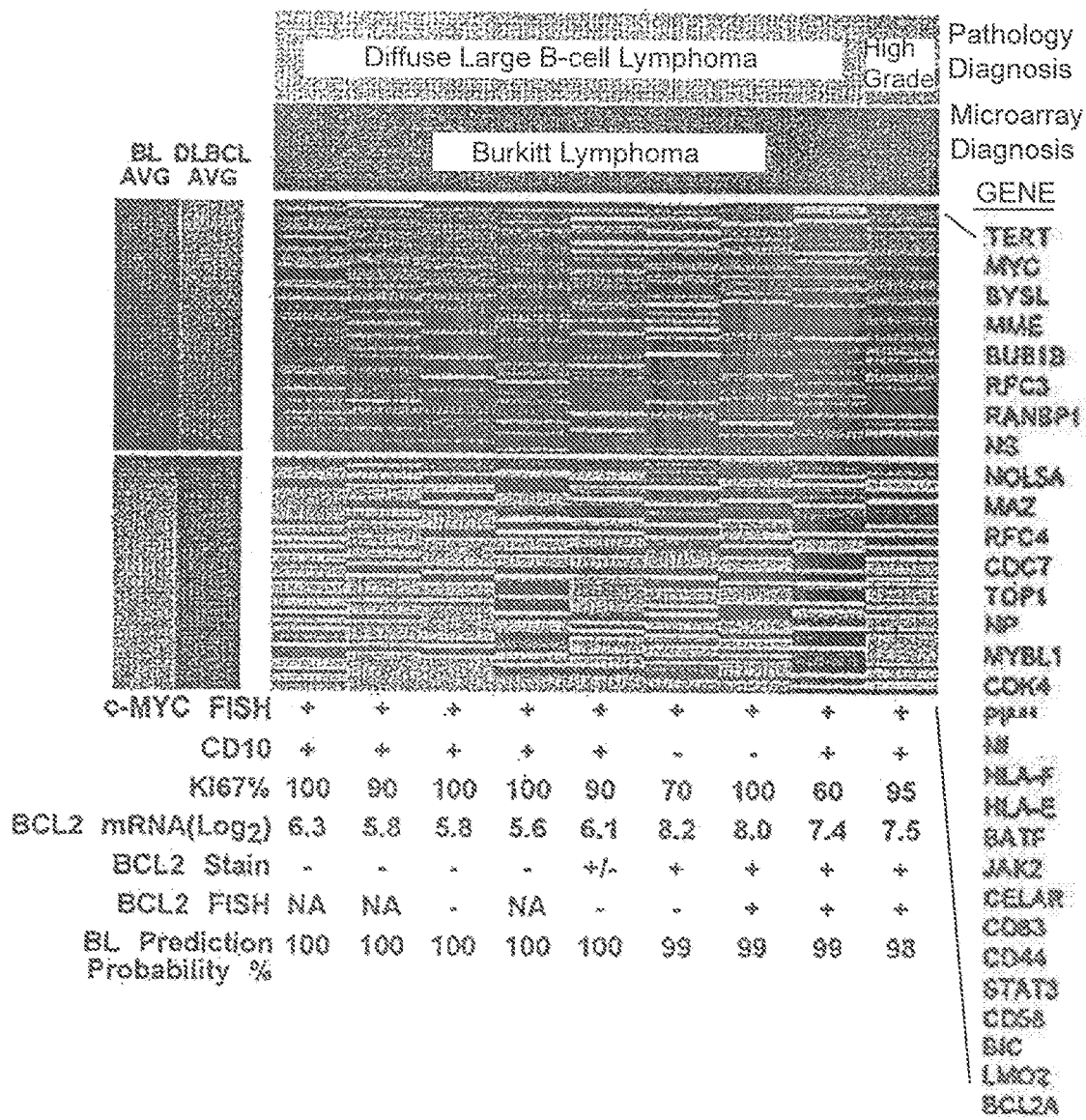
Figure 36B:
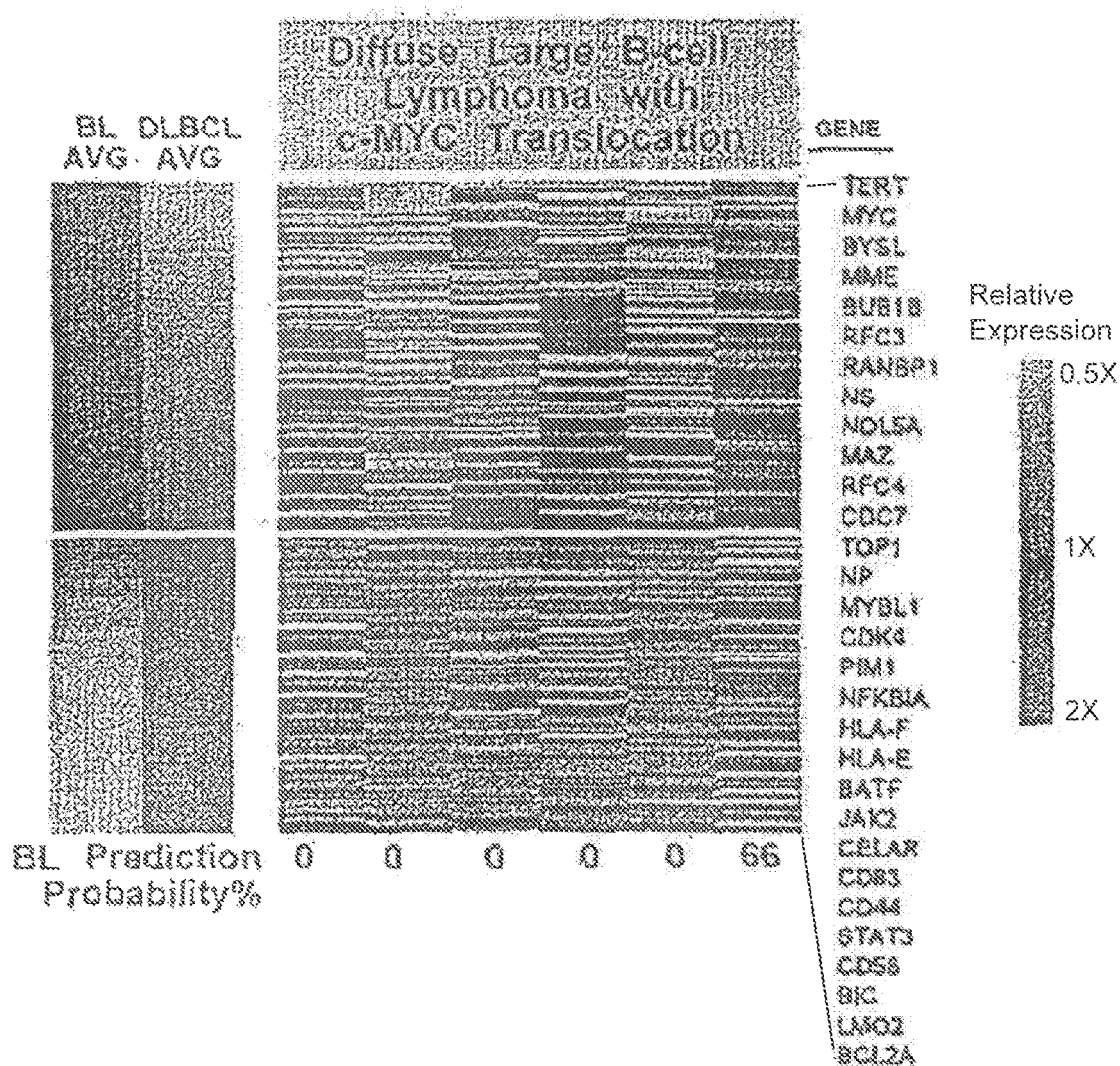

FIGS. 36A and 36B: Performance of a molecular predictor of BL. FIG. 36A. Gene expression in the nine BL-discrepant cases for which the pathology-based diagnosis and the gene expression-based diagnosis were not in agreement. Expression of the BL-predictor genes in these samples is compared to the average expression of these genes in BL and DLBCL. For each sample, immunophenotype, BCL2 mRNA and protein expression, and t(14;18) FISH results are depicted at the bottom of the panel. Also shown is the probability that each sample is BL based on gene expression. FIG. 36B. Expression of the BL-predictor genes in the six DLBCL samples known to harbor a translocation involving the c-myc gene. Expression of these genes in the samples is compared to the average expression in BL and DLBCL The probability that each sample is BL based on gene expression is shown.

Figure 37E:
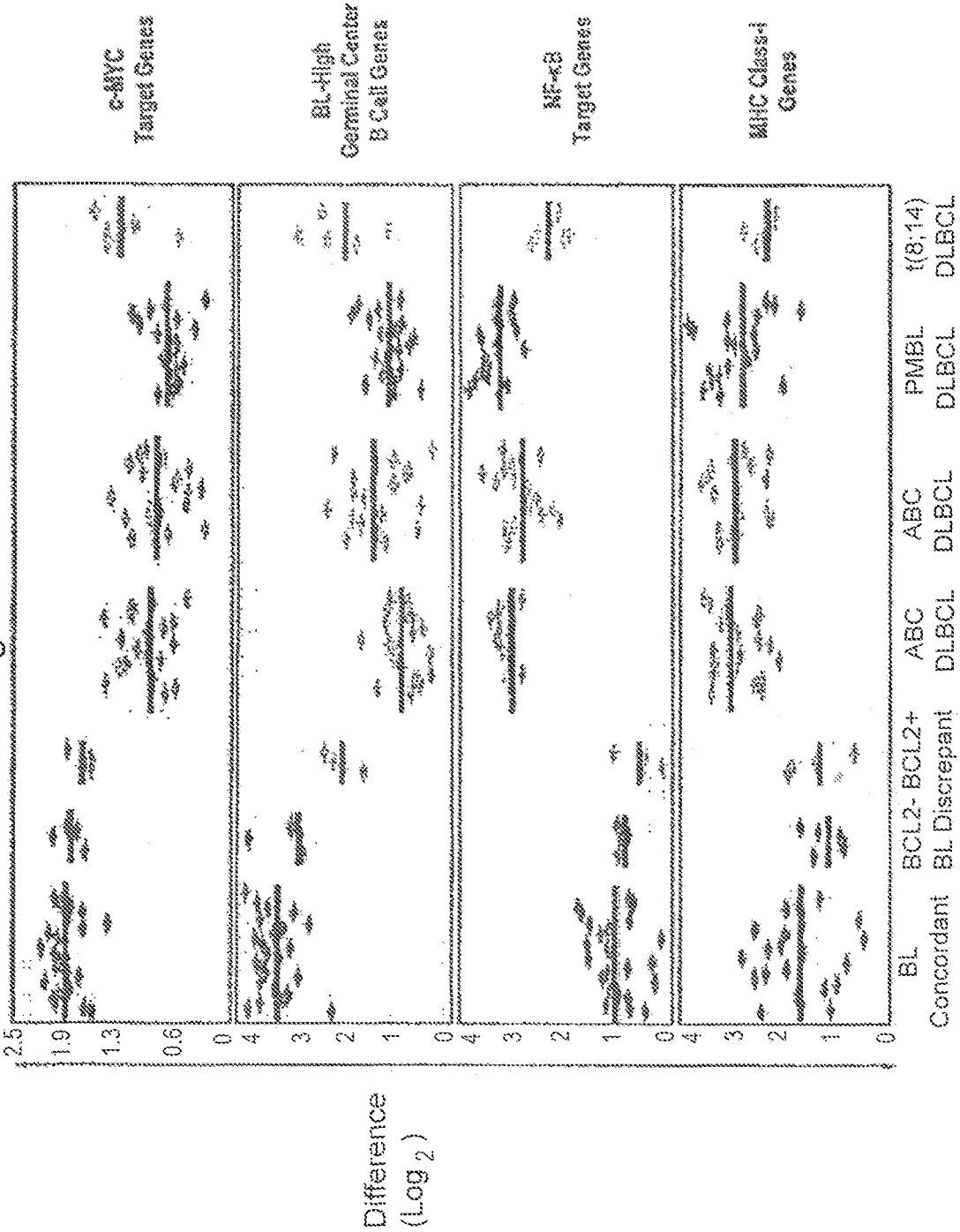

FIGS. 37A-37E: Relative expression of gene expression signatures among lymphoma subtypes. FIG. 37A. Average relative expression of c-myc end its target genes for BL and each molecular subtype of DLBCL (ABC, GCB, and PMBL). All expression data are shown over a 4-fold range. The color scale is identical to that in FIG. 36. FIG. 37B. Expression of genes related to normal GCB cell differentiation among the lymphoma subtypes. "BL-high" genes are expressed at 2-fold or higher levels in BL compared to GCB (P<0.001). "BL-low" genes are expressed at 2-fold or higher levels in GCB compared to BL (P<0.001). The "BL-GCB" genes are not differentially expressed between BL and GCB. FIG. 37C. Relative expression among lymphoma types of genes that encode MHC class-1 proteins. FIG. 37D. Relative expression among the lymphoma types of genes that are targets of the NF-κB signaling pathway. FIG. 37E. Average expression of each of the four gene expression signatures among the lymphoma samples according to their classification by the BL-predictor.

Figure 38A:
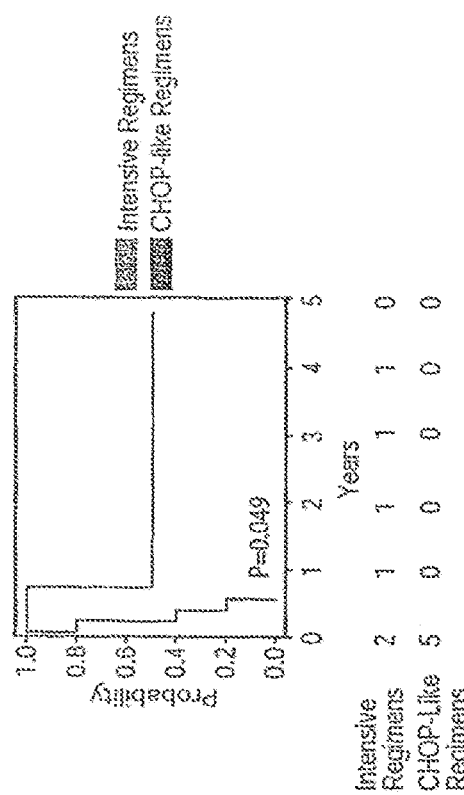
Figure 38B:
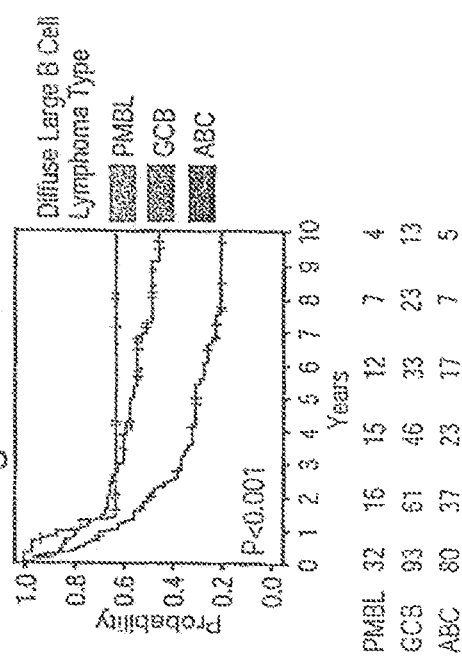
Figure 38C:
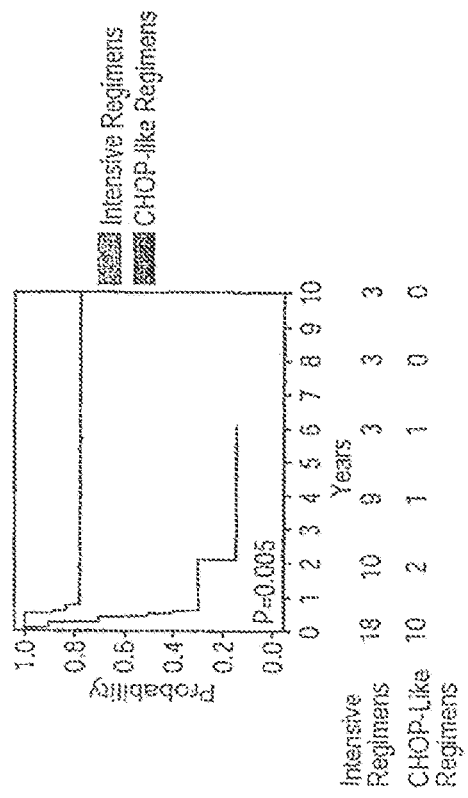
Figure 38D:
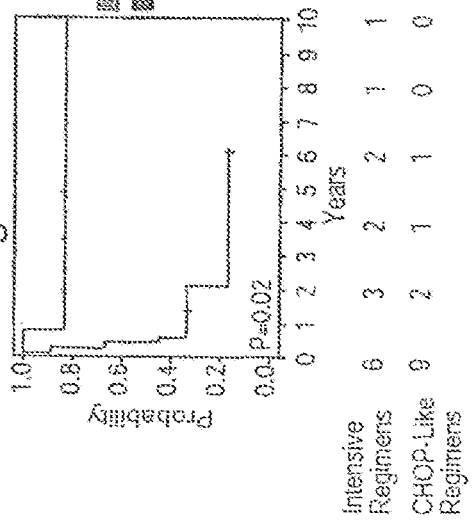

FIGS. 38A-38D: Survival analysis in BL and DLBCL FIG. 38A. Kaplan-Meier plot of overall survival for all patients with a gene expression-based diagnosis of BL, subdivided by treatment received. FIG. 38B. Kaplan-Meier plot of overall survival for adults with a gene expression-based diagnosis of BL, subdivided by treatment received. FIG. 38C. Kaplan-Meier plot of overall survival for all BL-discrepant patients, subdivided by treatment received. FIG. 38D. Kaplan-Meier plot of overall survival for all patients assigned to the three molecular subgroups of DLBCL.

DETAILED DESCRIPTION

The following description is merely intended to illustrate various embodiments of the invention. As such, the specific modifications discussed are not to be construed limitations on the scope of the invention. It will be apparent to one skilled in the art that various equivalents, changes, and modifications may be made without departing from the scope of the invention, and it us understood that such embodiments are to be included herein.

Abbreviations

The following abbreviations are used herein: ABC, activated B-cell-like diffuse large B cell lymphoma; ASCT, autologous stem cell transplant; AWD, alive with disease; BL, Burkitt lymphoma; BM, bone marrow; CGH, comparative genome hybridization; CHOP, cyclophosphamide, doxorubtcine, vincristine, and prednisone; CI, confidence interval; CNS, central nervous system; COP, cyclophosphamide, vincristine; and prednisone; $C_T$, cycle threshold; DLBCL, diffuse large B-cell lymphoma; DOD, dead of disease; ECOG, Eastern Cooperative Oncology Group; EST, expressed sequence tag; FACS, fluorescence-activated cell sorting; FH, follicular hyperplasia; FISH, fluorescence in-situ hybridization; FL, follicular lymphoma; GC, germinal center, GGB, germinal center B-cell-like diffuse large B cell lymphoma; GI gastrointestinal; IPI, International Prognostic Index; LPC, lymphoplasmacytic lymphoma; LPS, linear predictor score; MALT, mucosa-associated lymphoid tissue lymphomas; MCL, mantle cell lymphoma; MHC, major histocompatibility complex; NA, not available or not applicable; NK, natural killer; NMZ, nodal marginal zone lymphoma; PB, peripheral blood; PCR, polymerase chain reaction; PMBL, primary mediastinal B-cell lymphoma; PR, partial response; PTLD, post-transplant lympho proliferative disorder; REAL, Revised European-American Lymphoma; RPA, RNase protection assay; RQ-PCR, real-time quantitative PCR; RR, relative risk of death; RT-PCR, reverse transcriptase polymerase chain reaction; SAGE, serial analysis of gene expression; SLL, small lymphocytic lymphoma; SMZL, splenic marginal zone lymphoma; WHO, World Health Organization.

Definitions

The term "lymphoproliferative disorder" as used herein refers to any tumor of lymphocytes, and may refer to both malignant and benign tumors. The terms "lymphoma" and "lymphoid malignancy" as used herein refer specifically to malignant tumors derived from lymphocytes and lymphoblasts. Examples of lymphomas include, but are not limited to, follicular lymphoma (FL), Burkitt lymphoma (BL), mantle cell lymphoma (MCL), follicular hyperplasia (FH), smallcell lymphocytic lymphoma (SLL), mucosa-associated lymphoid tissue lymphoma (MALT), splenic lymphoma, multiple myeloma, lymphoplasmacytic lymphoma, post-transplant lymphoproliferative disorder (PTLD), lymphoblastic lymphoma, nodal marginal zone lymphoma (NMZ), germinal canter B cell-like diffuse large B cell lymphoma (GGB), activated B cell-like diffuse large B cell lymphoma (ABC) and primary mediastinal B cell lymphoma (PMBL).

The phrase "lymphoma type" (or simply "type") as used herein refers to a diagnostic classification of a lymphoma. The phrase may refer to a broad lymphoma class (e.g., DLBCL, FL, MCL, etc.) or to a subtype or subgroup falling within a broad lymphoma class (e.g., GCB DLBCL, ABC DLBCL).

The phrase "gene expression data" as used herein refers to information regarding the relative or absolute level of expression of a gene or set of genes in a cell or group of cells. The level of expression of a gene may be determined based on the Jevel of RNA, such as mRNA, encoded by the gene. Alternatively, the level of expression may be determined based on the level of a polypeptide or fragment thereof encoded by the gene, "Gene expression data" may be acquired for an individual cell, or for a group of cells such as a tumor or biopsy sample.

The term "microarray," "array," or "chip" refers to a plurality of nucleic acid probes coupled to the surface of a substrate in different known locations. The substrate is preferably solid. Microarrays have been generally described in the art in, for example, U.S. Pat. No. 5,143,854 (Plrrung), U.S. Pat. No. 5,424,188 (Fodor), U.S. Pat. No. 5,445,934 (Fodor), U.S. Pat. No. 5,677,195 (Winkler), U.S. Pat. No.

5,744,305 (Fodor), U.S. Pat. No. 5,800,992 (Fodor), U.S. Pat. No. 6,040,193 (Winkler), and Fodor et al. 1991. Light-directed, spatially addressable parallel chemical synthesis. Science, 251; 767-777. Each of these references is incorporated by reference herein in their entirety.

The term "gene expression signature" or "signature" as used herein refers to a group of coordinately expressed genes. The genes making up this signature may be expressed in a specific cell lineage, stage of differentiation, or during a particular biological response. The genes can reflect biological aspects of the tumors in which they are expressed, such as the cell of origin of the cancer, the nature of the non-malignant cells in the biopsy, and the oncogenic mechanisms responsible for the cancer (Shaffer 2001). Examples of gene expression signatures include lymph node (Shaffer 2001), proliferation (Rosenwald 2002), MHC class II, ABC DLBCL high, B-cell differentiation, T-cell, macrophage, immune response-1, immune response-2, and germinal center B cell.

The phrase "survival predictor score" as used herein refers to a score generated by a multivariate model used to predict survival based on gene expression-A subject with a higher survival predictor score is predicted to have poorer survival than a subject with a lower survival predictor score.

The term "survival" as used herein may refer to the probability or likelihood of a subject surviving for a particular period of time. Alternatively, it may refer to the likely term of survival for a subject, such as expected mean or median survival time for a subject with a particular gene expression pattern.

The phrase "linear predictor score" or "LPS" as used herein refers to a score that denotes the probability that a sample belongs to a particular lymphoma type. An LPS may be calculated using an equation such as:

$$LPS(S) = \sum_{j=0} t_j S_j,$$

where $S_j$ is the expression of gene j from gene set G in a sample S, and $t_j$ is a scale factor representing the difference in expression of gene j between a first lymphoma type and a second lymphoma type. Alternatively, a linear predictor score may be generated by other methods including but not limited to linear discriminant analysis (Dudolt 2002), support vector machines (Furey 2000), or shrunken centroids (Tibshiranl 2002)

The phrase "scale factor" as used herein refers to a factor that defines the relative difference in expression of a particular gene between two samples. An example of a scale factor is a t-score generated by a Student's t-test.

The phrase "lymphoma subject," wherein "lymphoma" is a specific lymphoma type (e.g., "follicular lymphoma subject"), may refer to a subject that has been diagnosed with a particular lymphoma by any method known in the art or discussed herein. This phrase may also refer to a subject with a known or suspected predisposition or risk of developing a particular lymphoma type.

The gene expression profile of a cancer cell or biopsy sample at a specific timepoint may provide the basis for better classification of cancer subtypes, more accurate prediction of cancer survival, and more specifically, tailored-therapies. Disclosed herein are a variety of methods for identifying, diagnosing, and/or classifying a lymphoma, lymphoid malignancy, or lymphoproliferative disorder based on its gene expression patterns. Also disclosed are methods for predicting survival in a subject diagnosed with a particular lymphoma type or subtype using gene expression data. The information obtained using these methods will be useful in evaluating the optimal therapeutic approach to be employed for a particular subject suffering from cancer.

The pattern of expression of a particular gene is closely connected to the biological role and effect of its gene product. For this reason, the systematic study of variations in gene expression provides an alternative approach for linking specific genes with specific diseases and for recognizing heritable gene variations that are important for immune function. For example, allelic differences in the regulatory region of a gene may influence the expression levels of that gene. An appreciation for such quantitative traits in the immune system may help elucidate the genetics of autoimmune diseases and lymphoprollferative disorders.

Genes that encode components of the same multi-subunit protein complex are often coordinately regulated. Coordinate regulation is also observed among genes whose products function in a common differentiation program or in the same physiological response, pathway. Recent application of gene expression profiling to the immune system has shown that lymphocyte differentiation and activation are accompanied by parallel changes in expression among hundreds of genes. Gene expression databases may be used to interpret the pathological changes in gene expression that accompany autoimmunity, immune deficiencies, cancers of immune cells and of normal immune responses.

Scanning and interpreting large bodies of relative gene expression data is a formidable task. This task is greatly facilitated by algorithms designed to organize the data in a way that highlights systematic features, and by visualization tools that represent the differential expression of each gene as varying intensities and hues of color (Elsen 1998). The development of microarrays, which are capable of generating massive amounts of expression data in a single experiment, has greatly increased the need for faster and more efficient methods of analyzing large-scale expression data sets. In order to effectively utilize microarray gene expression data for the identification and diagnosis of lymphoma and for the prediction of survival in lymphoma patients, new algorithms must be developed to identify important information and convert it to a mare manageable format. In addition, the microarrays used to generate this data should be streamlined to incorporate probe sets that are useful for diagnosis and survival prediction. Disclosed herein are various methods and compositions that address both of these issues.

Mathematical analysis of gene expression data is a rapidly evolving science based on a rich mathematics of pattern recognition developed in other contexts (Kohonen 1997). Mathematical analysis of gene expression generally has three goals. First, it may be used to identify groups of genes that are coordinately regulated within a biological system. Second, it may be used to recognize and interpret similarities between biological samples on the basis of similarities in gene expression patterns. Third, it may be used to recognize and identify those features of a gene expression pattern that are related to distinct biological processes or phenotypes.

Mathematical analysis of gene expression data often begins by establishing the expression pattern for each gene on an array across n experimental samples. The expression pattern of each gene can be represented by a point in n-dimensional space, with each coordinate specified by an expression measurement in one of the n samples (Elsen 1998). A clustering algorithm that uses distance metrics can then be applied to locale clusters of genes in this n-dimensional space. These clusters indicate genes with similar patterns of variation in expression over a series of experiments. Clustering methods that have been applied to microarray data in the past include hierarchical clustering (Elsen 1998), self-organizing maps (SOMs) (Tamayo 1999), k-means (Tavazole 1999), and deterministic annealing (Alon 1999). A variety of different algorithms, each emphasizing distinct orderly features of the data, may be required to glean the maximal biological insight from a set of samples (Alizadeh 1998). One such algorithm, hierarchical clustering, begins by determining the gene expression correlation coefficients for each pair of the n genes studied. Genes with similar gene expression correlation coefficients are grouped next to one another in a hierarchical fashion. Generally, genes with similar expression patterns under a particular set of conditions encode protein products that play related roles in the physiological adaptation to those conditions. Novel genes of unknown function that are clustered with a large group of functionally related genes are likely to participate in the same biological process. Likewise, the other clustering methods mentioned herein may also group genes together that encode proteins with related biological function.

Gene expression maps may be constructed by organizing gene expression data from multiple samples using any of the various clustering algorithms outlined herein. The ordered tables of data may then be displayed graphically in a way that allows researchers and clinicians to assimilate both the choreography of gene expression on a broad scale and the fine distinctions in expression of individual genes.

In such a gene expression map, genes that are clustered together reflect a particular biological function, and are termed gene expression signatures (Shaffer 2001). One general type of gene expression signature includes genes that are characteristically expressed in a particular cell type or at a particular stage of cellular differentiation or activation. Another general type of gene expression signature includes genes that are regulated in their expression by a particular biological process such as proliferation, or by the activity of a particular transcription factor or signaling pathway.

The pattern of gene expression in a biological sample provides a distinctive and accessible molecular picture of its functional state and identity (DeRisi 1997; Cho 1998; Chu 1998; Holstege 1998; Spellman 1998). Each cell transduces variations in its environment, internal state, and developmental state into readily measured and recognizable variations in its gene expression patterns. Two different samples that have related gene expression patterns are therefore likely to be biologically and functionally similar to one another. Some biological processes are reflected by the expression of genes in a specific gene expression signature, as described above. The expression of a specific gene expression signature in a sample can provide important biological insights into its cellular composition and the function of various intracellular pathways within those cells.

The present invention discloses a variety of gene expression signatures related to the clinical outcome of lymphoma patients. While several of these signatures share a name with a previously disclosed signature, each of the gene expression signatures disclosed herein comprises a novel combination of genes. For example, the lymph node signature disclosed herein includes genes encoding extracellular matrix components and genes that are characteristically expressed in macrophage, NK, and T cells (e.g., α-Actinin, collagen type III α 1, connective tissue growth factor, fibronectin, KIAA0233, urokinase plasminogen activator). The proliferation signature includes genes that are characteristically expressed by cells that are rapidly multiplying or proliferating (e.g., c-myc, E21G3, NPM3, BMP6). The MHC class II signature includes genes that interact with lymphocytes in order to allow the recognition of foreign antigens (e.g., HLA-DPα, HLA-DQα, HLA-DRα, HLA-DRβ). The immune response-1 signature includes genes encoding T cell markers (e.g., CD7, CD8B1, ITK, LEF1, STAT4), as well as genes that are highly expressed in macrophages (e.g., ACTN1, TNFSF13B). The immune response-2 signature includes genes known to be preferentially expressed in macrophages and/or dendritic cells (e.g., TLR6, FCGR1A, SEPT10, LGMN, C3AR1). The germinal center B cell signature includes genes known to be overexpressed at this stage of B cell differentiation (e.g., MME, MEF2C, BCL6, LMO2, PRSPAP2, MBD4, EBF, MYBL1).

Databases of gene expression signatures have proven quite useful in elucidating the complex gene expression patterns of various cancers. For example, expression of genes from the germinal center B-cell signature in a lymphoma biopsy suggests that the lymphoma is derived from this stage of B cell differentiation. In the same lymphoma biopsy, the expression of genes from the T cell signature can be used to estimate the degree of infiltration of the tumor by host T cells, while the expression of genes from the proliferation signature can be used to quantitate the tumor cell proliferation rate. In this manner, gene expression signatures provide an "executive summary" of the biological properties of a tumor specimen. Gene expression signatures can also be helpful in interpreting the results of a supervised analysis of gene expression data. Supervised analysis generates a long list of genes with expression patterns that are correlated with survival. Gene expression signatures can be useful in assigning these "predictive" genes to functional categories. In building a multivariate model of survival based on gene expression data, this functional categorization helps to limit the inclusion of multiple genes in the model that measure the same aspect of tumor biology.

Gene expression profiles can be used to create multivariate models for predicting survival. The methods for creating these models are called "supervised" because they use clinical data to guide the selection of genes to be used in the prognostic classification. For example, a supervised method might identify genes with expression patterns that correlate with the length of overall survival following chemotherapy. The general method used to create a multivariate model for predicting survival may utilize the following steps:

1. Identify genes with expression patterns that are univariately associated with a particular clinical outcome using a Cox proportional hazards model. Generally, a univariate p-value of <0.01 is considered the cut-off for significance. These genes are termed "predictor" genes.
2. Within a set of predictor genes, identify gene expression signatures.
3. For each gene expression signature that is significantly-associated with survival, average the expression of the component genes within this signature to generate a gene expression signature value.
4. Build a multivariate Cox model of clinical outcome using the gene expression signature values.
5. If possible, include additional genes in the model that do not belong to a gene expression signature but which add to the statistical power of the model.

This approach has been utilized in the present invention to create novel survival prediction models for FL, DLBCL, and MCL. Each of these models generates a survival predictor score, with a higher score being associated with worse clinical outcome. Each of these models may be used separately to predict survival. Alternatively, these models may be used in conjunction with one or more other models, disclosed herein or in other references, to predict survival.

A first FL survival predictor was generated using gene expression data obtained using Affymetrix U133A and U133B microarrays. This predictor incorporated immune response-1 and immune response-2 gene expression signatures. Fitting the Cox proportional hazards model to the gene expression signature values obtained from these signatures resulted in the following model:

Survival predictor score=[(2.71*immune response-2 gene expression signature value)]−[(2.36×immune response-1 gene expression signature value)].

A second FL survival predictor was generated using gene expression data obtained using Affymetrix U133A and U133B microarrays. This predictor incorporated macrophage, T-cell, and B-cell differentiation gene expression signatures. Fitting the Cox proportional hazards model to the gene expression signature values obtained from these signatures resulted in the following model;

Survival predictor score=[2.053*(macrophage gene expression signature value)]−[2.344*(T-cell gene expression signature value)]−[0.729*(B-cell differentiation gene expression signature value)].

A third FL survival predictor was generated using gene expression data obtained using the Lymph Dx microarray. This predictor incorporated macrophage, T-cell, and B-cell differentiation gene expression signatures. Fitting the Cox proportional hazards model to the gene expression signature values obtained from these signatures resulted in the following model:

Survival predictor score=[1.51*(macrophage gene expression signature value)]−[2.11*(T-cell gene expression signature value)]−[0.505*(B-cell differentiation gene expression signature value)].

A first DLBCL survival predictor was generated using gene expression data obtained using Affymetrix U133A and U133B microarrays. This predictor incorporated ABC DLBCL high, lymph node, end MHC class II gene expression signatures. Fitting the Cox proportional hazards model to the gene expression signature values obtained from these signatures resulted in the following model:

Survival predictor score=[0.586*(ABC DLBCL high gene expression signature value)]−[0.468*(fymph node gene expression signature value)]−0.336*(MHC class II gene expression signature value)].

A second DLBCL survival predictor was generated using gene expression data obtained using the Lymph Dx microarray. This predictor incorporated lymph node, proliferation, germinal center B-cell, and MHC class II gene expression signatures. Fitting the Cox proportional hazards model to the gene expression signature values obtained from these signatures resulted in the following model:

Survival predictor score=[−0.4337*(lymph node gene expression signature value)]+[0.09*(proliferation gene expression signature value)]−[0.4144*(germinal center B-cell gene expression signature value)]−[0.2006*(MHC class II gene expression signature value)].

A third DLBCL survival predictor was generated using gene expression data obtained using the Lymph Dx microarray. This predictor incorporated lymph node, germinal center B cell, and MHC class II gene expression signatures. Fitting the Cox proportional hazards model to the gene expression signature values obtained from these signatures resulted in the following model:

Survival predictor score=[−0.32*(lymph node gene expression signature value)]−[0.176*(germinal center B-cell gene expression signature value)]−[0.206*(MHC class II gene expression signature value)].

A method of refining a DLBCL survival predictor was developed based on analysis of characteristic chromosomal alterations in DLBCL cases. Malignant lymphomas are generally characterized by distinctive recurrent primary chromosomal translocations such as the t(11;14) or t(14;18), in MCL and PL, respectively. By identifying genomic imbalances, comparative genomic hybridization (CGH) has the potential to detect less well-characterized chromosomal aberrations in lymphomas that may play an important role in development and progression of the disease, in DLBCL, previous cytogenetic studies have identified a plethora of clonal chromosomal aberrations, some of which are associated with particular morphological or clinical manifestations (Yunis 1989; Monni 1996; Rao 1998; Cigudosa 1999; Schlegelberger 1999; Berglund 2002; Dave 2002; Nanjangud 2002; Bea 2004).

CGH was used to identify chromosomal alterations n 224 DLBCL samples that had previously been broken into subtypes based on gene expresslon data obtained using a Lymphochip microarray. Chromosomal alterations were observed in 164 of the 224 cases. Certain alterations were differentially distributed among subtypes. For example, gains of chromosome arm 3q were observed in around a fourth of ABC samples, but were never observed in GCB samples and were observed only once in PMBL samples. Similarly, gains of 18q21-q22 were observed in around a third of ABC samples, but were observed in only 10% and 16% of GCB and PMBL samples, respectively. Genomic gains of 3q and 18q have previously been correlated with shorter survival in DLBCL patients (Bea 2004). The present findings provide a clear explanation for this observation, namely that both abnormalities are statistically associated with ABC, which has a worse prognosis than other DLBCL subtypes (Alizadeh 2000; Rosenwald 2002; Rosenwald 2003b). Alternatively, these genetic alterations may themselves contribute at least in part to the ABC gene expression phenotype and its inferior prognosis.

Other chromosomal abnormalities were found to occur more frequently in one DLBCL subtype than another, but without being restricted to a single subtype. For example, deletions of 6q21-q22 occurred in 40% was observed in 40% of ABC samples and 22% of GCB samples, but never in PMBL samples. Gains and amplifications of 12cen-q15 were observed most frequently. In GCB samples, but were also observed at a low frequency in both ABC and PMBL samples. These results suggest that certain oncogenic pathways are shared by various DLBCL subtypes, but nonetheless are more frequently utilized in different subtypes.

The distinct patterns of genomic alterations observed across different DLBCL subtypes are consistent with recent studies showing a correlation between gene copy number changes and expression of genes located within the involved genomic regions (Phillips 2001; Vfrtaneva 2001; Hyman 2002; Pollack 2002; Orsetti 2004).

The relationship between chromosome gains/amplifications and the expression profile of genes located within the gained/amplified regions was examined by RQ-PCR for four chromosomal regions commonly over represented in GCB and ABC tumors: 2p14-p16, 3q27-qter, 12q12-q15, and 18q21-q22. A strong impact of genomic gain's and amplifications on gene expression was observed. 25-75% of genes located within these chromosomal segments were overexpressed in those tumors with increased DNA copy number.

For many genes, expression levels were significantly higher in samples with gains or amplifications versus samples with normal DNA profiles, which suggests a direct effect of copy number on mRNA expression levels. However, not all genes in overrepresented chromosomal regions were more highly expressed. This suggests that either the individual genes were not amplified or that the functional background of the cell was not appropriate for expression of the gene. For example, REL was significantly overexpressed in GGB samples with overrepresentation of 2p14-p16, but not in ABC samples with overrepresentation of this region. Quantitative PCR analysis confirmed that the REL locus was amplified in virtually all GCB samples with overrepresentation of the 2p14-p16 region. However, REL was not amplified in any of the ABC samples with gains or amplifications of 2p14-p16, indicating that genes other than REL may be targeted by 2p14-p16 gains in ABC. Interestingly, mRNA expression of BCL11A, which is located very close to REL, was not influenced by 2p14-p16 gains in GCB or ABC samples, despite the fact that quantitative PCR analysis showed amplification and gains of the BCL11A locus in both subtypes.

Gene expression studies showed that chromosomal alterations in DLBCL cases are correlated with expression of certain gene expression signatures. Unexpectedly, this correlation was seen not only in gene expression signatures that reflect variation within malignant cells (proliferation and MHC class II signatures), but also in gene expression signatures that reflect the nature of non-malignant DLBCL tumors (T cell and lymph node signatures). The proliferation signature, which is more highly expressed in proliferating than in quiescent cells, was increased in DLBCL samples with genomic loss in 6q21 and gains in several bands of chromosome 3. The MHC class II signature, which reflects the coordinate regulation of all MHC class II genes in malignant DLBCL cells, was decreased in DLBCL samples with gains of 3p11-p12. The T cell signature, which reflects the infiltration of tumors by T cells, was decreased in DLBCL samples with gains of cytobands in chromosomes 7, 11, 12, and X or losses in 6q and 17p. The lymph node signature, which reflects a host response characterized by abundant expression of extracellular matrix components and infiltration of tumors with immune cells other than T cells, was increased in DLBCL samples with Xp21 gains and decreased in samples with gains in several cytobands of chromosome 3.

Previous studies have suggested that specific genetic alterations are relevant to predicting survival in DLBCL cases (Yunls 1989; Bea 2004). However, the present study shows that only gains in certain regions of chromosome 3 are significantly associated with inferior survival after adjusting for multiple variable comparisons. Specifically, gains involving 3p11-p12 were found to have prognostic value that was statistically independent of previously defined DLBCL survival predictors based on optimal gene expression-based models (Rosenwald 2002). This information can be used to create a refilled DLBCL survival predictor. For example, a survival predictor score may be calculated using an equation such as:

Survival predictor score=[0.241*(proliferation gene expression signature value)]+[0.310*(BMP6 expression value)]−[0.290*(germinal center B cell gene expression signature value)]−[0.311* (MHC class II gene expression signature value)]−[0.249*(lymph node gene expression signature value)].

wherein a higher survival predictor score is associated with worse survival. The DLBCL sample may then be assayed for gains or amplifications in the 3p11-p12 using any method, such as for example CGH. The identification of such gains or amplifications corresponds to a decrease. In survival, and may be used to adjust the survival predictor score accordingly. Alternatively, identification of a gain or amplification of 3p11-p12 may be used as a stand-alone indicator of worse survival for a DLBCL patient in the absence of additional gene expression data.

An MCL survival predictor was generated using gene expression data obtained using Affymetrix U133A, Asymetrix U133B, and Lymph Dx microarrays. This predictor incorporated a proliferation gene expression signature. Fitting the Cox proportional hazards model to the gene expression signature values obtained from these signatures resulted in the following model;

Survival predictor score=[1.66*(proliferation gene expression signature value)].

Gene expression data can also be used to diagnose and identify lymphoma types. In an embodiment of the present invention, a statistical method based on Bayesian analysis was developed to classify lymphoma specimens according to their gene expression profiles. This method does not merely assign a tumor to a particular lymphoma type, but also determines the probability that the tumor belongs to that lymphoma type. Many different methods have been formulated to predict cancer subgroups (Golub 1999; Ramaswamy 2001; Dudolt 2002; Radmacher 2002). These methods assign tumors to one of two subgroups based on expression of a set of differentially expressed genes. However, they do not provide a probability of membership in a subgroup. By contrast, the method disclosed herein used Bayes' rule to estimate this probability, thus allowing one to vary the probability cut-off for assignment of a tumor to a particular subgroup. In tumor types in which unknown additional subgroups may exist, the present method allows samples that do not meet the gene expression criteria of known subgroups to fall into an unclassified group with intermediate probability. A cancer subgroup predictor of the type described herein may be used clinically to provide quantitative diagnostic information for an individual cancer patient. This information can in turn be used to provide a predictor of treatment outcome for a particular cancer patient.

For any two lymphoma types A and B, there is a set of genes with significantly higher expression in type A than type B, and a set of genes with significantly lower expression in type A than in type B. By observing the expression of these genes in an unknown sample, it is possible to determine to which of the two types the ample belongs. Evaluating the likelihood that a particular sample belongs to one or the other lymphoma type by Bayesian analysis may be done using the following steps:

1. Identify those genes that are most differentially expressed between the two lymphoma types. This can be done by selecting those genes with the largest t-statistic between the two lymphoma types. The genes in this step may be subdivided into gene expression signatures in certain cases, with genes from each signature analyzed separately.

2. Create a series of linear predictor score (LPS) for samples belonging to either lymphoma type.
3. Evaluate the LPS for each sample in a training set, and estimate the distribution of these scores within each lymphoma type according to a normal distribution.
4. Use Bayes' rule to evaluate the probability that each subsequent sample belongs to one or the other lymphoma type.

If only two types of lymphoma are being distinguished, then a single probability score is sufficient to discriminate between the two types. However, if more than two lymphoma types are being distinguished, multiple scores will be needed to highlight specific differences between the types.

A novel microarray termed the Lymph Dx microarray is disclosed herein for the identification and diagnosis of various lymphoma types. The Lymph Dx microarray contains cDNA probes corresponding to approximately 2,653 genes, fewer than the number seen on microarrays that have been used previously for lymphoma diagnosis. The reduced number of probes on the Lymph Dx microarray is the result of eliminating genes that are less useful for the identification of lymphoma types and predicting clinical outcome. This reduction allows for simplified analysis of gene expression data. The genes represented on the Lymph Dx microarray can be divided into four broad categories: 1,101 lymphoma predictor genes identified previously using the Affymetrix U133 microarray, 171 outcome predictor genes, 167 new genes not found on the Affymetrix U133 microarray, and 1,121 named genes. A list of the probe sets on the Lymph Dx microarray is presented in Table 2, contained in the file "Table_0002_LymphDx_Probe_List.txt."

Figure 1:
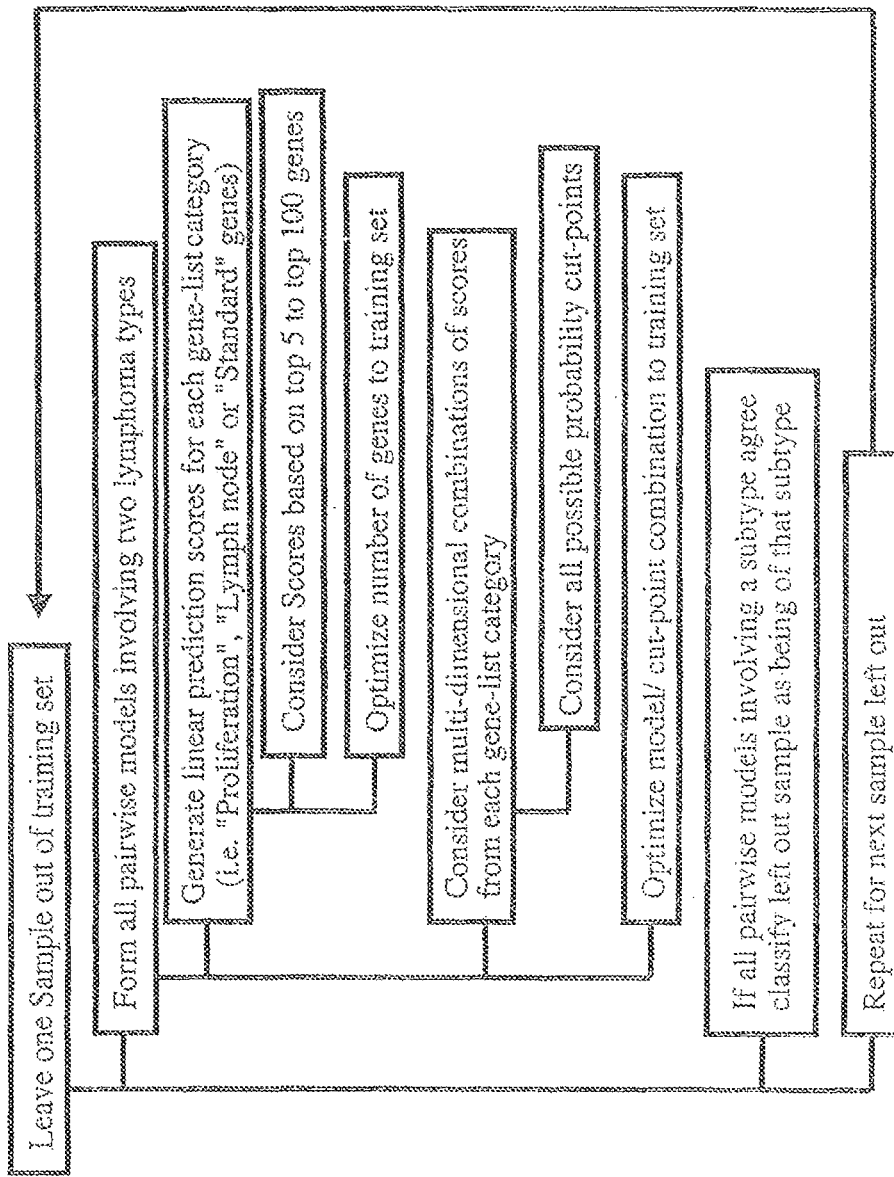
FIG. 1: Method for identifying lymphoma type. Flow chart depicts a general method for identifying lymphoma type using gene expression data.

Gene expression data obtained using the Lymph Dx microarray may be used to identify and classify lymphomas using Bayesian analysis using a strategy similar to that set forth above. In certain embodiments, this strategy may include additional steps designed to optimize the number of genes used and the cut-off points between lymphoma types. A general overview of such a method is presented in FIG. 1. Each gene represented on the Lymph Dx microarray was placed into one of three gene-list categories based on its correlation with the lymph node or proliferation gene expression signatures: lymph node, proliferation, or standard. These signatures were identified by clustering of the DLBCL cases using hierarchical clustering and centroid-correlation of 0.35. Standard genes were those with expression patterns that did not correlate highly with expression of the lymph node or proliferation signatures. Lymph Dx gene expression data was first used to identify samples as FL, MCL, SLL, FH, or DLBCL/BL, then to identify DLBCL/BL samples as ABG, GCB, PMBL, or BL. For each stage, a series of pair-wise models was created, with each model containing a different pair of lymphoma types (e.g., FL vs. MCL, SLL vs. FH, etc.). For each pair, the difference in expression of each gene on the microarray was measured, and a t-statistic was generated representing this difference. Genes from each gene-list category were ordered based on their t-statistic, and those with the largest t-statistics were used to generate a series of LPSs for samples belonging to either lymphoma type. The number of genes used to generate the LPSs was optimized by repeating the calculation using between five and 100 genes from each gene-list category. The number of genes from each category used in the final LPS calculation was that which gave rise to the largest difference in LPS between the two lymphoma types. Once the number of genes in each gene-list category was optimized, four different LPSs were calculated for each sample. The first included genes from the standard gene-list category only, the second included genes from the proliferation and standard gene-list categories, the third included genes from the lymph node and standard gene-list categories, and the fourth included genes from all three categories. The probability q that a sample X belongs to the first lymphoma type of a pair-wise model can then be calculated using an equation:

$$q = \frac{\phi(LPS(X); \hat{\mu}_1, \hat{\sigma}_1)}{\phi(LPS(X); \hat{\mu}_1, \hat{\sigma}_1) + \phi(LPS(X); \hat{\mu}_2, \hat{\sigma}_2)}$$

LPS(X) is the LPS for sample X, $\phi(x; \mu, \sigma)$ is the normal density function with mean $\mu$ and standard deviation $\sigma$. $\hat{\mu}_1$ and $\hat{\sigma}_1$ are the mean and variance of the LPSs for samples belonging to the first lymphoma type, and $\hat{\mu}_2$ and $\hat{\sigma}_2$ are the mean and variance of the LPSs for samples belonging to the second lymphoma type. Samples with high q values were classified as the first lymphoma type, samples with low q values were classified as the second lymphoma type, and samples with middle range q values were deemed unclassified. To determine the proper cut-off point between high, low, and middle q values, every possible cut-off point between adjacent samples was analyzed by an equaltion:

3.99*[(% of type 1 misidentified as type 2)+(% of type 2 misidentified as type 1)]+[(% of type 1 unclassified)+(% of type 2 misidentified)].

This equation was used to favor the assignment of a sample to an "unclassified" category rather than to an incorrect lymphoma type. The final cut-off points were those which minimized this equation. The coefficient of 3.99 was chosen arbitrarily to allow an additional classification error only if the adjustment resulted in four or more unclassified samples becoming correctly classified. The coefficient can be varied to achieve a different set of trade-offs between the number of unclassified and unidentified samples.

To ensure that the accuracy of the model was not a result of overfitting, each model was validated by leave-one-out cross-validation. This entailed removing each sample of known lymphoma type from the data one at a time, and then determining whether the model could predict the missing sample. This process confirmed the accuracy of the prediction method.

Bayesian analysis has been used herein to classify lymphoma samples as DLBCL or BL based on gene expression data. BL is characterized by a high degree of proliferation and deregulation of the c-myc gene (Jaffe 2001). The diagnostic distinction between BL and DLBCL is critically important because there are significant differences in their clinical management. Lower-dose chemotherapy regimens typically used to treat DLBCL (e.g., CHOP) are not adequate to treat BL (Bishop 2000; Buller 1993), which requires intensive chemotherapy regimens (Pees 1992; Magrath 1996; Thomas 1999; Mead 2002; Divine 2005). Furthermore, prophylactic intrathecal chemotherapy or systemic chemotherapy that crosses the blood-brain barrier, which are unnecessary in most cases of DLBCL, are essential in the treatment of BL due the high risk of central nervous system involvement (Soussain 1995; Bishop 2000).

The diagnosis of BL relies on morphology, immunophenotype, and cytogenetics (Jaffe 2001). However, DLBCL and BL can have overlapping morphology and immunophenotype, and the characteristic t(8;14) translocation of BL (Nerl 1988; Gerbitz 1999; Hecht 2000) is also found in 5-10% of DLBCL cases (Kramer 1998). Since DLBCL is over 20 times more common than BL (Morton 2005), most aggressive lymphomas with t(8;14) are not BL. Thus, the distinction between BL and DLBCL can be difficult and may lead to incorrect clinical decisions and adverse outcomes.

The term Burkitt-like lymphoma has been used to refer to cases that have some features in common with BL. However, the most recent WHO guidelines (Jaffe 2005) have eliminated Burkitt-like lymphoma as a separate diagnostic category. Burkitt-like lymphoma is now synonymous with the term atypical BL, which is reserved for those cases that share the genetic abnormality and immunophenotype of BL but have atypical morphology. It is not clear whether atypical BL is biologically difference from BL or if it merely represents a morphologic variant.

A gene expression-based predictor of BL that diagnoses classic BL with 100% accuracy and/distinguishes it from DLBCL has been developed. Surprisingly, eight cases that were given a pathological diagnosis of DLBCL were similar to BL by gene expression and had other molecular and clinical characteristics of BL.

Compared to DLBCL, BL was found to have high expression of the c-myc target gene expression signature and the GC B cell gene expression signature, and low expression of the NF-κB target gene expression signature and the MHC class I gene expression signature. A number of aggressive lymphomas that had been classified as DLBCL by an expert panel of hematopathologlsts (n=8) were reclassified as BL based on gene expression analysis: All eight of these cases had c-myc translocations and resembled BL with respect to all four gene expression signatures that distinguished BL from DLBCL, suggesting that these cases represent BL that cannot be reliably diagnosed by current methods. Consistent with previous studies (Butler 1993; Magrath 1996; Smeland 2004), patients classified as BL by gene expression had poor outcome with lower dose chemotherapy regimens, yet could be cured with intensive regimes.

The translocation of the c-myc gene and its consequent deregulation is a key oncogenic event in the genesis of BL and, accordingly, expression of the c-myc target gene expression signature distinguished BL from DLBCL. However, c-myc translocations also occur in 5-10% of DLBCL. It is therefore noteworthy that the gene expression-based predictor disclosed herein did not classify any of six DLBCL cases bearing a c-myc translocation as BL. Thus, c-myc deregulation by translocation and the attendant overexpression of c-myc target genes are not sufficient to create the phenotype of BL. Rather, it is likely that additional differences in the molecular pathogenesis of BL and DLBCL contribute to their clinical differences.

In keeping with this notion, BL and DLBCL were found to differ in the expression of three gene expression signatures in addition to the c-myc target gene signature. Both BL and GCB are thought to originate from a germinal center B cell (Mann 1976; Alizadeh 2000). Surprisingly, however, there were subsets of germinal center B cell genes that were differentially expressed between BL and GCB.

NF-κB target genes were expressed at very low levels in BL as compared to the DLBCL subtypes. These genes are also known to be expressed at lower levels in GCB than in ABC and PMBL (Rosenwald 2003b; Savage 2003; Feuerhake 2005; Lam 2005). However, BL was found to express NF-κB target genes at levels even lower than those of GCB. It is unclear at present whether this low expression reflects differences in the malignant cells or in tumor-infiltrating immune cells.

BL tumors expressed MHC class I genes at very low levels compared with DLBCL tumors. Previous studies have documented the loss of MHC class I molecules in some BL-derived cell lines (Voltz 1989), but the mechanism underlying this downmodulation is unclear at present.

The gene expression signatures that distinguish BL and DLBCL provide insight into the nine BL-discrepant cases that were classified as BL by gene expression but DLBCL by the panel of hematopathologists. The five BL-discrepant that were BCL2-negative were indistinguishable from the BL-concordant cases in the expression of all four gene expression signatures. Therefore, these cases bear all the hallmarks of BL but cannot be distinguished using current methodologies. Interestingly, BL-discrepant cases that were BCL2-positive resembled the BL-concordant cases with respect to three gene expression signatures, but had lower expression of the BL-high GC B cell signature. This phenotype was also observed in the BCL2-positive BL-concordant cases. Cases carrying dual translocations t(8;14) and t(14;18) have been described previously as having a very aggressive course and a poor prognosis (Macpherson 1999). The data presented herein confirm that CHOP-like regimens are not adequate to treat such patients.

The method of distinguishing BL and DLBCL disclosed herein provides a more quantitative and reproducible diagnosis of BL than is afforded by current methods based on morphology and immunophenotype. Such a method is clinically important because BL is a curable malignancy. Previous studies have shown that BL patients treated with CHOP-like chemotherapy regimens fare significantly worse than those who receive intensive regimens (Butler 1993; Magrath 1996; Smeland 2004). The results disclosed herein reveal that this also true for cases that were diagnosed as DLBCL pathologically but as BL based on gene expression. Correct identification of these cases will greatly enhance the formulation of treatment options for these BL-discrepant patients.

The methods discussed herein for identifying and classifying lymphoma subtypes have been used to identify and characterize cases of cyclin D1-negative MCL. Cyclin D1 overexpression has generally been considered essential to MCL pathogenesis, in fact, the current WHO guidelines for diagnosing MCL rely on morphologic examination and immunophenotyping, and require demonstration of cyclin D1 overexpression and/or the t(11;14)(q13;q32) for confirmation. Several suspected cases of cyclin-D1 MCL have been identified in recent studies, but these cases have been controversial and difficult to substantiate. Most reported cases of cyclin D1-negative MCL have been attributed to suboptimal immunostaining, inadequate genetic or molecular analyses, or misdiagnosis.

Nevertheless, in a recent study of 99 lymphomas, seven cases were identified that were morphologically consistent with MCL but lacked cyclin D1 expression as measured by quantitative RT-PCR and Lymphochip cDNA microarray analyses (Rosenwald 2003). Other than cyclin D1, these cases exhibited characteristic MCL gene expression signatures as determined by cDNA microarray analysis, and were therefore classified as cyclin D1-negative MCL. One of these seven cases had the characteristic t(11;14)(q13;q32) as determined by FISH analysis, and expressed cyclin D1 as determined by immunohistochemical staining. Thus, this case was determined to be a false negative and was reclassified as cyclin D1-positive MCL. Additional gene expression profiling analysis was performed using U133A/B microarrays, and the algorithm for diagnosing MCL was refined. Using this refined algorithm, four of the six remaining cyclin D1-negative cases were determined to be unclassifiable B-cell lymphomas, and were thus excluded from additional study. The two remaining cases and four newly identified cases were used for the current studies.

The present disclosure confirms and extends previous findings regarding the identification of cyclin D1-negative MCL. Six cases of MCL have been confirmed herein as negative for cyclin D1 mRNA expression by quantitative RT-PCR, microarray analysis, and immunostaining. These cases also lack the characteristic IGH/CCND1 fusion by FISH analysis. Nonetheless, all six cases exhibit the characteristic pathologic features of MCL and, more importantly, shared the characteristic MCL gene expression profile by microarray analysis. Therefore, these cases are regarded as bona fide cases of cyclin D1-negative MCL. The existence of such cases sheds new light on the pathobiology of MCL and challenges the idea that cyclin D1 overexpression is essential to MCL pathogenesis. It is also shown herein that patients with cyclin D1-negative MCL have clinical and pathologic features similar to those with cyclin D1-positive MCL. In particular, tumors in both groups have similar growth patterns and common cytological and immunohistochemical features. Similar age and sex distribution, stage, serum LDH levels, extranodal sites, IPI scores, response to initial treatment, and overall survival are observed in the cyclin D1-positive and cyclin D1-negative groups.

Recent studies have reported 23 cyclin D1-negative cases among 151 cases of lymphoma with the morphological features of MCL based on immunohistochemical staining (Yatabe 2000). Conventional cytogenetics was performed on only three of these 23 cases, and all three were negative for the t(11;14)(q13;q32). However, FISH or quantitative RT-PCR analysis was not performed on any of these cases. Compared to the 128 cyclin D1-positive MCL cases, the 23 cyclin D1-negative cases exhibited significantly better overall survival. Another recent study identified three cases of apparent cyclin D1-negative MCL by immunostains and compared them to 14 cases of typical cyclin D1-positive MCL (Hashimoto 2002). This study suggested that cyclin D1-negative MCL is a more indolent form of MCL. However, neither of these studies provided convincing evidence that the cyclin D1-negative MCL disclosed therein were true cases of MCL. In fact, the Yatabe et al. study notes that some of the cases identified as cyclin D1-negative MCL might actually be marginal zone B-cell lymphomas or atypical small lymphocytic lymphomas (Yatabe 2000). The results presented herein represent the first demonstration of characteristic MCL gene expression signature in a set of cyclin D1-negative MCL cases. No significant difference in clinical features was identified between these cases and cyclin D1-positive MCL.

The pathogenic mechanisms involved in the development of the cyclin D1-negative MCL are currently unknown. Since the oncogenic effect of overexpressed cyclin D1 is considered to be cell cycle deregulation, other proteins involved in cell cycle control, especially the G1 to S phase transition, were examined. The D-type cyclins, D1, D2 and D3, are all positive promoters of cell cycle progression from the G1 to S phase. The D-type cyclins are similar in structure and biochemical function (In aba 1992), but are expressed in a lineage-specific manner (Sherr 1994). There is considerable redundancy in the growth promoting function af the D-type cyclins, since only limited phenotypic consequences due to the absence of either cyclin D1, D2, or D3 are seen in gene knock-out mice (Sicinski 1995; Stcinskl 1996; Ciemerych 2002; Sicinska 2003). In non-neoplastic lymph nodes and tonsils, cyclin D2 is found mainly in intermolecular T-cells, whereas cyclin D3 is found in centroblasts in lymphoid follicles and in scattered B cells and T cells of the interfollicular areas (Teramoto 1999). However, cyclin D1 is not expressed in non-neoplastic T-cells or B-cells (Rosenberg 1991; Yang 1994). In low-grade B-cell malignancies, overexpression of cyclin D2 mRNA was observed by Northern blot analysis in 29 of 34 CLL cases and in all seven LPC cases, but not in two cases of MCL (Delmer 1995). Cyclin D3 appears tobe expressed more ubiquitously in B-cell malignancies, including FL, marginal zone lymphoma, and DLBCL (Ciemerych 2002), but is usually not expressed in lymphoid malignancies with either cyclin D1 or D2 overexpression (Ott 1997; Doglioni 1998; Suzuki 1999). In the current study, overexpression of either cyclin D2 or D3 was observed in all six cases of cyclin D1-negative MCL, indicating an important substitute role for these cyclins in the pathogenesis of cyclin D1-negative MCL. However, the mechanism of cyclin D2 or D3 up-regulation in these cases remains unclear. No chromosomal translocations or gene amplifications involving the cyclin D2 or D3 gene loci by FISH analysis were identified in these cases. The findings herein are consistent with several previous studies which suggested that deregulation of cyclin D2 or D3 expression is often due to epigenetic mechanisms (Andreasson 1998; Bergsagel 2003; Pruned 2003).

Deregulation of other genes or factors important in cell cycle control could also play a role in the pathogenesis of such cases. These may include deregulation of $p27^{kip1}$, up-regulation of cyclin E, inactivation of the RB gene, deletion of the $p16^{INK4a}/p14^{ARF}$ locus, as well as involvement of other genes. The $p27^{kip1}$ protein regulates cellular progression from G1 into S phase by inhibiting the cyclin E/CDK2 complex (Polyak 1994). Regulation of $p27^{kip1}$ occurs primarily through posttranscriptional mechanisms, including sequestration by cyclin D1 or cyclin D3 (Lin 2003; Quintanilla-Martinez 2003) or proteasomal degradation (Chlarle 2000). In a prior study, expression of $p27^{kip1}$ as assessed by immunostains was noted in only five of 40 cases of typical MCL, but was found in eight of ten cases of blastic MCL (Quintanilla-Martinez 1998). In the current study, down-regulation of $p27^{kip1}$ protein expression was seen in all six cases, similar to that seen in typical cyclin D1-positive MCL.

The E-type cyclins, including cyclin E1 and E2, are also important in the G1 phase of the cell cycle. When combined with CDK2, cyclin E promotes the hyper-phosphorylation of RB protein, and thereby facilitates the entry of cells into S phase (Sherr 1996). However, none of the present cases were positive for cyclin E expression, arguing against a role for cyclin E in the pathogenesis of cyclin D1-negative MCL. Inactivation of the RB tumor suppressor gene has been implicated in the development of various types of human malignancy. However, RB protein expression was identified in all of our cases and the expression levels were similar to those seen in cyclin D1-positive MCL. The present findings are consistent with a previous study concluding that RB protein appears to be normally regulated in MCL (Jares 1996). The present study also investigated whether deletions of the tumor suppressor genes $p16^{INK4a}$ and $p14^{ARF}$ play a role in cyclin D1-negative MCL. $p16^{INK4a}$ regulates the G1/S phase transition by forming binary complexes with CDK 4 and 6, thereby preventing these subunits from association with D-type cyclins (Sherr 2002). Deletion of $p16^{INK4a}$ or cyclin D1 overexpression may therefore promote the G1/S phase transition by the same mechanism. An important function of $p14^{ARF}$ is to augment p53 function by antagonizing MDM2, and loss of $p14^{ARF}$ function may contribute to the enhanced proliferation in tumor cells (Sherr 2002). As has been shown previously, INK4a/ARF locus deletions occur in up to 21% (18/85) cases, of MCL and are preferentially observed among the more proliferative cases (Rosenwald 2003).

However, deletion of the INK4a/ARF locus was not identified in any of the six cases, arguing against a role for $p16^{INK4a}/p14^{ARF}$ in the pathogenesis of cyclin D1-negative MCL.

The classification of a lymphoproliferative disorder in accordance with embodiments of the present invention may be used in combination with any other effective classification feature or set of features. For example, a disorder may be classified by a method of the present invention in conjunction with WHO suggested guidelines, morphological properties, histochemical properties, chromosomal structure, genetic mutation, cellular proliferation: rates, immunoreactivity, clinical presentation, and/or response to chemical, biological, or other agents. Embodiments of the present invention may be used in lieu of or in conjunction with other methods for lymphoma diagnosis, such as immunohistochemistry, flow cytometry, FISH for translocations, or viral diagnostics.

Accurate determination of lymphoma type in a subject allows for better selection and application of therapeutic methods. Knowledge about the exact lymphoma affecting a subject allows a clinician to select therapies or treatments that are most appropriate and useful for that subject, while avoiding therapies that are nonproductive or even counterproductive. For example, CNS prophylaxis may be useful for treating BL but not DLBCL, CHOP treatment may be useful for treating DLBCL but not biastic MCL (Fisher 1993; Khouri 1998), and subjects with follicular lymphoma frequently receive treatment while subjects with follicular hyperplasia do not. In each of these situations, the lymphoma types or subtypes in question can be difficult to distinguish using prior art diagnostic methods. The diagnostic and identification methods of the present invention allow for more precise delineation between these lymphomas, which simplifies the decision of whether to pursue a particular therapeutic option. Likewise, the survival prediction methods disclosed in the present invention also allow for better selection of therapeutic options. A subject with a very low survival predictor score (i.e., very good prognosis) may not receive treatment, but may instead be subjected to periodic check-ups and diligent observation. As survival predictor scores increase (i.e., prognosis gets worse), subjects may receive more intensive treatments. Those subjects with the highest survival predictor scores (i.e., very poor prognosis) may receive experimental treatments or treatments with novel agents. Accurate survival prediction using the methods disclosed herein provides an improved tool for selecting treatment options and for predicting the likely clinical outcome of those options.

Any effective method of quantifying the expression of at least one gene, gene set, or group of gene sets may be used to acquire gene expression data for use in embodiments of the present invention. For example, gene expression data may be measured or estimated using one or more microarrays. The microarrays may be of any effective type, including but not limited to nucleic acid based or antibody based. Gene expression may also be measured by a variety of other techniques, including but not limited to PCR, quantitative RT-PCR, real-time PCR, RNA amplification, in situ hybridization, immunohistochemistry, immunocytochemistry, FACS, serial analysis of gene expression (SAGE) (Velcufescu 1995), Northern blot hybridization, or western blot hybridization.

Nucleic acid microarrays generally comprise nucleic acid probes derived from individual genes and placed in an ordered array on a support. This support may be, for example, a glass slide, a nylon membrane, or a silicon wafer. Gene expression patterns in a sample are obtained by hybridizing the microarray with the gene expression product from the sample. This gene expression product may be for example, total cellular mRNA, rRNA, or cDNA obtained by reverse transcription of total cellular mRNA. The gene expression product from a sample is labeled with a radioactive, fluorescent, or other label to allow for detection. Following hybridization, the microarray is washed, and hybridization of gene expression product to each nucleic acid probe on the microarray is detected and quantified using a detection device such as a phosphorimager or scanning confocal microscope.

There are two broad classes of microarrays: cDNA and oligonucleotide arrays. cDNA arrays consist of hundreds or thousands of cDNA probes immobilized on a solid support. These cDNA probes are usually 100 nucleotides or greater in size. There are two commonly used designs for cDNA arrays. The first is the nitrocellulose filter array, which is generally prepared by robotic spotting of purified DNA fragments or lysates of bacteria containing cDNA clones onto a nitrocellulose filter (Southern 1992; Southern 1994; Gress 1996; Pietu 1996). The other commonly used cDNA arrays is fabricated by robotic spotting of PCR fragments from cDNA clones onto glass microscope slides (Schena 1995; DeRisi 1996; Schena 1996; Shalon 1996; DeRisi 1997; Heller 1997; Lashkari 1997). These cDNA microarrays are simultaneously hybridized with two fluorescent cDNA probes, each labeled with a different fluorescent dye (typically Cy3 or Cy5). In this format, the relative mRNA expression in two samples is directly compared for each gene on the microarray. Oligonucleotide arrays differ from cDNA arrays in that the probes are 20- to 25-mer oligonucleotides. Oligonucleotide arrays are generally produced by in situ oligonucleotide synthesis in conjunction with photolithographic masking techniques (Pease 1994; Upshutz 1995; Chee 1996; Lockhart 1996; Wodlcka 1997). The solid support for oligonucleotide arrays is typically a glass or silicon surface.

Methods and techniques applicable to array synthesis and use have been described in, for example, U.S. Pat. No. 5,143,854 (Pirrung), U.S. Pat. No. 5,242,974 (Holmes), U.S. Pat. No. 5,252,743 (Barrett), U.S. Pat. No. 5,324,633 (Fodor), U.S. Pat. No. 5,384,261 (Winkler), U.S. Pat. No. 5,424,186 (Fodor), U.S. Pat. No. 5,445,934 (Fodor), U.S. Pat. No. 5,451,683 (Barrett), U.S. Pat. No. 5,482,867 (Barrett), U.S. Pat. No. 5,491,074 (Aldwin), U.S. Pat. No. 5,527,681 (Holmes), U.S. Pat. No. 5,550,215 (Holmes), U.S. Pat. No. 5,571,639 (Hubbell), U.S. Pat. No. 5,578,832 (Trulson), U.S. Pat. No. 5,593,839 (Hubbell), U.S. Pat. No. 5,599,695 (Pease), U.S. Pat. No. 5,624,711 (Sundberg), U.S. Pat. No. 5,631,734 (Stern), U.S. Pat. No. 5,795,716 (Chee), U.S. Pat. No. 5,831,070 (Pease), U.S. Pat. No. 5,837,832 (Chee), U.S. Pat. No. 5,856,101 (Hubbell), U.S. Pat. No. 5,858,659 (Sapolsky), U.S. Pat. No. 5,936,324 (Montagu), U.S. Pat. No. 5,968,740 (Fodor), U.S. Pat. No. 5,974,164 (Chee). U.S. Pat. No. 5,981,185 (Matson), U.S. Pat. No. 5,981,956 (Stern), U.S. Pat. No. 6,025,601 (Trulson), U.S. Pat. No. 6,033,860 (Lockhart), U.S. Pat. No. 6,040,193 (Winkler), U.S. Pat. No. 6,090,555 (Flekowsky), and U.S. Pat. No. 6,410,229 (Lockhart), and U.S. Patent Application Publication No. 20030104411 (Fodor). Each of the above patents and applications is incorporated by reference herein in its entirety.

Microarrays may generally be produced using a variety of techniques, such as mechanical or light directed synthesis methods that incorporate a combination of photolithographic methods and solid phase synthesis methods. Techniques for the synthesis of microarrays using mechanical synthesis methods are described in, for example, U.S. Pat. No. 5,384,261 (Winkler) and U.S. Pat. No. 6,040,193 (Winkler). Although a planar array surface is preferred, the microarray may be fabricated on a surface of virtually any shape, or even on a multiplicity of surfaces. Microarrays may be nucleic acids on beads, gels, polymeric surfaces, fibers such as fiber optics, glass or any other appropriate substrate. See, for example, U.S. Pat. No. 5,708,153 (Dower); U.S. Pat. No. 5,770,358 (Dower); U.S. Pat. No. 5,789,162 (Dower); U.S. Pat. No. 5,800,992 (Fodor); and U.S. Pat. No. 6,040,193 (Winkler), each of which is incorporated by reference herein in its entirety.

Microarrays may be packaged in such a manner as to allow for diagnostic use, or they can be an all-inclusive device. See, for example, U.S. Pat. No. 5,856,174 (Upshutz) and U.S. Pat. No. 5,922,591 (Anderson), both of which are incorporated by reference herein in their entirety.

Microarrays directed to a variety of purposes are commercially available from Asymetrix (Affymetrix, Santa Clara, Calif.). For instance, these microarrays may be used for genotyping and gene expression monitoring for a variety of eukaryotic and prokaryote species.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing froth the scope of the invention. It will be understood that many variations can be made in the procedures herein described while still remaining within the bounds of the present invention. It is the intention of the inventors that such variations are included within the scope of the invention.

EXAMPLES

Example 1: Collection and Analysis of Gene Expression Data Using Affymetrix U133A and U133B Microarrays 568 cell samples representing various forms of human lymphoid malignancies were obtained by biopsy using known methods described in the literature. The samples were reviewed by a panel of hematopathologists and classified into the following lymphoma types based on current diagnostic criteria:
  231 diffuse large B cell lymphomas (DLBCL)
  191 follicular lymphomas (FL)
  26 Burkitt lymphomas (BL)
  21 mantle cell lymphoma (MCL)
  18 follicular hyperplasias (FH)
  17 small cell lymphocytic lymphomas (SLL)
  16 mucosa-associated lymphoid tissue lymphomas (MALT)
  13 splenic lymphomas (Splenic)
  10 cyclin-D1 negative lymphomas with MCL morphology (CD1negMCL)
  9 multiple myeloma (Mult_Wyeloma)
  6 lymphoplasmacytlc lymphomas (LPC)
  4 post-transplant lymphoproliferative disorders (PTLD)
  3 lymphoblastic lymphomas (Lymbl)
  3 nodal marginal zone lymphomas (NMZ)
The 231 DLBCL samples were subdivided into the following lymphoma types based on gene expression (see below):
  88 germinal center B cell-like (GCB)
  78 activated B cell-like (ABC)
  33 primary mediastinal B cell lymphoma (PMBL)
  32 samples for which the subtype could not be determined (UC_DLBCL)
The 16 MALT samples were subdivided into the following four group based on tumor origin:
  9 from the gastric region (MALT_gastric)
  1 from the salivary gland (MALT_salivary)
  1 from the lung (MALT_lung)
  1 from the tonsil (MALT_tonsil)
  4 of unknown origin (MALT_unk)
Each of the 568 cell samples was given a unique sample ID number consisting of the lymphoma type followed by a unique numerical identifier. For example, "ABC_304" refers to an ABC DLBCL sample numbered 304. Cells were purified and RNA was isolated from the purified cells according to known methods described in the literature.

Aliquots of RNA from each sample were applied to Affymetrix U133A and Affymetrix U133B microarrays according to standard Affymetrix protocol. The U133A and U133B microarrays are divided into probe sets, with each probe set consisting of up to 69 oligonucleotide probes 25 nucleotides in length. Each probe set represents a distinct human gene. Information pertaining to these microarrays is available at www.affymetrix.com. Each microarray was scanned using an Affymetrix scanner; which records signal intensity for every probe on the microarray. This information can be transformed into summary signal values for each probe set using a number of different algorithms, including MAS 5.0, D-chip (Li 2001), or Bioconductor's RMA algorithms (Irlzarry 2003). The images produced by the scanner were evaluated by Affymetrix MAS 5.0 software and stored as tables in .txt format. Since each sample was scanned on both microarrays, there are two .txt files for each sample. Each .txt file was given a unique name consisting of the table number, sample ID number (discussed above), and a letter denoting the microarray used. For example, Table_0588_ABC_304_A.txt is the .txt file for Table 588, which contains data for sample ID number ABC_304 from the U133A array. The data for each sample tested is contained in Tables 3-1138.

The signal value for each probe on the U133A and U133B microarrays was normalized to a target value of 500, and the base-2 log of the normalized values was used for the following analyses. Log-signal values for each probe set are presented in Tables 1139-1706, contained in files with the title format "Table_No._NAME_log_signal.txt," where NAME refers to the sample ID number (e.g., ABC_304). The first column provides the UNIQID for the probe set, while the second column provides the log-signal value.

Log-signal files were statistically analyzed using S+ software and the S+ subtype predictor script contained in the file entitled "Subtype_Predictor.txt," located in the computer program listing appendix contained on CD number 22 of 22. Although the log-signal values were analyzed using S+ software and the above algorithm, any effective software/ algorithm combination may be used. Tables 1707-1721 provide descriptive statistical characteristics for each of the lymphoma types tested except for CD1negMCL, non-gastric MALT, and UC_DLBCL. Table 1722 provides statistical characteristics for all MALT samples combined, while Table 1723 does likewise for all DLBCL samples.

The files containing Tables 1707-1723 have the title format "Table_No._TYPE_Stats.txt," where TYPE refers to the lymphoma type. Each row of these tables represents a particular probe set. The first column of each table provides the UNIQID for the probe set, while the second column provides the average log-signal for the probe set over all samples of a particular lymphoma type. The third column provides the log-fold change in expression of the probe set between the lymphoma type in question and a second lymphoma type. For example, if log fold.ABC.vs.GCB is −0.21 for gene X, expression of gene X in the ABC samples is, on average, 0.86 (i.e., $2^{-0.21}$) times greater than expression of gene X in the GCB samples. The fourth column provides a two-sided P-value derived from a t-test of the log signals of the two lymphoma types compared in column three. If, for example, P.value.ABC.vs.GCB was 0.00001 for gene X, this would indicate that the observed difference in expression of gene X between ABC and GCB would only occur approximately one time in 100,000 if there was no actual difference in gene X expression between the two lymphoma types. The remainder of the columns can be read as pairs that repeat the pattern of columns three and four, presenting the log-fold change and P-value of the difference in expression of the probe set for the lymphoma type in question versus all other lymphoma types being tested. Tables 1710, 1715, and 1723 (corresponding to FL, MCL, and DLBCL, respectively) contain two additional columns entitled "TYPE_Cox_coefficient" and "TYPE_Cox_P_value." The content of these columns Ia discussed in the following examples.

Example 2: Collection of Gene Expression Data Using the Novel Lymph Dx Microarray The novel Lymph Dx microarray contains cDNA probes corresponding to approximately 2,734 genes. 174 of these are "housekeeping" genes present for quality control, since they represent genes that are most variably expressed across ell lymphoma samples. Other genes represented on the microarray were selected for their utility in identifying particular lymphoma samples and predicting survival in those samples. The genes represented on the Lymph Dx microarray can be divided into four broad categories; 1,101 lymphoma predictor genes identified previously using the Affymetrix U133 microarray, 171 outcome predictor genes identified using the Affymetrix U133 microarray, 167 genes not found on the Affymetrix U133 microarray but represented on the Lymphochip microarray (Alizadeh 1999), and 1,121 named genes. The types of genes making up each of these broad categories are summarized in Table 1724, below, while the specific genes represented on the Lymph Dx microarray are listed in Table 2, contained in the file "Table_0002_LymphDx_Probe_List.txt."

TABLE 1724

| Gene type | Number of genes |
|---|---|
| Lymphoma predictor genes | 1101 |
| Subtype specific | 763 |
| Lymph node signature | 178 |
| Proliferation signature | 160 |
| Outcome predictor genes | 171 |
| DLBCL | 79 |
| FL | 81 |
| MCL | 11 |
| New genes not on U133 | 167 |
| Lymphochip lymphoma predictor genes | 84 |
| EBV and HHV8 viral genes | 18 |
| BCL-2/cyclin D1/INK4a specialty probes | 14 |
| Named genes missing from U133 | 51 |
| Named genes | 1121 |

TABLE 1724-continued

| Gene type | Number of genes |
|---|---|
| Protein kinase | 440 |
| Interleukin | 35 |
| Interleukin receptor | 29 |
| Chemokine | 51 |
| Chemokine receptor | 29 |
| TNF family | 26 |
| TNF receptor family | 51 |
| Adhesion | 45 |
| Surface marker | 264 |
| Oncogene/tumor suppressor | 49 |
| Apoptosis | 46 |
| Drug target | 10 |
| Regulatory | 46 |

Cell samples representing various forms of human lymphoid malignancy were obtained by biopsy using known methods described in the literature. These 634 biopsy samples were reviewed by a panel of hematopathologists and classified into the following lymphoma types based on current diagnostic criteria:
  201 diffuse large B-cell lymphomas(DLBCL)
  191 follicular lymphomas (FL)
  60 Burtott lymphomas (BL)
  21 mantle cell lymphomas (MCL)
  30 primary mediastinal B cell lymphoma (PMBL)
  18 follicular hyperplasias (FH)
  18 small cell lymphocytic lymphomas (SLL)
  17 mucosa-associated lymphoid tissue lymphomas (MALT), including 9 gastric MALTs (GMALT)
  16 chronic lymphocytic leukemias (CLL)
  13 splenic lymphomas (SPL)
  11 lymphoplasmacytic lymphomas (LPC)
  11 transformed DLBCL (trDLBCL) (DLBCL that arose from an antecedent FL)
  10 cyclin D1 negative lymphomas with MCL morphology (CD1N)
  6 peripheral T-cell lymphoma (PTCL)
  4 post-transplant lymphoproliferative disorders (PTLD)
  4 nodal marginal zone lymphomas (NMZ)
  3 lymphoblastic lymphomas (LBL)
Each of the 634 samples was given a unique sample ID number consisting of the lymphoma type followed by a unique numerical identifier. For example, "BL_2032_52748" refers to a Burkitt lymphoma sample with the numerical identifier 2032_52748. Cells were purified and RNA was isolated from the purified cells according to known methods described in the literature.

Aliquots of purified RNA from each sample were applied to the Lymph Dx microarrays according to standard Affymetrix microarray protocol. Each microarray was scanned on an Affymetrix scanner. This scanner produced an image of the microarray, which was then evaluated by Affymetrix MAS 5.0 software. This information was stored in tables in .txt format. Each of these .txt files was given a unique name consisting of the table number, the sample ID number (discussed above), and the UNIQID for identifying the array data in the National Cancer Institute Database. For example, Table_1725_BL_2032_52748.txt is the .txt file for Table 1725, which contains data for sample ID number BL_2032. The data for each sample analyzed is contained in Tables 1725-2358. The signal intensity for each probe on the microarray can be transformed into summary signal values for each probe set through a number of different algorithms, including but not limited to MAS 5.0, D-chip (Li 2001), or Bioconductor's RMA algorithms (Irizarry 2003).

Figure 2:
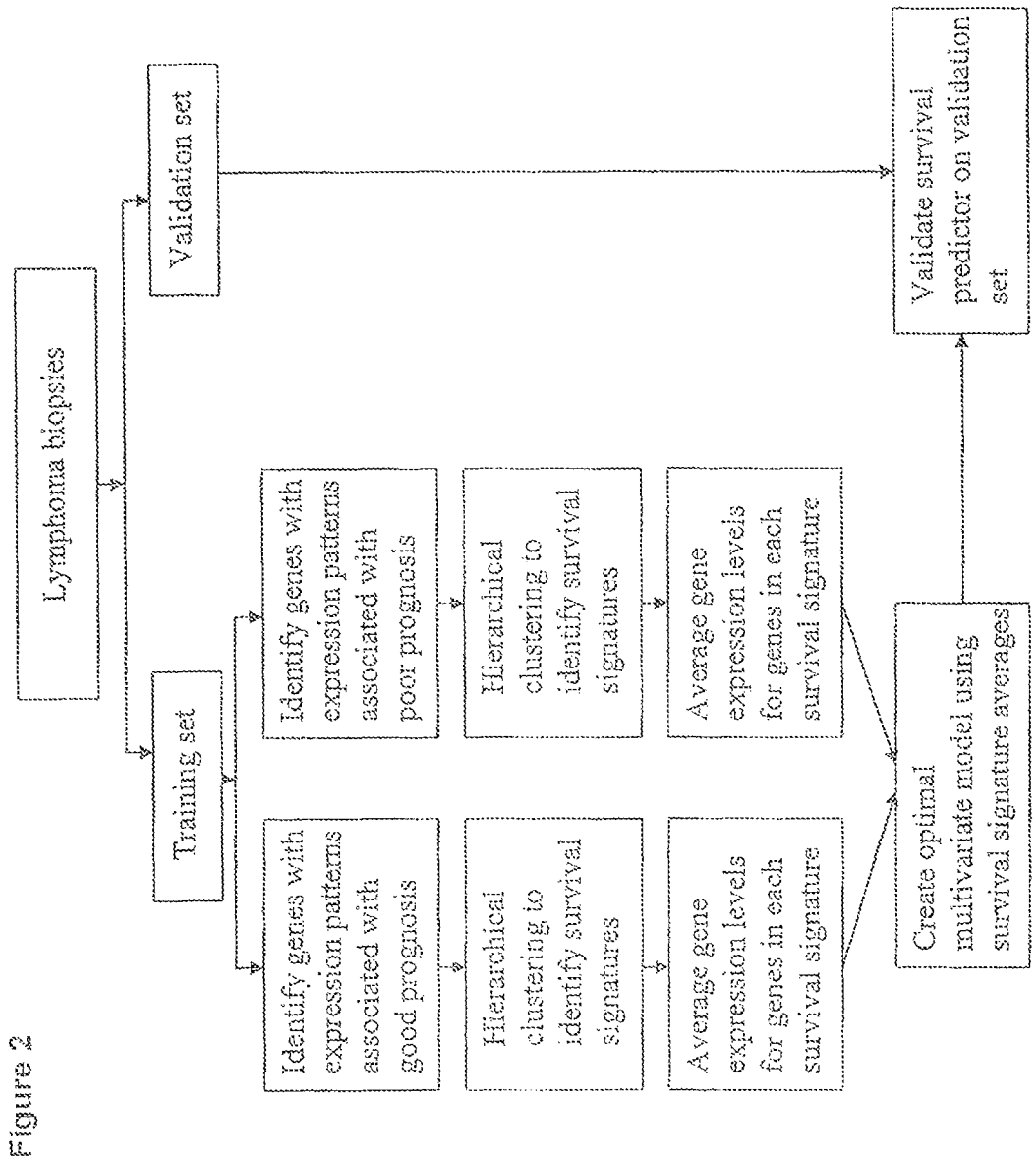
FIG. 2: Survival signature analysis. Flow chart depicts method for developing a lymphoma survival predictor based on gene expression patterns.

Example 3: Development of a First FL Survival Predictor Using Gene Expression Data from Affymetrix U133A and U133B Microarrays An analytical method entitled Survival Signature Analysis was developed to create survival prediction models for lymphoma. This method is summarized in FIG. 2. The key feature of this method is the identification of gene expression signatures. Survival Signature Analysis begins by identifying genes whose expression patterns are statistically associated with survival. A hierarchical clustering algorithm is then used to identify subsets of these genes with correlated expression patterns across the lymphoma samples. These subsets are operationally defined as "survival-associated signatures." Evaluating a limited number of survival-associated signatures mitigates the multiple comparison problems that are inherent in the use of large-scale gene expression data sets to create statistical models of survival (Ransohoff 2004).

Figure 3:
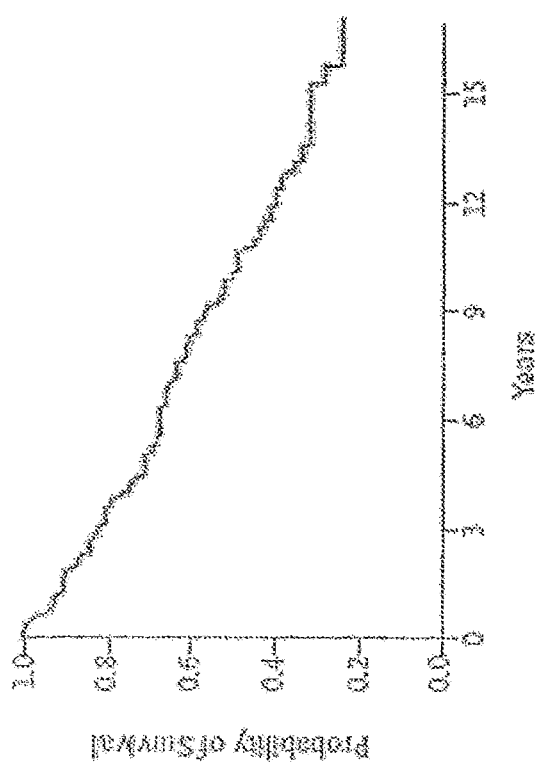
FIG. 3: FL survival data. Survival data for 191 subjects diagnosed with FL. Median age at diagnosis was 51 years (ranging from 23 to 81 years), and the subjects had a median follow-up of 6.6 years (8.1 years for survivors, with a range of <1 to 26.2 years).
Figure 4:
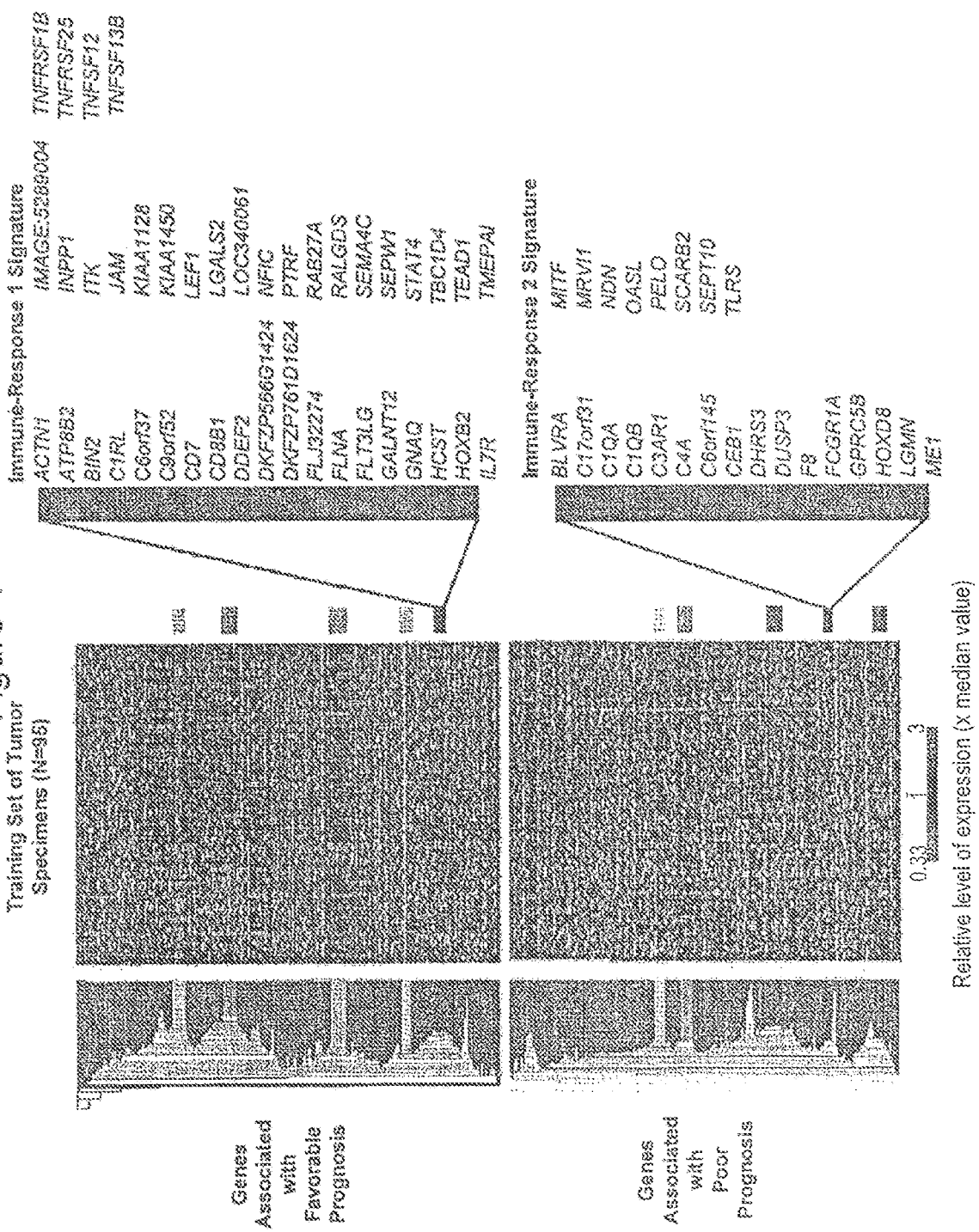
FIG. 4: Hierarchical clustering of survival associated genes in FL samples. Each column represents a single FL sample, while each row represents a single gene. Relative gene expression is depicted according to the color scale at the bottom of the figure. The dendrogram to the left indicates the degree to which the expression pattern of each gene is correlated with that of the other genes. The colored bars indicate sets of coordinated regulated genes defined as gene expression signatures. Genes comprising the immune response-1 and immune response-2 gene expression signature are listed on the right.

FL samples were divided into two equivalent groups: a training set (95 samples) for developing the survival prediction model, and a validation set (96 samples) for evaluating the reproducibility of the model. The overall survival of this cohort is depicted in FIG. 3. The median age at diagnosis was 51 years (ranging from 23 to 81 years), and the patients had a median follow-up of 6.6 years (8.1 years for survivors, with a range of <1 to 28.2 years). Gene expression data from Affymetrix U133A and U133B microarrays was obtained for each sample. Within the training set, a Cox proportional hazards model was used to identify "survival predictor" genes, which were genes whose expression levels were associated with long survival (good prognosis genes) or short survival (poor prognosis genes). A hierarchical clustering algorithm (Eisen 1998) was used to identify gene expression signatures within the good and poor prognosis genes according to their expression pattern across all samples. Ten gene expression signatures were observed within either the good prognosis or poor prognosis gene sets (FIG. 4). The expression level of every component gene in each of these ten gene expression signatures was averaged to create a gene expression signature value.

To create a multivariate model of survival, different combinations of the ten gene expression signature values were generated and evaluated for their ability to predict survival within the training set. Among models consisting of two signatures, an exceptionally strong statistical synergy was observed between one signature from the good prognosis group and one signature from the poor prognosis group. These signatures were deemed "immune response-1" and "immune response-2," respectively, based on the biological function of certain genes within each signature. The immune response-1 gene expression signature included genes encoding T cell markers (e.g., CD7, CD8B1, ITK, LEF1, STAT4) and genes that are highly expressed in macrophages (e.g., ACTN1, TNFSF13B). The immune response-1 signature is not merely a surrogate for the number of T cells in the FL biopsy sample because many other standard T cell genes (e.g., CD2, CD4, LAT, TRIM, SH2D1A) were not associated with survival. The immune response-2 gene expression signature included genes known to be preferentially expressed in macrophages and/or dendritic cells (e.g., TLR5, FCGR1A, SEPT10, LGMN, C3AR1). Table 2359 lists the genes that were used to generate the gene expression signature values for the immune response-1 and immune response-2 signatures.

TABLE 2359

| Signature | UNIQID | Unigene ID Build 167 (http://www.ncbi.nlm.nih.gov/UniGene) | Gene symbol |
|---|---|---|---|
| Immune response-1 | 1095985 | 83883 | TMEPAI |
| Immune response-1 | 1096579 | 117339 | HCST |
| Immune response-1 | 1097255 | 380144 | |
| Immune response-1 | 1097307 | 379754 | LOC340061 |
| Immune response-1 | 1097329 | 528675 | TEAD1 |
| Immune response-1 | 1097561 | 19221 | C20orf112 |
| Immune response-1 | 1098152 | 377588 | KIAA1450 |
| Immune response-1 | 1098405 | 362807 | IL7R |
| Immune response-1 | 1098548 | 436639 | NFIC |
| Immune response-1 | 1098893 | 43577 | ATP8B2 |
| Immune response-1 | 1099053 | 376041 | |
| Immune response-1 | 1100871 | 48353 | |
| Immune response-1 | 1101004 | 2969 | SKI |
| Immune response-1 | 1103303 | 49605 | C9orf52 |
| Immune response-1 | 1107713 | 171806 | |
| Immune response-1 | 1115194 | 270737 | TNFSF13B |
| Immune response-1 | 1119251 | 433941 | SEPW1 |
| Immune response-1 | 1119838 | 469951 | GNAQ |
| Immune response-1 | 1119924 | 32309 | INPP1 |
| Immune response-1 | 1120196 | 173802 | TBC1D4 |
| Immune response-1 | 1120267 | 256278 | TNFRSF1B |
| Immune response-1 | 1121313 | 290432 | HOXB2 |
| Immune response-1 | 1121406 | NA | TNFSF12 |
| Immune response-1 | 1121720 | 80642 | STAT4 |
| Immune response-1 | 1122956 | 113987 | LGALS2 |
| Immune response-1 | 1123038 | 119000 | ACTN1 |
| Immune response-1 | 1123092 | 437191 | PTRF |
| Immune response-1 | 1123875 | 428 | FLT3LG |
| Immune response-1 | 1124760 | 419149 | JAM3 |
| Immune response-1 | 1128356 | 415792 | C1RL |
| Immune response-1 | 1128395 | 7188 | SEMA4C |
| Immune response-1 | 1132104 | 173802 | TBC1D4 |
| Immune response-1 | 1133408 | 12802 | DDEF2 |
| Immune response-1 | 1134069 | 405667 | CD8B1 |
| Immune response-1 | 1134751 | 106185 | RALGDS |
| Immune response-1 | 1134945 | 81897 | KIAA1128 |
| Immune response-1 | 1135743 | 299558 | TNFRSF25 |
| Immune response-1 | 1135968 | 119000 | ACTN1 |
| Immune response-1 | 1136048 | 299558 | TNFRSF25 |
| Immune response-1 | 1136087 | 211576 | ITK |
| Immune response-1 | 1137137 | 195464 | FLNA |
| Immune response-1 | 1137289 | 36972 | CD7 |
| Immune response-1 | 1137534 | 36972 | CD7 |
| Immune response-1 | 1139339 | 47099 | GALNT12 |
| Immune response-1 | 1139461 | 14770 | BIN2 |
| Immune response-1 | 1140391 | 44865 | LEF1 |
| Immune response-1 | 1140524 | 10784 | C6orf37 |
| Immune response-1 | 1140759 | 298530 | RAB27A |
| Immune response-2 | 1118755 | 127826 | EPOR |
| Immune response-2 | 1118966 | 19196 | LOC51619 |
| Immune response-2 | 1121053 | 1690 | FGFBP1 |
| Immune response-2 | 1121267 | 334629 | SLN |
| Immune response-2 | 1121331 | 8980 | TESK2 |
| Immune response-2 | 1121766 | 396566 | MPP3 |
| Immune response-2 | 1121852 | 421391 | LECT1 |
| Immune response-2 | 1122624 | 126378 | ABCG4 |
| Immune response-2 | 1122679 | 232770 | ALOXE3 |
| Immune response-2 | 1122770 | 66578 | CRHR2 |
| Immune response-2 | 1123767 | 1309 | CD1A |
| Immune response-2 | 1123841 | 389 | ADH7 |
| Immune response-2 | 1126097 | 498015 | |
| Immune response-2 | 1126380 | 159408 | |
| Immune response-2 | 1126628 | 254321 | CTNNA1 |
| Immune response-2 | 1126836 | 414410 | NEK1 |
| Immune response-2 | 1127277 | 121494 | SPAM1 |
| Immune response-2 | 1127519 | NA | |
| Immune response-2 | 1127648 | 285050 | |
| Immune response-2 | 1128483 | 444359 | SEMA4G |
| Immune response-2 | 1128818 | 115830 | HS3ST2 |
| Immune response-2 | 1129012 | 95497 | SLC2A9 |
| Immune response-2 | 1129582 | 272236 | C21orf77 |

TABLE 2359-continued

| Signature | UNIQID | Unigene ID Build 167 (http://www.ncbi.nlm.nih.gov/UniGene) | Gene symbol |
|---|---|---|---|
| Immune response-2 | 1129658 | 58356 | PGLYRP4 |
| Immune response-2 | 1129705 | 289368 | ADAM19 |
| Immune response-2 | 1129867 | 283963 | G6PC2 |
| Immune response-2 | 1130003 | 432799 | |
| Immune response-2 | 1130388 | 19196 | LOC51619 |
| Immune response-2 | 1131837 | 156114 | PTPNS1 |
| Immune response-2 | 1133843 | 6682 | SLC7A11 |
| Immune response-2 | 1133949 | 502092 | PSG9 |
| Immune response-2 | 1134447 | 417628 | CRHR1 |
| Immune response-2 | 1135117 | 512646 | PSG6 |
| Immune response-2 | 1136017 | 1645 | CYP4A11 |
| Immune response-2 | 1137478 | 315235 | ALDOB |
| Immune response-2 | 1137745 | 26776 | NTRK3 |
| Immune response-2 | 1137768 | 479985 | |
| Immune response-2 | 1138476 | 351874 | HLA-DOA |
| Immune response-2 | 1138529 | 407604 | CRSP2 |
| Immune response-2 | 1138601 | 149473 | PRSS7 |
| Immune response-2 | 1139862 | 251383 | CHST4 |
| Immune response-2 | 1140189 | 287369 | IL22 |
| Immune response-2 | 1140389 | 22116 | CDC14B |

Although the immune response-1 and immune response-2 gene expression signatures taken individually were not ideal predictors of survival, the binary model formed by combining the two was more predictive of survival in the training set than any other binary model (p<0.001). Using this binary model as an anchor, other signatures were added to the model using a step up procedure (Drapner 1966). Of the remaining eight signatures, only one signature contributed significantly to the model in the training set (p<0.01), resulting in a three-variable model for survival. This model was associated with survival in a highly statistically significant fashion in both the training (p<0.001) and validation sets (p=0.003). However, only the immune response-1 and immune response-2 gene expression signatures contributed to the predictive power of the model in both the training set and the validation set. The predictive power of each of these signatures is summarized in Table 2360.

TABLE 2360

| Gene expression signature | Contribution of signature to model in validation set (p-value) | Relative risk of death among patients in validation set (95% C.I.) | Effect of increased expression on survival |
|---|---|---|---|
| Immune response-1 | <0.001 | 0.15 (0.05-0.46) | Favorable |
| Immune response-2 | <0.001 | 9.35 (3.02-28.9) | Poor |

Based on this information, the third signature was removed from the model and the two-signature model was used to generate a survival predictor score using the following equation:

Survival predictor score=[(2.71*immune response-2 gene expression signature value)]−[(2.36×immune response-1 gene expression signature value)].

A higher survival predictor score was associated with worse outcome. The two-signature model was associated with survival in a statistically significant fashion in both the training set (p<0.001) and the validation set (p<0.001), which demonstrated that the model was reproducible. For the 187 FL samples with available clinical data, the survival predictor score had a mean of 1.6 and a standard deviation of 0.894, with each unit increase in the predictor score corresponding to a 2.5 fold increase in the relative risk of death. Data for all 191 samples is shown in Table 2361.

TABLE 2361

| Sample ID # | Set | Length of follow-up (years) | Status at follow-up | Immune response-1 signature value | Immune response-2 signature value | Survival predictor score |
|---|---|---|---|---|---|---|
| FL_1073 | Training | 7.68 | Dead | 9.20 | 8.67 | 1.77 |
| FL_1074 | Training | 4.52 | Dead | 9.10 | 8.57 | 1.74 |
| FL_1075 | Validation | 4.52 | Dead | 8.97 | 8.69 | 2.38 |
| FL_1076 | Training | 3.22 | Dead | 9.20 | 8.55 | 1.44 |
| FL_1077 | Training | 7.06 | Alive | 9.80 | 8.46 | −0.20 |
| FL_1078 | Training | 4.95 | Alive | 9.32 | 8.23 | 0.30 |
| FL_1080 | Training | 6.05 | Alive | 9.45 | 8.94 | 1.93 |
| FL_1081 | Validation | 6.61 | Alive | 9.00 | 8.22 | 1.05 |
| FL_1083 | Training | 10.01 | Alive | 9.82 | 8.72 | 0.47 |
| FL_1085 | Validation | 8.84 | Alive | 9.31 | 8.58 | 1.29 |
| FL_1086 | Validation | 1.98 | Dead | 9.49 | 9.09 | 2.22 |
| FL_1087 | Training | 8.19 | Alive | 9.98 | 9.27 | 1.57 |
| FL_1088 | Validation | 5.30 | Alive | 9.22 | 8.47 | 1.20 |
| FL_1089 | Training | 10.72 | Alive | 9.42 | 8.35 | 0.40 |
| FL_1090 | Validation | 10.20 | Alive | 9.27 | 8.37 | 0.82 |
| FL_1097 | Validation | 8.79 | Dead | 9.87 | 8.92 | 0.87 |
| FL_1098 | Validation | 5.34 | Dead | 9.33 | 8.81 | 1.87 |
| FL_1099 | Training | 7.65 | Alive | 9.73 | 9.04 | 1.54 |
| FL_1102 | Validation | 13.20 | Dead | 9.45 | 8.89 | 1.79 |
| FL_1104 | Training | 8.42 | Dead | 9.30 | 8.27 | 0.48 |
| FL_1106 | Validation | 7.94 | Alive | 9.13 | 9.19 | 3.36 |
| FL_1107 | Training | 5.01 | Dead | 9.41 | 9.32 | 3.07 |
| FL_1183 | Training | 11.56 | Dead | 9.31 | 8.53 | 1.16 |
| FL_1184 | Training | 6.93 | Dead | 9.66 | 8.83 | 1.13 |
| FL_1185 | Validation | 7.02 | Dead | 9.23 | 9.09 | 2.86 |
| FL_1186 | Training | 1.34 | Dead | 9.01 | 8.84 | 2.68 |
| FL_1416 | Validation | 6.21 | Alive | 9.50 | 8.67 | 1.08 |
| FL_1417 | Training | 2.40 | Dead | 8.47 | 8.39 | 2.73 |
| FL_1418 | Validation | 3.59 | Alive | 8.94 | 8.42 | 1.72 |
| FL_1419 | Training | 3.85 | Alive | 9.82 | 8.56 | 0.03 |
| FL_1422 | Training | 5.72 | Alive | 9.46 | 8.49 | 0.68 |
| FL_1425 | Validation | 4.26 | Alive | 8.93 | 8.50 | 1.98 |

TABLE 2361-continued

| Sample ID # | Set | Length of follow-up (years) | Status at follow-up | Immune response-1 signature value | Immune response-2 signature value | Survival predictor score |
|---|---|---|---|---|---|---|
| FL_1426 | Training | 7.32 | Alive | 9.08 | 8.26 | 0.97 |
| FL_1427 | Training | 5.22 | Alive | 8.57 | 8.28 | 2.22 |
| FL_1428 | Validation | 5.41 | Dead | 9.22 | 8.44 | 1.10 |
| FL_1432 | Training | 3.68 | Alive | 9.22 | 8.95 | 2.51 |
| FL_1436 | Training | 9.08 | Dead | 9.48 | 8.63 | 1.02 |
| FL_1440 | Training | 7.85 | Alive | 9.07 | 8.35 | 1.22 |
| FL_1445 | Training | 9.24 | Dead | 8.67 | 8.66 | 3.01 |
| FL_1450 | Validation | 0.65 | Dead | 9.83 | 9.99 | 3.86 |
| FL_1472 | Validation | 16.72 | Alive | 8.85 | 8.49 | 2.10 |
| FL_1473 | Training | 15.07 | Alive | 9.75 | 8.50 | 0.02 |
| FL_1474 | Validation | 2.75 | Dead | 9.34 | 9.10 | 2.62 |
| FL_1476 | Validation | 4.08 | Dead | 9.51 | 8.87 | 1.60 |
| FL_1477 | Training | 0.59 | Dead | 9.64 | 9.06 | 1.83 |
| FL_1478 | Training | 12.47 | Dead | 9.60 | 8.87 | 1.39 |
| FL_1479 | Training | 2.29 | Dead | 8.71 | 9.07 | 4.01 |
| FL_1480 | Training | 16.29 | Alive | 9.40 | 6.67 | 1.30 |
| FL_1579 | Training | 8.22 | Dead | 8.81 | 8.44 | 2.10 |
| FL_1580 | Training | 19.30 | Alive | 9.58 | 8.52 | 0.49 |
| FL_1581 | Training | 9.52 | Dead | 9.08 | 9.02 | 3.00 |
| FL_1582 | Validation | 1.30 | Dead | 8.40 | 8.18 | 2.36 |
| FL_1583 | Training | 15.26 | Dead | 9.47 | 8.79 | 1.48 |
| FL_1584 | Training | 15.73 | Dead | 9.44 | 8.55 | 0.89 |
| FL_1585 | Validation | 0.01 | Alive | 8.96 | 8.53 | 1.96 |
| FL_1586 | Validation | 3.11 | Alive | 9.38 | 8.55 | 1.03 |
| FL_1588 | Training | 0.49 | Dead | 9.52 | 9.06 | 2.08 |
| FL_1589 | Training | 3.15 | Alive | 9.72 | 8.74 | 0.72 |
| FL_1591 | Training | 11.22 | Alive | 9.49 | 8.62 | 0.97 |
| FL_1594 | Validation | 11.19 | Alive | 9.25 | 8.59 | 1.47 |
| FL_1595 | Training | 8.03 | Alive | 9.75 | 9.60 | 3.01 |
| FL_1598 | Validation | 2.80 | Dead | 8.81 | 8.33 | 1.79 |
| FL_1599 | Validation | 6.17 | Alive | 9.48 | 8.65 | 1.06 |
| FL_1603 | Training | 5.17 | Dead | 9.66 | 9.75 | 3.63 |
| FL_1604 | Training | 3.98 | Dead | 9.24 | 8.86 | 2.20 |
| FL_1606 | Validation | 4.22 | Dead | 9.45 | 9.18 | 2.57 |
| FL_1607 | Validation | 8.12 | Alive | 9.40 | 8.60 | 1.13 |
| FL_1608 | Validation | 9.70 | Alive | 8.92 | 8.41 | 1.72 |
| FL_1610 | Validation | 2.05 | Dead | 9.33 | 9.35 | 3.32 |
| FL_1611 | Validation | 10.15 | Alive | 9.42 | 8.69 | 1.31 |
| FL_1616 | Training | 2.36 | Dead | 9.38 | 8.82 | 1.78 |
| FL_1617 | Validation | 7.85 | Alive | 8.96 | 8.49 | 1.87 |
| FL_1619 | Validation | 9.24 | Dead | 9.43 | 8.56 | 0.94 |
| FL_1620 | Validation | 9.36 | Dead | 9.14 | 8.35 | 1.04 |
| FL_1622 | Training | 14.01 | Alive | 9.23 | 8.53 | 1.33 |
| FL_1623 | Training | 9.72 | Alive | 9.67 | 8.93 | 1.38 |
| FL_1624 | Validation | 3.98 | Dead | 9.05 | 8.50 | 1.70 |
| FL_1625 | Validation | 11.16 | Alive | 8.98 | 8.47 | 1.75 |
| FL_1626 | Validation | 6.47 | Dead | 8.59 | 8.14 | 1.76 |
| FL_1628 | Validation | 0.82 | Dead | 9.80 | 8.72 | 0.51 |
| FL_1637 | Validation | 18.81 | Alive | 9.95 | 9.58 | 2.48 |
| FL_1638 | Validation | 4.06 | Alive | 9.13 | 8.88 | 2.51 |
| FL_1639 | Training | 4.75 | Alive | 9.53 | 8.89 | 1.62 |
| FL_1643 | Training | 0.77 | Dead | 9.73 | 9.06 | 1.58 |
| FL_1644 | Validation | 3.84 | Alive | 9.55 | 8.68 | 0.98 |
| FL_1645 | Training | 3.56 | Alive | 9.49 | 8.70 | 1.18 |
| FL_1646 | Training | 1.97 | Dead | 9.25 | 8.61 | 1.50 |
| FL_1647 | Training | 1.22 | Dead | 9.12 | 8.89 | 2.55 |
| FL_1648 | Training | 11.01 | Alive | 9.13 | 8.12 | 0.46 |
| FL_1652 | Training | 3.72 | Dead | 9.50 | 9.14 | 2.35 |
| FL_1654 | Validation | 0.30 | Dead | 8.74 | 8.28 | 1.82 |
| FL_1655 | Training | 8.45 | Alive | 9.51 | 8.85 | 1.53 |
| FL_1656 | Validation | 9.36 | Alive | 9.06 | 8.58 | 1.87 |
| FL_1657 | Training | 10.09 | Alive | 9.53 | 8.46 | 0.44 |
| FL_1660 | Training | 2.32 | Alive | 8.81 | 8.38 | 1.91 |
| FL_1661 | Validation | 1.48 | Alive | 9.86 | 8.90 | 0.85 |
| FL_1662 | Validation | 0.74 | Dead | 9.57 | 9.15 | 2.21 |
| FL_1664 | Validation | 4.53 | Dead | 9.34 | 8.62 | 1.31 |
| FL_1669 | Training | 4.40 | Dead | 8.87 | 8.58 | 2.30 |
| FL_1670 | Training | 1.88 | Alive | 9.64 | 9.45 | 2.86 |
| FL_1675 | Training | 4.57 | Alive | 9.36 | 8.46 | 0.84 |
| FL_1681 | Validation | 4.23 | Alive | 9.52 | 8.63 | 0.91 |
| FL_1683 | Validation | 4.03 | Dead | 9.95 | 9.10 | 1.19 |
| FL_1684 | Training | 2.88 | Dead | 9.53 | 8.73 | 1.18 |
| FL_1716 | Validation | 9.69 | Alive | 8.95 | 8.35 | 1.50 |
| FL_1717 | Validation | 2.01 | Dead | 9.35 | 8.88 | 1.98 |
| FL_1718 | Training | 10.35 | Alive | 9.23 | 8.13 | 0.26 |
| FL_1719 | Validation | 7.70 | Dead | 9.13 | 8.50 | 1.49 |

TABLE 2361-continued

| Sample ID # | Set | Length of follow-up (years) | Status at follow-up | Immune response-1 signature value | Immune response-2 signature value | Survival predictor score |
|---|---|---|---|---|---|---|
| FL_1720 | Training | 3.91 | Dead | 8.78 | 8.88 | 3.33 |
| FL_1729 | Training | 8.06 | Alive | 9.35 | 8.65 | 1.39 |
| FL_1732 | Validation | 0.71 | Dead | 7.81 | 8.59 | 4.86 |
| FL_1761 | Validation | 10.83 | Alive | 9.31 | 8.55 | 1.22 |
| FL_1764 | Training | 0.42 | Dead | 9.25 | 8.87 | 2.21 |
| FL_1768 | Training | 13.04 | Alive | 9.42 | 8.47 | 0.72 |
| FL_1771 | Training | 9.26 | Dead | 9.09 | 8.67 | 2.06 |
| FL_1772 | Validation | 13.64 | Dead | 9.49 | 8.49 | 0.61 |
| FL_1788 | Training | 1.00 | Dead | 9.09 | 9.13 | 3.29 |
| FL_1790 | Training | 1.42 | Alive | 9.85 | 9.40 | 2.22 |
| FL_1792 | Validation | 2.01 | Dead | 9.33 | 8.72 | 1.61 |
| FL_1795 | Training | 0.71 | Dead | 10.19 | 9.27 | 1.08 |
| FL_1797 | Validation | 7.17 | Alive | 9.34 | 8.92 | 2.14 |
| FL_1799 | Training | 14.18 | Alive | 9.32 | 8.63 | 1.38 |
| FL_1810 | Validation | 9.91 | Alive | 8.66 | 8.41 | 2.35 |
| FL_1811 | Validation | 3.04 | Alive | 9.38 | 8.27 | 0.29 |
| FL_1825 | Training | 2.98 | Alive | 9.46 | 9.07 | 2.25 |
| FL_1827 | Training | 3.66 | Alive | 9.80 | 8.84 | 0.83 |
| FL_1828 | Validation | 11.51 | Alive | 8.99 | 8.09 | 0.72 |
| FL_1829 | Validation | 4.11 | Alive | 9.57 | 8.73 | 1.08 |
| FL_1830 | Validation | 5.65 | Dead | 9.01 | 8.68 | 2.25 |
| FL_1833 | Training | 11.95 | Alive | 9.74 | 8.67 | 0.51 |
| FL_1834 | Validation | 16.92 | Alive | 9.22 | 8.72 | 1.88 |
| FL_1835 | Validation | 12.49 | Alive | 9.26 | 8.83 | 2.10 |
| FL_1836 | Validation | 12.24 | Alive | 9.55 | 8.64 | 0.85 |
| FL_1837 | Validation | 0.55 | Dead | 9.47 | 8.84 | 1.62 |
| FL_1838 | Validation | 2.54 | Alive | 9.90 | 9.12 | 1.34 |
| FL_1839 | Training | 4.48 | Alive | 8.56 | 8.32 | 2.34 |
| FL_1841 | Training | 0.88 | Dead | 9.32 | 9.10 | 2.66 |
| FL_1842 | Validation | 4.56 | Alive | 9.73 | 8.87 | 1.07 |
| FL_1844 | Validation | 13.39 | Alive | 9.41 | 8.55 | 0.98 |
| FL_1845 | Training | 12.92 | Dead | 9.89 | 9.04 | 1.16 |
| FL_1846 | Validation | 1.80 | Dead | 9.79 | 9.61 | 2.93 |
| FL_1848 | Training | 12.52 | Alive | 9.78 | 8.81 | 0.82 |
| FL_1851 | Training | 4.08 | Dead | 9.43 | 9.01 | 2.18 |
| FL_1853 | Validation | 12.50 | Alive | 9.28 | 8.54 | 1.25 |
| FL_1854 | Validation | 13.81 | Alive | 9.32 | 8.84 | 1.98 |
| FL_1855 | Validation | 9.96 | Dead | 9.31 | 8.39 | 0.75 |
| FL_1857 | Validation | 8.39 | Dead | 9.80 | 9.14 | 1.65 |
| FL_1861 | Validation | 8.18 | Dead | 9.47 | 8.57 | 0.88 |
| FL_1862 | Validation | 7.22 | Dead | 8.98 | 8.33 | 1.44 |
| FL_1863 | Validation | 10.77 | Dead | 9.31 | 8.86 | 2.00 |
| FL_1864 | Training | 14.25 | Alive | 9.98 | 9.12 | 1.17 |
| FL_1866 | Training | 10.72 | Dead | 9.93 | 8.94 | 0.79 |
| FL_1870 | Validation | 6.41 | Dead | 10.01 | 9.22 | 1.36 |
| FL_1873 | Training | 7.78 | Dead | 9.39 | 8.66 | 1.30 |
| FL_1874 | Validation | 3.15 | Dead | 9.38 | 8.74 | 1.53 |
| FL_1876 | Validation | 15.07 | Alive | 9.59 | 8.72 | 0.98 |
| FL_1879 | Training | 7.13 | Dead | 9.25 | 8.62 | 1.53 |
| FL_1880 | Validation | 12.84 | Dead | 8.82 | 8.35 | 1.82 |
| FL_1882 | Training | 8.84 | Dead | 9.43 | 8.76 | 1.49 |
| FL_1884 | Validation | 11.92 | Dead | 9.48 | 9.14 | 2.41 |
| FL_1885 | Validation | 15.49 | Alive | 9.70 | 8.85 | 1.11 |
| FL_1887 | Training | 5.14 | Dead | 9.47 | 8.57 | 0.87 |
| FL_1888 | Training | 15.08 | Alive | 9.83 | 8.97 | 1.11 |
| FL_1890 | Training | 3.03 | Dead | 9.29 | 9.05 | 2.60 |
| FL_1894 | Training | 11.37 | Dead | 9.01 | 8.64 | 2.13 |
| FL_1896 | Training | 12.03 | Alive | 9.80 | 8.56 | 0.08 |
| FL_1897 | Training | 9.63 | Alive | 9.02 | 8.33 | 1.29 |
| FL_1898 | Training | 5.20 | Alive | 8.82 | 8.25 | 1.54 |
| FL_1900 | Validation | 7.38 | Alive | 9.13 | 8.26 | 0.85 |
| FL_1903 | Validation | 28.25 | Alive | 9.07 | 8.46 | 1.54 |
| FL_1904 | Validation | 7.36 | Alive | 9.16 | 8.53 | 1.50 |
| FL_1905 | Validation | 3.68 | Dead | 9.25 | 8.38 | 0.87 |
| FL_1906 | Training | 2.35 | Dead | 8.04 | 8.69 | 4.56 |
| FL_1907 | Validation | 2.35 | Dead | 8.11 | 8.21 | 3.11 |
| FL_1910 | Training | 13.84 | Alive | 9.36 | 8.72 | 1.56 |
| FL_1912 | Validation | 0.73 | Dead | 9.30 | 9.21 | 3.02 |
| FL_1913 | Training | 2.57 | Alive | 9.77 | 8.51 | 0.01 |
| FL_1916 | Validation | 11.61 | Alive | 9.22 | 8.49 | 1.24 |
| FL_1918 | Validation | 9.95 | Dead | 9.54 | 8.77 | 1.26 |
| FL_1919 | Training | 10.84 | Dead | 9.51 | 8.81 | 1.44 |
| FL_735 | Validation | 11.05 | Dead | 8.81 | 8.23 | 1.53 |
| FL_738 | Validation | 10.15 | Dead | 9.19 | 8.79 | 2.13 |
| FL_739 | Training | 10.80 | Dead | 9.29 | 8.77 | 1.85 |
| FL_878 | Validation | 3.87 | Dead | 8.85 | 8.54 | 2.26 |

TABLE 2361-continued

| Sample ID # | Set | Length of follow-up (years) | Status at follow-up | Immune response-1 signature value | Immune response-2 signature value | Survival predictor score |
|---|---|---|---|---|---|---|
| FL_879 | Training | 4.34 | Dead | 8.95 | 8.74 | 2.56 |
| FL_886 | Validation | 3.29 | Alive | 9.43 | 8.72 | 1.40 |
| FL_888 | Validation | 1.32 | Dead | 8.76 | 8.49 | 2.34 |
| FL_1627 | Training | NA | NA | 9.60 | 8.51 | 0.40 |
| FL_1429 | Training | NA | NA | 8.69 | 8.28 | 1.93 |
| FL_1850 | Validation | NA | NA | 9.75 | 8.83 | 0.92 |
| FL_1735 | Validation | NA | NA | 7.32 | 8.30 | 5.24 |

Figure 5:
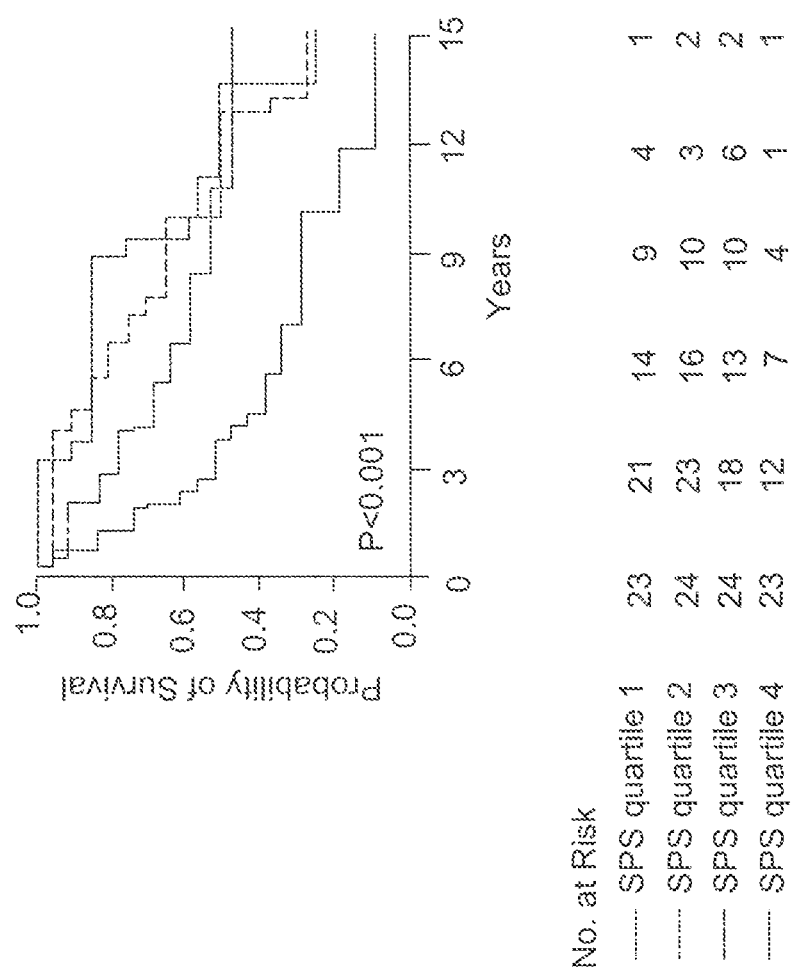

In order to visualize the predictive power of the model, the FL samples were ranked according to their survival predictor scores and divided into four quartiles, Kaplan-Meier plots of overall survival showed clear differences in survival rate in the validation set (FIG. 5). The median survival for each of the four quartiles is set forth in Table 2362.

TABLE 2362

| Quartile | Median survival (years) |
|---|---|
| 1 | 13.6 |
| 2 | 11.1 |
| 3 | 10.8 |
| 4 | 3.9 |

Various clinical variables were found to be significantly associated with survival, including the IPI and some of its components and the presence of B-symptoms. The gene expression-based model was independent of each of these variables at predicting survival. These clinical variables and the relative risk of death associated with each are summarized in Table 2363.

TABLE 2363

| Clinical variable | Criteria | % of patients[1] Training set | % of patients[1] Validation set | Univariate (clinical variable only) relative risk of death among patients in validation set RR[2] (95% C.I.) | p-value | Multivariate (clinical variable + survival predictor score) relative risk of death among patients in validation set RR[2] (95% C.I.) | p-value |
|---|---|---|---|---|---|---|---|
| Age | 60 | 64.5 | 70.2 | 1.90 (1.02-3.56) | 0.044 | 2.21 (1.48-3.29) | <0.001 |
|  | >60 | 35.5 | 29.8 |  |  |  |  |
| Stage | I-II | 33.3 | 25 | 1.31 (0.65-2.64) | 0.447 | 2.31 (1.61-3.52) | <0.001 |
|  | III-IV | 66.7 | 75 |  |  |  |  |
| Extranodal sites (#) | 2 | 5.4 | 20.2 | 1.58 (0.83-2.99) | 0.163 | 2.21 (1.48-3.30) | <0.001 |
|  | <2 | 94.6 | 79.8 |  |  |  |  |
| LDH | Normal | 77.1 | 66.2 | 1.77 (0.97-3.24) | 0.065 | 2.40 (1.57-3.67) | <0.001 |
|  | Greater than normal | 22.9 | 33.8 |  |  |  |  |
| ECOG performance status | 2 | 9.4 | 12.5 | 2.05 (0.89-4.71) | 0.090 | 2.17 (1.40-3.35) | <0.001 |
|  | <2 | 90.6 | 87.5 |  |  |  |  |
| Gender | Male | 42 | 65 | 1.62 (0.90-2.90) | 0.105 | 2.17 (1.45-3.25) | <0.001 |
|  | Female | 68 | 35 |  |  |  |  |
| B-symptoms | Present | 17.2 | 21.3 | 2.05 (1.08-3.89) | 0.029 | 2.10 (1.37-3.23) | <0.001 |
|  | Absent | 82.8 | 78.7 |  |  |  |  |
| Grade[3] | 1 | 45 | 43.4 | N/A | 0.118 | 2.55 (1.63-3.99) | <0.001 |
|  | 2 | 34.8 | 33.3 | 2.03 (1.04-3.96) |  |  |  |
|  | 3 | 20.2 | 23.3 | 1.39 (0.65-2.98) |  |  |  |
| Int'l, Prognostic Index[4] | Scores 0-1 | 63.1 | 47.5 | N/A | 0.029 | 2.28 (1.46-3.57) | <0.001 |
|  | Scores 2-3 | 33.3 | 45 | 2.07 (1.07-4.00) |  |  |  |
|  | Scores 4-5 | 3.6 | 7.5 | 3.73 (1.18-11.18) |  |  |  |

[1]Due to rounding, percentages may not total 100
[2]Relative risk of death (RR) based on 2-fold increase in expression
[3]RR for grades 2 and 3 calculated with respect to risk of death for grade 1. The p-value is calculated for all grades.
[4]RR for scores 2-3 and 4-5 calculated with respect to risk of death for scores 0-1.
The p-value is calculated for all grades.

The samples in the validation set were divided into three groups based on their IPI score, and the relationship between survival and IPI score was visualized by Kaplan-Meier plot (FIG. 6). Among validation set samples from the low-riak (IPI 0-1) and intermediate risk (IPI 2-3) IPI groups, the gene-expression-based survival predictor could stratify patients into groups differing by more than 5 years with regards to median survival (FIG. 7). The high-risk IPI group (IPI 4-5) comprised less than 5% of the samples, and was omitted from this analysis. These results demonstrate that the gene expression-based model is not merely acting as a surrogate for clinical variables that are known to predict survival in FL, but rather it identifies distinct biological attributes of the tumors that are associated with survival.

Example 4: Development of a Second FL Survival Predictor Using Gene Expression Data from Affymetrix U133A and U133B Microarrays 191 FL were divided into two equivalent groups: a training set (95 samples) for developing the survival prediction model, and a validation set (96 samples) for evaluating the reproducibility of the model. Gene expression data from Affymetrix U133A and U133B microarrays was obtained for each of the samples. A Cox proportional hazards model was used to identify survival predictor genes whose expression levels were associated with long survival (good prognosis genes) or short survival (poor prognosis genes) in the training set. The correlation between expression and survival for each gene on the microarrays is provided in the final two columns of Table 1710. The first of these two columns ("FL_Cox_coefficient") provides a Cox coefficient indicating the extent to which a 2-fold increase in expression of a particular gene affects mortality. A positive Cox coefficient indicates increasing mortality with increasing expression of the gene, white a negative Cox coefficient indicates decreasing mortality with increasing expression of the gene. The second of these two columns provides a Cox p-value indicating the estimated probability that the increase or decrease in survival associated with the gene would occur by chance if there was no connection between the expression of the gene and survival.

A hierarchical clustering algorithm (Eisen 1998) was used to identify gene expression signatures within the good and poor prognosis genes according to their expression pattern across all samples. Eight clusters of coordinated regulated genes were observed within the good prognosis gene set and six clusters were observed in the poor prognosis gene sets. The expression level of every component gene in each of these gene expression signatures was averaged to create a gene expression signature value. After averaging, only ten of the gene expression signatures were found to be significantly associated with survival in the training set ($p<0.01$); To create a multivariate model of survival, different combinations of these ten gene expression signature averages were generated and evaluated for their ability to predict survival within the training set. Among models consisting of two signatures, an exceptionally strong statistical synergy was noted between one signature from the good prognosis group and one from the poor prognosis group. These gene expression signatures were termed "T-cell" and "macrophage" based on the biological function of certain genes within each signature. The T-cell gene expression signature included genes that were typically expressed in T-cells, while the macrophage gene expression signature included a number of genes typically expressed in macrophages. Although these two signatures taken individually were not the best predictors of survival, the binary model formed by combining the two was more predictive than any combination of three signatures that did not contain these two signatures. Using these two signatures as an anchor, other signatures were added to the model using a step up procedure (Drapner 1966). Only one of the remaining eight signatures, termed the B-cell differentiation signature, contributed significantly to the model in the training set ($p=0.054$). The B-cell differentiation signature included a number of genes that appear to be involved in B-cell signal transduction. Table 2364 lists the genes that were used to generate the gene expression signature values for the T-cell, macrophage, and B-cell differentiation gene expression signatures.

TABLE 2364

| Signature | UNIQID | Unigene ID Build 167 (http://www.ncbi.nlm.nih.gov/UniGene) | Gene symbol |
| --- | --- | --- | --- |
| B-cell differentiation | 1119350 | 331141 | ALDH2 |
| B-cell differentiation | 1130922 | 459987 | ANP32B |
| B-cell differentiation | 1130923 | 459987 | ANP32B |
| B-cell differentiation | 1099291 | 130774 | C9orf105 |
| B-cell differentiation | 1102859 | 446195 | FLJ42418 |
| B-cell differentiation | 1120976 | 245644 | GCHFR |
| B-cell differentiation | 1098862 | 303669 | MGC26694 |
| B-cell differentiation | 1111070 | 202201 | |
| B-cell differentiation | 1105935 | | |
| B-cell differentiation | 1139017 | 274424 | NANS |
| B-cell differentiation | 1108988 | 3532 | NLK |
| B-cell differentiation | 1114726 | 3532 | NLK |
| B-cell differentiation | 1097897 | 266175 | PAG |
| B-cell differentiation | 1097901 | 266175 | PAG |
| B-cell differentiation | 1119813 | 155342 | PRKCD |
| B-cell differentiation | 1123298 | 20191 | SIAH2 |
| B-cell differentiation | 1101439 | 63335 | TERF2 |
| B-cell differentiation | 1120316 | 63335 | TERF2 |
| B-cell differentiation | 1096035 | 105794 | UGCGL1 |
| T-cell | 1134945 | 81897 | KIAA1128 |
| T-cell | 1134069 | 405667 | CD8B1 |
| T-cell | 1137809 | 405667 | CD8B1 |
| T-cell | 1119251 | 433941 | SEPW1 |
| T-cell | 1096579 | 117339 | HCST |
| T-cell | 1101004 | 2969 | SKI |
| T-cell | 1137137 | 195464 | FLNA |

TABLE 2364-continued

| Signature | UNIQID | Unigene ID Build 167 (http://www.ncbi.nlm.nih.gov/UniGene) | Gene symbol |
|---|---|---|---|
| T-cell | 1100871 | 48353 | |
| T-cell | 1139461 | 14770 | BIN2 |
| T-cell | 1128395 | 7188 | SEMA4C |
| T-cell | 1119880 | 442844 | FMOD |
| T-cell | 1130676 | 194431 | KIAA0992 |
| T-cell | 1130668 | 194431 | KIAA0992 |
| T-cell | 1135968 | 119000 | ACTN1 |
| T-cell | 1097329 | 528675 | TEAD1 |
| T-cell | 1098548 | 436639 | NFIC |
| T-cell | 1123038 | 119000 | ACTN1 |
| T-cell | 1128356 | 415792 | C1RL |
| T-cell | 1133408 | 12802 | DDEF2 |
| T-cell | 1140524 | 10784 | C6orf37 |
| T-cell | 1119838 | 469951 | GNAQ |
| T-cell | 1097255 | 380144 | |
| T-cell | 1098152 | 377588 | KIAA1450 |
| T-cell | 1115194 | 270737 | TNFSF13B |
| T-cell | 1124760 | 419149 | JAM3 |
| T-cell | 1120267 | 256278 | TNFRSF1B |
| T-cell | 1137289 | 36972 | CD7 |
| T-cell | 1137534 | 36972 | CD7 |
| T-cell | 1097307 | 379754 | LOC340061 |
| T-cell | 1123613 | 97087 | CD3Z |
| T-cell | 1121720 | 80642 | STAT4 |
| T-cell | 1120196 | 173802 | TBC1D4 |
| T-cell | 1136087 | 211576 | ITK |
| T-cell | 1132104 | 173802 | TBC1D4 |
| T-cell | 1140391 | 44865 | LEF1 |
| T-cell | 1098405 | 362807 | IL7R |
| T-cell | 1135743 | 299558 | TNFRSF25 |
| T-cell | 1136048 | 299558 | TNFRSF25 |
| T-cell | 1123875 | 428 | FLT3LG |
| T-cell | 1098893 | 43577 | ATP8B2 |
| T-cell | 1097561 | 19221 | C20orf112 |
| T-cell | 1122956 | 113987 | LGALS2 |
| T-cell | 1121406 | | TNFSF12 |
| T-cell | 1125532 | | |
| T-cell | 1138538 | 2014 | TRD |
| T-cell | 1103303 | 49605 | C9orf52 |
| T-cell | 1119924 | 32309 | INPP1 |
| Macrophage | 1123682 | 114408 | TLR5 |
| Macrophage | 1099124 | 355455 | SEPT10 |
| Macrophage | 1123401 | 50130 | NDN |
| Macrophage | 1134379 | 150833 | C4A |
| Macrophage | 1137481 | 150833 | C4A |
| Macrophage | 1132220 | 448805 | GPRC5B |
| Macrophage | 1119400 | 181046 | DUSP3 |
| Macrophage | 1131119 | 349656 | SCARB2 |
| Macrophage | 1123566 | 155935 | C3AR1 |
| Macrophage | 1138443 | 77424 | FCGR1A |
| Macrophage | 1127943 | 9641 | C1QA |
| Macrophage | 1119998 | 8986 | C1QB |
| Macrophage | 1132433 | 14732 | ME1 |
| Macrophage | 1119260 | 18069 | LGMN |
| Macrophage | 1098278 | 166017 | MITF |

The three signatures were used to generate a survival predictor score using the following equation:

Survival predictor score=[2.053*(macrophage gene expression signature value)]−[2.344*(T-cell gene expression signature value)]−[0.729*(B-cell differentiation gene expression signature value)].

A higher, survival predictor score was associated with worse outcome. According to a likelihood ratio test adjusted for the number of variables included, this model was significant in predicting survival in both the training set ($p=1.8 \times 10^{-8}$) and the validation set ($p=2.0 \times 10^{-5}$). For the 187 FL samples with available clinical data, the survival predictor score had a mean of −11.9 and a standard deviation of 0.9418, with each unit increase in the predictor score corresponding to a 2.5 fold increase in the relative risk of death. Data for all 191 samples is shown in Table 2385.

TABLE 2365

| Sample ID # | Set | B cell differentiation signature value | T-cell signature value | Macrophage signature value | Survival predictor score |
|---|---|---|---|---|---|
| FL_1073 | Training | 9.70 | 9.14 | 8.58 | −10.89 |
| FL_1074 | Training | 11.11 | 9.06 | 8.52 | −11.84 |
| FL_1075 | Validation | 11.23 | 8.92 | 8.75 | −11.15 |
| FL_1076 | Training | 10.02 | 9.21 | 8.59 | −11.25 |
| FL_1077 | Training | 9.94 | 9.77 | 8.44 | −12.82 |
| FL_1078 | Training | 10.67 | 9.32 | 8.21 | −12.76 |
| FL_1080 | Training | 10.62 | 9.44 | 8.88 | −11.64 |
| FL_1081 | Validation | 10.38 | 9.00 | 8.09 | −12.04 |
| FL_1083 | Training | 10.29 | 9.77 | 8.74 | −12.47 |
| FL_1085 | Validation | 9.87 | 9.24 | 8.43 | −11.55 |

TABLE 2365-continued

| Sample ID # | Set | B cell differ- entiation signature value | T-cell signature value | Macrophage signature value | Survival predictor score |
|---|---|---|---|---|---|
| FL_1086 | Validation | 10.03 | 9.50 | 9.02 | −11.06 |
| FL_1087 | Training | 9.83 | 9.98 | 9.37 | −11.31 |
| FL_1088 | Validation | 10.57 | 9.21 | 8.29 | −12.27 |
| FL_1089 | Training | 10.30 | 9.38 | 8.27 | −12.53 |
| FL_1090 | Validation | 9.74 | 9.24 | 8.20 | −11.93 |
| FL_1097 | Validation | 9.57 | 9.82 | 8.80 | −11.93 |
| FL_1098 | Validation | 11.08 | 9.40 | 8.97 | −11.69 |
| FL_1099 | Training | 10.23 | 9.70 | 9.12 | −11.46 |
| FL_1102 | Validation | 9.66 | 9.46 | 8.90 | −10.93 |
| FL_1104 | Training | 10.72 | 9.19 | 8.20 | −12.53 |
| FL_1106 | Validation | 11.11 | 9.17 | 9.57 | −9.96 |
| FL_1107 | Training | 9.70 | 9.42 | 9.55 | −9.54 |
| FL_1183 | Training | 9.85 | 9.25 | 8.44 | −11.54 |
| FL_1184 | Training | 10.12 | 9.57 | 8.86 | −11.63 |
| FL_1185 | Validation | 10.75 | 9.21 | 9.13 | −10.68 |
| FL_1186 | Training | 9.76 | 8.88 | 8.83 | −9.80 |
| FL_1416 | Validation | 9.94 | 9.45 | 8.59 | −11.77 |
| FL_1417 | Training | 10.12 | 8.53 | 8.43 | −10.08 |
| FL_1418 | Validation | 9.35 | 8.86 | 8.27 | −10.59 |
| FL_1419 | Training | 10.20 | 9.76 | 8.53 | −12.81 |
| FL_1422 | Training | 10.22 | 9.48 | 8.40 | −12.43 |
| FL_1425 | Validation | 9.61 | 8.89 | 8.58 | −10.23 |
| FL_1426 | Training | 10.80 | 9.06 | 8.13 | −12.41 |
| FL_1427 | Training | 10.27 | 8.56 | 8.13 | −10.87 |
| FL_1428 | Validation | 10.76 | 9.25 | 8.38 | −12.32 |
| FL_1432 | Training | 10.51 | 9.17 | 9.04 | −10.59 |
| FL_1436 | Training | 9.69 | 9.40 | 8.61 | −11.42 |
| FL_1440 | Training | 9.82 | 9.04 | 8.21 | −11.50 |
| FL_1445 | Training | 9.24 | 8.69 | 8.62 | −9.41 |
| FL_1450 | Validation | 9.70 | 9.88 | 10.37 | −8.93 |
| FL_1472 | Validation | 10.78 | 8.96 | 8.51 | −11.40 |
| FL_1473 | Training | 9.99 | 9.70 | 8.41 | −12.75 |
| FL_1474 | Validation | 10.21 | 9.27 | 9.05 | −10.59 |
| FL_1476 | Validation | 9.82 | 9.44 | 8.78 | −11.27 |
| FL_1477 | Training | 9.32 | 9.61 | 9.03 | −10.78 |
| FL_1478 | Training | 10.19 | 9.60 | 8.81 | −11.83 |
| FL_1479 | Training | 10.69 | 8.78 | 9.09 | −9.71 |
| FL_1480 | Training | 10.10 | 9.42 | 8.70 | −11.57 |
| FL_1579 | Training | 10.15 | 8.82 | 8.24 | −11.15 |
| FL_1580 | Training | 10.31 | 9.59 | 8.50 | −12.54 |
| FL_1581 | Training | 9.91 | 8.96 | 9.05 | −9.66 |
| FL_1582 | Validation | 9.73 | 8.31 | 8.06 | −10.03 |
| FL_1583 | Training | 10.95 | 9.45 | 8.86 | −11.95 |
| FL_1584 | Training | 9.98 | 9.38 | 8.46 | −11.89 |
| FL_1585 | Validation | 10.53 | 8.88 | 8.46 | −11.11 |
| FL_1586 | Validation | 10.00 | 9.30 | 8.42 | −11.81 |
| FL_1588 | Training | 9.59 | 9.41 | 8.94 | −10.68 |
| FL_1589 | Training | 10.29 | 9.68 | 8.73 | −12.27 |
| FL_1591 | Training | 10.44 | 9.45 | 8.56 | −12.18 |
| FL_1594 | Validation | 10.01 | 9.25 | 8.56 | −11.41 |
| FL_1595 | Training | 9.61 | 9.75 | 9.65 | −10.07 |
| FL_1598 | Validation | 11.18 | 8.80 | 8.31 | −11.71 |
| FL_1599 | Validation | 10.55 | 9.48 | 8.60 | −12.24 |
| FL_1603 | Training | 9.40 | 9.60 | 9.77 | −9.31 |
| FL_1604 | Training | 9.92 | 9.21 | 8.90 | −10.54 |
| FL_1606 | Validation | 9.87 | 9.45 | 9.17 | −10.52 |
| FL_1607 | Validation | 9.76 | 9.37 | 8.50 | −11.63 |
| FL_1608 | Validation | 9.92 | 8.90 | 8.39 | −10.85 |
| FL_1610 | Validation | 10.02 | 9.38 | 9.74 | −9.30 |
| FL_1611 | Validation | 10.18 | 9.41 | 8.69 | −11.64 |
| FL_1616 | Training | 9.62 | 9.33 | 8.85 | −10.71 |
| FL_1617 | Validation | 9.90 | 8.95 | 8.39 | −10.98 |
| FL_1619 | Validation | 9.98 | 9.37 | 8.47 | −11.85 |
| FL_1620 | Validation | 9.43 | 8.95 | 8.12 | −11.19 |
| FL_1622 | Training | 9.84 | 9.15 | 8.31 | −11.56 |
| FL_1623 | Training | 9.95 | 9.61 | 8.97 | −11.37 |
| FL_1624 | Validation | 10.55 | 9.06 | 8.43 | −11.61 |
| FL_1625 | Validation | 10.00 | 8.89 | 8.23 | −11.22 |
| FL_1626 | Validation | 11.05 | 8.62 | 8.10 | −11.62 |
| FL_1628 | Validation | 10.08 | 9.81 | 8.66 | −12.57 |
| FL_1637 | Validation | 9.77 | 9.95 | 9.59 | −10.76 |
| FL_1638 | Validation | 10.25 | 9.20 | 9.07 | −10.41 |
| FL_1639 | Training | 10.29 | 9.52 | 8.99 | −11.35 |
| FL_1643 | Training | 9.80 | 9.72 | 9.00 | −11.46 |
| FL_1644 | Validation | 9.51 | 9.46 | 8.61 | −11.43 |
| FL_1645 | Training | 9.39 | 9.46 | 8.70 | −11.15 |
| FL_1646 | Training | 9.90 | 9.25 | 8.52 | −11.42 |
| FL_1647 | Training | 9.51 | 9.12 | 8.95 | −9.92 |
| FL_1648 | Training | 10.02 | 9.18 | 7.86 | −12.67 |
| FL_1652 | Training | 9.62 | 9.39 | 9.19 | −10.16 |
| FL_1654 | Validation | 10.32 | 8.59 | 8.10 | −11.02 |
| FL_1655 | Training | 10.12 | 9.53 | 8.75 | −11.74 |
| FL_1656 | Validation | 10.54 | 9.08 | 8.55 | −11.42 |
| FL_1657 | Training | 10.53 | 9.53 | 8.55 | −12.46 |
| FL_1660 | Training | 10.24 | 8.75 | 8.27 | −10.99 |
| FL_1661 | Validation | 10.08 | 9.85 | 9.00 | −11.97 |
| FL_1662 | Validation | 9.85 | 9.56 | 9.49 | −10.11 |
| FL_1664 | Validation | 10.16 | 9.35 | 8.48 | −11.92 |
| FL_1669 | Training | 9.48 | 8.76 | 8.28 | −10.45 |
| FL_1670 | Training | 9.76 | 9.66 | 9.66 | −9.92 |
| FL_1675 | Training | 10.57 | 9.28 | 8.41 | −12.18 |
| FL_1681 | Validation | 10.48 | 9.52 | 8.66 | −12.19 |
| FL_1683 | Validation | 9.88 | 9.92 | 9.07 | −11.83 |
| FL_1684 | Training | 9.64 | 9.53 | 8.85 | −11.20 |
| FL_1716 | Validation | 9.90 | 8.91 | 8.22 | −11.23 |
| FL_1717 | Validation | 9.87 | 9.34 | 8.95 | −10.71 |
| FL_1718 | Training | 10.00 | 9.21 | 7.98 | −12.49 |
| FL_1719 | Validation | 9.87 | 9.06 | 8.42 | −11.14 |
| FL_1720 | Training | 10.70 | 8.77 | 8.92 | −10.05 |
| FL_1729 | Training | 10.50 | 9.23 | 8.65 | −11.53 |
| FL_1732 | Validation | 9.91 | 7.68 | 8.54 | −7.69 |
| FL_1761 | Validation | 9.81 | 9.22 | 8.39 | −11.54 |
| FL_1764 | Training | 9.81 | 9.24 | 8.77 | −10.80 |
| FL_1768 | Training | 10.12 | 9.36 | 8.50 | −11.86 |
| FL_1771 | Training | 9.92 | 9.12 | 8.68 | −10.79 |
| FL_1772 | Validation | 9.72 | 9.42 | 8.43 | −11.87 |
| FL_1788 | Training | 9.65 | 9.05 | 9.12 | −9.51 |
| FL_1790 | Training | 9.58 | 9.83 | 9.48 | −10.56 |
| FL_1792 | Validation | 9.79 | 9.29 | 8.67 | −11.11 |
| FL_1795 | Training | 9.58 | 10.18 | 9.33 | −11.69 |
| FL_1797 | Validation | 9.93 | 9.26 | 8.79 | −10.90 |
| FL_1799 | Training | 10.49 | 9.28 | 8.64 | −11.65 |
| FL_1810 | Validation | 10.06 | 8.55 | 8.21 | −10.52 |
| FL_1811 | Validation | 9.84 | 9.37 | 8.08 | −12.56 |
| FL_1825 | Training | 10.49 | 9.44 | 9.03 | −11.24 |
| FL_1827 | Training | 10.06 | 9.76 | 8.84 | −12.08 |
| FL_1828 | Validation | 10.55 | 8.93 | 7.67 | −12.87 |
| FL_1829 | Validation | 9.85 | 9.58 | 8.65 | −11.87 |
| FL_1830 | Validation | 10.80 | 8.99 | 8.67 | −11.15 |
| FL_1833 | Training | 10.41 | 9.83 | 8.82 | −12.52 |
| FL_1834 | Validation | 10.81 | 9.25 | 8.63 | −11.85 |
| FL_1835 | Validation | 9.36 | 9.25 | 8.91 | −10.21 |
| FL_1836 | Validation | 10.58 | 9.58 | 8.61 | −12.50 |
| FL_1837 | Validation | 10.22 | 9.47 | 8.76 | −11.68 |
| FL_1838 | Validation | 10.51 | 9.89 | 9.19 | −11.98 |
| FL_1839 | Training | 10.79 | 8.54 | 8.19 | −11.09 |
| FL_1841 | Training | 10.32 | 9.31 | 9.18 | −10.48 |
| FL_1842 | Validation | 10.36 | 9.69 | 8.92 | −11.95 |
| FL_1844 | Validation | 10.92 | 9.43 | 8.49 | −12.65 |
| FL_1845 | Training | 9.87 | 9.87 | 9.06 | −11.73 |
| FL_1846 | Validation | 9.66 | 9.81 | 9.93 | −9.63 |
| FL_1848 | Training | 9.82 | 9.74 | 8.70 | −12.14 |
| FL_1851 | Training | 9.89 | 9.47 | 9.03 | −10.87 |
| FL_1853 | Validation | 9.96 | 9.28 | 8.54 | −11.49 |
| FL_1854 | Validation | 9.97 | 9.29 | 8.73 | −11.12 |
| FL_1855 | Validation | 9.95 | 9.33 | 8.42 | −11.85 |
| FL_1857 | Validation | 10.35 | 9.81 | 9.28 | −11.50 |
| FL_1861 | Validation | 9.73 | 9.46 | 8.43 | −11.96 |
| FL_1862 | Validation | 10.42 | 8.94 | 8.22 | −11.69 |
| FL_1863 | Validation | 10.79 | 9.29 | 8.82 | −11.54 |
| FL_1864 | Training | 9.67 | 9.97 | 9.07 | −11.80 |
| FL_1866 | Training | 10.19 | 9.88 | 8.89 | −12.33 |
| FL_1870 | Validation | 9.78 | 10.07 | 9.30 | −11.63 |
| FL_1873 | Training | 10.09 | 9.41 | 8.77 | −11.40 |
| FL_1874 | Validation | 10.05 | 9.33 | 8.69 | −11.37 |
| FL_1876 | Validation | 10.15 | 9.59 | 8.67 | −12.08 |
| FL_1879 | Training | 9.73 | 9.21 | 8.58 | −11.06 |
| FL_1880 | Validation | 10.02 | 8.79 | 8.35 | −10.77 |

TABLE 2365-continued

| Sample ID # | Set | B cell differentiation signature value | T-cell signature value | Macrophage signature value | Survival predictor score |
|---|---|---|---|---|---|
| FL_1882 | Training | 9.59 | 9.44 | 8.80 | −11.05 |
| FL_1884 | Validation | 9.76 | 9.51 | 9.26 | −10.38 |
| FL_1885 | Validation | 10.48 | 9.66 | 8.75 | −12.32 |
| FL_1887 | Training | 9.98 | 9.42 | 8.47 | −11.96 |
| FL_1888 | Training | 9.73 | 9.83 | 8.99 | −11.67 |
| FL_1890 | Training | 10.06 | 9.33 | 8.98 | −10.76 |
| FL_1894 | Training | 9.85 | 8.99 | 8.75 | −10.29 |
| FL_1896 | Training | 10.21 | 9.80 | 8.51 | −12.94 |
| FL_1897 | Training | 10.67 | 8.99 | 8.26 | −11.90 |
| FL_1898 | Training | 9.59 | 8.77 | 8.21 | −10.68 |
| FL_1900 | Validation | 10.12 | 9.10 | 8.10 | −12.08 |
| FL_1903 | Validation | 11.08 | 8.99 | 8.39 | −11.93 |
| FL_1904 | Validation | 10.20 | 9.16 | 8.30 | −11.87 |
| FL_1905 | Validation | 9.73 | 9.21 | 8.22 | −11.80 |
| FL_1906 | Training | 9.95 | 8.15 | 8.44 | −9.01 |
| FL_1907 | Validation | 10.12 | 7.95 | 7.99 | −9.62 |
| FL_1910 | Training | 11.03 | 9.38 | 8.74 | −12.10 |
| FL_1912 | Validation | 9.83 | 9.38 | 9.36 | −9.95 |
| FL_1913 | Training | 9.81 | 9.75 | 8.43 | −12.69 |
| FL_1916 | Validation | 9.83 | 9.18 | 8.40 | −11.43 |
| FL_1918 | Validation | 9.86 | 9.52 | 8.79 | −11.45 |
| FL_1919 | Training | 9.87 | 9.53 | 8.79 | −11.48 |
| FL_735 | Validation | 10.48 | 8.73 | 8.23 | −11.20 |
| FL_738 | Validation | 11.05 | 9.10 | 8.75 | −11.43 |
| FL_739 | Training | 9.66 | 9.25 | 8.74 | −10.78 |
| FL_878 | Validation | 10.61 | 8.92 | 8.65 | −10.89 |
| FL_879 | Training | 9.92 | 8.94 | 8.78 | −10.14 |
| FL_886 | Validation | 10.16 | 9.41 | 8.63 | −11.73 |
| FL_888 | Validation | 9.35 | 8.76 | 8.38 | −10.15 |
| FL_1627 | Training | 9.82 | 9.48 | 8.49 | −11.94 |
| FL_1429 | Training | 10.06 | 8.70 | 8.14 | −11.01 |
| FL_1850 | Validation | 9.58 | 9.73 | 8.70 | −11.93 |
| FL_1735 | Validation | 9.60 | 7.46 | 8.42 | −7.19 |

In order to visualize the predictive power of the model, the FL samples were ranked according to their survival predictor scores and divided into four quartiles. Kaplan-Meier plots of overall survival showed clear differences in survival rate in the validation set (FIG. 8). The median survival for each of the four quartiles is set forth in Table 2366.

TABLE 2366

| Quartile | Median survival (yrs.) | 5-year survival | 10-year survival |
|---|---|---|---|
| 1 | NR | 94% | 79% |
| 2 | 11.6 | 82% | 62% |
| 3 | 8.8 | 69% | 39% |
| 4 | 3.9 | 38% | 22% |

Example 5: Development of a Third FL Survival Predictor Using Gene Expression Data from the Lymph Dx Microarray 191 FL samples were divided into two equivalent groups: a training set for developing the survival prediction model, and a validation set for evaluating the reproducibility of the model. Gene expression data from the Lymph Dx microarray was obtained for those genes listed in Table 2364, above. This gene expression data was used to calculate gene expression signature values for the macrophage, T-cell, and B-cell differentiation gene expression signatures, and these signature values were used to generate a survival predictor score using the following equation:

Survival predictor score=[1.51*(macrophage gene expression signature value)]−[2.11*(T-cell gene expression signature value)]−[0.505*(B-cell differentiation gene expression signature value)].

A higher survival predictor score was associated with worse outcome. For the 187 FL samples with available clinical data, the survival predictor score had a mean of −10.1 and a standard deviation 0.69, with each unit increase in the predictor score corresponding to a 2.7 fold increase in the relative risk of death. Data for all 191 samples is shown in Table 2367.

TABLE 2367

| Sample ID # | Set | B cell differentiation signature value | T-cell signature value | Macrophage signature value | Survival predictor score |
|---|---|---|---|---|---|
| FL_1073 | Training | 8.26 | 8.17 | 7.36 | −10.30 |
| FL_1074 | Training | 9.53 | 8.12 | 7.56 | −10.53 |
| FL_1075 | Validation | 9.81 | 8.00 | 7.99 | −9.77 |
| FL_1076 | Training | 8.46 | 8.10 | 7.62 | −9.86 |
| FL_1077 | Training | 8.45 | 8.66 | 7.32 | −11.49 |
| FL_1078 | Training | 9.23 | 8.32 | 7.32 | −11.18 |
| FL_1080 | Training | 9.18 | 8.37 | 7.86 | −10.42 |
| FL_1081 | Validation | 8.96 | 8.01 | 6.94 | −10.96 |
| FL_1083 | Training | 8.72 | 8.66 | 7.89 | −10.75 |
| FL_1085 | Validation | 8.34 | 8.17 | 7.54 | −10.07 |
| FL_1086 | Validation | 8.50 | 8.35 | 7.94 | −9.94 |
| FL_1087 | Training | 8.02 | 8.88 | 8.48 | −10.00 |
| FL_1088 | Validation | 9.10 | 8.15 | 7.38 | −10.65 |
| FL_1089 | Training | 8.76 | 8.31 | 7.35 | −10.86 |
| FL_1090 | Validation | 8.18 | 8.23 | 7.43 | −10.28 |
| FL_1097 | Validation | 8.07 | 8.81 | 7.90 | −10.73 |
| FL_1098 | Validation | 9.53 | 8.30 | 8.09 | −10.11 |
| FL_1099 | Training | 8.44 | 8.56 | 8.26 | −9.86 |
| FL_1102 | Validation | 7.92 | 8.43 | 7.94 | −9.80 |
| FL_1104 | Training | 9.17 | 8.07 | 7.21 | −10.78 |
| FL_1106 | Validation | 9.71 | 8.15 | 8.77 | −8.85 |
| FL_1107 | Training | 8.16 | 8.44 | 8.60 | −8.95 |
| FL_1183 | Training | 8.49 | 8.15 | 7.23 | −10.56 |
| FL_1184 | Training | 8.81 | 8.49 | 7.91 | −10.43 |
| FL_1185 | Validation | 9.31 | 8.19 | 8.06 | −9.80 |
| FL_1186 | Training | 8.43 | 7.87 | 7.83 | −9.04 |
| FL_1416 | Validation | 8.42 | 8.34 | 7.63 | −10.34 |
| FL_1417 | Training | 8.65 | 7.51 | 7.05 | −9.58 |
| FL_1418 | Validation | 7.96 | 7.82 | 7.22 | −9.62 |
| FL_1419 | Training | 8.80 | 8.71 | 7.55 | −11.43 |
| FL_1422 | Training | 8.63 | 8.35 | 7.39 | −10.83 |
| FL_1425 | Validation | 8.21 | 7.92 | 7.62 | −9.36 |
| FL_1426 | Training | 9.39 | 8.09 | 7.15 | −11.01 |
| FL_1427 | Training | 8.66 | 7.51 | 7.00 | −9.65 |
| FL_1428 | Validation | 9.33 | 8.18 | 7.39 | −10.81 |
| FL_1432 | Training | 8.98 | 8.17 | 7.93 | −9.81 |
| FL_1436 | Training | 8.04 | 8.17 | 7.35 | −10.20 |
| FL_1440 | Training | 8.29 | 7.82 | 7.15 | −9.89 |
| FL_1445 | Training | 8.04 | 7.78 | 7.63 | −8.94 |
| FL_1450 | Validation | 8.25 | 8.81 | 9.52 | −8.39 |
| FL_1472 | Training | 9.29 | 7.88 | 7.33 | −10.26 |
| FL_1473 | Training | 8.49 | 8.57 | 7.52 | −11.03 |
| FL_1474 | Validation | 8.59 | 8.09 | 8.53 | −8.54 |
| FL_1476 | Validation | 8.25 | 8.39 | 7.71 | −10.23 |
| FL_1477 | Training | 7.94 | 8.57 | 7.88 | −10.21 |
| FL_1478 | Training | 8.57 | 8.40 | 7.88 | −10.16 |
| FL_1479 | Training | 9.15 | 7.83 | 7.87 | −9.27 |
| FL_1480 | Training | 8.25 | 8.38 | 7.44 | −10.63 |
| FL_1579 | Training | 8.70 | 7.73 | 7.43 | −9.48 |
| FL_1580 | Training | 8.86 | 8.46 | 7.64 | −10.79 |
| FL_1581 | Training | 8.41 | 7.89 | 8.08 | −8.69 |
| FL_1582 | Validation | 8.20 | 7.42 | 6.99 | −9.24 |
| FL_1583 | Training | 9.34 | 8.34 | 7.94 | −10.32 |
| FL_1584 | Training | 8.50 | 8.33 | 7.75 | −10.17 |
| FL_1585 | Validation | 9.08 | 7.98 | 7.72 | −9.72 |
| FL_1586 | Validation | 8.52 | 8.25 | 7.36 | −10.61 |
| FL_1588 | Training | 7.97 | 8.35 | 7.73 | −9.98 |
| FL_1589 | Training | 8.85 | 8.48 | 7.76 | −10.66 |
| FL_1591 | Training | 8.92 | 8.36 | 7.77 | −10.42 |
| FL_1594 | Validation | 8.54 | 8.22 | 7.74 | −9.96 |
| FL_1595 | Training | 8.05 | 8.82 | 8.68 | −9.57 |
| FL_1598 | Validation | 9.74 | 7.81 | 6.97 | −10.88 |

TABLE 2367-continued

| Sample ID # | Set | B cell differentiation signature value | T-cell signature value | Macrophage signature value | Survival predictor score |
|---|---|---|---|---|---|
| FL_1599 | Validation | 9.13 | 8.42 | 7.69 | −10.77 |
| FL_1603 | Training | 7.97 | 8.66 | 8.90 | −8.86 |
| FL_1604 | Training | 8.47 | 8.14 | 7.75 | −9.75 |
| FL_1606 | Validation | 8.34 | 8.32 | 8.11 | −9.51 |
| FL_1607 | Validation | 8.33 | 8.30 | 7.39 | −10.57 |
| FL_1608 | Validation | 8.35 | 7.88 | 6.98 | −10.31 |
| FL_1610 | Validation | 8.48 | 8.35 | 8.86 | −8.52 |
| FL_1611 | Validation | 8.54 | 8.33 | 7.64 | −10.37 |
| FL_1616 | Training | 8.03 | 8.39 | 7.67 | −10.18 |
| FL_1617 | Validation | 8.30 | 7.85 | 7.52 | −9.40 |
| FL_1619 | Validation | 8.53 | 8.31 | 7.64 | −10.32 |
| FL_1620 | Validation | 8.09 | 7.99 | 7.17 | −10.11 |
| FL_1622 | Training | 8.14 | 8.10 | 7.36 | −10.09 |
| FL_1623 | Training | 8.45 | 8.52 | 8.15 | −9.93 |
| FL_1624 | Validation | 9.13 | 8.12 | 7.46 | −10.49 |
| FL_1625 | Validation | 8.53 | 7.94 | 7.17 | −10.23 |
| FL_1626 | Validation | 9.63 | 7.67 | 7.17 | −10.22 |
| FL_1628 | Validation | 8.63 | 8.76 | 7.95 | −10.86 |
| FL_1637 | Validation | 8.07 | 8.81 | 8.79 | −9.38 |
| FL_1638 | Validation | 8.52 | 8.18 | 8.19 | −9.18 |
| FL_1639 | Training | 8.70 | 8.33 | 7.89 | −10.06 |
| FL_1643 | Training | 8.26 | 8.62 | 8.01 | −10.26 |
| FL_1644 | Validation | 8.28 | 8.33 | 7.77 | −10.02 |
| FL_1645 | Training | 7.84 | 8.32 | 7.68 | −9.91 |
| FL_1646 | Training | 8.40 | 8.26 | 7.71 | −10.01 |
| FL_1647 | Training | 8.10 | 8.04 | 7.92 | −9.10 |
| FL_1648 | Training | 8.33 | 8.08 | 6.87 | −10.90 |
| FL_1652 | Training | 8.15 | 8.33 | 8.37 | −9.07 |
| FL_1654 | Validation | 8.67 | 7.62 | 7.03 | −9.85 |
| FL_1655 | Training | 8.53 | 8.41 | 7.75 | −10.36 |
| FL_1656 | Validation | 9.09 | 8.09 | 7.62 | −10.16 |
| FL_1657 | Training | 8.95 | 8.44 | 7.58 | −10.89 |
| FL_1660 | Training | 8.82 | 7.79 | 7.26 | −9.93 |
| FL_1661 | Validation | 8.56 | 8.79 | 8.17 | −10.53 |
| FL_1662 | Validation | 8.30 | 8.47 | 8.69 | −8.93 |
| FL_1664 | Validation | 8.62 | 8.23 | 7.56 | −10.31 |
| FL_1669 | Training | 7.89 | 7.67 | 7.39 | −9.02 |
| FL_1670 | Training | 8.01 | 8.54 | 8.64 | −9.03 |
| FL_1675 | Training | 9.00 | 8.21 | 7.36 | −10.76 |
| FL_1681 | Validation | 8.83 | 8.39 | 7.59 | −10.72 |
| FL_1683 | Validation | 8.14 | 8.85 | 7.97 | −10.74 |
| FL_1684 | Training | 7.99 | 8.42 | 7.84 | −9.97 |
| FL_1716 | Validation | 8.28 | 7.90 | 7.26 | −9.88 |
| FL_1717 | Validation | 8.27 | 8.21 | 7.89 | −9.60 |
| FL_1718 | Training | 8.50 | 8.17 | 7.15 | −10.75 |
| FL_1719 | Validation | 8.35 | 8.02 | 7.21 | −10.26 |
| FL_1720 | Training | 9.03 | 7.65 | 8.01 | −8.61 |
| FL_1729 | Training | 8.97 | 8.27 | 7.69 | −10.37 |
| FL_1732 | Validation | 8.49 | 6.82 | 7.71 | −7.02 |
| FL_1761 | Validation | 8.36 | 8.19 | 7.29 | −10.49 |
| FL_1764 | Training | 8.52 | 8.24 | 7.94 | −9.69 |
| FL_1768 | Training | 8.70 | 8.25 | 7.63 | −10.28 |
| FL_1771 | Training | 8.55 | 8.19 | 7.65 | −10.04 |
| FL_1772 | Validation | 8.30 | 8.38 | 7.41 | −10.71 |
| FL_1788 | Training | 8.14 | 8.06 | 8.11 | −8.87 |
| FL_1790 | Training | 7.95 | 8.69 | 8.36 | −9.74 |
| FL_1792 | Validation | 8.16 | 8.20 | 7.64 | −9.88 |
| FL_1795 | Training | 7.94 | 9.08 | 8.37 | −10.54 |
| FL_1797 | Validation | 8.17 | 8.21 | 7.87 | −9.57 |
| FL_1799 | Training | 9.02 | 8.21 | 7.77 | −10.14 |
| FL_1810 | Validation | 8.43 | 7.52 | 7.06 | −9.47 |
| FL_1811 | Validation | 8.33 | 8.24 | 7.07 | −10.93 |
| FL_1825 | Training | 8.90 | 8.39 | 7.97 | −10.18 |
| FL_1827 | Training | 8.47 | 8.77 | 7.96 | −10.76 |
| FL_1828 | Validation | 9.13 | 7.87 | 6.76 | −11.01 |
| FL_1829 | Validation | 8.34 | 8.51 | 7.59 | −10.71 |
| FL_1830 | Validation | 9.26 | 8.04 | 7.62 | −10.13 |
| FL_1833 | Training | 8.82 | 8.86 | 7.88 | −11.26 |
| FL_1834 | Validation | 9.25 | 8.17 | 7.62 | −10.39 |
| FL_1835 | Validation | 7.71 | 8.16 | 8.01 | −9.02 |
| FL_1836 | Validation | 9.06 | 8.52 | 7.59 | −11.09 |
| FL_1837 | Validation | 8.57 | 8.33 | 7.37 | −10.79 |
| FL_1838 | Validation | 8.78 | 8.72 | 8.04 | −10.69 |
| FL_1839 | Training | 9.27 | 7.36 | 7.37 | −9.08 |
| FL_1841 | Training | 8.66 | 8.35 | 8.17 | −9.64 |
| FL_1842 | Validation | 8.62 | 8.50 | 8.02 | −10.19 |
| FL_1844 | Validation | 9.37 | 8.40 | 7.47 | −11.18 |
| FL_1845 | Training | 8.33 | 8.84 | 8.30 | −10.32 |
| FL_1846 | Validation | 8.11 | 8.75 | 9.06 | −8.89 |
| FL_1848 | Training | 8.19 | 8.60 | 7.91 | −10.33 |
| FL_1851 | Training | 8.37 | 8.50 | 8.15 | −9.84 |
| FL_1853 | Validation | 8.37 | 8.14 | 7.43 | −10.19 |
| FL_1854 | Validation | 8.50 | 8.29 | 7.96 | −9.78 |
| FL_1855 | Validation | 8.63 | 8.34 | 7.54 | −10.58 |
| FL_1857 | Validation | 8.73 | 8.82 | 8.45 | −10.26 |
| FL_1861 | Validation | 8.21 | 8.50 | 7.50 | −10.77 |
| FL_1862 | Validation | 8.98 | 7.96 | 7.31 | −10.28 |
| FL_1863 | Validation | 9.30 | 8.22 | 7.86 | −10.18 |
| FL_1864 | Training | 8.13 | 8.93 | 8.27 | −10.46 |
| FL_1866 | Training | 8.62 | 8.78 | 7.91 | −10.93 |
| FL_1870 | Validation | 8.18 | 8.97 | 8.52 | −10.18 |
| FL_1873 | Training | 8.55 | 8.30 | 8.00 | −9.74 |
| FL_1874 | Training | 8.43 | 8.20 | 7.59 | −10.10 |
| FL_1876 | Validation | 8.48 | 8.52 | 7.70 | −10.64 |
| FL_1879 | Training | 8.29 | 8.21 | 7.66 | −9.94 |
| FL_1880 | Validation | 8.56 | 7.76 | 7.34 | −9.61 |
| FL_1882 | Training | 8.02 | 8.40 | 7.71 | −10.14 |
| FL_1884 | Validation | 8.14 | 8.46 | 8.42 | −9.24 |
| FL_1885 | Validation | 8.88 | 8.57 | 7.78 | −10.81 |
| FL_1887 | Training | 8.38 | 8.39 | 7.38 | −10.78 |
| FL_1888 | Training | 8.14 | 8.74 | 8.07 | −10.37 |
| FL_1890 | Training | 8.45 | 8.24 | 8.11 | −9.41 |
| FL_1894 | Training | 8.38 | 7.97 | 7.82 | −9.25 |
| FL_1896 | Training | 8.63 | 8.71 | 7.52 | −11.37 |
| FL_1897 | Training | 9.01 | 7.91 | 6.93 | −10.78 |
| FL_1898 | Training | 8.08 | 7.75 | 7.09 | −9.74 |
| FL_1900 | Validation | 8.61 | 7.94 | 6.84 | −10.77 |
| FL_1903 | Validation | 9.63 | 7.96 | 7.30 | −10.64 |
| FL_1904 | Validation | 8.79 | 8.14 | 7.15 | −10.82 |
| FL_1905 | Validation | 8.22 | 8.24 | 7.36 | −10.43 |
| FL_1906 | Training | 8.40 | 7.40 | 7.24 | −8.93 |
| FL_1907 | Validation | 8.61 | 7.11 | 6.59 | −9.40 |
| FL_1910 | Training | 9.47 | 8.28 | 7.63 | −10.73 |
| FL_1912 | Validation | 8.32 | 8.45 | 8.52 | −9.18 |
| FL_1913 | Training | 8.24 | 8.60 | 7.23 | −11.41 |
| FL_1916 | Validation | 8.31 | 8.04 | 7.27 | −10.19 |
| FL_1918 | Validation | 8.30 | 8.49 | 7.78 | −10.37 |
| FL_1919 | Training | 8.05 | 8.42 | 8.00 | −9.75 |
| FL_735 | Validation | 9.03 | 7.83 | 7.41 | −9.88 |
| FL_738 | Validation | 9.54 | 8.07 | 7.65 | −10.30 |
| FL_739 | Training | 8.14 | 8.09 | 7.69 | −9.57 |
| FL_878 | Validation | 9.17 | 7.91 | 7.70 | −9.69 |
| FL_879 | Training | 8.37 | 7.96 | 7.67 | −9.45 |
| FL_886 | Validation | 8.59 | 8.38 | 7.67 | −10.44 |
| FL_888 | Validation | 7.85 | 7.71 | 7.07 | −9.56 |
| FL_1627 | Training | 8.26 | 8.17 | 7.36 | −10.30 |
| FL_1429 | Training | 9.53 | 8.12 | 7.56 | −10.53 |
| FL_1850 | Validation | 9.81 | 8.00 | 7.99 | −9.77 |
| FL_1735 | Validation | 8.46 | 8.10 | 7.62 | −9.86 |

In order to visualize the predictive power of the model, the FL samples were ranked according to their survival predictor scores and divided into four quartiles. Kaplan-Meier plots of overall survival showed clear differences in survival rate in the validation set (FIG. 9).

Example 6: Development of a First DLBCL Survival Predictor Using Gene Expression Data from Affymetrix U133A and U133B Microarrays Gene expression data from Affymetrix U133A and U133B microarrays was obtained for 231 DLBCL samples. The follow-up time and status at follow-up for each of the subjects from whom these samples were acquired is listed in Table 2368. Table 2368 also indicates which samples were used in creating the survival predictor.

TABLE 2368

| Sample ID # | Length of follow-up (years) | Status at follow-up | Used in creating survival predictor? |
|---|---|---|---|
| ABC_1000 | 0.69 | Dead | Yes |
| ABC_1002 | 0.28 | Dead | Yes |
| ABC_1023 | 5.57 | Dead | Yes |
| ABC_1027 | 0.25 | Dead | Yes |
| ABC_1031 | 6.64 | Dead | Yes |
| ABC_1034 | 2.31 | Dead | Yes |
| ABC_1038 | 0.71 | Dead | Yes |
| ABC_1043 | 2.31 | Dead | Yes |
| ABC_1045 | 2.26 | Dead | Yes |
| ABC_1055 | 7.81 | Alive | Yes |
| ABC_1057 | 2.13 | Dead | Yes |
| ABC_1059 | 2.00 | Dead | Yes |
| ABC_1061 | 1.04 | Dead | Yes |
| ABC_1946 | 0.68 | Dead | No |
| ABC_1994 | 1.21 | Dead | No |
| ABC_2001 | 1.32 | Dead | No |
| ABC_304 | 1.31 | Dead | Yes |
| ABC_305 | 0.82 | Alive | Yes |
| ABC_309 | 2.80 | Alive | Yes |
| ABC_413 | 0.60 | Dead | Yes |
| ABC_428 | 11.38 | Alive | Yes |
| ABC_432 | 0.38 | Dead | Yes |
| ABC_446 | 2.82 | Dead | Yes |
| ABC_462 | 7.49 | Dead | Yes |
| ABC_477 | 1.70 | Dead | Yes |
| ABC_481 | 10.75 | Alive | Yes |
| ABC_482 | 7.72 | Alive | Yes |
| ABC_538 | 0.34 | Dead | Yes |
| ABC_541 | 4.11 | Alive | Yes |
| ABC_544 | 1.31 | Dead | Yes |
| ABC_547 | 0.05 | Dead | Yes |
| ABC_577 | 1.65 | Alive | Yes |
| ABC_616 | 0.99 | Dead | Yes |
| ABC_626 | 2.49 | Dead | Yes |
| ABC_633 | 2.02 | Alive | Yes |
| ABC_642 | 0.34 | Dead | Yes |
| ABC_644 | 0.31 | Dead | Yes |
| ABC_645 | 6.08 | Dead | Yes |
| ABC_646 | 2.59 | Dead | Yes |
| ABC_651 | 2.34 | Alive | Yes |
| ABC_652 | 0.01 | Dead | Yes |
| ABC_660 | 0.20 | Dead | Yes |
| ABC_663 | 0.62 | Dead | Yes |
| ABC_668 | 6.44 | Alive | Yes |
| ABC_676 | 1.00 | Dead | Yes |
| ABC_678 | 0.06 | Dead | Yes |
| ABC_687 | 0.94 | Dead | Yes |
| ABC_689 | 2.54 | Dead | Yes |
| ABC_692 | 10.53 | Alive | Yes |
| ABC_694 | 4.83 | Alive | Yes |
| ABC_700 | 5.40 | Dead | Yes |
| ABC_702 | 4.13 | Dead | Yes |
| ABC_704 | 9.67 | Alive | Yes |
| ABC_709 | 0.47 | Dead | Yes |
| ABC_712 | 3.26 | Dead | Yes |
| ABC_714 | 2.45 | Dead | Yes |
| ABC_717 | 0.42 | Dead | Yes |
| ABC_725 | 0.96 | Dead | Yes |
| ABC_726 | 7.62 | Alive | Yes |
| ABC_730 | 1.03 | Dead | Yes |
| ABC_753 | 0.04 | Dead | Yes |
| ABC_756 | 7.21 | Alive | Yes |
| ABC_771 | 6.80 | Dead | Yes |
| ABC_779 | 0.35 | Dead | Yes |
| ABC_800 | 0.33 | Dead | Yes |
| ABC_807 | 0.31 | Dead | Yes |
| ABC_809 | 0.51 | Dead | Yes |
| ABC_816 | 1.86 | Dead | Yes |
| ABC_820 | 1.59 | Dead | Yes |
| ABC_823 | 0.16 | Dead | Yes |
| ABC_835 | 1.22 | Dead | Yes |
| ABC_839 | 0.29 | Dead | Yes |
| ABC_841 | 10.14 | Alive | Yes |
| ABC_858 | 3.58 | Dead | Yes |
| ABC_872 | 5.00 | Alive | Yes |
| ABC_875 | 8.45 | Alive | Yes |
| ABC_912 | 16.79 | Alive | Yes |
| ABC_996 | 0.21 | Dead | Yes |
| GCB_1005 | 5.77 | Alive | Yes |
| GCB_1008 | 6.46 | Alive | Yes |
| GCB_1009 | 9.68 | Alive | Yes |
| GCB_1021 | 14.59 | Alive | Yes |
| GCB_1025 | 2.86 | Dead | Yes |
| GCB_1026 | 6.94 | Dead | Yes |
| GCB_1037 | 0.23 | Dead | Yes |
| GCB_1039 | 2.05 | Dead | Yes |
| GCB_1049 | 1.33 | Dead | Yes |
| GCB_1051 | 0.12 | Dead | Yes |
| GCB_1058 | 0.42 | Dead | Yes |
| GCB_1060 | 6.45 | Alive | Yes |
| GCB_1990 | 0.06 | Dead | No |
| GCB_1991 | 1.01 | Dead | No |
| GCB_2017 | 0.08 | Dead | No |
| GCB_2018 | 0.17 | Dead | No |
| GCB_2095 | 0.97 | Alive | No |
| GCB_412 | 12.12 | Alive | Yes |
| GCB_415 | 5.38 | Dead | Yes |
| GCB_421 | 1.24 | Dead | Yes |
| GCB_424 | 10.62 | Dead | Yes |
| GCB_433 | 0.76 | Dead | Yes |
| GCB_434 | 10.53 | Alive | Yes |
| GCB_438 | 8.15 | Alive | Yes |
| GCB_459 | 9.65 | Alive | Yes |
| GCB_470 | 11.17 | Alive | Yes |
| GCB_479 | 7.24 | Alive | Yes |
| GCB_492 | 11.29 | Alive | Yes |
| GCB_517 | 3.03 | Dead | Yes |
| GCB_523 | 8.36 | Alive | Yes |
| GCB_524 | 5.88 | Alive | Yes |
| GCB_529 | 1.06 | Dead | Yes |
| GCB_533 | 0.71 | Dead | Yes |
| GCB_537 | 4.99 | Dead | Yes |
| GCB_543 | 3.47 | Alive | Yes |
| GCB_545 | 1.10 | Dead | Yes |
| GCB_549 | 2.68 | Dead | Yes |
| GCB_550 | 21.78 | Alive | Yes |
| GCB_553 | 0.82 | Dead | Yes |
| GCB_565 | 9.11 | Dead | Yes |
| GCB_572 | 14.24 | Alive | Yes |
| GCB_617 | 5.88 | Alive | Yes |
| GCB_618 | 5.65 | Alive | Yes |
| GCB_619 | 8.76 | Alive | Yes |
| GCB_623 | 2.43 | Alive | Yes |
| GCB_627 | 1.27 | Dead | Yes |
| GCB_654 | 7.37 | Alive | Yes |
| GCB_661 | 0.56 | Alive | Yes |
| GCB_669 | 7.11 | Alive | Yes |
| GCB_672 | 6.78 | Alive | Yes |
| GCB_674 | 7.22 | Alive | Yes |
| GCB_675 | 6.02 | Alive | Yes |
| GCB_681 | 9.70 | Alive | Yes |
| GCB_688 | 0.33 | Dead | Yes |
| GCB_695 | 0.15 | Dead | Yes |
| GCB_698 | 3.88 | Alive | Yes |
| GCB_701 | 3.90 | Alive | Yes |
| GCB_710 | 1.08 | Dead | Yes |
| GCB_711 | 3.93 | Dead | Yes |
| GCB_722 | 3.32 | Alive | Yes |
| GCB_724 | 1.40 | Dead | Yes |
| GCB_731 | 10.18 | Alive | Yes |
| GCB_742 | 4.09 | Alive | Yes |
| GCB_744 | 8.86 | Alive | Yes |
| GCB_745 | 1.33 | Dead | Yes |
| GCB_747 | 15.41 | Alive | Yes |
| GCB_749 | 10.40 | Alive | Yes |
| GCB_758 | 1.10 | Dead | Yes |
| GCB_772 | 2.48 | Alive | Yes |
| GCB_777 | 4.27 | Dead | Yes |
| GCB_792 | 5.53 | Alive | Yes |
| GCB_795 | 3.43 | Alive | Yes |

TABLE 2368-continued

| Sample ID # | Length of follow-up (years) | Status at follow-up | Used in creating survival predictor? |
|---|---|---|---|
| GCB_797 | 6.87 | Dead | Yes |
| GCB_803 | 1.45 | Dead | Yes |
| GCB_810 | 11.72 | Alive | Yes |
| GCB_817 | 2.76 | Dead | Yes |
| GCB_818 | 0.10 | Dead | Yes |
| GCB_819 | 0.72 | Dead | Yes |
| GCB_821 | 9.47 | Alive | Yes |
| GCB_832 | 4.01 | Alive | Yes |
| GCB_836 | 4.29 | Alive | Yes |
| GCB_840 | 3.40 | Alive | Yes |
| GCB_847 | 4.16 | Alive | Yes |
| GCB_860 | 3.03 | Dead | Yes |
| GCB_871 | 0.41 | Dead | Yes |
| GCB_874 | 0.12 | Dead | Yes |
| GCB_995 | 6.65 | Alive | Yes |
| PMBL_1006 | 7.12 | Alive | Yes |
| PMBL_1024 | 19.83 | Alive | Yes |
| PMBL_1048 | 7.70 | Alive | Yes |
| PMBL_1053 | 1.04 | Dead | Yes |
| PMBL_1920 | 1.97 | Alive | No |
| PMBL_1921 | 4.16 | Alive | No |
| PMBL_1923 | 1.60 | Alive | No |
| PMBL_1924 | 6.11 | Alive | No |
| PMBL_1935 | 12.42 | Alive | No |
| PMBL_1941 | 0.71 | Alive | No |
| PMBL_1942 | 0.88 | Alive | No |
| PMBL_1943 | 8.96 | Alive | No |
| PMBL_1945 | 0.84 | Dead | No |
| PMBL_1948 | 7.96 | Alive | No |
| PMBL_1949 | 4.28 | Alive | No |
| PMBL_1989 | 1.33 | Dead | No |
| PMBL_1992 | 1.00 | Dead | No |
| PMBL_1993 | 1.33 | Dead | No |
| PMBL_2002 | 6.62 | Alive | No |
| PMBL_2019 | 0.99 | Dead | No |
| PMBL_2020 | 2.08 | Alive | No |
| PMBL_2092 | 1.27 | Alive | No |
| PMBL_484 | 1.40 | Dead | Yes |
| PMBL_546 | 0.78 | Dead | Yes |
| PMBL_570 | 14.40 | Alive | Yes |
| PMBL_621 | 8.14 | Alive | Yes |
| PMBL_638 | 0.70 | Dead | Yes |
| PMBL_691 | 0.32 | Dead | Yes |
| PMBL_791 | 1.33 | Dead | Yes |
| PMBL_824 | 12.24 | Alive | Yes |
| PMBL_906 | 16.80 | Alive | Yes |
| PMBL_994 | 4.79 | Alive | Yes |
| PMBL_998 | 9.11 | Alive | Yes |
| UC_DLBCL_1001 | 0.33 | Dead | Yes |
| UC_DLBCL_1004 | 6.72 | Alive | Yes |
| UC_DLBCL_1007 | 2.26 | Dead | Yes |
| UC_DLBCL_1018 | 0.03 | Dead | Yes |
| UC_DLBCL_1041 | 3.13 | Dead | Yes |
| UC_DLBCL_1054 | 12.34 | Alive | Yes |
| UC_DLBCL_306 | 2.69 | Alive | Yes |
| UC_DLBCL_310 | 0.97 | Alive | Yes |
| UC_DLBCL_449 | 9.16 | Alive | Yes |
| UC_DLBCL_452 | 9.17 | Alive | Yes |
| UC_DLBCL_458 | 1.18 | Dead | Yes |
| UC_DLBCL_460 | 9.02 | Alive | Yes |
| UC_DLBCL_491 | 4.47 | Dead | Yes |
| UC_DLBCL_528 | 1.64 | Alive | Yes |
| UC_DLBCL_615 | 4.94 | Alive | Yes |
| UC_DLBCL_625 | 5.24 | Alive | Yes |
| UC_DLBCL_664 | 0.62 | Dead | Yes |
| UC_DLBCL_671 | 3.35 | Alive | Yes |
| UC_DLBCL_682 | 0.11 | Dead | Yes |
| UC_DLBCL_683 | 7.42 | Alive | Yes |
| UC_DLBCL_684 | 1.92 | Dead | Yes |
| UC_DLBCL_748 | 1.01 | Dead | Yes |
| UC_DLBCL_751 | 9.99 | Alive | Yes |
| UC_DLBCL_808 | 0.37 | Dead | Yes |
| UC_DLBCL_831 | 11.02 | Dead | Yes |
| UC_DLBCL_834 | 1.64 | Dead | Yes |
| UC_DLBCL_838 | 0.00 | Dead | Yes |
| UC_DLBCL_851 | 0.05 | Dead | Yes |
| UC_DLBCL_854 | 1.51 | Dead | Yes |
| UC_DLBCL_855 | 1.67 | Alive | Yes |
| UC_DLBCL_856 | 0.60 | Dead | Yes |

The correlation between expression of each gene represented on the microarrays and survival was estimated using a Cox proportional hazards model. The results of this survival analysis are provided in the final two columns of Table 1723. The first of these two columns ("DLBCL_Cox_coefficient") provides a Cox coefficient indicating the extent to which a 2-fold increase in expression of a particular gene affects mortality. A positive Cox coefficient indicates increasing mortality with increasing expression of the gene, while a negative Cox coefficient indicates decreasing mortality with increasing expression of the gene. The second of these two columns ("DLBCL_Cox_P_value") provides a Cox p-value indicating the estimated probability that the increase or decrease in survival associated with the gene would occur by chance if there was no connection between the expression of the gene and survival.

Genes that were significantly correlated with survival (p<0.001) were grouped into gene expression signatures using a hierarchical clustering algorithm. The expression level of every component gene in each of these gene expression signatures was averaged for each sample to create a gene expression signature value. A step-up procedure (Drapner 1966) was applied to determine the optimal number of gene signatures to use in the survival predictor model. First, the gene expression signature that was most significantly associated with survival was included in the model. Next, the gene expression signature with the second highest association with survival was added to the model to form a two-component model. This procedure was repeated until there was no gene expression signature to add to the model with a p-value of <0.05.

The final prediction model incorporated gene expression signature values from three gene expression signatures. The first gene expression signature added to the model was termed "ABC DLBCL high," because it included genes that were more highly expressed in ABC than in GCB (Rosenwald 2002). The second gene expression signature added to the model was termed "lymph node," because it reflected the response of non-tumor cells in the lymph node to the malignant lymphoma cells. The final gene expression signature added to the model was termed "MHC class II," because it included all of the genes encoding the MHC class II alpha and beta chains. Table 2369 shows the genes that were averaged to form each of these signatures.

TABLE 2369

| Signature | UNIQID | Gene symbol | Survival p-value |
|---|---|---|---|
| ABC DLBCL high | 1134271 | POU5F1 | 3.09E−05 |
| ABC DLBCL high | 1121564 | DRIL1 | 4.06E−05 |
| ABC DLBCL high | 1119889 | PDCD4 | 7.28E−05 |
| ABC DLBCL high | 1133300 | CTH | 1.23E−04 |
| ABC DLBCL high | 1106030 | MGC:50789 | 1.70E−04 |
| ABC DLBCL high | 1139301 | FLJ20150 | 4.49E−04 |
| ABC DLBCL high | 1122131 | CHST7 | 5.18E−04 |
| ABC DLBCL high | 1114824 | LIMD1 | 5.20E−04 |
| ABC DLBCL high | 1100161 | LOC142678 | 6.24E−04 |
| ABC DLBCL high | 1120129 | TLE1 | 6.95E−04 |
| Lymph node | 1097126 | TEM8 | 5.14E−09 |
| Lymph node | 1120880 | LTBP2 | 9.80E−07 |

TABLE 2369-continued

| Signature | UNIQID | Gene symbol | Survival p-value |
|---|---|---|---|
| Lymph node | 1098898 | FLJ31056 | 1.09E−06 |
| Lymph node | 1123376 | RARRES2 | 1.68E−06 |
| Lymph node | 1128945 | SLC12A8 | 2.90E−06 |
| Lymph node | 1130994 | DPYSL3 | 3.37E−06 |
| Lymph node | 1124429 | SULF1 | 3.53E−06 |
| Lymph node | 1099358 | FLJ39971 | 4.09E−06 |
| Lymph node | 1130509 | SPARC | 6.23E−06 |
| Lymph node | 1095985 | TMEPAI | 7.07E−06 |
| Lymph node | 1123038 | ACTN1 | 7.90E−06 |
| Lymph node | 1133700 | CDH11 | 8.20E−06 |
| Lymph node | 1122101 | TFEC | 9.66E−06 |
| Lymph node | 1124296 | SDC2 | 9.99E−06 |
| MHC Class II | 1123127 | HLA-DRA | 1.21E−06 |
| MHC Class II | 1136777 | HLA-DQA1 | 3.45E−06 |
| MHC Class II | 1137771 | HLA-DRB1 | 3.95E−06 |
| MHC Class II | 1134281 | HLA-DRB4 | 2.70E−05 |
| MHC Class II | 1136573 | HLA-DPA1 | 2.92E−05 |
| MHC Class II | 1132710 | HLA-DRB3 | 7.09E−05 |

Fitting the Cox proportional hazards model to the three gene expression signature values resulted in the following model:

Survival predictor score=[0.586*(ABC DLBCL high gene expression signature value)]−[0.468* (lymph node gene expression signature value)]− [0.336*(MHC Class II gene expression signature value)].

A higher survival predictor score was associated with worse outcome. According to a likelihood ratio test adjusted for the number of variables included, this model was significant in predicting survival at $p=2.13\times10^{-10}$. In order to visualize the predictive power of the model, the 205 samples used to create the model were ranked according to their survival predictor scores and divided into four quartiles, Kaplan-Meier plots of overall survival probability show clear differences in survival rate between these four quartiles (FIG. 10). The five-year survival probabilities for each quartile are set forth in Table 2370.

TABLE 2370

| Quartile | 5-year survival |
|---|---|
| 1 | 83% |
| 2 | 59% |
| 3 | 33% |
| 4 | 17% |

Example 7: Development of a Second DLBCL Survival Predictor Using Gene Expression Data from the Lymph Dx Microarray A DLBCL survival model: based on gene expression had been developed previously using proliferation, germinal center B-cell, lymph node, and MHC class II gene expression signatures and the expression of the single gene BMP-6 (Rosenwald 2002). BMP-6 expression was poorly measured on the Lymph Dx microarray, but genes associated with each of these four gene expression signatures exhibited associations with survival similar to those observed using Lymphochip microarrays. DLBCL samples were divided into two groups: a training set (100 samples) for developing the survival prediction model, and a validation set (100 samples) for evaluating the reproducibility of the model. Gene expressed in the training set samples were clustered, and lymph node, germinal center B-cell, MHC class II, and proliferation gene expression signatures were identified. Within each signature, expression of genes that were associated with survival (p<0.01) was averaged to generate a gene expression signature value for each signature. Table 2371 lists the genes that were used to generate the gene expression signature value for each signature.

TABLE 2371

| Signature | UNIQID | Unigene ID Build 167 (http://www.ncbi.nlm.nih.gov/UniGene) | Gene symbol |
|---|---|---|---|
| Germinal center B-cell | 1099686 | 117721 | |
| Germinal center B-cell | 1099711 | 243596 | |
| Germinal center B-cell | 1103390 | 271752 | BPNT1 |
| Germinal center B-cell | 1106025 | 49500 | KIAA0746 |
| Germinal center B-cell | 1128287 | 300063 | ASB13 |
| Germinal center B-cell | 1132520 | 283063 | LMO2 |
| Germinal center B-cell | 1138192 | 126608 | NR3C1 |
| Germinal center B-cell | 1529318 | 291954 | |
| Germinal center B-cell | 1529344 | 317970 | SERPINA11 |
| Germinal center B-cell | 1529352 | 446195 | |
| Germinal center B-cell | 1096570 | 409813 | ANUBL1 |
| Germinal center B-cell | 1097897 | 266175 | PAG |
| Germinal center B-cell | 1097901 | 266175 | PAG |
| Germinal center B-cell | 1098611 | 433611 | PDK1 |
| Germinal center B-cell | 1100581 | 155024 | BCL6 |
| Germinal center B-cell | 1115034 | 387222 | NEK6 |
| Germinal center B-cell | 1120090 | 155024 | BCL6 |
| Germinal center B-cell | 1120946 | 25209 | MAPK10 |
| Germinal center B-cell | 1121248 | 54089 | BARD1 |
| Germinal center B-cell | 1123105 | 434281 | PTK2 |
| Germinal center B-cell | 1125456 | 300592 | MYBL1 |
| Germinal center B-cell | 1128694 | 171466 | ELL3 |
| Germinal center B-cell | 1128787 | 114611 | C7orf10 |
| Germinal center B-cell | 1132122 | 307734 | MME |
| Germinal center B-cell | 1136269 | 101474 | MAST2 |
| Germinal center B-cell | 1136702 | 155584 | KIAA0121 |
| Germinal center B-cell | 1139230 | 29724 | PLEKHF2 |
| Germinal center B-cell | 1529292 | NA | |
| Germinal center B-cell | 1529295 | 116441 | |
| Lymph node | 1097126 | 274520 | ANTXR1 |
| Lymph node | 1099028 | 334838 | FNDC1 |

TABLE 2371-continued

| Signature | UNIQID | Unigene ID Build 167 (http://www.ncbi.nlm.nih.gov/UniGene) | Gene symbol |
|---|---|---|---|
| Lymph node | 1099358 | 93135 | |
| Lymph node | 1101478 | 146246 | MGC45780 |
| Lymph node | 1103497 | 50115 | |
| Lymph node | 1121029 | 412999 | CSTA |
| Lymph node | 1124429 | 409602 | SULF1 |
| Lymph node | 1135068 | 71719 | PDLIM3 |
| Lymph node | 1136051 | 520937 | CSF2RA |
| Lymph node | 1136172 | 38084 | SULT1C1 |
| MHC class II | 1136777 | 387679 | HLA-DQA1 |
| MHC class II | 1136877 | 409934 | HLA-DQB1 |
| Proliferation | 1096903 | 437460 | FLJ10385 |
| Proliferation | 1120583 | 153768 | RNU3IP2 |
| Proliferation | 1123289 | 5409 | POLR1C |
| Proliferation | 1131808 | 75447 | RALBP1 |
| Proliferation | 1133102 | 360041 | FRDA |
| Proliferation | 1136595 | 404814 | VDAC1 |

Table 2372 lists p-values for the association of each signature with survival in the training set, the validation set, and overall.

TABLE 2372

| Signature | Training set | Validation set | Overall |
|---|---|---|---|
| Lymph node | $4.0 \times 10^{-5}$ | $2.3 \times 10^{-6}$ | $6.8 \times 10^{-10}$ |
| Proliferation | $8.1 \times 10^{-5}$ | $3.4 \times 10^{-3}$ | $2.1 \times 10^{-6}$ |
| Germinal center B-cell | $6.2 \times 10^{-6}$ | $2.1 \times 10^{-3}$ | $5.0 \times 10^{-8}$ |
| MHC class II | $2.4 \times 10^{-2}$ | $2.7 \times 10^{-3}$ | $3.1 \times 10^{-4}$ |

The four gene expression signatures were used to generate a survival predictor score using the following equation:

Survival predictor score=[−0.4337*(lymph node gene expression signature value)]+[0.09*(proliferation gene expression signature value)]−[0.4144*(germinal center B-cell gene expression signature value)]−[0.2006*(MHC class II gene expression signature value)].

A higher survival predictor score was associated with worse outcome. For the 200 DLBCL samples used to generate the model, the survival predictor score had a mean of 5.7 and a standard deviation of 0.78, with each unit increase in the predictor score corresponding to an approximately 2.7 fold increase in the relative risk of death. Data for all 200 samples is presented in Table 2373.

TABLE 2373

| Sample ID # | Set | Lymph node signature value | Proliferation signature value | Germinal center B-cell signature value | MHC class II signature value | Survival predictor score |
|---|---|---|---|---|---|---|
| ABC_1000 | Validation | 6.50 | 8.92 | 7.60 | 11.50 | −5.08 |
| ABC_1002 | Validation | 7.00 | 8.58 | 7.27 | 12.54 | −5.50 |
| ABC_1023 | Validation | 7.43 | 8.99 | 6.80 | 11.42 | −5.05 |
| ABC_1027 | Training | 5.68 | 9.00 | 6.87 | 12.31 | −4.70 |
| ABC_1031 | Validation | 8.02 | 9.00 | 7.17 | 11.68 | −5.53 |
| ABC_1034 | Validation | 6.06 | 9.61 | 6.72 | 11.83 | −4.58 |
| ABC_1038 | Training | 6.83 | 8.97 | 7.17 | 12.30 | −5.23 |
| ABC_1043 | Training | 6.96 | 9.01 | 6.77 | 12.29 | −5.11 |
| ABC_1045 | Validation | 8.18 | 8.21 | 6.77 | 12.07 | −5.66 |
| ABC_1055 | Validation | 5.58 | 9.16 | 7.30 | 13.05 | −4.76 |
| ABC_1057 | Training | 7.33 | 8.94 | 7.74 | 12.05 | −5.53 |
| ABC_1059 | Validation | 9.02 | 8.46 | 7.15 | 11.35 | −6.08 |
| ABC_1061 | Training | 7.13 | 9.18 | 7.09 | 12.28 | −5.21 |
| ABC_304 | Validation | 5.92 | 8.80 | 6.78 | 12.76 | −4.84 |
| ABC_305 | Training | 5.92 | 8.74 | 7.50 | 11.89 | −4.91 |
| ABC_309 | Validation | 8.86 | 8.39 | 7.62 | 12.53 | −6.46 |
| ABC_413 | Validation | 6.45 | 9.32 | 6.55 | 9.04 | −4.16 |
| ABC_428 | Training | 7.52 | 9.19 | 7.98 | 10.25 | −5.51 |
| ABC_432 | Validation | 6.48 | 9.33 | 7.45 | 9.56 | −4.56 |
| ABC_446 | Training | 7.91 | 9.42 | 7.41 | 10.55 | −5.46 |
| ABC_462 | Validation | 6.41 | 8.85 | 6.67 | 13.36 | −5.03 |
| ABC_477 | Validation | 6.26 | 9.02 | 6.69 | 12.45 | −4.89 |
| ABC_481 | Training | 8.18 | 8.30 | 7.35 | 11.98 | −5.91 |
| ABC_482 | Training | 8.59 | 9.01 | 7.66 | 12.35 | −6.16 |
| ABC_538 | Validation | 8.06 | 8.84 | 7.17 | 11.83 | −5.69 |
| ABC_541 | Training | 6.14 | 8.52 | 7.42 | 10.59 | −4.71 |
| ABC_544 | Training | 6.91 | 9.03 | 6.82 | 11.87 | −4.89 |
| ABC_547 | Validation | 5.80 | 8.96 | 7.14 | 11.38 | −4.60 |
| ABC_577 | Validation | 7.84 | 8.65 | 8.16 | 11.95 | −5.94 |
| ABC_616 | Validation | 6.03 | 9.05 | 7.36 | 12.64 | −4.84 |
| ABC_626 | Validation | 7.48 | 9.22 | 7.25 | 11.11 | −5.27 |

TABLE 2373-continued

| Sample ID # | Set | Lymph node signature value | Proliferation signature value | Germinal center B-cell signature value | MHC class II signature value | Survival predictor score |
|---|---|---|---|---|---|---|
| ABC_633 | Training | 7.74 | 8.35 | 7.39 | 12.45 | −5.80 |
| ABC_642 | Training | 5.71 | 8.82 | 6.41 | 13.80 | −4.62 |
| ABC_644 | Validation | 6.64 | 9.15 | 7.05 | 13.28 | −5.20 |
| ABC_645 | Training | 8.44 | 8.81 | 7.93 | 13.39 | −6.43 |
| ABC_646 | Validation | 5.94 | 9.11 | 6.71 | 11.60 | −4.63 |
| ABC_652 | Validation | 5.87 | 8.85 | 6.88 | 12.73 | −4.77 |
| ABC_660 | Training | 5.19 | 9.34 | 6.64 | 10.17 | −3.86 |
| ABC_663 | Training | 5.69 | 9.02 | 7.33 | 12.82 | −4.91 |
| ABC_668 | Validation | 7.12 | 9.28 | 7.03 | 10.57 | −4.91 |
| ABC_676 | Training | 4.95 | 8.90 | 7.09 | 13.32 | −4.61 |
| ABC_678 | Training | 5.84 | 9.11 | 7.34 | 11.26 | −4.41 |
| ABC_687 | Validation | 5.15 | 9.89 | 6.56 | 10.46 | −3.76 |
| ABC_689 | Training | 6.49 | 8.86 | 7.10 | 12.56 | −4.88 |
| ABC_692 | Validation | 7.32 | 8.96 | 7.25 | 11.57 | −5.32 |
| ABC_694 | Validation | 8.28 | 9.21 | 8.01 | 12.41 | −6.23 |
| ABC_700 | Training | 7.29 | 8.97 | 7.55 | 12.10 | −5.48 |
| ABC_702 | Validation | 7.60 | 8.66 | 6.86 | 12.55 | −5.45 |
| ABC_704 | Training | 7.07 | 8.92 | 7.03 | 12.83 | −5.35 |
| ABC_709 | Validation | 5.92 | 8.58 | 6.37 | 13.40 | −4.66 |
| ABC_712 | Validation | 5.79 | 9.12 | 6.34 | 12.02 | −4.23 |
| ABC_714 | Training | 7.49 | 8.88 | 7.49 | 11.97 | −5.54 |
| ABC_717 | Training | 7.17 | 9.45 | 7.01 | 11.34 | −5.05 |
| ABC_725 | Training | 6.71 | 9.01 | 6.52 | 12.76 | −4.86 |
| ABC_726 | Validation | 6.91 | 8.72 | 6.71 | 11.91 | −4.90 |
| ABC_730 | Validation | 6.28 | 9.22 | 7.28 | 12.14 | −4.88 |
| ABC_753 | Training | 8.84 | 9.64 | 7.05 | 13.00 | −5.22 |
| ABC_756 | Training | 7.67 | 8.45 | 7.59 | 12.48 | −5.85 |
| ABC_771 | Training | 6.98 | 8.76 | 6.91 | 12.20 | −5.18 |
| ABC_779 | Training | 6.73 | 9.32 | 6.78 | 9.82 | −4.44 |
| ABC_800 | Validation | 8.75 | 8.31 | 7.45 | 11.91 | −6.04 |
| ABC_807 | Training | 5.50 | 9.53 | 6.92 | 7.56 | −3.79 |
| ABC_809 | Training | 7.40 | 8.70 | 7.68 | 10.83 | −5.50 |
| ABC_816 | Training | 5.20 | 9.91 | 7.65 | 10.64 | −4.14 |
| ABC_820 | Training | 6.71 | 8.94 | 6.55 | 11.98 | −4.85 |
| ABC_823 | Validation | 5.58 | 9.26 | 6.44 | 10.09 | −3.97 |
| ABC_835 | Validation | 6.95 | 8.68 | 8.04 | 12.31 | −5.59 |
| ABC_839 | Training | 6.63 | 9.17 | 7.23 | 11.89 | −5.04 |
| ABC_841 | Validation | 6.35 | 9.51 | 7.52 | 13.19 | −5.28 |
| ABC_858 | Training | 7.63 | 8.51 | 7.12 | 11.74 | −5.42 |
| ABC_872 | Training | 6.78 | 8.73 | 7.41 | 12.47 | −5.44 |
| ABC_875 | Training | 7.59 | 8.81 | 7.20 | 11.26 | −5.25 |
| ABC_912 | Validation | 7.01 | 8.55 | 7.45 | 12.79 | −5.64 |
| ABC_996 | Validation | 5.00 | 9.53 | 6.70 | 10.02 | −3.94 |
| GCB_1005 | Validation | 8.28 | 8.67 | 9.11 | 13.27 | −6.98 |
| GCB_1008 | Training | 8.17 | 8.59 | 9.83 | 12.83 | −7.06 |
| GCB_1009 | Training | 6.63 | 9.02 | 10.07 | 12.28 | −6.19 |
| GCB_1021 | Validation | 6.44 | 8.83 | 9.34 | 13.20 | −6.15 |
| GCB_1025 | Validation | 7.87 | 8.48 | 9.27 | 12.37 | −6.57 |
| GCB_1026 | Training | 7.71 | 8.30 | 9.81 | 13.52 | −6.85 |
| GCB_1037 | Training | 4.95 | 8.83 | 9.35 | 12.57 | −5.22 |
| GCB_1039 | Training | 7.63 | 8.65 | 9.01 | 13.28 | −6.47 |
| GCB_1049 | Validation | 8.54 | 8.61 | 8.12 | 12.60 | −6.41 |
| GCB_1051 | Validation | 6.26 | 9.09 | 9.48 | 12.76 | −5.97 |
| GCB_1058 | Validation | 7.12 | 8.89 | 8.34 | 12.80 | −5.85 |
| GCB_1060 | Validation | 8.27 | 8.84 | 8.94 | 12.96 | −6.75 |
| GCB_412 | Training | 7.22 | 8.33 | 8.50 | 13.09 | −6.09 |
| GCB_415 | Training | 9.01 | 8.62 | 8.38 | 11.99 | −6.47 |
| GCB_421 | Training | 7.59 | 7.89 | 7.49 | 12.20 | −5.80 |
| GCB_424 | Training | 9.29 | 8.42 | 8.51 | 12.44 | −6.79 |
| GCB_433 | Training | 8.45 | 8.34 | 8.02 | 12.64 | −6.54 |
| GCB_434 | Training | 8.46 | 8.55 | 9.17 | 12.54 | −6.98 |
| GCB_438 | Validation | 8.14 | 8.71 | 9.13 | 12.51 | −6.67 |
| GCB_459 | Validation | 8.98 | 8.39 | 8.42 | 11.37 | −6.49 |
| GCB_470 | Validation | 7.72 | 8.57 | 8.67 | 12.23 | −6.12 |
| GCB_479 | Validation | 6.86 | 8.25 | 7.13 | 13.07 | −5.35 |
| GCB_492 | Training | 8.01 | 8.61 | 9.51 | 12.34 | −6.63 |
| GCB_517 | Validation | 8.57 | 8.73 | 7.99 | 12.76 | −6.48 |
| GCB_523 | Training | 5.96 | 8.56 | 8.74 | 12.77 | −5.72 |
| GCB_524 | Training | 8.51 | 8.09 | 8.76 | 12.51 | −6.57 |
| GCB_529 | Training | 5.12 | 9.17 | 8.88 | 10.77 | −4.86 |
| GCB_533 | Training | 8.88 | 8.81 | 8.36 | 12.44 | −6.60 |
| GCB_537 | Validation | 7.42 | 8.19 | 9.73 | 13.29 | −6.68 |
| GCB_543 | Validation | 8.49 | 8.02 | 8.66 | 12.08 | −6.45 |
| GCB_545 | Training | 8.65 | 8.28 | 6.90 | 12.90 | −6.13 |

TABLE 2373-continued

| Sample ID # | Set | Lymph node signature value | Proliferation signature value | Germinal center B-cell signature value | MHC class II signature value | Survival predictor score |
|---|---|---|---|---|---|---|
| GCB_549 | Validation | 6.87 | 8.24 | 8.65 | 12.15 | −6.00 |
| GCB_550 | Validation | 8.98 | 8.29 | 8.76 | 12.24 | −6.94 |
| GCB_553 | Validation | 8.51 | 8.64 | 8.62 | 12.63 | −6.69 |
| GCB_565 | Validation | 7.97 | 8.79 | 9.79 | 13.42 | −6.98 |
| GCB_572 | Training | 7.61 | 8.60 | 9.39 | 12.58 | −6.42 |
| GCB_617 | Validation | 8.31 | 7.89 | 7.54 | 13.17 | −6.12 |
| GCB_618 | Training | 5.66 | 8.97 | 9.20 | 13.32 | −5.54 |
| GCB_619 | Validation | 7.83 | 8.65 | 9.34 | 12.12 | −6.36 |
| GCB_623 | Training | 7.16 | 8.88 | 9.26 | 12.35 | −6.21 |
| GCB_627 | Validation | 8.13 | 8.83 | 8.62 | 11.85 | −6.31 |
| GCB_654 | Training | 6.30 | 9.60 | 8.45 | 10.00 | −4.88 |
| GCB_661 | Validation | 8.46 | 8.51 | 8.18 | 12.66 | −6.33 |
| GCB_669 | Training | 7.88 | 8.65 | 8.59 | 12.32 | −6.19 |
| GCB_672 | Training | 8.29 | 8.61 | 8.14 | 12.41 | −6.21 |
| GCB_674 | Validation | 8.36 | 8.62 | 7.76 | 12.33 | −6.14 |
| GCB_675 | Validation | 6.01 | 9.52 | 8.90 | 10.12 | −5.09 |
| GCB_681 | Training | 9.25 | 8.72 | 8.72 | 12.59 | −6.89 |
| GCB_688 | Validation | 6.97 | 9.01 | 9.90 | 9.94 | −5.99 |
| GCB_695 | Validation | 8.80 | 8.73 | 9.23 | 12.45 | −6.84 |
| GCB_698 | Validation | 9.27 | 8.35 | 8.85 | 11.99 | −6.96 |
| GCB_701 | Training | 7.77 | 7.93 | 8.68 | 13.10 | −6.33 |
| GCB_710 | Validation | 6.12 | 8.78 | 7.65 | 13.19 | −5.24 |
| GCB_711 | Training | 7.57 | 8.80 | 8.43 | 11.44 | −5.84 |
| GCB_722 | Training | 7.78 | 8.31 | 8.93 | 12.61 | −6.51 |
| GCB_724 | Training | 7.88 | 9.08 | 8.74 | 11.53 | −6.21 |
| GCB_731 | Validation | 7.72 | 8.92 | 9.08 | 12.20 | −6.46 |
| GCB_742 | Validation | 8.33 | 8.55 | 8.58 | 12.95 | −6.70 |
| GCB_744 | Training | 8.02 | 8.64 | 9.36 | 11.85 | −6.52 |
| GCB_745 | Training | 8.47 | 8.34 | 8.93 | 11.95 | −6.67 |
| GCB_747 | Validation | 7.64 | 8.48 | 8.32 | 13.06 | −6.27 |
| GCB_749 | Training | 7.57 | 8.61 | 9.40 | 12.55 | −6.56 |
| GCB_758 | Validation | 5.66 | 8.77 | 7.89 | 12.51 | −4.63 |
| GCB_772 | Validation | 8.52 | 7.81 | 7.95 | 12.25 | −6.34 |
| GCB_777 | Validation | 7.52 | 8.65 | 8.57 | 11.69 | −6.10 |
| GCB_792 | Training | 8.14 | 8.64 | 9.21 | 12.08 | −6.65 |
| GCB_795 | Validation | 9.19 | 8.17 | 8.81 | 11.60 | −6.92 |
| GCB_797 | Validation | 7.50 | 8.62 | 8.08 | 12.84 | −6.09 |
| GCB_803 | Validation | 6.19 | 8.65 | 9.49 | 13.18 | −6.11 |
| GCB_810 | Training | 8.46 | 8.32 | 8.10 | 13.13 | −6.50 |
| GCB_817 | Training | 6.93 | 8.51 | 9.49 | 11.09 | −6.04 |
| GCB_818 | Training | 7.18 | 8.96 | 8.08 | 12.23 | −5.76 |
| GCB_819 | Validation | 7.16 | 8.97 | 8.06 | 13.22 | −5.79 |
| GCB_821 | Validation | 8.13 | 8.59 | 8.90 | 12.41 | −6.61 |
| GCB_832 | Training | 7.83 | 8.35 | 8.71 | 12.47 | −6.37 |
| GCB_836 | Validation | 7.84 | 8.99 | 8.50 | 11.46 | −5.85 |
| GCB_840 | Training | 8.24 | 7.75 | 7.40 | 11.74 | −5.77 |
| GCB_847 | Training | 7.82 | 8.17 | 8.97 | 12.55 | −6.51 |
| GCB_860 | Training | 7.12 | 8.39 | 9.34 | 11.54 | −6.10 |
| GCB_871 | Training | 5.59 | 9.60 | 7.28 | 11.16 | −4.23 |
| GCB_874 | Training | 8.53 | 9.14 | 8.95 | 11.65 | −6.47 |
| GCB_995 | Validation | 6.98 | 8.68 | 8.54 | 12.22 | −5.76 |
| PMBL_1006 | Validation | 7.34 | 8.51 | 7.66 | 10.94 | −5.33 |
| PMBL_1024 | Validation | 7.62 | 8.48 | 8.56 | 10.89 | −5.96 |
| PMBL_1048 | Validation | 8.68 | 8.16 | 7.23 | 12.18 | −6.08 |
| PMBL_1053 | Training | 7.02 | 8.28 | 8.24 | 11.12 | −5.31 |
| PMBL_484 | Training | 7.15 | 8.45 | 7.01 | 13.62 | −5.41 |
| PMBL_546 | Validation | 8.19 | 7.88 | 7.66 | 11.73 | −6.06 |
| PMBL_570 | Training | 9.34 | 8.21 | 8.48 | 12.70 | −6.86 |
| PMBL_621 | Training | 8.08 | 8.60 | 9.14 | 12.96 | −6.72 |
| PMBL_638 | Training | 7.56 | 8.26 | 8.00 | 11.37 | −5.75 |
| PMBL_691 | Validation | 6.48 | 8.92 | 8.40 | 10.17 | −5.04 |
| PMBL_791 | Validation | 7.72 | 8.65 | 8.94 | 11.56 | −6.16 |
| PMBL_824 | Validation | 8.06 | 8.01 | 7.76 | 13.28 | −6.11 |
| PMBL_994 | Training | 9.15 | 8.36 | 7.46 | 12.43 | −6.29 |
| PMBL_998 | Training | 6.70 | 8.35 | 9.24 | 13.19 | −6.20 |
| UC_DLBCL_1001 | Validation | 6.74 | 8.43 | 7.10 | 12.76 | −5.31 |
| UC_DLBCL_1004 | Validation | 7.54 | 8.75 | 8.01 | 13.09 | −6.10 |
| UC_DLBCL_1007 | Training | 9.97 | 8.44 | 7.64 | 12.97 | −6.85 |
| UC_DLBCL_1018 | Training | 6.42 | 8.38 | 6.97 | 12.71 | −5.03 |
| UC_DLBCL_1041 | Validation | 5.76 | 8.69 | 6.78 | 13.36 | −4.71 |
| UC_DLBCL_1054 | Training | 8.92 | 8.65 | 8.51 | 11.48 | −6.59 |
| UC_DLBCL_306 | Validation | 7.85 | 8.90 | 8.31 | 12.36 | −6.23 |
| UC_DLBCL_310 | Training | 8.14 | 8.80 | 7.63 | 12.27 | −6.03 |
| UC_DLBCL_449 | Validation | 9.03 | 8.48 | 7.07 | 12.17 | −6.01 |

TABLE 2373-continued

| Sample ID # | Set | Lymph node signature value | Proliferation signature value | Germinal center B-cell signature value | MHC class II signature value | Survival predictor score |
|---|---|---|---|---|---|---|
| UC_DLBCL_458 | Training | 5.92 | 8.53 | 8.28 | 9.60 | −4.96 |
| UC_DLBCL_460 | Validation | 7.92 | 9.08 | 8.30 | 12.29 | −6.13 |
| UC_DLBCL_491 | Training | 7.65 | 8.33 | 7.35 | 12.39 | −5.53 |
| UC_DLBCL_528 | Validation | 6.99 | 8.56 | 7.36 | 11.63 | −5.35 |
| UC_DLBCL_615 | Validation | 7.11 | 8.32 | 8.77 | 12.80 | −6.10 |
| UC_DLBCL_625 | Training | 8.93 | 7.78 | 7.85 | 12.62 | −6.46 |
| UC_DLBCL_664 | Training | 7.62 | 8.15 | 8.17 | 12.72 | −6.04 |
| UC_DLBCL_671 | Training | 8.09 | 8.48 | 7.61 | 11.53 | −5.78 |
| UC_DLBCL_682 | Training | 7.38 | 8.35 | 7.14 | 12.33 | −5.43 |
| UC_DLBCL_683 | Training | 7.91 | 8.36 | 7.78 | 12.57 | −6.02 |
| UC_DLBCL_684 | Validation | 8.06 | 8.63 | 8.29 | 12.76 | −6.29 |
| UC_DLBCL_748 | Validation | 5.38 | 8.57 | 7.45 | 9.55 | −4.23 |
| UC_DLBCL_751 | Training | 6.33 | 8.65 | 8.88 | 13.14 | −5.74 |
| UC_DLBCL_808 | Training | 7.42 | 9.01 | 7.44 | 13.09 | −5.63 |
| UC_DLBCL_831 | Validation | 8.33 | 8.30 | 7.46 | 11.58 | −5.84 |
| UC_DLBCL_834 | Training | 6.98 | 9.09 | 8.61 | 11.77 | −5.66 |
| UC_DLBCL_838 | Validation | 7.25 | 8.40 | 7.23 | 12.56 | −5.36 |
| UC_DLBCL_851 | Validation | 6.28 | 9.05 | 6.78 | 8.19 | −4.10 |
| UC_DLBCL_854 | Validation | 7.36 | 8.50 | 7.39 | 12.59 | −5.53 |
| UC_DLBCL_855 | Training | 8.31 | 7.94 | 7.49 | 12.08 | −6.07 |
| UC_DLBCL_856 | Validation | 5.65 | 9.01 | 8.52 | 9.32 | −4.68 |

In order to visualize the predictive power of the model, the 200 samples were ranked according to their survival predictor scores and divided into four quartiles. Kaplan-Meier plots of overall survival probability show clear differences in survival rate between these four quartiles (FIG. 11).

Example 8: Development of a Third DLBCL Survival Predictor Using Gene Expression Data from the Lymph Dx Microarray The number of genes used to generate the DLBCL survival predictor in Example 7 was reduced in order to create a survival predictor compatible with RT-PCR. The list of genes from the lymph node and germinal center B-cell gene expression signatures was narrowed to those three genes from each signature that were most closely correlated with the lymph node and germinal center B-cell gene expression signature values, respectively. The genes from the proliferation gene expression signature did not add significantly to the reduced gene survival prediction model, so they were removed entirely. The expression of genes within each signature was averaged on the logs scale to generate a gene expression signature value for each signature. Table 2374 lists the genes that were used to generate these gene expression signature values.

Table 2376 lists p-values for association of each signature with survival in the training set, the validation set, and overall.

TABLE 2375

| Signature | Training set | Validation set | Overall |
|---|---|---|---|
| Lymph node | $6.1 \times 10^{-6}$ | 0.0021 | $2.1 \times 10^{-17}$ |
| Germinal center B-cell | $3.5 \times 10^{-4}$ | 0.0099 | $2.7 \times 10^{-5}$ |
| MHC class II | 0.024 | 0.0026 | 0.00031 |

The three gene expression signatures were used to generate a survival predictor score using the following equation:

Survival predictor score=[−0.32*(lymph node gene expression signature value)]−[0.176*(germinal center B-cell gene expression signature value)]−[0.206*(MHC class II gene expression signature value)].

A higher survival predictor score was associated with worse outcome. For the 200 DLBCL samples used to generate the model, the survival predictor score had a mean of 6.54 and a standard deviation of 0.69, with each unit increase in the predictor score corresponding to an approximately 2.7 fold increase in the relative risk of death. Data for all 200 samples is presented in Table 2376.

TABLE 2374

| Signature | UNIQID | Unigene ID Build 167 http://www.ncbi.nlm.nih.gov/UniGene | Gene symbol |
|---|---|---|---|
| Germinal center B-cell | 1099686 | 117721 | |
| Germinal center B-cell | 1529318 | 291954 | |
| Germinal center B-cell | 1529344 | 317970 | SERPINA11 |
| Lymph node | 1097126 | 274520 | ANTXR1 |
| Lymph node | 1099358 | 93135 | |
| Lymph node | 1121029 | 412999 | CSTA |
| MHC class II | 1136777 | 387679 | HLA-DQA1 |
| MHC class II | 1136877 | 409934 | HLA-DQB1 |

TABLE 2376

| Sample ID # | Set | Lymph node signature value | Germinal center B-cell signature value | MHC class II signature value | Survival predictor score |
|---|---|---|---|---|---|
| ABC_1000 | Validation | 8.08 | 5.68 | 11.50 | −5.96 |
| ABC_1002 | Validation | 8.32 | 6.06 | 12.54 | −6.31 |
| ABC_1023 | Validation | 9.36 | 4.74 | 11.42 | −6.18 |
| ABC_1027 | Training | 7.41 | 4.90 | 12.31 | −5.77 |
| ABC_1031 | Validation | 9.40 | 5.23 | 11.68 | −6.33 |
| ABC_1034 | Validation | 7.47 | 4.92 | 11.83 | −5.69 |
| ABC_1038 | Training | 7.89 | 5.84 | 12.30 | −6.09 |
| ABC_1043 | Training | 7.84 | 4.66 | 12.29 | −5.86 |
| ABC_1045 | Validation | 9.31 | 4.66 | 12.07 | −6.29 |
| ABC_1055 | Validation | 6.46 | 6.38 | 13.05 | −5.88 |
| ABC_1057 | Training | 9.13 | 7.93 | 12.05 | −6.80 |
| ABC_1059 | Validation | 10.93 | 4.82 | 11.35 | −6.68 |
| ABC_1061 | Training | 8.18 | 5.04 | 12.28 | −6.04 |
| ABC_304 | Validation | 7.31 | 6.47 | 12.76 | −6.10 |
| ABC_305 | Training | 7.02 | 6.60 | 11.89 | −5.86 |
| ABC_309 | Validation | 10.47 | 7.00 | 12.53 | −7.16 |
| ABC_413 | Validation | 7.99 | 4.80 | 9.04 | −5.26 |
| ABC_428 | Training | 9.43 | 7.59 | 10.25 | −6.47 |
| ABC_432 | Validation | 7.29 | 8.16 | 9.56 | −5.74 |
| ABC_446 | Training | 9.49 | 5.46 | 10.55 | −6.17 |
| ABC_462 | Validation | 7.72 | 4.97 | 13.36 | −6.10 |
| ABC_477 | Validation | 7.16 | 3.69 | 12.45 | −5.51 |
| ABC_481 | Training | 9.75 | 6.89 | 11.98 | −6.80 |
| ABC_482 | Training | 10.51 | 7.64 | 12.35 | −7.25 |
| ABC_538 | Validation | 8.79 | 5.00 | 11.83 | −6.13 |
| ABC_541 | Training | 7.70 | 5.80 | 10.59 | −5.67 |
| ABC_544 | Training | 8.90 | 3.98 | 11.87 | −5.99 |
| ABC_547 | Validation | 7.05 | 5.18 | 11.38 | −5.51 |
| ABC_577 | Validation | 9.93 | 8.05 | 11.95 | −7.06 |
| ABC_616 | Validation | 7.34 | 4.54 | 12.64 | −5.75 |
| ABC_626 | Validation | 8.78 | 6.77 | 11.11 | −6.29 |
| ABC_633 | Training | 9.63 | 5.02 | 12.45 | −6.53 |
| ABC_642 | Training | 7.31 | 4.95 | 13.80 | −6.05 |
| ABC_644 | Validation | 7.72 | 5.35 | 13.28 | −6.15 |
| ABC_645 | Training | 9.77 | 6.21 | 13.39 | −6.98 |
| ABC_646 | Validation | 7.39 | 3.75 | 11.60 | −5.41 |
| ABC_652 | Validation | 7.51 | 4.53 | 12.73 | −5.82 |
| ABC_660 | Training | 5.85 | 3.55 | 10.17 | −4.59 |
| ABC_663 | Training | 7.04 | 5.06 | 12.82 | −5.78 |
| ABC_668 | Validation | 8.00 | 5.65 | 10.57 | −5.73 |
| ABC_676 | Training | 6.53 | 4.29 | 13.32 | −5.59 |
| ABC_678 | Training | 6.87 | 7.48 | 11.26 | −5.83 |
| ABC_687 | Validation | 6.39 | 3.78 | 10.46 | −4.87 |
| ABC_689 | Training | 8.29 | 5.07 | 12.56 | −6.13 |
| ABC_692 | Validation | 8.10 | 5.26 | 11.57 | −5.90 |
| ABC_694 | Validation | 9.67 | 8.15 | 12.41 | −7.09 |
| ABC_700 | Training | 8.37 | 6.75 | 12.10 | −6.36 |
| ABC_702 | Validation | 8.44 | 4.59 | 12.55 | −6.09 |
| ABC_704 | Training | 8.51 | 4.34 | 12.83 | −6.13 |
| ABC_709 | Validation | 7.47 | 4.54 | 13.40 | −5.95 |
| ABC_712 | Validation | 7.12 | 3.99 | 12.02 | −5.46 |
| ABC_714 | Training | 9.57 | 7.03 | 11.97 | −6.77 |
| ABC_717 | Training | 8.33 | 5.54 | 11.34 | −5.98 |
| ABC_725 | Training | 8.04 | 4.40 | 12.76 | −5.97 |
| ABC_726 | Validation | 7.79 | 4.18 | 11.91 | −5.68 |
| ABC_730 | Validation | 8.13 | 7.36 | 12.14 | −6.40 |
| ABC_753 | Training | 9.24 | 6.60 | 13.00 | −6.80 |
| ABC_756 | Training | 9.51 | 5.21 | 12.48 | −6.53 |
| ABC_771 | Training | 8.08 | 4.74 | 12.20 | −5.93 |
| ABC_779 | Training | 8.11 | 4.09 | 9.82 | −5.34 |
| ABC_800 | Validation | 10.34 | 4.83 | 11.91 | −6.61 |
| ABC_807 | Training | 6.58 | 4.44 | 7.56 | −4.44 |
| ABC_809 | Training | 9.29 | 5.72 | 10.83 | −6.21 |
| ABC_816 | Training | 6.36 | 6.36 | 10.64 | −5.35 |
| ABC_820 | Training | 8.10 | 4.79 | 11.98 | −5.90 |
| ABC_823 | Validation | 6.63 | 4.85 | 10.09 | −5.05 |
| ABC_835 | Validation | 9.17 | 7.78 | 12.31 | −6.84 |
| ABC_839 | Training | 8.06 | 4.97 | 11.89 | −5.90 |
| ABC_841 | Validation | 8.05 | 6.24 | 13.19 | −6.39 |
| ABC_858 | Training | 9.02 | 4.86 | 11.74 | −6.16 |
| ABC_872 | Training | 8.67 | 5.85 | 12.47 | −6.37 |
| ABC_875 | Training | 9.60 | 5.59 | 11.26 | −6.37 |
| ABC_912 | Validation | 7.99 | 7.74 | 12.79 | −6.56 |
| ABC_996 | Validation | 6.89 | 6.23 | 10.02 | −5.36 |
| GCB_1005 | Validation | 9.02 | 9.56 | 13.27 | −7.30 |
| GCB_1008 | Training | 9.27 | 10.49 | 12.83 | −7.46 |
| GCB_1009 | Training | 7.80 | 10.09 | 12.28 | −6.80 |
| GCB_1021 | Validation | 8.73 | 9.20 | 13.20 | −7.13 |
| GCB_1025 | Validation | 9.94 | 9.97 | 12.37 | −7.49 |
| GCB_1026 | Training | 9.54 | 10.20 | 13.52 | −7.63 |
| GCB_1037 | Training | 6.34 | 8.79 | 12.57 | −6.17 |
| GCB_1039 | Training | 8.71 | 9.94 | 13.28 | −7.27 |
| GCB_1049 | Validation | 10.53 | 8.18 | 12.60 | −7.41 |
| GCB_1051 | Validation | 7.63 | 10.18 | 12.76 | −6.86 |
| GCB_1058 | Validation | 8.61 | 9.04 | 12.80 | −6.98 |
| GCB_1060 | Validation | 10.23 | 9.38 | 12.96 | −7.59 |
| GCB_412 | Training | 8.79 | 7.92 | 13.09 | −6.90 |
| GCB_415 | Training | 10.72 | 8.57 | 11.99 | −7.41 |
| GCB_421 | Training | 9.23 | 5.26 | 12.20 | −6.39 |
| GCB_424 | Training | 11.14 | 8.46 | 12.44 | −7.62 |
| GCB_433 | Training | 9.26 | 8.52 | 12.64 | −7.07 |
| GCB_434 | Training | 9.73 | 10.13 | 12.54 | −7.48 |
| GCB_438 | Validation | 9.60 | 9.99 | 12.51 | −7.41 |
| GCB_459 | Validation | 10.51 | 7.75 | 11.37 | −7.07 |
| GCB_470 | Validation | 9.56 | 6.63 | 12.23 | −6.74 |
| GCB_479 | Validation | 7.77 | 4.71 | 13.07 | −6.01 |
| GCB_492 | Training | 8.82 | 9.52 | 12.34 | −7.04 |
| GCB_517 | Validation | 9.92 | 6.96 | 12.76 | −7.03 |
| GCB_523 | Training | 6.59 | 9.17 | 12.77 | −6.35 |
| GCB_524 | Training | 10.00 | 7.83 | 12.51 | −7.16 |
| GCB_529 | Training | 5.61 | 7.93 | 10.77 | −5.41 |
| GCB_533 | Training | 9.55 | 5.54 | 12.44 | −6.59 |
| GCB_537 | Validation | 8.25 | 10.25 | 13.29 | −7.18 |
| GCB_543 | Validation | 9.92 | 8.85 | 12.06 | −7.21 |
| GCB_545 | Training | 9.69 | 4.91 | 12.90 | −6.62 |
| GCB_549 | Validation | 7.86 | 8.88 | 12.15 | −6.58 |
| GCB_550 | Validation | 10.64 | 9.53 | 12.24 | −7.60 |
| GCB_553 | Validation | 10.14 | 9.05 | 12.63 | −7.44 |
| GCB_565 | Validation | 9.08 | 10.80 | 13.42 | −7.57 |
| GCB_572 | Training | 8.93 | 10.03 | 12.58 | −7.21 |
| GCB_617 | Validation | 9.27 | 7.80 | 13.17 | −7.05 |
| GCB_618 | Training | 7.23 | 9.11 | 13.32 | −6.66 |
| GCB_619 | Validation | 9.63 | 9.63 | 12.12 | −7.27 |
| GCB_623 | Training | 8.94 | 9.07 | 12.35 | −7.00 |
| GCB_627 | Validation | 9.72 | 8.33 | 11.85 | −7.02 |
| GCB_654 | Training | 7.04 | 5.60 | 10.00 | −5.30 |
| GCB_661 | Validation | 10.27 | 7.92 | 12.66 | −7.29 |
| GCB_669 | Training | 9.15 | 9.29 | 12.32 | −7.10 |
| GCB_672 | Training | 9.69 | 7.36 | 12.41 | −6.95 |
| GCB_674 | Validation | 9.93 | 6.23 | 12.33 | −6.81 |
| GCB_675 | Validation | 7.48 | 8.46 | 10.12 | −5.97 |
| GCB_681 | Training | 10.77 | 9.52 | 12.59 | −7.72 |
| GCB_688 | Validation | 8.01 | 10.17 | 9.94 | −6.40 |
| GCB_695 | Validation | 10.58 | 9.38 | 12.45 | −7.60 |
| GCB_698 | Validation | 10.44 | 9.00 | 11.99 | −7.39 |
| GCB_701 | Training | 9.38 | 9.27 | 13.10 | −7.33 |
| GCB_710 | Validation | 6.96 | 5.59 | 13.19 | −5.93 |
| GCB_711 | Training | 9.28 | 8.49 | 11.44 | −6.82 |
| GCB_722 | Training | 8.93 | 9.51 | 12.61 | −7.13 |
| GCB_724 | Training | 9.51 | 8.39 | 11.53 | −6.90 |
| GCB_731 | Validation | 8.82 | 9.19 | 12.20 | −6.95 |
| GCB_742 | Validation | 9.95 | 9.37 | 12.95 | −7.50 |
| GCB_744 | Training | 10.23 | 10.11 | 11.85 | −7.49 |
| GCB_745 | Training | 10.29 | 9.71 | 11.95 | −7.46 |
| GCB_747 | Validation | 9.83 | 9.79 | 13.06 | −7.56 |
| GCB_749 | Training | 8.57 | 10.27 | 12.55 | −7.14 |
| GCB_758 | Validation | 6.88 | 5.69 | 12.51 | −5.78 |
| GCB_772 | Validation | 9.92 | 7.28 | 12.25 | −6.98 |
| GCB_777 | Validation | 9.03 | 9.63 | 11.69 | −6.99 |
| GCB_792 | Training | 9.49 | 9.06 | 12.08 | −7.12 |
| GCB_795 | Validation | 11.12 | 9.02 | 11.60 | −7.54 |
| GCB_797 | Validation | 8.42 | 5.90 | 12.84 | −6.38 |
| GCB_803 | Validation | 7.33 | 10.11 | 13.18 | −6.84 |
| GCB_810 | Training | 10.00 | 8.22 | 13.13 | −7.35 |
| GCB_817 | Training | 8.60 | 10.16 | 11.09 | −6.82 |
| GCB_818 | Training | 9.14 | 7.78 | 12.23 | −6.81 |
| GCB_819 | Validation | 9.08 | 8.63 | 13.22 | −7.15 |
| GCB_821 | Validation | 10.05 | 9.81 | 12.41 | −7.50 |

TABLE 2376-continued

| Sample ID # | Set | Lymph node signature value | Germinal center B-cell signature value | MHC class II signature value | Survival predictor score |
|---|---|---|---|---|---|
| GCB_832 | Training | 8.83 | 6.91 | 12.47 | −6.61 |
| GCB_836 | Validation | 9.49 | 7.86 | 11.46 | −6.78 |
| GCB_840 | Training | 9.45 | 5.02 | 11.74 | −6.33 |
| GCB_847 | Training | 9.41 | 8.77 | 12.55 | −7.14 |
| GCB_860 | Training | 9.02 | 6.66 | 11.54 | −6.43 |
| GCB_871 | Training | 6.60 | 4.46 | 11.16 | −5.20 |
| GCB_874 | Training | 10.39 | 9.13 | 11.65 | −7.33 |
| GCB_995 | Validation | 8.52 | 9.35 | 12.22 | −6.89 |
| PMBL_1006 | Validation | 8.72 | 4.67 | 10.94 | −5.86 |
| PMBL_1024 | Validation | 9.30 | 8.47 | 10.89 | −6.71 |
| PMBL_1048 | Validation | 10.30 | 4.98 | 12.18 | −6.68 |
| PMBL_1053 | Training | 8.75 | 9.78 | 11.12 | −6.81 |
| PMBL_484 | Training | 8.25 | 4.96 | 13.62 | −6.32 |
| PMBL_546 | Validation | 9.66 | 6.07 | 11.73 | −6.57 |
| PMBL_570 | Training | 10.58 | 8.54 | 12.70 | −7.50 |
| PMBL_621 | Training | 9.39 | 9.94 | 12.96 | −7.43 |
| PMBL_638 | Training | 9.81 | 8.35 | 11.37 | −6.95 |
| PMBL_691 | Validation | 8.37 | 7.51 | 10.17 | −6.10 |
| PMBL_791 | Validation | 9.29 | 8.65 | 11.56 | −6.88 |
| PMBL_824 | Validation | 9.87 | 7.19 | 13.28 | −7.16 |
| PMBL_994 | Training | 11.27 | 6.73 | 12.43 | −7.35 |
| PMBL_998 | Training | 7.92 | 8.34 | 13.19 | −6.72 |
| UC_DLBCL_1001 | Validation | 8.25 | 5.63 | 12.76 | −6.26 |
| UC_DLBCL_1004 | Validation | 9.01 | 7.01 | 13.09 | −6.81 |
| UC_DLBCL_1007 | Training | 11.42 | 6.73 | 12.97 | −7.51 |
| UC_DLBCL_1018 | Training | 7.77 | 4.58 | 12.71 | −5.91 |
| UC_DLBCL_1041 | Validation | 7.90 | 4.33 | 13.38 | −6.05 |
| UC_DLBCL_1054 | Training | 10.41 | 8.72 | 11.48 | −7.23 |
| UC_DLBCL_306 | Validation | 9.42 | 6.54 | 12.36 | −6.71 |
| UC_DLBCL_310 | Training | 9.97 | 5.50 | 12.27 | −6.69 |
| UC_DLBCL_449 | Validation | 10.01 | 5.37 | 12.17 | −6.65 |
| UC_DLBCL_458 | Training | 7.50 | 5.79 | 9.60 | −5.40 |
| UC_DLBCL_460 | Validation | 10.26 | 8.27 | 12.29 | −7.27 |
| UC_DLBCL_491 | Training | 9.43 | 4.73 | 12.39 | −6.40 |
| UC_DLBCL_528 | Validation | 8.42 | 6.19 | 11.63 | −6.18 |
| UC_DLBCL_615 | Validation | 8.44 | 9.01 | 12.80 | −6.92 |
| UC_DLBCL_625 | Training | 10.43 | 8.27 | 12.62 | −7.39 |
| UC_DLBCL_664 | Training | 9.80 | 8.74 | 12.72 | −7.29 |
| UC_DLBCL_671 | Training | 9.42 | 5.26 | 11.53 | −6.32 |
| UC_DLBCL_682 | Training | 9.01 | 4.73 | 12.33 | −6.26 |
| UC_DLBCL_683 | Training | 8.85 | 8.23 | 12.57 | −6.87 |
| UC_DLBCL_684 | Validation | 9.62 | 8.78 | 12.76 | −7.25 |
| UC_DLBCL_748 | Validation | 7.60 | 5.79 | 9.55 | −5.42 |
| UC_DLBCL_751 | Training | 6.40 | 9.91 | 13.14 | −6.50 |
| UC_DLBCL_808 | Training | 9.44 | 7.01 | 13.09 | −6.95 |
| UC_DLBCL_831 | Validation | 9.45 | 5.81 | 11.58 | −6.43 |
| UC_DLBCL_834 | Training | 8.52 | 7.66 | 11.77 | −6.50 |
| UC_DLBCL_838 | Validation | 8.49 | 4.60 | 12.56 | −6.11 |
| UC_DLBCL_851 | Validation | 7.50 | 4.82 | 8.19 | −4.94 |
| UC_DLBCL_854 | Validation | 8.35 | 5.82 | 12.59 | −6.29 |
| UC_DLBCL_855 | Training | 9.56 | 5.44 | 12.08 | −6.51 |
| UC_DLBCL_856 | Validation | 6.81 | 7.49 | 9.32 | −5.42 |

In order to visualize the predictive power of the model, the 200 samples were ranked according to their survival predictor scores and divided into four quartiles. Kaplan-Meier plots of overall survival probability show clear differences in survival rate between these four quartiles (FIG. 12).

Example 9: Development of a Refined DLBCL Survival Predictor Based on Genomic Alterations Comparative genomic hybridization (CGH) was performed on 224 DLBCL samples for which gene expression profiles had previously been obtained using a Lymphochip (Rosenwald 2002). Of these 224 samples, 87 had been classified as GCB based on the Lymphochip expression data, 77 had been classified as ABC, 19 had been classified as PMBL, and 41 were unclassified (Wright 2003). Clinical data was available for each subject from whom the samples had been obtained (Rosenwald 2002). All patients had received anthracycline-based chemotherapy. Median follow-up was 2.7 years and 58% of patients died during this period. The median age of the patients was 60 years and 54% were men 16% of patients had Ann Arbor stage I disease and 30%, 19%, and 35% had Stage II, III, and IV, respectively. 38% of DLBCL patients (78 cases) with available data were in the low-risk IPI group (IPI 0-1), 48% (99 cases) were in the intermediate-risk IPI group (IPI 2-3), and 14% (30 cases) were in the high-risk IPI group (IPI 4-5).

CGH was carried out using a commercially available felt (Vysis, Downers Grove, Ill.). Hybridization and digital image acquisition, processing, and evaluation were performed on a Cytovision Ultra workstation (Applied Imaging, Sunderland, UK) as described previously (Bea 1999). Signal ratios greater than 1.25 were considered chromosomal gains, while signal ratios less than 0.75 were considered chromosomal losses. Ratios exceeding 1.5 and/or strong focal signals with a ratio profile showing overrepresentation were considered genomic amplifications. All CGH data are available at http://www.ncbi.nlm.nih.gov/sky.

CGH alterations in individual cytobands were treated as categorical variables and their associations with DLBCL subgroups or gene: expression signatures were analyzed as follows. Preliminary analyses did not reveal significant differences in the effects of gains and amplifications, so they were treated as equivalent chromosomal abnormalities. Since a large number of individual chromosomal abnormalities were analyzed, there was a danger that some of the abnormalities would appear to be significant purely by chance. To avoid such false positives, a stepwise permutation test that generated nominal p-values accounting for multiple hypothesis testing was used (Westfall 1993; Simon 2003). This test takes into account the correlation between different chromosomal abnormalities. Differences in abnormality frequency between subtypes were detected using a chi squared test. Differences in gene expression signature measures affected by genomic imbalances were detected using a t-test. To further reduce the effects of multiple comparisons, only those chromosomal abnormalities that were present in a substantial portion of the data were analyzed. For the subgroup analysis, only those alterations that had a frequency of >20% in one or more of the DLBCL subgroups were considered. For correlation with gene expression signatures, chromosomal abnormalities were only considered if they occurred in at least 5% of all DLBCL samples. P-values for the association between gene expression levels (as a continuous variable) and genomic imbalances (amplification vs. gain vs. normal copy number) were calculated using an ANOVA test. P-values of <0.01 were considered significant to account for multiple comparisons. Overall survival was modeled using a Cox proportional hazards approach and visualized using the Kaplan-Meier method. The P values were adjusted for multiple comparisons, with the follow-up time and status at follow-up being permuted. Once an abnormality was found to be significant univariately, a likelihood ratio test was used to determine whether this variable added significantly to the survival model based on gene expression.

FIG. 29 shows the results of CGH analysis for GCB (A), ABC (B), and PMBL (C) samples (Bea 2005). Overall, chromosomal alterations were observed in 164 of the 224 patients (73%). A summary of the most common alterations is set forth in Table 2415.

TABLE 2415

|  | Overall (n = 224) | ABC (n = 77) | GCB (n = 87) | PMBL (n = 19) | Unclassified (n = 41) |
|---|---|---|---|---|---|
| Samples exhibiting alterations | 164 (73%) | 63 (81%) | 63 (72%) | 16 (84%) | 22 (54%) |
| Mean number of alterations | 3.3 | 4.5 | 3.1 | 3.3 | 1.7 |
| Mean number of gains | 1.9 | 2.5 | 1.6 | 2.1 | 1.0 |
| Mean number of amplifications | 0.3 | 0.4 | 0.3 | 0.4 | 0.0 |
| Mean number of losses | 1.2 | 1.6 | 1.1 | 0.8 | 0.6 |
| Gains |  |  |  |  |  |
| Xp | 27 (12%) | 12 (16%) | 12 (14%) | 3 (16%) | 0 |
| 1q25-q32 | 26 (12%) | 9 (12%) | 9 (10%) | 1 (5%) | 7 (17%) |
| 2p14-p16+ | 39 (17%) | 12 (15%) | 15 (17%) | 9 (47%) | 3 (7%) |
| Trisomy 3+ | 14 (6%) | 12 (15%) | 0 | 1 (5%) | 1 (2%) |
| 3p+ | 28 (12%) | 24 (31%) | 1 (1%) | 1 (5%) | 2 (5%) |
| 3q* | 22 (10%) | 20 (26%) | 0 | 1 (5%) | 1 (2%) |
| 3q27-qter* | 35 (16%) | 26 (33%) | 4 (5%) | 3 (16%) | 2 (5%) |
| 6p | 30 (13%) | 13 (17%) | 11 (13%) | 1 (5%) | 5 (12%) |
| 7p | 22 (10%) | 8 (10%) | 13 (15%) | 1 (5%) | 0 |
| 7q | 25 (11%) | 10 (13%) | 13 (15%) | 1 (5%) | 1 (2%) |
| 8q23-qter | 23 (10%) | 8 (10%) | 10 (11%) | 2 (11 %) | 3 (7%) |
| 9p* | 14 (6%) | 5 (6%) | 0 | 7 (37%) | 2 (5%) |
| 12p | 19 (8%) | 4 (5%) | 14 (16%) | 1 (5%) | 0 |
| 12q12# | 24 (11%) | 4 (5%) | 18 (21%) | 1 (5%) | 1 (2%) |
| 12q22-qter | 22 (10%) | 7 (9%) | 13 (15%) | 1 (5%) | 1 (2%) |
| 18q21-q22+ | 42 (19%) | 26 (34%) | 9 (10%) | 3 (16%) | 4 (10%) |
| Losses |  |  |  |  |  |
| 6q16 | 50 (22%) | 26 (34%) | 19 (22%) | 0 | 5 (12%) |
| 6q21-q22+ | 55 (25%) | 31 (40%) | 19 (22%) | 0 | 5 (12%) |
| 8p22-pter | 19 (8%) | 8 (10%) | 3 (3%) | 3 (16%) | 5 (12%) |
| 17p | 22 (10%) | 14 (18%) | 7 (8%) | 0 | 1 (2%) |

*P < 0.001;
+P < 0.05;
P = 0.059; unclassified tumors were not included in statistical analysis The number of alterations did not differ statistically between GCB (3.1±3.7, n=87), ABC (4.5±4.5, n=77), PMBL (3.3±2.7, n=19) and unclassified DLBCL (1.7±2.2, n=41). Among samples exhibiting alterations, 81% exhibited more than one. The most frequent alteration in those samples exhibiting only a single alteration was loss of 6q (n=8), with two minimally lost regions in 6q21-q22 and 6q25-qter. These deletions may represent early events in the development of these lymphomas.

Irrespective of the DLBCL subgroup, the most frequent alterations were loss of 6q22-q22 (25%), loss of 6q16 (22%), gain of 18q21-q22 (19%), gain of 2p14-p16 (47%), gain of 3q27-qter (16%), gain of 6p (13%), and gain of Xp, 1q25-q32, and 3p (12% each). Amplifications were identified in 33 different chromosomal regions, most frequently in 2p14-p16 and 18q21-q22 (11 and 20 cases, respectively). Some alterations occurred frequently in the same tumors, suggesting that they may be part of a recurrent lymphogenesis pathway. For example, 17 of 26 ABC samples with 3q27-qter gains also exhibited 18q21-q22 gains (P=0.0001, odds ratio: 9.23; 95% CI 3.14-27.2).

Notably, several chromosomal alterations were differentially distributed among DLBCL subgroups (FIG. 29D). ABC exhibited characteristic and recurrent gains of chromosome 3, gains and amplification of 18q21-q22, and loss of 6q21-q22. Gains of the whole 3q arm and trisomy 3, which were observed in 26% and 15% of ABC samples, respectively, were never observed in GCB and observed only once in PMBL. Gains of 18q21-q22 were observed in 34% of ABC samples, versus only 10% and 16% of GCB and PMBL samples, respectively. Amplification of 18q21, which contains the BCL2 gene, was also more frequent in ABC (18%) than in GCB or PMBL (5% each). Previous studies utilizing PCR-based and FISH methods found that the t(14;18) translocation, which involves the BCL2 gene, occurs in GCB but never in ABC (Huang 2002; Iqbal 2004). Interestingly, 3 of the 4 GCB samples exhibiting amplification of 18q21 also exhibited the t(14;18) translocation (the remaining case was not analyzed for this translocation). High expression of the BCL2 gene is a characteristic feature of ABC, but only occurs in GCB that have the t(14;18) translocation (Alizadeh 2000; Huang 2002; Rosenwald 2002). Together, these data suggest that amplification of the 18q21 region occurs preferentially in lymphomas that have the ability to express the BCL2 gene.

GCB samples were characterized by more frequent gains of 12q12 compared to ABC and PMBL, although this increase did not reach statistical significance (21% for GCB vs. 5% for both ABC and PMBL, P=0.059). PMBL samples were characterized by frequent gains of 9p21-pter (37% for PMBL vs. 0% for GCB and 6% for ABC, P<0.001) and 2p14-p16 (47% for PMBL vs, 17% for GCB and 11% for ABC, P<0.02) compared to GCB and ABC. Taken together, these data further demonstrate that GCB, ABC, and PMBL are genetically distinct.

To confirm some of the more frequent DLBCL chromosomal alterations identified by CGH, real-time quantitative PCR (RQ-PCR) was used to quantify the copy number of select genes from the following regions; 2p14-16 (REL, BCL11A), 12q13-q14 (SAS, CDK4, MDM2), 3q27 (RFC4, BCL6, and 18q21 (MADH4, MALT1, BCL2). RQ-PCR was performed using the ABI Prism 7700 Sequence Detector System (Applied Biosystems). $\beta_2$-microglobulin ($\beta_2$M) was used as a reference gene. Each assay was analyzed using the comparative cycle threshold ($C_T$) method, using the arithmetic formula provided by the manufacturer. To determine the cut-off values for a genomic gain/amplification in each probe set, eight DNA samples from peripheral blood or placenta of healthy subjects was studied. The cut-off value for a genomic gain was determined to be the mean ratio plus three standard deviation units (approximately 1.3 for each gene). A ratio between the cut-off value and 2 was considered a gain, while a ratio of greater than 2 was considered an amplification. A subset of samples were also investigated using albumin (ALB) as a reference gene. The results between the two control genes were totally concordant in 87% of the cases, and partially concordant in 13% of the cases. For the four samples that CGH had shown contained alterations in the $\beta_2$M locus (15q21.1), ALB was used as the sole reference gene.

REL was found to be amplified in virtually all GCB samples in which high-level 2p14-16 amplifications had been observed by CGH. The copy number of BCL11A was increased in all but one of these cases, albeit usually at lower levels than REL. Although CGH had shown high-level 2p14-16 amplifications in two ABC samples, RQ-PCR showed merely a gain in REL for these two samples. BCL1IA was amplified in one of these samples and gained in the other. These results confirm the previous observation that REL may not to the primary target of amplification in ABC (Rosenwald 2002). CDK4 and SAS, which map to 12q13-q14, were frequently gained or amplified in GCB samples that had exhibited 12q gains by CGH, whereas MDM2 was less commonly altered in these samples. In contrast, all three ABC sample with 12q13-q14 gains exhibited gains of CDK4, although less frequently than gains of SAS or MDM2. RPC4 and BCL6, located in 3q27, were gained or amplified in all ABC and GCB samples in which 3q27-qter gains or amplifications had been observed by CGH. MALT1 and BCL2 were commonly gained or amplified in ABC and GCB samples that had exhibited 18q21 gains, by CGH, while MADH4 was less frequently altered.

To determine the influence of these chromosomal alterations, on locus-specific gene expression, mRNA levels of genes located in four recurrently gained/amplified regions (2p14-p16, 3q27-qter, 12q12-q15, and 18q21-q22) were correlated with copy number changes. It was found that each of these chromosomal alterations was associated with a higher expression levels for a subset of genes within the region, but these genes differed between DLBCL subgroups.

14 genes were mapped to the chromosomal region 2p14-p16. GCB and ABC samples with increased genomic copy numbers in this region showed significant overexpression of 8 (57%) and 5 (36%) of these 14 genes, respectively (FIGS. 30A and 30B). Four of the genes (VRK2, XPO1, SLC14A, and ACTR2) were significantly overexpressed in both GCB and ABC samples (FIGS. 30A and 2B). In contrast, REL, ASHA2, MDH1, and UGP2 were only overexpressed in GCB-DLBCL with 2p14-p16 gains (FIG. 30A).

GCB and ABC samples with gains/amplifications in the 12q12-q15 region showed significant overexpression of 10 (19%) and 12 (23%) of the >52 genes represented on the Lymphochip microarray. Five of these genes were overexpressed in both GCB and ABC samples (SENP1, MCRS1, MARS, SAS, and CDK4) (FIG. 30F). Most of the overexpressed genes clustered to the chromosomal region 12q13.

7 (33%) of the 21 genes mapping to chromosome 3q27-qter were significantly overexpressed in ABC (FIG. 30C), versus only 2 (13%) in GCB. Similarly, 9 (75%) of the 12 genes mapping to chromosome 18q21-q22 were significantly overexpressed in ABC (FIG. 30E), versus only 4 (33%) in GCB (FIG. 30D). All 4 18q21-q22 genes overexpressed in GCB (MADH2, MADH4, LOC51320, and PMAIP1) were also overexpressed in ABC.

To determine whether the various genetic alterations identified in DLBCL samples influence previously defined gene expression signatures, gene expression signature averages were created for each DLBCL, and then evaluated within tumors with specific chromosomal alterations (Bea 2005). Statistically significant associations were observed between several chromosomal alterations and the proliferation, lymph node, T-cell, and MHC class II gene expression signatures. In particular, gains of various cytobands of chromosome 3 and losses in 6q21 were both associated with increased expression of the proliferation gene expression signature (FIG. 31). Copy number gains of the chromosomal regions 3p12 and 3q12 were associated with decreased expression of the MHC class II gene expression signature. Genetic losses of 6q21 and other cytobands of chromosome 6, as well as losses of 17p13, gains of Xp11, gains of 11q24-q25, gains of 12q12, and gains of several cytobands in 7p and 7q all decreased expression of the T-cell gene expression signature. Finally, gains of Xp21 were associated with increased expression of the lymph node gene expression signature, while gains of 3q22 or several additional cytobands in 3p and 3q were associated with decreased expression of lymph node gene expression signature.

The prognostic value of each DLBCL chromosomal alteration was analyzed across all DLBCL samples and within each DLBCL subtype separately. Although several chromosomal alterations were individually associated with a significant increase or decrease in overall survival rate, only gains within certain regions of chromosome 3 were significantly associated with shorter overall survival after adjustment for multiple comparisons in the whole series of patients. These regions were 3p11-p12, 3q11-q13, 3q21-q24, and 3q25-q27.

Previously, a gene expression-based DLBCL survival predictor had been developed using four gene expression signatures and BMP6 (Rosenwald 2002). This survival predictor had the following formula;

$$\text{Survival predictor score} = [0.241*(\text{proliferation gene expression signature value})] + [0.310*(\text{BMP6})] - [0.290*(\text{germinal center B cell gene expression signature value})] - [0.311*(\text{MHC class II gene expression signature value})] - [0.249*(\text{lymph node gene expression signature value})].$$

This model could divide DLBCL patients into four quartile groups with 5-year survival rates of 73%, 71%, 34%, and 15%. To determine whether the chromosome 3 gains discussed above could improve this survival predictor, a multivariate analysis was performed. In this analysis, chromosome 3 gains involving the 3p11-p12 region had an independent prognostic value and improved survival predictions obtained using gene expression data alone (FIG. 32). Cases with gains of 3p11-p12 were primarily, those that had been categorized in the least favorable quartile survival group using gene expression data alone. However, several cases with 3p11-p12 gains had been included in the more favorable quartile survival groups based on gene expression data. These cases had a significantly worse clinical prognosis than would have been predicted by gene expression data alone.

Example 10: Development of an MCL Survival Predictor Using Gene Expression Data from Affymetrix U133A and U133B Microarrays The connection between higher expression of proliferation genes and worse survival in MCL had previously been documented and validated (Rosenwald 2003a). A cluster of proliferation genes had been identified in the DLBCL samples used to create the DLBCL survival predictor described in Example 7. By averaging the expression of these genes, a proliferation gene expression signature value had been developed for the DLBCL samples. The correlation of this signature with each probe set on the U133A and U133B microarrays was determined, and the 22 genes for which the correlation was greater than 0.5 were labeled proliferation genes. The correlation between expression of these proliferation genes and survival in 21 MCL samples was estimated using the Cox proportional hazards model. Table 2377 lists these 21 MCL samples.

TABLE 2377

| Sample ID # | Length of follow-up (years) | Status at follow-up | Used in creating survival predictor? |
|---|---|---|---|
| MCL_1012 | 3.19 | Alive | Yes |
| MCL_1091 | 3.03 | Alive | Yes |
| MCL_1114 | 0.59 | Dead | Yes |
| MCL_1128 | 0.43 | Dead | Yes |
| MCL_1150 | 3.21 | Dead | Yes |
| MCL_1162 | 0.78 | Alive | Yes |

TABLE 2377-continued

| Sample ID # | Length of follow-up (years) | Status at follow-up | Used in creating survival predictor? |
|---|---|---|---|
| MCL__1166 | 0.53 | Dead | Yes |
| MCL__1194 | 0.55 | Alive | Yes |
| MCL__885 | 1.19 | Alive | Yes |
| MCL__918 | 1.95 | Dead | Yes |
| MCL__924 | 5.48 | Dead | Yes |
| MCL__925 | 7.23 | Alive | Yes |
| MCL__926 | 5.18 | Dead | Yes |
| MCL__936 | 2.80 | Alive | Yes |
| MCL__939 | 1.07 | Dead | Yes |
| MCL__953 | 2.31 | Dead | Yes |
| MCL__956 | 1.40 | Dead | Yes |
| MCL__964 | 0.75 | Alive | Yes |
| MCL__966 | 0.21 | Dead | Yes |
| MCL__968 | 1.59 | Dead | Yes |
| MCL__970 | 5.02 | Dead | Yes |

Out of the 22 proliferation genes, 11 were significant at a 0.001 level. The expression level of these 11 genes in each of the 21 MCL samples was averaged to generate a proliferation gene expression signature value. No other genes represented on the U133A or U133B microarrays correlated with MCL survival to an extent greater than would be expected by chance, so the final model included only proliferation genes. The 11 genes used to generate the model are presented in Table 2378.

TABLE 2378

| Signature | UNIQID | Gene Symbol |
|---|---|---|
| Proliferation | 1097290 | CIRH1A |
| Proliferation | 1101295 | FLJ40629 |
| Proliferation | 1119729 | TK1 |
| Proliferation | 1120153 | LMNB1 |
| Proliferation | 1120494 | CDC6 |
| Proliferation | 1124745 | KIAA0056 |
| Proliferation | 1126148 | DKFZp586E1120 |
| Proliferation | 1130618 | TPI1 |
| Proliferation | 1134753 | WHSC1 |
| Proliferation | 1139654 | ECT2 |
| Proliferation | 1140632 | IMAGE: 52707 |

A survival predictor score for MCL was generated using the following equation:

Survival predictor score=1.66*(proliferation gene expression signature value).

This model was associated with survival in a statistically significant manner (p=0.00018). To illustrate the significance of the model in predicting survival, the 21 MCL samples were divided into two equivalent groups based on their survival predictor scores. Those samples with survival predictor scores above the median were placed in the high proliferation group, while those with survival predictor scores below the median were placed in the low proliferation group. FIG. 13 illustrates the Kaplan Meier survival estimates for these two groups. Median survival for the high proliferation group was 1.07 years, while median survival for the low proliferation group was 5.18 years.

Example 11: Development of an MCL Survival Predictor Using Gene Expression Data from the Lymph Dx Microarray A set of 21 genes associated with proliferation and poor prognosis in MCL had been identified previously (Rosenwald 2003a). Of these 21 genes, only four were represented on the Lymph Dx microarray. In order to find a larger set of genes on the Lymph Dx microarray associated With survival in MCL, Lymphochip expression data (Rosenwald 2003a) was re-analyzed and another set of proliferation genes whose expression levels were correlated with poor survival in MCL were identified. Thirteen of these genes were represented on the Lymph Dx microarray (median expression >6 on $log_2$ scale). These 13 genes are listed in Table 2379.

TABLE 2379

| Signature | UNIQID | Unigene ID Build 167 http://www.ncbi.nlm.nih.gov/UniGene | Gene symbol |
|---|---|---|---|
| Proliferation | 1119294 | 156346 | TOP2A |
| Proliferation | 1119729 | 164457 | TK1 |
| Proliferation | 1120153 | 89497 | LMNB1 |
| Proliferation | 1121276 | 24529 | CHEK1 |
| Proliferation | 1123358 | 442658 | AURKB |
| Proliferation | 1124178 | 446579 | HSPCA |
| Proliferation | 1124563 | 249441 | WEE1 |
| Proliferation | 1130799 | 233952 | PSMA7 |
| Proliferation | 1131274 | 374378 | CKS1B |
| Proliferation | 1131778 | 396393 | UBE2S |
| Proliferation | 1132449 | 250822 | STK6 |
| Proliferation | 1135229 | 367676 | DUT |
| Proliferation | 1136585 | 80976 | MKI67 |

The expression levels of the 13 genes listed in Table 2379 on the Lymph Dx microarray were transformed into the $log_2$ scale and averaged to form a proliferation gene expression signature value. This was used to generate a survival predictor score using the following equation:

Survival predictor score=1.66*(proliferation gene expression signature value).

For the 21 MCL samples analyzed, the survival predictor score had a mean of 14.85 and a standard deviation of 1.13, Even in this limited sample set, the survival predictor score was significantly associated with prognosis (p=0.0049), with each unit increase in the score corresponding to a 2.7 fold increase in the relative risk of death. Data for all 21 samples is shown in Table 2380.

TABLE 2380

| Sample ID # | Proliferation signature value | Survival predictor score |
|---|---|---|
| MCL__1012 | 8.83 | 14.658 |
| MCL__1091 | 8.81 | 14.625 |

TABLE 2380-continued

| Sample ID # | Proliferation signature value | Survival predictor score |
|---|---|---|
| MCL_1114 | 10.39 | 17.247 |
| MCL_1128 | 10.12 | 16.799 |
| MCL_1150 | 8.33 | 13.828 |
| MCL_1162 | 8.15 | 13.529 |
| MCL_1166 | 9.40 | 15.604 |
| MCL_1194 | 7.44 | 12.350 |
| MCL_885 | 8.68 | 14.409 |
| MCL_918 | 9.33 | 15.488 |
| MCL_924 | 8.35 | 13.861 |
| MCL_925 | 8.86 | 14.708 |
| MCL_926 | 8.14 | 13.512 |
| MCL_936 | 8.56 | 14.21 |
| MCL_939 | 9.14 | 15.172 |
| MCL_953 | 9.25 | 15.355 |
| MCL_956 | 9.35 | 15.521 |
| MCL_964 | 9.74 | 16.168 |
| MCL_966 | 8.76 | 14.542 |
| MCL_968 | 9.10 | 15.106 |
| MCL_970 | 9.27 | 15.388 |

To illustrate the significance of the model in predicting survival, the 21 MCL samples were divided into two equivalent groups based on their survival predictor scores. Those samples with survival predictor scores above the median were placed in the high proliferation group, while those with survival predictor scores below the median were placed in the low proliferation group. FIG. 14 illustrates the Kaplan Meier survival estimates for these two groups.

Example 12: Identification of Lymphoma Samples as MCL Based on Bayesian Analysis of Gene Expression Data from Affymetrix U133A and U133B Microarrays A statistical method based on Bayesian analysis was developed to distinguish MCL samples from samples belonging to other lymphoma types based on gene expression profiling. This method was developed using the gene expression data obtained in Example 1 for the following lymphoma types: ABC, GCB, PMBL, BL, FH, FL, MALT, MCL, PTLD, SLL, and splenic marginal zone lymphoma (splenic). Tables 1707-1741 (discussed in Example 1) provide gene expression data for samples within each of these lymphoma types. Including the expression level of each gene and the difference in expression of each gene between types. Tables 1710, 1715, and 1723 (corresponding to FL, MCL, and DLBCL, respectively) include the correlation between expression of each gene and survival.

To determine the lymphoma type of a sample, a series of predictor models are generated. Each predictor model calculates the probability that the sample belongs to a first lymphoma type rather than a second lymphoma type. A method was developed to determine whether a sample was MCL, or one of the following lymphoma types: ABC, BL, FH, FL, GCB, MALT, PMBL, PTLD, SLL, or splenic. This method required ten different predictor models, each designed to determine whether the sample belonged to MCL or one of the other ten lymphoma types (e.g., MCL vs. ABC, MCL vs. BL, etc.).

Several of the lymphoma samples analyzed displayed a tendency towards elevated or reduced expression of genes from the lymph node and proliferation gene expression signatures. These genes are likely to be highly differentially expressed between the lymphoma types, but they do not serve as good predictor genes because they are often variably expressed within a single lymphoma type. For this reason, any gene that displayed a correlation with the proliferation or lymph node signatures was eliminated from consideration.

For each lymphoma type pair (e.g., MCL vs. ABC, MCL vs. FL, etc.), 20 genes were identified that exhibited the greatest difference in expression between MCL and the second lymphoma type according to a Student's t-test. The choice to use 20 genes was arbitrary. For each sample X, the 20 genes were used to generate a linear predictor score (LPS) according to the following formula:

$$LPS(X) = \sum_{j=1}^{20} t_j X_j,$$

where $X_j$ is the expression of gene j in sample X and $t_j$ is the t-statistic for the difference in expression of gene/between a first lymphoma type and a second lymphoma type. This is merely one method for generating an LPS. Others methods include linear discriminant analysis (Dudolt 2002), support vector machines (Furey 2000), or shrunken centroids (Tibshirani 2002). In addition, there is no requirement that a t-statistic be used as the scaling factor.

After an LPS had been formulated for each lymphoma sample, the mean and standard deviation of these LPS's was calculated for each lymphoma type. For a new sample X, Bayes' rule can be used to estimate the probability that the sample belongs to a first lymphoma type rather than a second lymphoma type (FIG. 16). In this example, Bayes' rule was used to calculate the probability q that sample X was MCL rather than a second lymphoma type using the following equation:

$$q(X \text{ is type } 1) = \frac{\phi(LPS(X); \hat{\mu}_1, \hat{\sigma}_1)}{\phi(LPS(X); \hat{\mu}_1, \hat{\sigma}_1) + \phi(LPS(X); \hat{\mu}_2, \hat{\sigma}_2)}$$

where type 1 is MCL, type 2 is one of the other nine lymphoma types, $\phi(x; \mu, \sigma)$ is the normal density function with mean $\mu$ and standard deviation $\sigma$, $\hat{\mu}_1$ and $\hat{\sigma}_1$ are the sample mean and variance of the LPS values for lymphoma type 1, and $\hat{\mu}_2$ and $\hat{\sigma}_2$ are the sample mean and variance of the LPS values for lymphoma type 2.

This method was used to develop ten predictor models, one for each pairing of MCL and a second lymphoma type. A sample was classified as MCL if each of the ten predictors generated at least a 90% probability that the sample was MCL. If any of the ten predictors indicated a probability of less than 90% the sample was classified as non-MCL.

The 10 sets of 20 genes that were included in these models and the t-statistics for each gene are presented in Tables 2381-2490.

TABLE 2381

| | MCL vs. ABC predictor genes | |
|---|---|---|
| UNIQID | Gene name | Scale Factor |
| 1103711 | *Homo sapiens* cDNA FLJ11833 fis, clone HEMBA1006579. | 17.88496416 |
| 1133111 | PDE9A -- phosphodiesterase 9A | 17.61579873 |
| 1137987 | PLXNB1 -- plexin B1 | 17.47030156 |
| 1132835 | SOX11 -- SRY (sex determining region Y)-box 11 | 16.89404131 |
| 1109505 | *Homo sapiens*, Similar to LOC168058, clone MGC: 39372 IMAGE: 5089466, mRNA, complete cds | 15.78111902 |
| 1139054 | LOC58486 -- transposon-derived Buster1 transposase-like protein | 15.77800815 |
| 1119361 | TIA1 -- TIA1 cytotoxic granule-associated RNA binding protein | 15.68070962 |
| 1115226 | KIAA1683 -- KIAA1683 protein | 15.67954057 |
| 1101211 | *Homo sapiens* cDNA: FLJ21960 fis, clone HEP05517. | 15.4183527 |
| 1118963 | *Homo sapiens* cDNA FLJ35653 fis, clone SPLEN2013690. | 15.36802586 |
| 1096503 | GL012 -- hypothetical protein GL012 | 14.64776335 |
| 1127849 | SNN -- stannin | 14.54859775 |
| 1099204 | *Homo sapiens* mRNA; cDNA DKFZp586K1922 (from clone DKFZp586K1922) | 14.32724822 |
| 1098840 | C3orf6 -- chromosome 3 open reading frame 6 | 14.10346944 |
| 1139444 | RABL2B -- RAB, member of RAS oncogene family-like 2B | 14.10016196 |
| 1106855 | KIAA1909 -- KIAA1909 protein | 13.9504946 |
| 1126695 | KIAA0484 -- KIAA0484 protein | 13.92285415 |
| 1120137 | FCGBP -- Fc fragment of IgG binding protein | 13.86147896 |
| 1133011 | TMSNB -- thymosin, beta, identified in neuroblastoma cells | 13.74377784 |
| 1133192 | GRP3 -- guanine nucleotide exchange factor for Rap1 | −17.09085725 |

TABLE 2382

| | MCL vs. BL predictor genes | |
|---|---|---|
| UNIQID | Gene name | Scale Factor |
| 1120900 | EPHB6 -- EphB6 | 13.43582327 |
| 1112061 | *Homo sapiens* cDNA FLJ90513 fis, clone NT2RP3004355. | 12.73065392 |
| 1109505 | *Homo sapiens*, Similar to LOC168058, clone MGC: 39372 IMAGE: 5089466, mRNA, complete cds | 12.63674985 |
| 1133099 | DNASE1L3 -- deoxyribonuclease I-like 3 | 12.43333984 |
| 1106855 | KIAA1909 -- KIAA1909 protein | 12.32623489 |
| 1110070 | ESTs | 12.05416064 |
| 1121739 | ZNF135 -- zinc finger protein 135 (clone pHZ-17) | 11.90460363 |
| 1098840 | C3orf6 -- chromosome 3 open reading frame 6 | 11.90309143 |
| 1132833 | SOX11 -- SRY (sex determining region Y)-box 11 | 11.60864812 |
| 1121693 | KIAA0450 -- KIAA0450 gene product | 11.33634052 |
| 1123760 | ILT7 -- leukocyte immunoglobulin-like receptor, subfamily A (without TM domain), member 4 | 11.18744726 |
| 1125964 | KIAA0792 -- KIAA0792 gene product | 11.14762675 |
| 1112306 | ESTs | 11.02434114 |
| 1096070 | DNMT3A -- DNA (cytosine-5-)-methyltransferase 3 alpha | 10.98991879 |
| 1129943 | *Homo sapiens*, similar to Zinc finger protein 85 (Zinc finger protein HPF4) (HTF1), clone IMAGE: 3352451, mRNA | 10.72494956 |
| 1118749 | PRKWNK1 -- protein kinase, lysine deficient 1 | 10.64623382 |
| 1098954 | FLJ13204 -- hypothetical protein FLJ13204 | 10.46164401 |
| 1134749 | PRKCBP1 -- protein kinase C binding protein 1 | 10.40948157 |
| 1131860 | BIN1 -- bridging integrator 1 | 10.31084561 |
| 1123148 | TGFBR2 -- transforming growth factor, beta receptor II (70/80 kDa) | 10.2956213 |

TABLE 2383

| | MCL vs. FH predictor genes | |
|---|---|---|
| UNIQID | Gene name | Scale Factor |
| 1132834 | SOX11 -- SRY (sex determining region Y)-box 11 | 24.3531072 |
| 1100873 | ESTs | 16.83342764 |
| 1109603 | ESTs | 13.02401995 |
| 1139411 | OSBPL10 -- oxysterol binding protein-like 10 | 12.54369577 |
| 1106855 | KIAA1909 -- KIAA1909 protein | 12.10316361 |

TABLE 2383-continued

MCL vs. FH predictor genes

| UNIQID | Gene name | Scale Factor |
|---|---|---|
| 1125193 | CNR1 -- cannabinoid receptor 1 (brain) | 12.070579 |
| 1137450 | ALOX5 -- arachidonate 5-lipoxygenase | 11.74571823 |
| 1100258 | KIAA1384 -- KIAA1384 protein | 11.60998697 |
| 1133167 | ZFD25 -- zinc finger protein (ZFD25) | 11.52931491 |
| 1136831 | PPFIBP2 -- PTPRF interacting protein, binding protein 2 (liprin beta 2) | 11.50062692 |
| 1138222 | NA | 10.99674674 |
| 1099437 | *Homo sapiens* mRNA; cDNA DKFZp667B1913 (from clone DKFZp667B1913) | 10.90797288 |
| 1140236 | SPAP1 -- SH2 domain containing phosphatase anchor protein 1 | 10.77082801 |
| 1114109 | DCAL1 -- dendritic cell-associated lectin-1 | 10.65867119 |
| 1098277 | PRICKLE1 -- prickle-like 1 (*Drosophila*) | 10.55457068 |
| 1135138 | CD24 -- CD24 antigen (small cell lung carcinoma cluster 4 antigen) | 10.41999962 |
| 1103304 | *Homo sapiens* clone CDABP0095 mRNA sequence | −10.46625233 |
| 1128460 | RDGBB -- retinal degeneration B beta | −10.91106245 |
| 1121953 | KIAA0125 -- KIAA0125 gene product | −11.22466255 |
| 1129281 | C14orf110 -- chromosome 14 open reading frame 110 | −15.54465448 |

TABLE 2384

MCL vs. FL predictor genes

| UNIQID | Gene name | Scale Factor |
|---|---|---|
| 1132835 | SOX11 -- SRY (sex determining region Y)-box 11 | 22.14208817 |
| 1096070 | DNMT3A -- DNA (cytosine-5-)-methyltransferase 3 alpha | 20.53740132 |
| 1103711 | *Homo sapiens* cDNA FLJ11833 fis, clone HEMBA1006579. | 20.49880004 |
| 1137987 | PLXNB1 -- plexin B1 | 18.38081568 |
| 1109505 | *Homo sapiens*, Similar to LOC168058, clone MGC: 39372 IMAGE: 5089466, mRNA, complete cds | 17.17812448 |
| 1098840 | C3orf6 -- chromosome 3 open reading frame 6 | 16.32703666 |
| 1130926 | C5orf13 -- chromosome 5 open reading frame 13 | 15.34261878 |
| 1096396 | SPG3A -- spastic paraplegia 3A (autosomal dominant) | 14.75437736 |
| 1132734 | COL9A3 -- collagen, type IX, alpha 3 | 14.684583 |
| 1139393 | OPN3 -- opsin 3 (encephalopsin, panopsin) | 14.39118445 |
| 1115537 | LOC84518 -- protein related with psoriasis | 14.18446144 |
| 1102215 | *Homo sapiens* cDNA FLJ11666 fis, clone HEMBA1004672. | 14.16246426 |
| 1124585 | *Homo sapiens* cDNA: FLJ21930 fis, clone HEP04301, highly similar to HSU90916 Human clone 23815 mRNA sequence. | −14.33315955 |
| 1137561 | HOXA1 -- homeo box A1 | −15.38404642 |
| 1100581 | *Homo sapiens* mRNA; cDNA DKFZp667A1115 (from clone DKFZp667A1115) | −15.91666634 |
| 1124646 | KIAA0084 -- KIAA0084 protein | −16.40577696 |
| 1114543 | ESTs | −17.60167863 |
| 1120090 | BCL6 -- B-cell CLL/lymphoma 6 (zinc finger protein 51) | −17.63091181 |
| 1123731 | RGS13 -- regulator of G-protein signalling 13 | −22.41602151 |
| 1133192 | GRP3 -- guanine nucleotide exchange factor for Rap1 | −27.28308723 |

TABLE 2385

MCL vs. GCB predictor genes

| UNIQID | Gene name | Scale Factor |
|---|---|---|
| 1098840 | C3orf6 -- chromosome 3 open reading frame 6 | 22.26488562 |
| 1132835 | SOX11 -- SRY (sex determining region Y)-box 11 | 17.76179754 |
| 1137987 | PLXNB1 -- plexin B1 | 16.86845147 |
| 1098954 | FLJ13204 -- hypothetical protein FLJ13204 | 16.65023669 |
| 1103711 | *Homo sapiens* cDNA FLJ11833 fis, clone HEMBA1006579. | 15.64719784 |
| 1096070 | DNMT3A -- DNA (cytosine-5-)-methyltransferase 3 alpha | 15.22540494 |
| 1139393 | OPN3 -- opsin 3 (encephalopsin, panopsin) | 14.64030565 |
| 1127849 | SNN -- stannin | 14.28242206 |
| 1098156 | Human HeLa mRNA isolated as a false positive in a two-hybrid-screen. | 14.00049272 |

TABLE 2385-continued

MCL vs. GCB predictor genes

| UNIQID | Gene name | Scale Factor |
| --- | --- | --- |
| 1128845 | FLJ20174 -- hypothetical protein FLJ20174 | 13.96064416 |
| 1129943 | *Homo sapiens*, similar to Zinc finger protein 85 (Zinc finger protein HPF4) (HTF1), clone IMAGE: 3352451, mRNA | 13.85404507 |
| 1140116 | DKFZP564B116 -- hypothetical protein DKFZp564B1162 | 13.81464172 |
| 1106855 | KIAA1909 -- KIAA1909 protein | 13.74521849 |
| 1120900 | EPHB6 -- EphB6 | 13.46567004 |
| 1127371 | *Homo sapiens* cDNA FLJ14046 fis, clone HEMBA1006461. | 13.45735668 |
| 1119361 | TIA1 -- TIA1 cytotoxic granule-associated RNA binding protein | 13.37376559 |
| 1120854 | EDG1 -- endothelial differentiation, sphingolipid G-protein-coupled receptor, 1 | 13.1047657 |
| 1098277 | PRICKLE1 -- prickle-like 1 (*Drosophila*) | 13.04993076 |
| 1140127 | TRIM34 -- tripartite motif-containing 34 | 12.66260609 |
| 1100581 | *Homo sapiens* mRNA; cDNA DKFZp667A1115 (from clone DKFZp667A1115) | −12.81251689 |

TABLE 2386

MCL vs. MALT predictor genes

| UNIQID | Gene name | Scale Factor |
| --- | --- | --- |
| 1132834 | SOX11 -- SRY (sex determining region Y)-box 11 | 20.7489202 |
| 1101987 | KIAA1909 -- KIAA1909 protein | 10.78991326 |
| 1100873 | ESTs | 10.11845036 |
| 1130764 | HNRPA0 -- heterogeneous nuclear ribonucleoprotein A0 | 9.432459453 |
| 1102178 | *Homo sapiens*, Similar to thymosin, beta, identified in neuroblastoma cells, clone MGC: 39900 IMAGE: 5247537, mRNA, complete cds | 9.035605572 |
| 1098277 | PRICKLE1 -- prickle-like 1 (*Drosophila*) | 9.003360784 |
| 1130926 | C5orf13 -- chromosome 5 open reading frame 13 | 8.712830747 |
| 1098694 | LOC112868 -- hypothetical protein LOC112868 | 8.309789856 |
| 1103711 | *Homo sapiens* cDNA FLJ11833 fis, clone HEMBA1006579. | 8.248526605 |
| 1138099 | NA | 8.107440225 |
| 1120854 | EDG1 -- endothelial differentiation, sphingolipid G-protein-coupled receptor, 1 | 8.045872672 |
| 1102215 | *Homo sapiens* cDNA FLJ11666 fis, clone HEMBA1004672. | 8.032351578 |
| 1121739 | ZNF135 -- zinc finger protein 135 (clone pHZ-17) | 8.020919565 |
| 1096070 | DNMT3A -- DNA (cytosine-5-)-methyltransferase 3 alpha | 7.964477216 |
| 1101211 | *Homo sapiens* cDNA: FLJ21960 fis, clone HEP05517. | 7.738742472 |
| 1120825 | CHL1 -- cell adhesion molecule with homology to L1CAM (close homolog of L1) | 7.516130116 |
| 1099437 | *Homo sapiens* mRNA; cDNA DKFZp667B1913 (from clone DKFZp667B1913) | 7.209041652 |
| 1096503 | GL012 -- hypothetical protein GL012 | 7.171540413 |
| 1135927 | LILRA2 -- leukocyte immunoglobulin-like receptor, subfamily A (with TM domain), member 2 | 7.134470829 |
| 1120645 | FADS3 -- fatty acid desaturase 3 | 7.039952979 |

TABLE 2387

MCL vs. PMBL predictor genes

| UNIQID | Gene name | Scale Factor |
| --- | --- | --- |
| 1132834 | SOX11 -- SRY (sex determining region Y)-box 11 | 28.17593839 |
| 1100873 | ESTs | 17.90004832 |
| 1096503 | GL012 -- hypothetical protein GL012 | 17.43982729 |
| 1098840 | C3orf6 -- chromosome 3 open reading frame 6 | 17.37421052 |
| 1124734 | NA | 16.73821457 |
| 1135102 | PRKCB1 -- protein kinase C, beta 1 | 16.67436366 |
| 1103711 | *Homo sapiens* cDNA FLJ11833 fis, clone HEMBA1006579. | 16.57202026 |
| 1140416 | TOSO -- regulator of Fas-induced apoptosis | 15.64802242 |
| 1121757 | ADRB2 -- adrenergic, beta-2-, receptor, surface | 15.57336633 |
| 1140236 | SPAP1 -- SH2 domain containing phosphatase anchor protein 1 | 15.20264513 |

TABLE 2387-continued

MCL vs. PMBL predictor genes

| UNIQID | Gene name | Scale Factor |
| --- | --- | --- |
| 1099140 | ESTs, Moderately similar to hypothetical protein FLJ20378 [Homo sapiens] [H. sapiens] | 15.11929571 |
| 1099549 | ESTs | 14.92883027 |
| 1139054 | LOC58486 -- transposon-derived Buster1 transposase-like protein | 14.63422275 |
| 1138818 | ILF3 -- interleukin enhancer binding factor 3, 90 kDa | 14.50621028 |
| 1109444 | ESTs, Highly similar to IL24_HUMAN Interleukin-24 precursor (Suppression of tumorigenicity 16 protein) (Melanoma differentiation associated protein 7) (MDA-7) [H. sapiens] | 14.20430672 |
| 1124534 | KIAA0553 -- KIAA0553 protein | 14.18537487 |
| 1098277 | PRICKLE1 -- prickle-like 1 (Drosophila) | 13.98526258 |
| 1131687 | TLK1 -- tousled-like kinase 1 | 13.97468703 |
| 1125112 | PLCL2 -- phospholipase C-like 2 | 13.85714318 |
| 1125397 | Homo sapiens cDNA FLJ33389 fis, clone BRACE2006871. | 13.85049805 |

TABLE 2388

MCL vs. PTLD predictor genes

| UNIQID | Gene name | Scale Factor |
| --- | --- | --- |
| 1109603 | ESTs | 19.95553782 |
| 1138222 | NA | 15.95397369 |
| 1135138 | CD24 -- CD24 antigen (small cell lung carcinoma cluster 4 antigen) | 15.89198725 |
| 1134230 | RASGRP2 -- RAS guanyl releasing protein 2 (calcium and DAG-regulated) | 15.80452978 |
| 1139411 | OSBPL10 -- oxysterol binding protein-like 10 | 14.32818885 |
| 1140416 | TOSO -- regulator of Fas-induced apoptosis | 13.89685188 |
| 1132834 | SOX11 -- SRY (sex determining region Y)-box 11 | 13.78424818 |
| 1121739 | ZNF135 -- zinc finger protein 135 (clone pHZ-17) | 13.02195529 |
| 1098156 | Human HeLa mRNA isolated as a false positive in a two-hybrid-screen. | 12.95032605 |
| 1099270 | Homo sapiens cDNA FLJ30555 fis, clone BRAWH2003818. | 12.7877735 |
| 1139012 | FLJ20373 -- hypothetical protein FLJ20373 | 12.70176225 |
| 1120654 | EDG1 -- endothelial differentiation, sphingolipid G-protein-coupled receptor, 1 | 12.25264341 |
| 1120985 | KIAA0053 -- KIAA0053 gene product | 12.04626201 |
| 1115952 | LOC146517 -- hypothetical protein LOC146517 | 11.96299478 |
| 1120825 | CHL1 -- cell adhesion molecule with homology to L1CAM (close homolog of L1) | 11.82402907 |
| 1131636 | SPOCK2 -- sparc/osteonectin, cwcv and kazal-like domains proteoglycan (testican) 2 | 11.80417657 |
| 1136706 | MYT1 -- myelin transcription factor 1 | 11.74962191 |
| 1113560 | Homo sapiens, clone IMAGE: 5725893, mRNA | 11.72049882 |
| 1133851 | P4HA1 -- procollagen-proline, 2-oxoglutarate 4-dioxygenase (proline 4-hydroxylase), alpha polypeptide 1 | −12.59876059 |
| 1137459 | BCAT1 -- branched chain aminotransferase 1, cytosolic | −14.00465411 |

TABLE 2389

MCL vs. SLL predictor genes

| UNIQID | Gene name | Scale Factor |
| --- | --- | --- |
| 1132834 | SOX11 -- SRY (sex determining region Y)-box 11 | 23.59602107 |
| 1101987 | KIAA1909 -- KIAA1909 protein | 14.50254794 |
| 1103711 | Homo sapiens cDNA FLJ11833 fis, clone HEMBA1006579. | 13.31375894 |
| 1096070 | DNMT3A -- DNA (cytosine-5-)-methyltransferase 3 alpha | 12.37453972 |
| 1130926 | C5orf13 -- chromosome 5 open reading frame 13 | 11.27840239 |
| 1120845 | FADS3 -- fatty acid desaturase 3 | 11.14057287 |
| 1138099 | NA | 10.92729287 |
| 1097887 | KIAA0303 -- KIAA0303 protein | 10.37913127 |
| 1099941 | ESTs | 10.33953409 |
| 1130373 | KIAA0303 -- KIAA0303 protein | 10.01524528 |
| 1110957 | SYNE2 -- spectrin repeat containing, nuclear envelope 2 | 9.865436185 |

TABLE 2389-continued

MCL vs. SLL predictor genes

| UNIQID | Gene name | Scale Factor |
| --- | --- | --- |
| 1130320 | ESTs | 9.807091644 |
| 1124373 | LPIN1 -- lipin 1 | 9.024985551 |
| 1128813 | KREMEN2 -- kringle containing transmembrane protein 2 | 8.903791941 |
| 1131130 | MARCKS -- myristoylated alanine-rich protein kinase C substrate | 8.688979176 |
| 1120825 | CHL1 -- cell adhesion molecule with homology to L1CAM (close homolog of L1) | 8.685132271 |
| 1119752 | BASP1 -- brain abundant, membrane attached signal protein 1 | 8.663402838 |
| 1131854 | GCLC -- glutamate-cysteine ligase, catalytic subunit | −8.761521136 |
| 1105801 | *Homo sapiens* mRNA; cDNA DKFZp686H1529 (from clone DKFZp686H1529) | −8.828675125 |
| 1097824 | MAP2 -- microtubule-associated protein 2 | −9.345688564 |

TABLE 2390

MCL vs. splenic predictor genes

| UNIQID | Gene name | Scale Factor |
| --- | --- | --- |
| 1106855 | KIAA1909 -- KIAA1909 protein | 14.48278638 |
| 1121739 | ZNF135 -- zinc finger protein 135 (clone pHZ-17) | 11.95918572 |
| 1111850 | *Homo sapiens* cDNA FLJ36977 fis, clone BRACE2006344. | 11.13464157 |
| 1098024 | KIAA1972 -- KIAA1972 protein | 10.10869886 |
| 1130764 | HNRPA0 -- heterogeneous nuclear ribonucleoprotein A0 | 10.06898534 |
| 1135342 | SHOX2 -- short stature homeobox 2 | 9.565884385 |
| 1097218 | MGC45400 -- hypothetical protein MGC45400 | 9.187725705 |
| 1117193 | RINZF -- zinc finger protein RINZF | 9.12522795 |
| 1139584 | PSMD10 -- proteasome (prosome, macropain) 26S subunit, non-ATPase, 10 | 9.066714773 |
| 1132834 | SOX11 -- SRY (sex determining region Y)-box 11 | 8.908574745 |
| 1131130 | MARCKS -- myristoylated alanine-rich protein kinase C substrate | 8.732921026 |
| 1131756 | PDCD4 -- programmed cell death 4 (neoplastic transformation inhibitor) | 8.441424593 |
| 1102187 | DKFZp586C102 -- hypothetical protein DKFZp586C1021 | 8.391861029 |
| 1098195 | DKFZp762C111 -- hypothetical protein DKFZp762C1112 | 8.349839204 |
| 1101211 | *Homo sapiens* cDNA: FLJ21960 fis, clone HEP05517. | 8.337208237 |
| 1136673 | GNAS -- GNAS complex locus | 8.254076655 |
| 1139116 | USP16 -- ubiquitin specific protease 16 | 8.179384251 |
| 1098694 | LOC112868 -- hypothetical protein LOC112868 | 7.935903681 |
| 1120519 | WWP2 -- Nedd-4-like ubiquitin-protein ligase | −7.881202253 |
| 1114916 | FLJ13993 -- hypothetical protein FLJ13993 | −8.33683119 |

With so many candidate predictor genes being utilized, it is possible to generate a predictor, model that accurately predicts every element of a training set but fails to perform on an independent sample. This occurs because the model incorporates and "learns" the individual characteristics of each sample in the training set. Leave-one-out cross-validation was used to verify that the prediction models generated above would work on independent samples that the models had not encountered previously, in this cross-validation method, a single sample is removed from the training set, and the predictor is developed again using the remaining data. The resulting model is then used to predict the sample that was removed. This method is repeated with each individual sample taken out. Since no sample is predicted from a model that includes that sample, this method provides an unbiased estimate of predictor accuracy.

When the predictors developed above were evaluated by leave-one-out cross-validation. All but one of the 21 MCL samples were correctly identified as MCL and none of the 489 non-MCL samples were mistakenly identified as MCL.

Example 13: Identification of Lymphoma Samples as MCL Based on Bayesian Analysis of Gene Expression Data from a Lymphochip Microarray Lymphoma samples with morphology consistent with MCL were identified by pathological review. Since t(11;14) translocation and cyclin D1 overexpression have been consistently associated with MCL, cyclin D1 mRNA levels were measured in each sample by quantitative RT-PCR. Of the 101 samples analyzed, 92 expressed cyclin D1 mRNA. These 92 samples, which were deemed the "core group" of MCLs, were divided into a training set and a validation set. Gene expression was measured in all 101 samples using a Lymphochip Microarray (Alizadeh 1999). For comparison, gene expression was measured in 20 samples identified as SLL. In addition, MCL expression data was compared to expression data obtained previously for GCB (134 cases) and ABC (83 cases) (Rosenwald 2002). Several thousand genes were differentially expressed between cyclin D1-positive MCL and the other lymphoma types with high statistical significance ($p<0.001$). A complete listing of these genes is available at http://llmpp.nih.gov/MCL.

Three different binary predictor models were developed: MCL vs. SLL, MCL vs. GCB, and MCL vs. ABC. Each of these models was designed to calculate the probability that a sample was MCL rather than the other lymphoma type in the pair. For each pair, the genes that were most differentially expressed between MCL and the other lymphoma type in the pair were identified, and the difference in expression between the lymphoma types was quantified using a Student's t-test. An LPS was then calculated for each sample using the following formula:

$$LPS(X) = \sum_{j=0} t_j X_j,$$

where $X_j$ is the expression of gene j in sample X and $t_j$ is the t-statistic for the difference in expression of gene j between the two lymphoma types in the pair. Cyclin D1 was excluded from the calculation of LPS so that the model could be used to identify potential MCL cases that were cyclin D1 negative.

After an LPS had been formulated for each lymphoma sample, the mean and standard deviation of these LPS's was calculated for each lymphoma type. For a new sample X, Bayes' rule can be used to estimate the probability q that the sample belongs to MCL rather than the second lymphoma type in the pair using the following equation:

$$q(X \text{ is } MCL) = \frac{\phi(LPS(X); \hat{\mu}_{MCL}, \hat{\sigma}_{MCL})}{\phi(LPS(X); \hat{\mu}_{MCL}, \hat{\sigma}_{MCL}) + \phi(LPS(X); \hat{\mu}_2, \hat{\sigma}_2)}$$

where $\phi(x; \mu, \sigma)$ is the normal density function with mean $\mu$ and standard deviation $\sigma$, $\hat{\mu}_{MCL}$ and $\hat{\sigma}_{MCL}$ are the sample mean and variance of the LPS values for MCL, and $\hat{\mu}_2$ and $\hat{\sigma}_2$ are the sample mean and variance of the LPS values for the second lymphoma type of the pair. A cut-off point of 90% was selected for assigning a sample to a particular lymphoma type. Every sample in the training set was classified correctly using this model (FIG. 16). When applied to the validation set, the model correctly classified 98% of the cyclin D1-positive MCL cases as MCL (FIG. 16).

This diagnostic test was applied to nine lymphoma cases that were morphologically consistent with MCL, but negative for cyclin D1 expression. Seven of these samples were classified as MCL, one was classified as GCB, and one was not assigned to any lymphoma type because none of the pairs generated a probability of 90% or greater.

Example 14: Classification of DLBCL Samples Based on Bayesian Analysis of Gene Expression Data from the Lymphochip Microarray A statistical method to classify DLBCL samples based on Bayesian analysis was developed using gene expression data obtained using the Lymphochip cDNA microarray (Rosenwald 2002); This data is available at http://llmpp.nih.gov/DLBCL. The data was divided into two sets; a training set used to create and optimize the prediction model, and a validation set to evaluate the performance of the model. The training set consisted of 42 ABC DLBCL samples and 67 GCB DLBCL samples, while the validation set consisted of 41 ABC DLBCL samples, 67 GCB DLBCL samples, and 57 type 3 DLBCL samples (Shipp 2002).

Genes that were listed as present on >50% of the samples were identified, and the signal value for these genes on each microarray was normalized to 1,000. After normalization, all signal values under 50 were set to 50. A $\log_2$ transformation was then performed on all the signal values.

An LPS for distinguishing between two lymphoma types was calculated for each sample X in the training set using an equation:

$$LPS(X) = \sum_j t_j X_j,$$

where $X_j$ represents the expression level of gene j and $t_j$ is a scaling factor whose value depends on the difference in expression of gene j between the two lymphoma types. The scaling factor used in this example was the t-statistic generated by a t test of the difference in gene j expression between two lymphoma types. Only those genes with the largest t-statistics were included when calculating the LPS for each sample. The list of genes used to generate the LPS was narrowed further by including only those genes that were most variably expressed within the training set. Only genes in the top third with respect to variance were included. Genes that displayed a correlation with proliferation or lymph node signatures (Shaffer 2001; Rosenwald 2002) were eliminated from consideration, because these genes are often variably expressed within samples from a single lymphoma type (Rosenwald 2002).

Since the LPS is a linear combination of gene expression values, its distribution within each lymphoma type should be approximately normal, provided that it includes a sufficient number of genes and the correlation structure of those genes is not extreme. The mean and variance of these normal distributions within a lymphoma type can then be estimated from the combined LPS's of all samples within the type. The LPS distribution of two lymphoma types can be used to estimate the probability that a new sample belongs to one of the types using Bayes' rule. The probability q that a sample Y belongs to lymphoma type 1 can be determined by an equation:

$$q(Y \text{ is subtype } 1) = \frac{\phi(LPS(Y); \hat{\mu}_1, \hat{\sigma}_1)}{\phi(LPS(Y); \hat{\mu}_1, \hat{\sigma}_1) + \phi(LPS(Y); \hat{\mu}_2, \hat{\sigma}_2)}$$

where $\phi(x; \mu, \sigma)$ is the normal density function with mean $\mu$ and standard deviation $\sigma$, $\hat{\mu}_1$ and $\hat{\sigma}_1$ are the sample mean and variance of the LPS values for lymphoma type 1, and $\hat{\mu}_2$ and $\hat{\sigma}_2$ are the sample mean and variance of the LPS values for lymphoma type 2. This calculation was used to determine the probability that each sample in the training set belonged to GCB or ABC. A sample was classified as a particular type if it had a 90% or greater probability of belonging to that type. The number of genes in the predictor model was optimized based on the accuracy with which the predictor classified samples into the ABC or GCB subtypes defined previously by hierarchical clustering (Rosenwald 2002). The final predictor incorporated 27 genes, and correctly classified 87% of the training set samples into the subtype to which they had been assigned by hierarchical clustering (FIG. 17). The genes included in the predictor are listed in Table 2391.

TABLE 2391

| UNIQID | Unigene ID Build 167 (http://www.ncbi.nlm.nih.gov/UniGene) | Gene symbol |
|---|---|---|
| 19375 | 235860 | FOXP1 |
| 19346 | 109150 | SH3BP5 |
| 19227 | 193857 | LOC96597 |
| 16049 | 439852 | IGHM |
| 32529 | 55098 | C3orf6 |
| 24729 | 127686 | IRF4 |
| 24899 | 81170 | PIM1 |
| 19348 | NA | NA |
| 27565 | 444105 | ENTPD1 |
| 17227 | 170359 | IL16 |
| 26919 | 118722 | FUT8 |
| 24321 | 171262 | ETV6 |
| 29385 | 167746 | BLNK |
| 16858 | 376071 | CCND2 |
| 31801 | 386140 | BMF |
| 19234 | 418004 | PTPN1 |
| 26385 | 307734 | MME |
| 24361 | 388737 | NA |
| 24570 | 446198 | NA |
| 24904 | 18166 | KIAA0870 |
| 24429 | 155024 | BCL6 |
| 28224 | 387222 | NEK6 |
| 27673 | 124922 | LRMP |
| 24376 | 317970 | SERPINA11 |
| 17496 | 300592 | MYBL1 |
| 17218 | 283063 | LMO2 |
| 28338 | 78877 | ITPKB |

Since the samples used to estimate the distribution of the LPS's were the same samples used to generate the model, there was a possibility of overfitting. Overfitting would result in a model that indicates a larger separation between the LPS's of two lymphoma types than would be found in independent data. To insure that overfitting was not taking place, the model was tested on the validation set. The reproducibility of the predictor model was verified by its ability to correctly classify 88% of the samples in the validation set (FIG. 18). Interestingly, 56% of the DLBCL samples that had been placed in the type 3 subtype by hierarchical clustering were classified as either ABC or GCB using this Bayesian model.

In previous experiments, the genes that were used to distinguish GCB and ABC were deliberately selected to include those that were preferentially expressed in normal GCB cells (Alizadeh 2000; Rosenwald 2002). In the present analysis, the predictor model was not biased a priori to include such genes. The ABC and GCB lymphoma types as defined by the Bayesian model were analyzed for differential expression of GCB cell restricted genes. Thirty seven genes were found to be both more highly expressed in GCB cells than at other stages of differentiation (p<0.001) and differentially expressed between DLBCL subtypes (p<0.001) (FIG. 19A). These 37 genes are listed in Table 2392.

TABLE 2392

| UNIQID | Unigene ID Build 167 (http://www.ncbi.nlm.nih.gov/UniGene) | Gene symbol |
|---|---|---|
| 28014 | 300592 | MYBL1 |
| 24376 | 317970 | SERPINA11 |
| 24429 | 155024 | BCL6 |
| 16886 | 124922 | LRMP |
| 27374 | 283063 | LMO2 |
| 29912 | 446198 | |
| 24510 | 266175 | PAG |
| 24854 | 439767 | TOX |
| 32171 | 307734 | MME |
| 24361 | 388737 | |
| 19365 | 171857 | Cyorf15a |
| 27292 | 272251 | KLHL5 |
| 24822 | 283794 | PCDHGC3 |
| 30923 | 446195 | |
| 24825 | 88556 | HDAC1 |
| 31696 | 91139 | SLC1A1 |
| 26976 | 434281 | PTK2 |
| 19279 | 49614 | GCET2 |
| 17866 | 1765 | LCK |
| 24386 | 437459 | MYO1E |
| 33013 | 293130 | VNN2 |
| 25126 | | |
| 30498 | 157441 | SPI1 |
| 26512 | 379414 | MFHAS1 |
| 26582 | 153260 | SH3KBP1 |
| 17840 | 132311 | MAP2K1 |
| 26000 | 25155 | NET1 |
| 24323 | 149342 | AICDA |
| 30922 | 435904 | C21orf107 |
| 30641 | 79299 | LHFPL2 |
| 19308 | 179608 | DHRS9 |
| 24455 | 405387 | |
| 30034 | 300208 | SEC231P |
| 24977 | 169939 | HS2ST1 |
| 24449 | 206097 | RRAS2 |
| 30763 | 446198 | |
| 27987 | 73792 | CR2 |

All but two (AICDA and DHRS9) of these 37 genes were more highly expressed in GCB than in ABC. This demonstrates that the DLBCL subtypes defined by the Bayesian predictor seem to differ with respect to their cell of origin, with GCB retaining the gene expression program of normal GCB cells.

ABC, on the other hand, displayed higher expression of genes characteristic of plasma cells (FIG. 19B). Twenty four genes were found to be both more highly expressed in plasma cells than in B cells at earlier developmental stages (p<0.001) and differentially expressed between the DLBCL subtypes (p<0.001). These 24 genes are listed in Table 2393.

TABLE 2393

| UNIQID | Unigene ID Build 167 (http://www.ncbi.nlm.nih.gov/UniGene) | Gene symbol |
|---|---|---|
| 16614 | 127686 | IRF4 |
| 26907 | 118722 | FUT8 |
| 31104 | 313544 | NS |
| 19219 | 355724 | CFLAR |
| 26174 | 28707 | SSR3 |
| 24566 | 169948 | KCNA3 |
| 34500 | 442808 | B4GALT2 |
| 26991 | 314828 | UPP1 |
| 30191 | 438695 | FKBP11 |
| 27402 | 259855 | EEF2K |
| 26096 | 434937 | PPIB |
| 15887 | 2128 | DUSP5 |
| 32440 | 512686 | C20orf69 |
| 34827 | 429975 | PM5 |
| 29232 | 437638 | XBP1 |
| 17763 | 76640 | RGC32 |
| 32163 | 445862 | RAB30 |
| 17814 | 5353 | CASP10 |
| 31460 | 409223 | SSR4 |
| 26693 | 83919 | GCS1 |
| 25130 | 409563 | PACAP |
| 16436 | 267819 | PPP1R2 |
| 31610 | 76901 | PDIR |
| 28961 | 212296 | ITGA6 |

The majority of these plasma cell-restricted genes were more highly expressed in ABC than in GCB. Eight of the 32 genes encode proteins that reside and function in the endoplasmic reticulum (ER) or Golgi apparatus, suggesting that ABCs have increased the intracellular machinery for protein secretion. These eight genes are denoted in the above list by the designation "ER" or "goigi" in parentheses. Another gene on this list, XBP-1 transcription factor, encodes a protein that is required for plasma cell differentiation (Reimold 2001) and is involved in the response to unfolded proteins in the ER (Calfon 2002). ABCs have not undergone full plasmacytic differentiation, however, because other key plasma cell genes such as Blimp-1 were not more highly expressed in ABC.

Example 15: Classification of DLBCL Samples Based on Bayesian Analysis of Gene Expression Data from the Affymetrix HU6860 Microarray The prediction method described in Example 14 above was applied to gene expression data from 58 DLBCL samples obtained using an Affymetrix HU6800 oligonucleotide microarray (Shipp 2002). This data is available at www.genome.wi.mit.edu/MPR/lymphoma. The first step in analyzing this data was to exclude all microarray features with a median signal value of <200 across the samples. Multiple microarray features representing the same gene were then averaged. Of the 27 genes in the DLBCL subtype predictor developed using the Lymphochip data (above), only 14 were represented on the Affymetrix array and passed this filtering process. These 14 genes (are listed in Table 2394.

TABLE 2394

| UNIQID | Unigene ID Build 167 (http://www.ncbi.nlm.nih.gov/UniGene) | Gene symbol |
|---|---|---|
| 24729 | 127686 | IRF4 |
| 17227 | 170359 | IL16 |
| 26907 | 118722 | FUT8 |
| 27565 | 444105 | ENTPD1 |
| 16858 | 376071 | CCND2 |
| 24899 | 81170 | PIM1 |
| 16947 | 418004 | PTPN1 |
| 16049 | 439852 | IGHM |
| 26385 | 307734 | MME |
| 27673 | 124922 | LRMP |
| 24429 | 155024 | BCL6 |
| 17218 | 283063 | LMO2 |
| 28338 | 78877 | ITPKB |
| 17496 | 300592 | MYBL1 |

These 14 genes were used to create a new DLBCL subtype predictor in which the LPS scaling coefficients were again calculated based on the DLBCL subtype distinction in the Lymphochip data set (Rosenwald 2002). To account for systematic measuring differences between the Affymetrix and Lymphochip microarrays, the expression value of each gene on the Affymetrix microarray was shifted and scaled to match the mean and variance of the corresponding expression values on the Lymphochip. The adjusted expression values for each of the 14 genes were then used to calculate LPS's for each sample. DLBCL subtype membership was again assigned on a cut-off of 90% certainty. Several observations suggested that the predictor identified ABC and GCB samples within the Affymetrix data set that were comparable to those found in the Lymphochip data set. First, the relative proportions of ABC (29%) and GCB (53%) were very similar to the corresponding proportions in the Lymphochip data set (34% and 49%, respectively). Second, 43 genes were found to be differentially expressed between the two DLBCL subtypes with high significance (p<0.001) in the Affymetrix data. This number is substantially higher than would be expected by chance, given that the Affymetrix microarray measures the expression of approximately 5,720 genes. The symbols for these 43 genes were: IGHM; TCF4; IRF4; CCND2; SLA; BATF; KIAA0171; PRKCB1; P2RX5; GOT2; SPIB; CSNK1E; PIM2; MARCKS; PIM1; TPM2; FUT8; CXCR4; SP140; BCL2; PTPN1; KIAA0084; HLA-DMB; ACP1; HLA-DQA1; RTVP1; VCL; RPL21; ITPKB; SLAM; KRT8; DCK; PLEK; SCA1; PSIP2; FAM3C; GPR18; HMG14; CSTB; SPINK2; LRMP; MYBL1; and LMO2. Third, the 43 genes differentially expressed between the types included 22 genes that were not used in the predictor but were represented on Lymphochip arrays. Fourteen of these 22 genes were differentially expressed on the Lymphochip array with high statistical significance (p<0.001). Finally, the expression of the c-rel gene was previously found to correspond to amplification of the c-rel genomic locus in DLBCL tumor cells, and oncogenic event occurring in GCB but not ABC (Rosenwald 2002). In the Affymetrix data set, c-rel was differentially expressed between the two subtypes (p=0.0025), and was highly expressed only in a subset of GCB's.

Example 16: Identification of DLBCL Samples as PMBL Based on Bayesian Analysis of Gene Expression Data from the Lymphochip Microarray 310 lymphoma biopsy samples identified as DLBCL by a panel of hematopathologists were divided into a 36 sample training set and a 274 sample validation set, with the validation set consisting of the DLBCL samples classified previously in Example 14. All patients from whom the sample's were derived had been treated with anthracycline-containing multiagent chemotherapy protocals, with some patients additionally receiving radiation therapy. The training set was profiled for gene expression using Lymphochip microarrays comprising 15,133 cDNA elements as described previously (Alizadeh 2000). This data is available at http://llmpp.nih.gov/PMBL. The validation set had previously been profiled using Lymphochip microarrays comprising 12,196 cDNA elements (Rosenwald 2002). This data is available at http://llmpp.nih.gov/DLBCL.

A hierarchical clustering algorithm (Elsen 1998) was used to organize the genes by their expression patterns across the 36 samples in the training set. A large group of genes that were more highly expressed in lymphomas with mediastinal involvement than in other DLBCLs was shown to be tightly clustered in the resulting dendrogram (FIG. 20A). This cluster of genes included two genes, MAL and FIG1, previously shown to be highly expressed in PMBL (Copie-Bergman 2002; Copie-Bergman 2003). Several of the lymphomas with mediastinal involvement did not express this set of putative PMBL signature genes, and it was, suspected that these samples were more likely to be conventional DLBCL than PMBL. Hierarchical clustering was used to organize the samples according to their expression of the PMBL signature genes, resulting in two major clusters of cases (FIG. 20B). One cluster contained 21 samples designated "PBML core" samples by virtue of their higher expression of PMBL signature genes. The other cluster contained some samples that had virtually no expression of these genes, and other samples that did express these genes but at lower levels than the PMBL core samples.

A gene expression-based method for distinguishing PMBL core cases from GCB and ABC DLBCL cases based on Bayesian analysis was developed using the methods described in Examples 14 and 15, A set of genes were selected that were differentially expressed between the PMBL core samples and both GCB and ABC (p<0.001). This set of genes included all of the PMBL signature genes identified by hierarchical clustering (FIG. 20A), as well as a large number of additional genes. Many of the genes in this set belonged to the lymph node gene expression signature (Alizadeh 2000; Rosenwald 2002). These genes were excluded from the final predictor because they might cause some DLBCL samples with higher expression of lymph node gene expression signature genes to be misclassified as PMBL. The list of PMBL distinction genes was refined by adding a requirement that they also be differentially expressed between the PMBL core samples and a subgroup of six DLBCL samples with higher expression of lymph node gene expression signature genes (p<0.001). The resulting set of 46 genes included 35 genes that were more highly expressed in PMBL and 11 genes that were more highly expressed in DLBCL (FIG. 21A). The 46 genes in this set were PDL2, SNFT, IL13RA1, FGFR1, FLJ10420, CCL17/TARC, TNFRSF8/CD30, E2F2, MAL, TNFSF4/OX40 ligand, IL411/Fig1, IMAGE:686580, BST2, FLJ31131, FCER2/CD23, SAMSN1, JAK2, FLJ00066, MST1R, TRAF1, SLAM, LV75, TNFRSF6/Fas, FNBP1, TLR7, TNFRSF17/BCMA, CDKN1A/p21CIP1, RGS9, IMAGE:1340506, NFKB2, KIAA0339, ITGAM, IL23A, SPINT2, MEF2A, PFDN6, ZNF141, IMAGE:4154313, IMAGE:825382, DLEU1, ITGAE, SH3BP5, BANK, TCL1A, PRKAR1B, and CARD11. A series of linear predictor scores were generated based on the expression of this gene set. Based on the distribution of linear predictor scores within; a particular lymphoma type, Bayes' rule can be used to estimate the probability that a particular sample belongs to either of the two types. An arbitrary probability cut-off of 90% or greater was used to classify a sample as a particular lymphoma type. All of the PMBL core samples were classified as PMBL using this method, as were six of the other lymphoma samples with mediastinal involvement. However, nine of the lymphoma samples with mediastinal involvement were classified as a DLBCL, as were all of the GCB and ABC samples.

In the validation set, 11 samples were identified on clinical grounds as being consistent with a diagnosis of PMBL, and the Bayesian model classified nine of these as PMBL (FIG. 21B). Interestingly, 12 of the remaining 263 DLBCL samples were classified as PMBL by the predictor. FIG. 21B shows that these cases were indistinguishable by gene expression from the nine cases diagnosed as PMBL on clinical grounds. As expected, the average expression of the PMBL predictor genes in the 249 samples classified as DLBCL was notably lower than in the 22 PMBL cases. Thus, PMBL represents a third subgroup of DLBCL than can be distinguished from ABC and GCB by gene expression profiling.

Table 2395 compares the clinical parameters of patients assigned to the PMBL, ABC, and GCB subgroups of DLBCL using this prediction method.

TABLE 2395

|  | ABC DLBCL | GCB DLBCL | PMBL Training set | PMBL Validation set | PMBL All cases | P value |
| --- | --- | --- | --- | --- | --- | --- |
| Median age | 66 | 61 | 33 | 33 | 33 | 4.4E−16 |
| Age <35 | 5% | 10% | 52% | 56% | 53% | 7.2E−14 |
| Age 35-60 | 29% | 38% | 44% | 28% | 37% |  |
| Age >60 | 66% | 52% | 4% | 17% | 9% |  |
| Gender = male | 59% | 53% | 44% | 50% | 47% | 0.38 |
| Female <35 | 2% | 3% | 32% | 39% | 35% | 1.1E−12 |
| Male <35 | 2% | 7% | 20% | 17% | 19% |  |
| Female 35-60 | 6% | 18% | 24% | 6% | 16% |  |
| Male 35-60 | 23% | 19% | 20% | 22% | 21% |  |
| Female >60 | 33% | 25% | 0% | 6% | 2% |  |
| Male >60 | 34% | 27% | 4% | 11% | 7% |  |

PMBL patients were significantly younger than other DLBCL patients, with a median age at diagnosis of 33 years compared with a median age of 66 and 61 years for ABC and GCB patients, respectively. Although there was no significant difference in gender distribution among the DLBCL subgroups, young women (<35 years) accounted for 35% of PMBL patients, more than any other DLBCL subgroup. Young men (<35 years) were also more frequently represented in the PMBL subgroup, accounting for 19% of the patients. Correspondingly, older men and women (age>60) were significantly underrepresented in the PMBL subgroup. These clinical characteristics were observed in both the training set and the validation set of PMBL cases, demonstrating that the PMBL predictor reproducibly identified a clinically distinct subgroup of DLBCL patients.

The PMBL subgroup defined by the PMBL predictor had a relatively favorable overall survival rate after therapy (FIG. 22). PMBL patients had a five-year survival rate of 84%, superior to the 46% rate seen in DLBCL patients as a whole (p=0.0067). The survival of the PMBL subgroup was significantly better than the 30% five-year survival rate of the ABC subgroup (FIG. 22; p=5.8E-5), but only marginally better than the 59% five-year survival rate of the GCB subgroup (p=0.18).

Example 17: Classification of Lymphomas Into Types Based on Bayesian Analysis of Gene Expression Data from the Lymph Dx Microarray Based on the clustering of the Lymph Dx microarray signals for the DLBCL samples, a cluster of "proliferation signature" genes and a cluster of "lymph node signature" genes were identified, the expression of these genes was averaged to form a proliferation signature and a lymph node signature. Each gene represented on the Lymph Dx microarray was placed into one of three "gene-list categories" based on its correlation with the proliferation or lymph node gene signatures. "Proliferation" genes were defined as those genes for which the correlation between their expression and the proliferation signature was greater than 0.35. Lymph node genes were defined as those genes for which the correlation between their expression and the lymph node signature was greater than 0.35. The remaining genes on the array were classified as standard genes. This classification resulted in 323 proliferation genes and 375 lymph node genes.

Two stages of lymphoma classification were performed using the gene expression data obtained for the above samples using the Lymph Dx microarray. The general procedure used to classify the samples is presented in flow chart form in FIG. 1.

For the first stage of expression analysis, the samples were divided into five types: FL, MCL, SLL, FH, and a class of aggressive lymphomas that included DLBCL and BL. Samples obtained from subjects with other diagnoses (e.g., MALT, LPC) were omitted from this analysis. Data from the Lymph Dx microarray was then used to compare gene expression in each possible lymphoma type pair (e.g., FH vs. FL, MCL vs. SLL, etc.). This resulted in the creation of ten "pair-wise models" (one for each possible lymphoma type pair) for predicting whether a sample fell into a particular lymphoma type.

For each lymphoma type pair, the difference in expression between the two; types for every gene on the microarray was calculated, and a t-statistic was generated to represent this difference. Within each gene-list category (proliferation, lymph node, and standard), individual genes were ordered based on the absolute value of their t-statistic. Only those genes that displayed a statistically significant difference in expression between the two types were included in the model. Those genes with largest absolute t-statistics in each gene-list category were then used to generate a linear predictor score (LPS) for each sample. For a sample X and a set of genes G, the LPS was defined as:

$$LPS(X) = \sum_{j=0} t_j X_j,$$

where $X_j$ is the expression of gene j in the sample and $t_j$ is the t-statistic representing the difference in expression of gene j between the two lymphoma types. This formulation of LPS, known as the compound coagulate predictor, has previously been used successfully (Radmacher 2002; Rosenwald 2003a; Wright 2003). Other ways to formulate an LPS include Fisher linear discriminant analysis (Dudolt 2002), weighted voting (Golub 1999), linear support vector machines (Ramaswamy 2001), and nearest shrunken centroids (Tibshirani 2002).

In order to optimize the number of genes used to generate the LPS, a series of LPS's were generated for each sample using between five and 100 genes from each gene-list category. The optimal number of genes is that number which generates a maximum t-statistic when comparing the LPS of two samples from different lymphoma types (FIG. 23). This optimization procedure was repeated for every geno-list category in every pair-wise model, meaning that 30 optimizations were performed in all.

It was recognized that for some pair-wise models, it would be useful to calculate LPS's using different combinations of gene-list categories. LPS's were calculated for each sample using four different combinations. In the first, LPS was calculated using the standard genes only. In the second, LPS's were calculated for both the standard and proliferation genes, but not for the lymph node genes. In the third, LPS's were calculated for both the standard and lymph node genes, but not the proliferation genes. In the fourth, LPS's were calculated using all three gene-list categories.

Depending on the number of gene-list categories included, between one and three LPS's were calculated for each sample in the pair-wise models. Thus, each sample could be thought of as a vector in a space of between one and three dimensions. Since the LPS's were sums of individual expressions, it was reasonable to approximate the distributions as normal. Multivariate normal distributions are defined by two quantities: a mean vector, which indicates the average value of each of the models within a given lymphoma type, and a covariance matrix, which indicates the magnitude and orientation spread of points away from this center. Both of these quantities can be estimated empirically from the observed data. FIG. 24 shows the Standard and Proliferation LPS's for the FL vs. DLBCL/BL pair-wise model. The dotted lines indicate the standard deviations from the fitted multivariate normal distributions.

Once the multidimensional distributions have been estimated, Bayes' rule (Bayes 1763) can be used to estimate the probability that a given sample belongs to one lymphoma type or another. Bayesian analysis of an LPS has been successfully employed in the past to distinguish DLBCL subtypes (Rosenwald 2003a, Wright 2003). For a sample X, the probability q of the sample belonging to a first lymphoma type rather than a second lymphoma type can be calculated using the formula:

$$q = \frac{\phi(LPS(X); \hat{\mu}_1, \hat{\sigma}_1)}{\phi(LPS(X); \hat{\mu}_1, \hat{\sigma}_1) + \phi(LPS(X); \hat{\mu}_2, \hat{\sigma}_2)}$$

where LPS(X) is the linear predictor score for sample X, $\phi(x, \mu, \sigma)$ is the normal density function with mean $\mu$ and standard deviation $\sigma$, $\hat{\mu}_1$ and $\hat{\sigma}_1$ are the mean and variance of the LPS's for the first lymphoma type, and $\hat{\mu}_2$ and $\hat{\sigma}_2$ are the mean and variance of the LPS's for the second lymphoma type. Using this equation, a single probability q value can be developed for each sample and for each of the four LPS combinations. This q value can then be used to classify a sample as a first lymphoma type, a second lymphoma type, or unclassified. Samples with the highest q values are classified as the first lymphoma type, while samples with the lowest q values are classified as the second lymphoma type. Samples with middle range q values are deemed unclassified. Classifying the samples in this manner requires two cut-off points: a lower cut-off point between the second lymphoma type and unclassified, and an upper cut-off point between unclassified and the first lymphoma type. To develop these cut-off points, samples were ordered by their q values, band each possible cut-off point between adjacent samples was considered. To ensure that the cut-off points were reasonable, the lower cut-off point was restricted to between 0.01 and 0.5 and the upper cut-off point was restricted to between 0.5 and 0.99.

Every cut-off point and model combination was analyzed by the following equation:

3.99*[(% of type 1 misidentified as type 2)+(% of type 2 misidentified as type 1)]+[(% of type 1 unclassified)+(% of type 2 misidentified)].

Using this equation, the cut-off point would be adjusted to allow an additional error only if this adjustment resulted in four or more unclassified samples becoming correctly classified. The final model and cut-off point for a given pair-wise analysis was that which minimized this equation. The equation utilizes percentages rather than the actual number of cases in order to account for the different number of samples in each class.

All cut-off points between a given pair of adjacent g-values will produce the same division of data. Since cut-off point optimality is defined in terms of dividing the data into subtypes, all cut-off points between a pair of borderline cases will be equally optimal, in choosing where to place the actual cut-off point values, values were chosen that would lead to a larger unclassified region. When the lower cut-off point was being defined, a value would be chosen that was ⅕ of the way from the smallest borderline case to the largest. When the upper cut-off point was being defined, a value would be chosen that was ⅘ of the way from the smallest borderline case to the largest. FIG. 25 illustrates the q-results of optimizing the cut-point for the FL versus DLBCL/BL samples. The optimal lower cut-off point for these samples was found at q=0.49, while the optimal upper cut-off point was found at q=0.84. FIG. 26 indicates; how this choice of cut-off points divided the space of LPS's.

The above procedures resulted in a series of pair-wise models for comparing every lymphoma type to every other lymphoma type. If there are n types, then there will be n−1 pair-wise models for each type. Since there were five lymphoma types in the stage 1 analysis, each type was involved in 4 pair-wise models. For instance, there were four different pair-wise models for MCL; MCL vs. FH, MCL vs. FL, MCL vs. SLL, and MCL vs. DLBCL/BL. For each sample tested, each pair-wise model will produce one of three possible results: 1) the sample belongs to the first lymphoma type of the pair-wise model, 2) the sample belongs to the second lymphoma type of the pair-wise model, or 3) the sample is unclassified. If each of the n−1 models agrees that the sample belongs to a particular lymphoma type, then the sample is designated as belonging to that type. If the n−1 models do not all agree that the sample belongs to a particular lymphoma type, the sample is designated as unclassified.

To ensure that the above methods did not result in overfitting (i.e., models that fit particular idiosyncrasies of the training set but fail when applied to independent data), the models were validated by leave-one-out cross-validation fashion (Hills 1966). Each sample was removed from the data one at a time, and a predictive model was developed as described above using the remaining data. This model was then used to predict the sample that was removed. Since the model being used to predict a given sample was generated from data that did not include that sample, this method provided an unbiased estimate of the accuracy of the model.

The results of the leave-one-out predictions are set forth in Tables 2396 and 2397, below. The rows in each table correspond to different sample groups, while the columns indicate the prediction results. The standard to which the prediction results were compared in this stage was the diagnoses of a panel of eight expert hematopathologists who used histological morphology and immunohistochemistry to classify the samples. Table 2396 provides classification results for the five lymphoma types tested (DLBCL/BL, FL, FH, MCL, SLL), while Table 2397 provides more specific results for classification of subtypes within these five lymphoma types. The results set forth in Table 2396 are also summarized in FIG. 27.

TABLE 2396

|  | DLBCL/BL | FL | FH | MCL | SLL | Unclassified | Total | % Correct | % Unclassified | % Error |
|---|---|---|---|---|---|---|---|---|---|---|
| DLBCL/BL | 249 | 6 | 0 | 0 | 0 | 7 | 262 | 95% | 2% | 3% |
| FL | 5 | 154 | 0 | 0 | 0 | 14 | 173 | 89% | 8% | 3% |
| FH | 0 | 0 | 17 | 0 | 0 | 0 | 17 | 100% | 0% | 0% |
| MCL | 0 | 0 | 0 | 22 | 0 | 0 | 22 | 100% | 0% | 0% |
| SLL | 0 | 0 | 0 | 0 | 14 | 0 | 14 | 100% | 0% | 0% |

TABLE 2397

|  | DLBCL/BL | FL | FH | MCL | SLL | Unclassified | Total | % Correct | % Unclassified | % Error |
|---|---|---|---|---|---|---|---|---|---|---|
| ABC | 78 | 0 | 0 | 0 | 0 | 0 | 78 | 100% | 0% | 0% |
| GCB | 77 | 4 | 0 | 0 | 0 | 4 | 85 | 91% | 5% | 5% |
| PMBL | 33 | 0 | 0 | 0 | 0 | 0 | 33 | 100% | 0% | 0% |
| Unclassified DLBCL | 27 | 1 | 0 | 0 | 0 | 2 | 30 | 90% | 7% | 3% |
| DLBCL (not yet subclassed) | 14 | 0 | 0 | 0 | 0 | 1 | 15 | 93% | 7% | 0% |
| BL | 20 | 1 | 0 | 0 | 0 | 0 | 21 | 95% | 0% | 5% |
| FL grade 1 | 1 | 78 | 0 | 0 | 0 | 3 | 82 | 95% | 4% | 1% |
| FL grade 2 | 2 | 58 | 0 | 0 | 0 | 3 | 63 | 92% | 5% | 3% |
| FL grade 3A | 2 | 18 | 0 | 0 | 0 | 8 | 28 | 64% | 29% | 7% |
| Combined FL grades 1, 2, 3A | 5 | 154 | 0 | 0 | 0 | 14 | 173 | 89% | 8% | 3% |
| FL grade 3B | 2 | 1 | 0 | 0 | 0 | 4 | 7 | 14% | 57% | 29% |
| FL unknown grade | 3 | 11 | 0 | 0 | 0 | 0 | 14 | 79% | 0% | 21% |
| FH | 0 | 0 | 17 | 0 | 0 | 0 | 17 | 100% | 0% | 0% |
| MCL | 0 | 0 | 0 | 22 | 0 | 0 | 22 | 100% | 0% | 0% |
| SLL | 0 | 0 | 0 | 0 | 14 | 0 | 14 | 100% | 0% | 0% |

As seen in Table 2396, perfect prediction of SLL, MCL, and FH samples was obtained. The success rate for predicting FL and the aggressive lymphomas (DLBCL/BL) was also very good, with only 3% of the samples being classified incorrectly. As seen in Table 2397, perfect prediction was also obtained for ABC and PMBL samples within the DLBCL samples.

Example 18: Classification of DLBCL/BL Samples Into Subtypes Based on Bayesian Analysis of Gene Expression Data from the Lymph Dx Microarray Samples identified as DLBCL/BL in Example 17 were subdivided into four types: ABC, GCB, PMBL, and BL. These samples were then used to generate six pair-wise models using the same procedure described in Example 17. The results of the leave-one-out predictions using these pair-wise models are set forth in Table 2398, below. Those results are also summarized in FIG. 28. The rows in the table correspond to different sample groups, while the columns indicate the prediction results. In this stage, the ability of the prediction method to identify BL was again measured against the diagnoses of hematopathologists. The ability of the prediction method to identify the various DLBCL subtypes, on the other hand, was measured against previous studies in which this distinction between subtypes was based on gene expression data from a Lymphochip microarray (Alizadeh 2000, Rosenwald 2002, Rosenwald 2003a, Wright 2003).

TABLE 2398

| | ABC | GCB | PMBL | BL | Unclassified | Total | % Correct | % Unclassified | % Error |
|---|---|---|---|---|---|---|---|---|---|
| ABC | 76 | 0 | 0 | 0 | 2 | 78 | 97% | 3% | 0% |
| GCB | 1 | 66 | 2 | 4 | 4 | 77 | 86% | 9% | 5% |
| PMBL | 0 | 2 | 27 | 0 | 4 | 33 | 82% | 12% | 6% |
| Unclassified DLBCL | 5 | 9 | 1 | 1 | 11 | 27 | NA | 41% | 4% |
| DLBCL (not yet subclassed) | 5 | 5 | 0 | 1 | 3 | 14 | NA | 21% | 7% |
| BL | 0 | 1 | 0 | 18 | 1 | 20 | 90% | 5% | 5% |
| FL grade 1 | 0 | 1 | 0 | 0 | 0 | 1 | | | |
| FL grade 2 | 0 | 1 | 0 | 0 | 1 | 2 | | | |
| FL grade 3A | 0 | 2 | 0 | 0 | 0 | 2 | | | |
| Combined FL grades 1, 2, 3A | 0 | 4 | 0 | 0 | 1 | 5 | | | |
| FL grade 3B | 0 | 1 | 0 | 0 | 1 | 2 | | | |
| FL unknown grade | 0 | 1 | 0 | 1 | 1 | 3 | | | |

As seen in Table 2398, only 1 of the 20 BL lymphoma samples was classified incorrectly. The classification of DLBCL into subtypes was also quite effective. All previously identified ABC subtype samples were again assigned to the ABC subtype, while only 5% of the GCB samples and 6% of the PMBL samples were assigned to a different subtype than they were assigned to previously.

The above classification was Implemented using S+ software end the S+ subtype predictor script contained in the file entitled "Subtype_Predictor.txt," located in the computer program listing-appendix contained on CD number 22 of 22. This S+ script implements the lymphoma prediction algorithm. When this script is pasted into an S+ script window and run in a working directory containing the data set files discussed below, it will produce a text file entitled "PredictionResults.txt," which indicates the results of the predictive algorithm. The other files in the computer program listing appendix contain the required data sets. In their required format, for carrying out the lymphoma type Identification described above. The file entitled "GeneData.txt" contains the gene expression values for each sample analyzed. This file is included in the working directory when the S+ subtype predictor script is run. The file entitled "GeneID.txt" contains information about the genes in the GeneData.txt file, and is also included in the working directory when the S+ subtype predictor script is run. This file indicates the UNIQID for each gene, as well as the extent to which the gene is associated with the lymph node and proliferation signatures ("LN.cor" and "pro.cor," respectively). The file entitled "SampleID.txt" contains information about the samples included in the "GeneData.txt" file, specifically the original classification of all the samples. This file is also included in the working directory when the S+ subtype predictor script is run. The file entitled "PredictionResults.txt" is an example of the productive output of the prediction algorithm.

After the above model was validated using leave-one-out cross-validation, the model was re-fit using all of the data to generate a final predictor that could be applied to a new set of data. Tables 2399-2414 indicate for each of the pair wise models the list of genes used, the weight given to each of those genes, the signature with which each gene was associated, the mean values and covariance matrices associated with the subtypes being compared, and the q-value cutpoints of the pair-wise model.

TABLE 2399

ABC vs. BL

| Signature | Scale | UNIQID | Unigene ID Build 167 http://www.ncbi.nlm.nih.gov/UniGene | Probe set | Gene symbol |
|---|---|---|---|---|---|
| Standard | −18.87 | 1101149 | 517226 | 229437_at | BIC |
| Standard | −17.4 | 1121452 | 227817 | 205681_at | BCL2A1 |

TABLE 2399-continued

| ABC vs. BL | | | | | |
|---|---|---|---|---|---|
| Standard | −16.42 | 1123163 | 421342 | 208991_at | STAT3 |
| Standard | −16.2 | 1121629 | 41691 | 205965_at | BATF |
| Standard | −15 | 1134095 | 89555 | 208018_s_at | HCK |
| Standard | −14.75 | 1132636 | 306278 | 204490_s_at | CD44 |
| Standard | −14.33 | 1119939 | 170087 | 202820_at | AHR |
| Standard | −14.25 | 1100138 | 278391 | 228234_at | TIRP |
| Standard | −14.02 | 1128626 | 501452 | 219424_at | EB13 |
| Standard | −13.89 | 1132883 | 432453 | 205027_s_at | MAP3K8 |
| Standard | −13.88 | 1134991 | 444105 | 209474_s_at | ENTPD1 |
| Standard | −13.37 | 1109913 | 355724 | 239629_at | CFLAR |
| Standard | −13.25 | 1120389 | 75367 | 203761_at | SLA |
| Standard | −12.99 | 1131497 | 114931 | 202295_s_at | CTSH |
| Standard | −12.71 | 1115071 | 390476 | 223218_s_at | MAIL |
| Standard | −12.46 | 1136329 | 132739 | 211675_s_at | HIC |
| Standard | −12.41 | 1128195 | 115325 | 218699_at | RAB7L1 |
| Standard | −12.37 | 1124381 | 440808 | 212288_at | FNBP1 |
| Standard | −12.30 | 1100562 | 26608 | 228737_at | C20orf100 |
| Standard | −12.24 | 1101272 | 179089 | 229584_at | DKFZp434 |
| Standard | −12.18 | 1128536 | 21126 | 219279_at | DOCK10 |
| Standard | −11.64 | 1098271 | 300670 | 226056_at | CDGAP |
| Standard | −11.41 | 1119566 | 433506 | 201954_at | ARPC1B |
| Standard | −11.11 | 1120651 | 80205 | 204269_at | PIM2 |
| Standard | −10.89 | 1098952 | 62264 | 226841_at | KIAA0937 |
| Standard | −10.80 | 1099939 | 488173 | 227983_at | MGC7036 |
| Standard | −10.67 | 1134270 | 352119 | 208284_x_at | GGT1 |
| Standard | −10.44 | 1134145 | 4750 | 208091_s_at | DKFZP564 |
| Standard | −10.39 | 1123437 | 73090 | 209636_at | NFKB2 |
| Standard | −10.17 | 1119884 | 418004 | 202716_at | PTPM1 |
| Standard | −10.14 | 1129269 | 62919 | 220358_at | SNFT |
| Standard | −10.13 | 1126293 | 504816 | 215348_at | TNFRSF5 |
| Standard | −10.12 | 1112344 | 163242 | 242408_at | |
| Standard | −10.10 | 1135550 | 221811 | 210550_s_at | RASGRF1 |
| Standard | −10.08 | 1135165 | 170359 | 209827_s_at | IL16 |
| Standard | −10.05 | 1120808 | 127686 | 204562_at | IRF4 |
| Standard | −10.01 | 1122067 | 72927 | 206693_at | IL7 |
| Standard | −9.97 | 1132004 | 415117 | 203217_s_at | SIAT9 |
| Standard | −9.86 | 1114824 | 193370 | 222762_x_at | LIMD1 |
| Standard | −9.87 | 1132034 | 410455 | 203271_s_at | UNC119 |
| Standard | −9.87 | 1099680 | 210387 | 227677_at | JAK3 |
| Standard | −9.86 | 1132830 | 31210 | 204908_at | BCL3 |
| Standard | −9.79 | 1099631 | 367639 | 227624_at | FLJ20032 |
| Standard | −9.78 | 1120267 | 256278 | 203508_at | TNFRSF1B |
| Standard | −9.77 | 1124167 | 378738 | 211986_at | MGC5395 |
| Standard | −9.73 | 1108970 | 140489 | 238604_at | |
| Standard | −9.71 | 1136216 | 512152 | 211528_x_at | HLA-G |
| Standard | −9.71 | 1120993 | 327 | 204912_at | IL10RA |
| Standard | −9.68 | 1100847 | 97411 | 229070_at | C6orf105 |
| Standard | −9.64 | 1123413 | 418291 | 209575_at | IL10RB |
| Standard | −9.62 | 1115704 | 350268 | 224569_s_at | IRF2BP2 |
| Standard | −9.58 | 1108237 | 126232 | 237753_at | |
| Standard | −9.55 | 1121695 | 511759 | 206082_at | HCP5 |
| Standard | −9.48 | 1101905 | 170843 | 230345_at | |
| Standard | −9.42 | 1119243 | 440165 | 201171_at | ATP6V0E |
| Standard | −9.39 | 1140457 | 210546 | 221658_s_at | IL21R |
| Standard | −9.32 | 1098506 | 193400 | 226333_at | IL6R |
| Standard | −9.31 | 1139805 | 414362 | 220230_s_at | CYB5R2 |
| Standard | −9.30 | 1139037 | 173380 | 218223_s_at | CKIP-1 |
| Standard | −9.28 | 1130533 | 76507 | 200706_s_at | LITAF |
| Standard | −9.15 | 1098678 | 386140 | 226530_at | BMF |
| Standard | −9.04 | 1133210 | 434374 | 205842_s_at | JAK2 |
| Standard | 9.05 | 1116432 | 409362 | 229356_x_at | KIAA1259 |
| Standard | 9.17 | 1097281 | 7037 | 224892_at | PLDN |
| Standard | 9.17 | 1140018 | 438482 | 220917_s_at | PWDMP |
| Standard | 9.30 | 1119997 | 367811 | 202951_at | STK38 |
| Standard | 9.41 | 1119817 | 409194 | 202561_at | TNKS |
| Standard | 9.55 | 1139842 | 133523 | 220367_s_at | SAP130 |
| Standard | 9.64 | 1132122 | 307734 | 203434_s_at | MME |
| Standard | 9.77 | 1119258 | 88556 | 201209_at | HDAC1 |
| Standard | 9.80 | 1128248 | 234149 | 218802_at | FLJ20647 |
| Standard | 10.38 | 1101211 | 287659 | 229513_at | STRBP |
| Standard | 10.52 | 1123419 | 170195 | 209590_at | BMP7 |
| Standard | 10.71 | 1133755 | 404501 | 207318_s_at | CDC2L5 |
| Standard | 10.80 | 1128192 | 102506 | 218696_at | EIF2AK3 |
| Standard | 10.85 | 1124786 | 22370 | 212847_at | NEXN |
| Standard | 10.92 | 1130114 | 445084 | 221965_at | MPHOSPH9 |
| Standard | 11.00 | 1126081 | 309763 | 215030_at | GRSF1 |
| Standard | 11.17 | 1118736 | 96731 | 38340_at | HIP1R |
| Standard | 11.26 | 1124613 | 296720 | 212599_at | AUTS2 |

TABLE 2399-continued

| | | ABC vs. BL | | | |
|---|---|---|---|---|---|
| Standard | 11.43 | 1125456 | 300592 | 213906_at | MYBL1 |
| Standard | 11.60 | 1097177 | 9691 | 224761_at | GNA13 |
| Standard | 12.11 | 1120400 | 152207 | 203787_at | SSBP2 |
| Standard | 12.12 | 1139266 | 76640 | 218723_s_at | RGC32 |
| Standard | 12.22 | 1100770 | 65578 | 228976_at | |
| Standard | 12.73 | 1131246 | 153752 | 201853_s_at | CDC25B |
| Standard | 13.48 | 1096503 | 21379 | 223522_at | C9orf45 |
| Standard | 14.50 | 1124920 | 6150 | 213039_at | ARHGEF1 |
| Standard | 15.03 | 1128360 | 445043 | 218988_at | SLC35E3 |
| Standard | 15.24 | 1099444 | 434489 | 227407_at | FLJ90013 |
| Standard | 21.03 | 1134582 | 78202 | 208794_s_at | SMARCA4 |

| Standard | | | | |
|---|---|---|---|---|
| Mean ABC | −4179.76 | Cut 1 | 0.20 | |
| Mean BL | −1894.68 | Cut 2 | 0.80 | |
| Covariance ABC | 53707.58 | | | |
| Covariance BL | 194887.5 | | | |

TABLE 2400

ABC vs. GCB

| Signature | Scale | UNIQID | Unigene ID Build 167 http://www.ncbi.nlm.nih.gov/UniGene | Probe set | Gene symbol |
|---|---|---|---|---|---|
| Standard | −15.31 | 1122645 | 158341 | 207641_at | TNFRSF13B |
| Standard | −14.56 | 1120651 | 80205 | 204269_at | PIM2 |
| Standard | −14.18 | 1120808 | 127686 | 204562_at | IRF4 |
| Standard | −13.84 | 1114824 | 193370 | 222762_x_at | LIMD1 |
| Standard | −13.44 | 1136687 | 59943 | 212345_s_at | CREB3L2 |
| Standard | −13.12 | 1139805 | 414362 | 220230_s_at | CYB5R2 |
| Standard | −12.23 | 1104552 | 193857 | 233483_at | LOC96597 |
| Standard | −12.19 | 1097236 | 235860 | 224837_at | FOXP1 |
| Standard | −12.06 | 1121629 | 41691 | 205965_at | BATF |
| Standard | −11.93 | 1128195 | 115325 | 218699_at | RAB7L1 |
| Standard | −11.72 | 1111503 | 502910 | 241383_at | KBRAS2 |
| Standard | −11.66 | 1134991 | 444105 | 209474_s_at | ENTPD1 |
| Standard | −11.27 | 1098678 | 386140 | 226530_at | BMF |
| Standard | −10.9 | 1131074 | 76894 | 201572_x_at | DCTD |
| Standard | −10.82 | 1135165 | 170359 | 209827_s_at | IL16 |
| Standard | −10.7 | 1132396 | 118722 | 203988_s_at | FUT8 |
| Standard | −10.54 | 1131541 | 310230 | 202369_s_at | TRAM2 |
| Standard | −10.47 | 1105759 | 171262 | 235056_at | ETV6 |
| Standard | −10.38 | 1121564 | 437783 | 205865_at | ARID3A |
| Standard | −10.16 | 1130472 | 192374 | 200599_s_at | TRA1 |
| Standard | −10.04 | 1132058 | 181999 | 203313_s_at | TGIF |
| Standard | −10.03 | 1105684 | 195155 | 234973_at | SLC38A5 |
| Standard | −9.95 | 1097735 | 26765 | 225436_at | LOC58489 |
| Standard | −9.94 | 1115071 | 390476 | 223218_s_at | MAIL |
| Standard | −9.85 | 1101149 | 517226 | 229437_at | BIC |
| Standard | −9.83 | 1119884 | 418004 | 202716_at | PTPN1 |
| Standard | −9.71 | 1134095 | 89555 | 208018_s_at | HCK |
| Standard | −9.68 | 1135550 | 221811 | 210550_s_at | RASGRF1 |
| Standard | −9.61 | 1098927 | 356216 | 226811_at | FLJ20202 |
| Standard | −9.6 | 1120389 | 75367 | 203761_at | SLA |
| Standard | −9.58 | 1133910 | 167746 | 207655_s_at | BLNK |
| Standard | 9.56 | 1118736 | 96731 | 38340_at | HIP1R |
| Standard | 9.58 | 1128860 | 323634 | 219753_at | STAG3 |
| Standard | 9.68 | 1134582 | 78202 | 208794_s_at | SMARCA4 |
| Standard | 9.7 | 1121853 | 98243 | 206310_at | SPINK2 |
| Standard | 10.14 | 1119256 | 88556 | 201209_at | HDAC1 |
| Standard | 10.19 | 1132122 | 307734 | 203434_s_at | MME |
| Standard | 10.23 | 1120400 | 152207 | 203767_at | SSBP2 |
| Standard | 10.48 | 1529344 | 317970 | Lymph_Dx_065_at | SERPINA11 |
| Standard | 10.64 | 1124613 | 296720 | 212599_at | AUTS2 |
| Standard | 10.72 | 1132159 | 147868 | 203521_s_at | ZNF318 |
| Standard | 10.98 | 1097901 | 266175 | 225626_at | PAG |
| Standard | 11.1 | 1128287 | 300063 | 218862_at | ASB13 |
| Standard | 12.26 | 1099686 | 117721 | 227684_at | |
| Standard | 12.45 | 1112674 | 310320 | 242794_at | MAML3 |
| Standard | 13.15 | 1120370 | 78877 | 203723_at | ITPKB |
| Standard | 14.23 | 1125456 | 300592 | 213906_at | MYBL1 |
| Lymph Node | 6.8 | 1097202 | 386779 | 224796_at | DDEF1 |
| Lymph Node | 6.85 | 1131755 | 241257 | 202729_s_at | LTBP1 |

TABLE 2400-continued

| | | ABC vs. GCB | | | |
|---|---|---|---|---|---|
| Lymph Node | 7.27 | 1136273 | 13775 | 211597_s_at | HOP |
| Lymph Node | 7.35 | 1119424 | 75485 | 201599_at | OAT |
| Lymph Node | 7.86 | 1095985 | 83883 | 222450_at | TMEPAI |
| Lymph Node | 8.02 | 1124875 | 18166 | 212975_at | KIAA0870 |
| Lymph Node | 8.32 | 1124655 | 79299 | 212658_at | LHFPL2 |
| Lymph Node | 8.62 | 1115034 | 387222 | 223158_s_at | NEK6 |
| Proliferation | −9.11 | 1120583 | 153768 | 204133_at | RNU3IP2 |
| Proliferation | −7.87 | 1135492 | 408615 | 210448_s_at | P2RX5 |
| Proliferation | −7.68 | 1127756 | 313544 | 217850_at | NS |
| Proliferation | −7.57 | 1097195 | 149931 | 224785_at | MGC29814 |
| Proliferation | −7.31 | 1127813 | 14317 | 217962_at | NOLA3 |
| Proliferation | −7.24 | 1138944 | 84753 | 218051_s_at | FLJ12442 |
| Proliferation | −6.99 | 1139226 | 266514 | 218633_x_at | FLJ11342 |
| Proliferation | −6.7 | 1137486 | 441069 | 214442_s_at | MIZ1 |
| Proliferation | −6.51 | 1133786 | 153591 | 207396_s_at | ALG3 |
| Proliferation | −6.45 | 1131150 | 75514 | 201695_s_at | NP |
| Proliferation | −6.45 | 1119076 | 268849 | 200681_at | GLO1 |
| Proliferation | −6.38 | 1115679 | 8345 | 224523_s_at | MGC4308 |
| Proliferation | −6.34 | 1110223 | 212709 | 239973_at | |
| Proliferation | −6.3 | 1529338 | 284275 | Lymph_Dx_058_s_at | PAK2 |
| Proliferation | −6.24 | 1135164 | 458360 | 209825_s_at | UMPK |
| Proliferation | −6.24 | 1128738 | 335550 | 219581_at | MGC2776 |
| Proliferation | −6.01 | 1099088 | 14355 | 226996_at | |
| Proliferation | −5.98 | 1123192 | 315177 | 209100_at | IFRD2 |
| Proliferation | −5.83 | 1116073 | 146161 | 227103_s_at | MGC2408 |
| Proliferation | 5.79 | 1097388 | 278839 | 225024_at | C20orf77 |
| Proliferation | 6.13 | 1124563 | 249441 | 212533_at | WEE1 |

| | Standard | Lymph Node | Proliferation | | |
|---|---|---|---|---|---|
| Mean ABC | −2226.57 | 476.67 | −1096.34 | Cut 1 | 0.50 |
| Mean GCB | −1352.02 | 547.18 | −1005.72 | Cut 2 | 0.74 |
| Covariance ABC | 33472.10 | 3418.91 | 4347.99 | | |
| | 3418.91 | 1296.05 | 846.32 | | |
| | 4347.99 | 846.32 | 1609.13 | | |
| Covariance GCB | 53751.59 | 466.34 | 751.08 | | |
| | 466.34 | 777.74 | 249.29 | | |
| | 751.08 | 249.29 | 1708.67 | | |

TABLE 2401

| | | | ABC vs. PMBL | | |
|---|---|---|---|---|---|
| Signature | Scale | UNIQID | Unigene ID Build 167 http://www.ncbi.nlm.nih.gov/UniGene | Probe set | Gene Symbol |
| Standard | −14.61 | 1097236 | 235860 | 224837_at | FOXP1 |
| Standard | −14.47 | 1104552 | 193857 | 233483_at | LOC96597 |
| Standard | −13.62 | 1122645 | 158341 | 207641_at | TNFRSF13B |
| Standard | −12.05 | 1135102 | 349845 | 209685_s_at | PRKCB1 |
| Standard | −11.65 | 1096499 | 293867 | 223514_at | CARD11 |
| Standard | −11.26 | 1124770 | 153261 | 212827_at | IGHM |
| Standard | −11.25 | 1125010 | 43728 | 213170_at | GPX7 |
| Standard | −11.13 | 1109545 | 63187 | 239231_at | |
| Standard | −10.99 | 1109220 | 445977 | 238880_at | GTF3A |
| Standard | −10.87 | 1131074 | 76894 | 201572_x_at | DCTD |
| Standard | −10.68 | 1134517 | 75807 | 208690_s_at | PDLIM1 |
| Standard | −10.63 | 1098604 | 32793 | 226444_at | SLC39A10 |
| Standard | −10.56 | 1131219 | 109150 | 201810_s_at | SH3BP5 |
| Standard | −10.52 | 1120651 | 80205 | 204269_at | PIM2 |
| Standard | −10.39 | 1133910 | 167746 | 207655_s_at | BLNK |
| Standard | −10.32 | 1099396 | 435949 | 227346_at | ZNFN1A1 |
| Standard | −10.25 | 1529297 | 132335 | Lymph_Dx_015_at | |
| Standard | −10.17 | 1107575 | 424589 | 237033_at | MGC52498 |
| Standard | −10.11 | 1117211 | 356509 | 233955_x_at | HSPC195 |
| Standard | 10.06 | 1129517 | −33 | 220712_at | |
| Standard | 10.29 | 1139950 | 437385 | 220731_s_at | FLJ10420 |
| Standard | 10.35 | 1097553 | 197071 | 225214_at | PSMB7 |
| Standard | 10.41 | 1119516 | 6061 | 201834_at | PRKAB1 |
| Standard | 10.47 | 1122772 | 66742 | 207900_at | CCL17 |
| Standard | 10.55 | 1132762 | 80395 | 204777_s_at | MAL |
| Standard | 10.77 | 1099265 | 375762 | 227193_at | |
| Standard | 10.81 | 1095996 | 288801 | 222482_at | SSBP3 |
| Standard | 11.14 | 1100770 | 65578 | 228976_at | |
| Standard | 11.19 | 1133801 | 181097 | 207426_s_at | TNFSF4 |

TABLE 2401-continued

ABC vs. PMBL

| Signature | Scale | UNIQID | Unigene | Probe set | Gene Symbol |
|---|---|---|---|---|---|
| Standard | 11.61 | 1099154 | 97927 | 227066_at | MOBKL2C |
| Standard | 11.63 | 1120370 | 78877 | 203723_at | ITPKB |
| Standard | 11.8 | 1112674 | 310320 | 242794_at | MAML3 |
| Standard | 12.57 | 1105178 | 283961 | 234284_at | GNG8 |
| Standard | 12.63 | 1124613 | 296720 | 212599_at | AUTS2 |
| Standard | 13.28 | 1106415 | 169071 | 235774_at | |
| Standard | 13.3 | 1121762 | 32970 | 206181_at | SLAMF1 |
| Standard | 13.6 | 1121853 | 98243 | 206310_at | SPINK2 |
| Lymph Node | 10.91 | 1105838 | 129837 | 235142_at | ZBTB8 |
| Lymph Node | 10.99 | 1136273 | 13775 | 211597_s_at | HOP |
| Lymph Node | 11.02 | 1099418 | 172792 | 227370_at | KIAA1946 |
| Lymph Node | 11.46 | 1124875 | 18166 | 212975_at | KIAA0870 |
| Lymph Node | 11.99 | 1120299 | 79334 | 203574_at | NFIL3 |
| Lymph Node | 12.49 | 1135871 | 104717 | 211031_s_at | CYLN2 |
| Lymph Node | 13.33 | 1121767 | 458324 | 206187_at | PTGIR |
| Proliferation | −13.17 | 1138944 | 84753 | 218051_s_at | FLJ12442 |
| Proliferation | −11.61 | 1116122 | 42768 | 227408_s_at | DKFZp761O0113 |
| Proliferation | −11.16 | 1110223 | 212709 | 239973_at | |
| Proliferation | −9.93 | 1120717 | 444159 | 204394_at | SLC43A1 |
| Proliferation | −9.54 | 1110099 | 116665 | 239835_at | TA-KRP |
| Proliferation | −9.49 | 1130942 | 445977 | 201338_x_at | GTF3A |
| Proliferation | −9.28 | 1123192 | 315177 | 209100_at | IFRD2 |
| Proliferation | −9.14 | 1135492 | 408615 | 210448_s_at | P2RX5 |
| Proliferation | −9.03 | 1120011 | 3068 | 202983_at | SMARCA3 |
| Proliferation | −9.01 | 1096738 | 87968 | 223903_at | TLR9 |
| Proliferation | −8.91 | 1108961 | 292088 | 238593_at | FLJ22531 |

|  | Standard | Lymph Node | Proliferation | | |
|---|---|---|---|---|---|
| Mean ABC | −849.47 | 531.79 | −1027.48 | Cut 1 | 0.20 |
| Mean PMBL | 27.99 | 750.84 | −872.43 | Cut 2 | 0.80 |
| Covariance ABC | 14028.46 | 3705.84 | 3118.60 | | |
|  | 3705.84 | 2326.91 | 1083.37 | | |
|  | 3118.60 | 1083.37 | 1589.42 | | |
| Covariance PMBL | 19425.29 | 5109.98 | 2199.28 | | |
|  | 5109.98 | 2084.28 | 620.86 | | |
|  | 2199.28 | 620.86 | 1028.44 | | |

TABLE 2402

BL vs. GCB

| Signature | Scale | UNIQID | Unigene ID Build 167 http://www.ncbi.nlm.nih.gov/UniGene | Probe set | Gene Symbol |
|---|---|---|---|---|---|
| Standard | −12.78 | 1131246 | 153752 | 201853_s_at | CDC25B |
| Standard | −11.35 | 1099444 | 434489 | 227407_at | FLJ90013 |
| Standard | −10.4 | 1116432 | 409362 | 229356_x_at | KIAA1259 |
| Standard | −10.3 | 1134582 | 78202 | 208794_s_at | SMARCA4 |
| Standard | −10.01 | 1133998 | 76884 | 207826_s_at | ID3 |
| Standard | −9.3 | 1126081 | 309763 | 215030_at | GRSF1 |
| Standard | −9.19 | 1096503 | 21379 | 223522_at | C9orf45 |
| Standard | −8.95 | 1529340 | −99 | Lymph_Dx_061_at | |
| Standard | −8.88 | 1138128 | 390428 | 216199_s_at | MAP3K4 |
| Standard | −8.8 | 1099152 | 351247 | 227064_at | MGC15396 |
| Standard | −8.69 | 1133757 | 6113 | 207320_x_at | STAU |
| Standard | −8.54 | 1116593 | 422889 | 230329_s_at | NUDT6 |
| Standard | −8.4 | 1130926 | 508741 | 201310_s_at | C5orf13 |
| Standard | −8.39 | 1135685 | 371282 | 210776_x_at | TCF3 |
| Standard | −8.39 | 1140520 | 11747 | 221741_s_at | C20orf21 |
| Standard | −8.34 | 1119802 | 7370 | 202522_at | PITPNB |
| Standard | −8.31 | 1096149 | 410205 | 222824_at | NUDT5 |
| Standard | −8.23 | 1124786 | 22370 | 212847_at | NEXN |
| Standard | −8.07 | 1098012 | 355669 | 225756_at | CSNK1E |
| Standard | −7.89 | 1116317 | 526415 | 228661_s_at | |
| Standard | −7.86 | 1109195 | 416155 | 238853_at | |
| Standard | −7.71 | 1134880 | 168799 | 209265_s_at | METTL3 |
| Standard | −7.66 | 1529298 | 136707 | Lymph_Dx_016_at | |
| Standard | −7.55 | 1128660 | 413071 | 219471_at | C13orf18 |
| Standard | −7.55 | 1138973 | 11270 | 218097_s_at | C10orf66 |
| Standard | −7.46 | 1127294 | 421986 | 217028_at | CXCR4 |
| Standard | 7.47 | 1134270 | 352119 | 208284_x_at | GGT1 |
| Standard | 7.48 | 1120743 | 79197 | 204440_at | CD83 |
| Standard | 7.5 | 1098179 | 163725 | 225956_at | LOC153222 |
| Standard | 7.55 | 1121400 | 223474 | 205599_at | TRAF1 |

TABLE 2402-continued

| | | | | BL vs. GCB | |
|---|---|---|---|---|---|
| Standard | 7.59 | 1114967 | 7905 | 223028_s_at | SNX9 |
| Standard | 7.6 | 1122087 | 72927 | 206693_at | IL7 |
| Standard | 7.64 | 1101905 | 170843 | 230345_at | |
| Standard | 7.77 | 1120700 | 410745 | 204362_at | SCAP2 |
| Standard | 7.8 | 1120572 | 84 | 204116_at | IL2RG |
| Standard | 7.84 | 1098271 | 300670 | 226056_at | CDGAP |
| Standard | 7.9 | 1115073 | 131315 | 223220_s_at | BAL |
| Standard | 7.9 | 1133210 | 434374 | 205842_s_at | JAK2 |
| Standard | 8 | 1129289 | 62919 | 220358_at | SNFT |
| Standard | 8.01 | 1131940 | 1103 | 203085_s_at | TGFB1 |
| Standard | 8.07 | 1098506 | 193400 | 226333_at | IL6R |
| Standard | 8.13 | 1120601 | 441129 | 204166_at | KIAA0963 |
| Standard | 8.21 | 1102540 | 434881 | 231093_at | FCRH3 |
| Standard | 8.24 | 1121695 | 611759 | 206082_at | HCP5 |
| Standard | 8.33 | 1136877 | 409934 | 212998_x_at | HLA-DQB1 |
| Standard | 8.37 | 1100138 | 278391 | 228234_at | TIRP |
| Standard | 8.46 | 1126293 | 504816 | 215346_at | TNFRSF5 |
| Standard | 8.46 | 1127805 | 360627 | 217947_at | CKLFSF6 |
| Standard | 8.59 | 1136573 | 914 | 211991_s_at | HLA-DPA1 |
| Standard | 8.62 | 1119111 | 35052 | 200804_at | TEGT |
| Standard | 8.7 | 1136329 | 132739 | 211675_s_at | HIC |
| Standard | 8.74 | 1123690 | 111805 | 210176_at | TLR1 |
| Standard | 8.81 | 1138677 | 390440 | 217436_x_at | |
| Standard | 8.89 | 1113993 | 131811 | 244286_at | |
| Standard | 8.89 | 1132651 | 439767 | 204529_s_at | TOX |
| Standard | 8.91 | 1119566 | 433506 | 201954_at | ARPC1B |
| Standard | 9.01 | 1128626 | 501452 | 219424_at | EBI3 |
| Standard | 9.17 | 1101272 | 179089 | 229584_at | DKFZp434H2111 |
| Standard | 9.33 | 1136777 | 387679 | 212671_s_at | HLA-DQA1 |
| Standard | 9.33 | 1109756 | 530304 | 239453_at | |
| Standard | 9.4 | 1136216 | 512152 | 211528_x_at | HLA-G |
| Standard | 9.4 | 1124381 | 440808 | 212288_at | FNBP1 |
| Standard | 9.46 | 1099680 | 210387 | 227677_at | JAK3 |
| Standard | 9.49 | 1109913 | 355724 | 239629_at | CFLAR |
| Standard | 9.56 | 1132636 | 306278 | 204490_s_at | CD44 |
| Standard | 9.59 | 1119243 | 440165 | 201171_at | ATP6V0E |
| Standard | 9.72 | 1101149 | 517226 | 229437_at | BIC |
| Standard | 9.8 | 1130674 | 381008 | 200905_x_at | HLA-E |
| Standard | 10.34 | 1119939 | 170087 | 202820_at | AHR |
| Standard | 10.44 | 1132883 | 432453 | 205027_s_at | MAP3K8 |
| Standard | 10.74 | 1121452 | 227817 | 205681_at | BCL2A1 |
| Standard | 10.84 | 1137360 | 429658 | 214196_s_at | CLN2 |
| Standard | 12.08 | 1132520 | 283063 | 204249_s_at | LMO2 |
| Standard | 12.33 | 1131497 | 114931 | 202295_s_at | CTSH |
| Standard | 13.58 | 1123163 | 421342 | 208991_at | STAT3 |
| Lymph Node | −9.1 | 1138136 | 433574 | 216215_s_at | RBM9 |
| Lymph Node | 8.78 | 1130121 | 411958 | 221978_at | HLA-F |
| Lymph Node | 9.22 | 1139830 | 221851 | 220330_s_at | SAMSN1 |
| Lymph Node | 9.23 | 1131705 | 386467 | 202638_s_at | ICAM1 |
| Lymph Node | 9.62 | 1130168 | 75626 | 222061_at | CD58 |
| Lymph Node | 9.66 | 1121844 | 83077 | 206295_at | IL18 |
| Lymph Node | 9.68 | 1121000 | 519033 | 204924_at | TLR2 |
| Lymph Node | 9.83 | 1102437 | 437023 | 230966_at | IL4I1 |
| Lymph Node | 10.71 | 1119475 | 296323 | 201739_at | SGK |
| Lymph Node | 11.09 | 1131786 | 375957 | 202803_s_at | ITGB2 |
| Proliferation | −11.07 | 1133141 | 344524 | 205677_s_at | DLEU1 |
| Proliferation | −10.04 | 1138259 | 89525 | 216484_x_at | HDGF |
| Proliferation | −9.74 | 1131578 | 202453 | 202431_s_at | MYC |
| Proliferation | −9.45 | 1137449 | 223745 | 214363_s_at | MATR3 |
| Proliferation | −9.43 | 1130468 | 166463 | 200594_x_at | HNRPU |
| Proliferation | −9.21 | 1138157 | 82563 | 216251_s_at | KIAA0153 |
| Proliferation | −9.15 | 1127756 | 313544 | 217850_at | NS |
| Proliferation | −9 | 1130433 | 246112 | 200058_s_at | U5-200KD |
| Proliferation | −8.76 | 1123108 | 108112 | 208828_at | POLE3 |
| Proliferation | −8.75 | 1128738 | 335550 | 219581_at | MGC2776 |
| Proliferation | −8.74 | 1122400 | 439911 | 207199_at | TERT |
| Proliferation | −8.66 | 1097948 | 69476 | 225684_at | LOC348235 |
| Proliferation | −8.6 | 1119460 | 76122 | 201696_at | SFRS4 |
| Proliferation | −8.6 | 1136401 | 27258 | 211761_s_at | SIP |
| Proliferation | −8.58 | 1099088 | 14355 | 226996_at | |
| Proliferation | −8.51 | 1134653 | 253536 | 208901_s_at | TOP1 |
| Proliferation | −8.49 | 1140584 | 294083 | 221932_s_at | C14orf87 |
| Proliferation | −8.43 | 1121309 | 23642 | 205449_at | HSU79266 |
| Proliferation | −8.43 | 1120385 | 36708 | 203755_at | BUB1B |
| Proliferation | −8.38 | 1136710 | 75782 | 212429_s_at | GTF3C2 |
| Proliferation | −8.36 | 1136605 | 448398 | 212064_x_at | MAZ |
| Proliferation | −8.24 | 1120697 | 323462 | 204355_at | DHX30 |
| Proliferation | −8.19 | 1127833 | 382044 | 218001_at | MRPS2 |

TABLE 2402-continued

| | | | BL vs. GCB | | | | |
|---|---|---|---|---|---|---|---|
| Proliferation | −8.11 | 1096903 | 437460 | 224185_at | FLJ10385 | | |
| Proliferation | −8.1 | 1120596 | 4854 | 204159_at | CDKN2C | | |
| Proliferation | −8.1 | 1120779 | 28853 | 204510_at | CDC7 | | |

| | Standard | Lymph Node | Proliferation | | |
|---|---|---|---|---|---|
| Mean BL | 1098.69 | 576.05 | −2392.12 | Cut 1 | 0.09 |
| Mean GCB | 2187.37 | 768.53 | −2129.35 | Cut 2 | 0.53 |
| Covariance BL | 75263.67 | 12684.43 | 15734.77 | | |
| | 12684.43 | 2650.81 | 2358.05 | | |
| | 15734.77 | 2358.05 | 4653.00 | | |
| Covariance GCB | 50548.22 | 9301.12 | 14182.83 | | |
| | 9301.12 | 2602.51 | 3028.21 | | |
| | 14182.83 | 3028.21 | 5983.04 | | |

TABLE 2403

BL vs. PMBL

| Signature | Scale | UNIQID | Unigene ID Build 167 http://www.ncbi.nlm.nih.gov/UniGene | Probe set | Gene Symbol |
|---|---|---|---|---|---|
| Standard | −13.54 | 1099444 | 434489 | 227407_at | FLJ90013 |
| Standard | −13.42 | 1096503 | 21379 | 223522_at | C9orf45 |
| Standard | −13.36 | 1130114 | 445084 | 221965_at | MPHOSPH9 |
| Standard | −13.27 | 1124786 | 22370 | 212847_at | NEXN |
| Standard | −13.27 | 1134582 | 78202 | 208794_s_at | SMARCA4 |
| Standard | −12.37 | 1096149 | 410205 | 222824_at | NUDT5 |
| Standard | −11.95 | 1130855 | 77515 | 201189_s_at | ITPR3 |
| Standard | −11.66 | 1529298 | 136707 | Lymph_Dx_016_at | |
| Standard | −11.35 | 1131246 | 153752 | 201853_s_at | CDC25B |
| Standard | −11.17 | 1136925 | 436939 | 213154_s_at | BICD2 |
| Standard | −11.08 | 1124188 | 282346 | 211987_at | TOP2B |
| Standard | −11.06 | 1133998 | 76884 | 207826_s_at | ID3 |
| Standard | −10.76 | 1139266 | 76640 | 218723_s_at | RGC32 |
| Standard | −10.74 | 1134880 | 168799 | 209265_s_at | METTL3 |
| Standard | −10.69 | 1140520 | 11747 | 221741_s_at | C20orf21 |
| Standard | −10.6 | 1109545 | 63187 | 239231_at | |
| Standard | −10.55 | 1106043 | 266331 | 235372_at | FREB |
| Standard | −10.52 | 1110214 | 144519 | 239964_at | TCL6 |
| Standard | −10.49 | 1098592 | 283707 | 226431_at | ALS2CR13 |
| Standard | −10.45 | 1109220 | 445977 | 238880_at | GTF3A |
| Standard | −10.41 | 1131263 | 249955 | 201877_s_at | PPP2R5C |
| Standard | 10.54 | 1122772 | 66742 | 207900_at | CCL17 |
| Standard | 10.59 | 1109913 | 355724 | 239629_at | CFLAR |
| Standard | 10.82 | 1119884 | 418004 | 202716_at | PTPN1 |
| Standard | 10.83 | 1135189 | 137569 | 209863_s_at | TP73L |
| Standard | 10.89 | 1123437 | 73090 | 209636_at | NFKB2 |
| Standard | 11.15 | 1124381 | 440806 | 212288_at | FNBP1 |
| Standard | 11.26 | 1108237 | 126232 | 237753_at | |
| Standard | 11.34 | 1101149 | 517226 | 229437_at | BIC |
| Standard | 11.77 | 1139774 | 15827 | 220140_s_at | SNX11 |
| Standard | 11.87 | 1123163 | 421342 | 208991_at | STAT3 |
| Standard | 11.93 | 1129269 | 62919 | 220358_at | SNFT |
| Standard | 12.03 | 1132636 | 306278 | 204490_s_at | CD44 |
| Standard | 12.1 | 1138677 | 390440 | 217436_x_at | |
| Standard | 12.2 | 1139950 | 437385 | 220731_s_at | FLJ10420 |
| Standard | 12.25 | 1134270 | 352119 | 208284_x_at | GGT1 |
| Standard | 12.27 | 1136216 | 512152 | 211528_x_at | HLA-G |
| Standard | 12.79 | 1121400 | 223474 | 205599_at | TRAF1 |
| Standard | 12.82 | 1119939 | 170087 | 202820_at | AHR |
| Standard | 13.12 | 1126293 | 504816 | 215346_at | TNFRSF5 |
| Standard | 13.44 | 1100138 | 278391 | 228234_at | TIRP |
| Standard | 13.74 | 1132883 | 432453 | 205027_s_at | MAP3K8 |
| Standard | 13.94 | 1131497 | 114931 | 202295_s_at | CTSH |
| Standard | 14.15 | 1121762 | 32970 | 206181_at | SLAMF1 |
| Standard | 14.51 | 1132520 | 283063 | 204249_s_at | LMO2 |
| Standard | 14.68 | 1121452 | 227817 | 205681_at | BCL2A1 |
| Standard | 15.24 | 1105178 | 283961 | 234284_at | GNG8 |
| Lymph Node | 10.95 | 1121205 | 2488 | 205269_at | LCP2 |
| Lymph Node | 11.22 | 1140845 | 21486 | AFFX-HUMISGF3A/M97935_3_at | STAT1 |
| Lymph Node | 11.45 | 1131068 | 118400 | 201564_s_at | FSCN1 |
| Lymph Node | 11.92 | 1131705 | 386467 | 202638_s_at | ICAM1 |
| Lymph Node | 12.06 | 1131038 | 81328 | 201502_s_at | NFKBIA |

TABLE 2403-continued

BL vs. PMBL

| | | | | | |
|---|---|---|---|---|---|
| Lymph Node | 12.49 | 1121444 | 153563 | 205668_at | LY75 |
| Lymph Node | 13.01 | 1123457 | 446304 | 209684_at | RIN2 |
| Lymph Node | 13.19 | 1140404 | 354740 | 221584_s_at | KCNMA1 |
| Lymph Node | 13.26 | 1124875 | 18166 | 212975_at | KIAA0870 |
| Lymph Node | 14.06 | 1102437 | 437023 | 230966_at | IL4I1 |
| Lymph Node | 14.11 | 1132766 | 82359 | 204781_s_at | TNFRSF6 |
| Lymph Node | 15.31 | 1121767 | 458324 | 206187_at | PTGIR |
| Lymph Node | 15.32 | 1135871 | 104717 | 211031_s_at | CYLN2 |
| Lymph Node | 15.34 | 1138652 | 444471 | 217388_s_at | KYNU |
| Lymph Node | 16.01 | 1139830 | 221851 | 220330_s_at | SAMSN1 |

| | Standard | Lymph Node | | |
|---|---|---|---|---|
| Mean BL | −66.97 | 1445.63 | Cut 1 | 0.20 |
| Mean PMBL | 1205.38 | 2041.25 | Cut 2 | 0.80 |
| Covariance BL | 35263.67 | 13424.88 | | |
| | 13424.88 | 7458.56 | | |
| Covariance PMBL | 12064.38 | 5113.74 | | |
| | 5113.74 | 3216.53 | | |

TABLE 2404

FH vs. DLBCL-BL

| Signature | Scale | UNIQID | Unigene ID Build 167 http://www.ncbi.nlm.nih.gov/UniGene | Probe set | Gene Symbol |
|---|---|---|---|---|---|
| Standard | −12.81 | 1104910 | 458262 | 233969_at | IGL@ |
| Standard | −11.54 | 1102898 | 145519 | 231496_at | FKSG87 |
| Standard | −11.46 | 1117298 | 449586 | 234366_x_at | |
| Standard | −11.46 | 1132973 | 169294 | 205255_x_at | TCF7 |
| Standard | −11.22 | 1133099 | 88646 | 205554_s_at | DNASE1L3 |
| Standard | −10.76 | 1131531 | 153647 | 202350_s_at | MATN2 |
| Standard | −10.59 | 1124283 | 406612 | 212144_at | UNC84B |
| Standard | −10.35 | 1099847 | 36723 | 227867_at | LOC129293 |
| Standard | −10.22 | 1136430 | 102950 | 211798_x_at | IGLJ3 |
| Standard | −10.05 | 1117394 | −13 | 234792_x_at | |
| Standard | −9.95 | 1133047 | 528338 | 205434_s_at | AAK1 |
| Standard | −9.95 | 1098865 | 250905 | 226741_at | LOC51234 |
| Standard | −9.82 | 1108515 | 98132 | 238071_at | LCN6 |
| Standard | −9.8 | 1131407 | 154248 | 202125_s_at | ALS2CR3 |
| Standard | −9.77 | 1128469 | 390817 | 219173_at | FLJ22686 |
| Standard | −9.7 | 1123875 | 428 | 210607_at | FLT3LG |
| Standard | −9.69 | 1131875 | 169172 | 202965_s_at | CAPN6 |
| Standard | −9.69 | 1135173 | 3781 | 209841_s_at | LRRN3 |
| Standard | −9.48 | 1099798 | 411081 | 227811_at | FGD3 |
| Standard | −9.41 | 1119046 | 349499 | 200606_at | DSP |
| Standard | −9.36 | 1122449 | 278694 | 207277_at | CD209 |
| Standard | −9.34 | 1114017 | 133255 | 244313_at | |
| Standard | −9.34 | 1122767 | 652 | 207892_at | TNFSF5 |
| Standard | −9.24 | 1123369 | 79025 | 209481_at | SNRK |
| Standard | −9.16 | 1098954 | 128905 | 226844_at | MOBKL2B |
| Standard | −9.14 | 1135513 | 421437 | 210481_s_at | CD209L |
| Standard | −9.08 | 1100904 | 426296 | 229145_at | LOC119504 |
| Standard | −8.99 | 1122738 | 81743 | 207840_at | CD160 |
| Standard | −8.94 | 1120925 | 204891 | 204773_at | IL11RA |
| Standard | 9.09 | 1123055 | 185726 | 208691_at | TFRC |
| Standard | 9.62 | 1134858 | 405954 | 209226_s_at | TNPO1 |
| Standard | 10.19 | 1123052 | 180909 | 208680_at | PRDX1 |
| Standard | 10.81 | 1124178 | 446579 | 211969_at | HSPCA |
| Lymph Node | −10.59 | 1137597 | 3903 | 214721_x_at | CDC42EP4 |
| Lymph Node | −9.69 | 1119684 | 439586 | 202242_at | TM4SF2 |
| Lymph Node | −9.25 | 1125593 | 8910 | 214180_at | MAN1C1 |
| Lymph Node | −8.44 | 1124318 | 21858 | 212190_at | SERPINE2 |
| Lymph Node | −8.09 | 1119448 | 212296 | 201656_at | ITGA6 |
| Lymph Node | −8.07 | 1125546 | 125036 | 214081_at | PLXDC1 |
| Lymph Node | −7.7 | 1097683 | 132569 | 225373_at | PP2135 |
| Lymph Node | −7.56 | 1101305 | 112742 | 229623_at | |
| Lymph Node | 7.45 | 1135240 | 436852 | 209955_s_at | FAP |
| Proliferation | 6.97 | 1135101 | 20830 | 209680_s_at | KIFC1 |
| Proliferation | 7.03 | 1130426 | 432607 | 200039_s_at | PSMB2 |
| Proliferation | 7.04 | 1130501 | 2795 | 200650_s_at | LDHA |
| Proliferation | 7.08 | 1130744 | 158688 | 201027_s_at | EIF5B |
| Proliferation | 7.23 | 1137506 | 75258 | 214501_s_at | H2AFY |
| Proliferation | 7.32 | 1131474 | 95577 | 202246_s_at | CDK4 |

TABLE 2404-continued

FH vs. DLBCL-BL

| | | | | | | | |
|---|---|---|---|---|---|---|---|
| Proliferation | 7.39 | 1130871 | 159087 | 201222_s_at | RAD23B | | |
| Proliferation | 7.42 | 1119375 | 381072 | 201489_at | PPIF | | |
| Proliferation | 7.47 | 1136595 | 404814 | 212038_s_at | VDAC1 | | |
| Proliferation | 7.7 | 1135858 | 90093 | 211015_s_at | HSPA4 | | |
| Proliferation | 7.78 | 1130527 | 184233 | 200692_s_at | HSPA9B | | |
| Proliferation | 7.78 | 1130820 | 151777 | 201144_s_at | EIF2S1 | | |
| Proliferation | 7.83 | 1115829 | 433213 | 225253_s_at | METTL2 | | |
| Proliferation | 7.84 | 1134699 | 439683 | 208974_x_at | KPNB1 | | |
| Proliferation | 7.87 | 1120274 | 31584 | 203517_at | MTX2 | | |
| Proliferation | 7.92 | 1136786 | 63788 | 212694_s_at | PCCB | | |
| Proliferation | 7.95 | 1097172 | 434886 | 224753_at | CDCA5 | | |
| Proliferation | 8.4 | 1138537 | −12 | 217140_s_at | | | |
| Proliferation | 8.53 | 1119488 | 154672 | 201761_at | MTHFD2 | | |
| Proliferation | 8.58 | 1130799 | 233952 | 201114_x_at | PSMA7 | | |
| Proliferation | 8.72 | 1135673 | 82159 | 210759_s_at | PSMA1 | | |
| Proliferation | 9.4 | 1114679 | 16470 | 222503_s_at | FLJ10904 | | |

| | Standard | Lymph Node | Proliferation | | |
|---|---|---|---|---|---|
| Mean FH | −2193.59 | −588.21 | 1571.78 | Cut 1 | 0.50 |
| Mean DLBCL-BL | −1448.27 | −441.91 | 1735.00 | Cut 2 | 0.92 |
| Covariance FH | 6729.73 | 1223.99 | 2541.22 | | |
| | 1223.99 | 405.22 | 293.72 | | |
| | 2541.22 | 293.72 | 1797.58 | | |
| Covariance DLBCL-BL | 17675.23 | 3642.41 | 4158.43 | | |
| | 3642.41 | 1379.81 | 1066.48 | | |
| | 4158.43 | 1066.48 | 2858.21 | | |

TABLE 2405

FH vs. FL

| Signature | Scale | UNIQID | Unigene ID Build 167 http://www.ncbi.nlm.nih.gov/UniGene | Probe set | Gene Symbol |
|---|---|---|---|---|---|
| Standard | −11.23 | 1117298 | 449586 | 234366_x_at | |
| Standard | −10.62 | 1121953 | 38365 | 206478_at | KIAA0125 |
| Standard | −10.6 | 1104910 | 458262 | 233969_at | IGL@ |
| Standard | −10.39 | 1136430 | 102950 | 211798_x_at | IGLJ3 |
| Standard | −9.96 | 1129281 | 395486 | 220377_at | C14orf110 |
| Standard | −9.73 | 1118835 | 102336 | 47069_at | ARHGAP8 |
| Standard | −9.21 | 1127807 | 7236 | 217950_at | NOSIP |
| Standard | −9.05 | 1128377 | 371003 | 219014_at | PLAC8 |
| Standard | −8.85 | 1101004 | 2969 | 229265_at | SKI |
| Standard | 9.06 | 1139411 | 368238 | 219073_s_at | OSBPL10 |
| Standard | 9.07 | 1120789 | 154729 | 204524_at | PDPK1 |
| Standard | 9.21 | 1136464 | 159428 | 211833_s_at | BAX |
| Standard | 9.29 | 1125279 | 445652 | 213575_at | TRA2A |
| Standard | 9.45 | 1529390 | 79241 | Lymph_Dx_120_at | BCL2 |
| Standard | 9.52 | 1132022 | 173911 | 203247_s_at | ZNF24 |
| Standard | 9.57 | 1139645 | 134051 | 219757_s_at | C14orf101 |
| Standard | 9.64 | 1137561 | 67397 | 214639_s_at | HOXA1 |
| Standard | 9.66 | 1114893 | 314623 | 222891_s_at | BCL11A |
| Standard | 10.38 | 1098095 | 131059 | 225852_at | ANKRD17 |
| Standard | 10.4 | 1134858 | 405954 | 209226_s_at | TNPO1 |
| Standard | 12.65 | 1101054 | 173328 | 229322_at | PPP2R5E |
| Standard | 12.79 | 1124178 | 446579 | 211969_at | HSPCA |
| Standard | 13.34 | 1135489 | 288178 | 210438_x_at | SSA2 |

| | Standard | | |
|---|---|---|---|
| Mean FH | 136.43 | Cut 1 | 0.50 |
| Mean FL | 640.38 | Cut 2 | 0.99 |
| Covariance FH | 10719.40 | | |
| Covariance FL | 9373.11 | | |

TABLE 2406

FH vs. MCL

| Signature | Scale | UNIQID | Unigene ID Build 167 http://www.ncbi.nlm.nih.gov/UniGene | Probe set | Gene Symbol |
|---|---|---|---|---|---|
| Standard | 13.05 | 1100258 | 88442 | 228377_at | KIAA1384 |
| Standard | 13.43 | 1529382 | 371468 | Lymph_Dx_111_at | CCND1 |
| Standard | 13.54 | 1106855 | 455101 | 236255_at | KIAA1909 |
| Standard | 13.73 | 1529308 | 193014 | Lymph_Dx_027_x_at | |
| Standard | 14.56 | 1100873 | 445884 | 229103_at | |
| Standard | 21.12 | 1132834 | 432638 | 204914_s_at | SOX11 |
| Lymph Node | −8.44 | 1130378 | 234434 | 44783_s_at | HEY1 |
| Lymph Node | −7.92 | 1123552 | 423077 | 209879_at | SELPLG |
| Lymph Node | −7.7 | 1131218 | 76753 | 201809_s_at | ENG |
| Lymph Node | −7.4 | 1097683 | 132569 | 225373_at | PP2135 |
| Lymph Node | −7.15 | 1136273 | 13775 | 211597_s_at | HOP |
| Lymph Node | 14.16 | 1134532 | 371468 | 208711_s_at | CCND1 |

| | Standard | Lymph Node | | |
|---|---|---|---|---|
| Mean FH | 451.68 | −282.65 | Cut 1 | 0.20 |
| Mean MCFL | 863.16 | −156.82 | Cut 2 | 0.80 |
| Covariance FH | 1617.92 | 222.89 | | |
| | 222.89 | 271.65 | | |
| Covariance MCL | 3154.38 | 917.30 | | |
| | 917.30 | 859.94 | | |

TABLE 2407

FH vs. SLL

| Signature | Scale | UNIQID | Unigene ID Build 167 http://www.ncbi.nlm.nih.gov/UniGene | Probe set | Gene Symbol |
|---|---|---|---|---|---|
| Standard | −13.14 | 1120765 | 343329 | 204484_at | PIK3C2B |
| Standard | −12.9 | 1097897 | 266175 | 225622_at | PAG |
| Standard | 12.72 | 1133195 | 274243 | 205805_s_at | ROR1 |
| Standard | 12.74 | 1140416 | 58831 | 221601_s_at | TOSO |
| Standard | 13.53 | 1131687 | 359280 | 202606_s_at | TLK1 |
| Standard | 13.57 | 1107044 | 163426 | 236458_at | |
| Standard | 14.43 | 1529389 | 79241 | Lymph_Dx_119_at | BCL2 |
| Standard | 14.51 | 1129026 | 135146 | 220007_at | FLJ13984 |
| Standard | 14.77 | 1136987 | 21695 | 213370_s_at | SFMBT1 |
| Standard | 14.79 | 1137109 | 469653 | 213689_x_at | RPL5 |
| Standard | 15.37 | 1529308 | 193014 | Lymph_Dx_027_x_at | |
| Standard | 15.82 | 1120832 | 57856 | 204604_at | PFTK1 |
| Standard | 17.37 | 1135550 | 221811 | 210550_s_at | RASGRF1 |
| Standard | 18.98 | 1122864 | 434384 | 208195_at | TTN |
| Lymph Node | −12.89 | 1123038 | 119000 | 208636_at | ACTN1 |
| Lymph Node | −12.8 | 1130378 | 234434 | 44783_s_at | HEY1 |
| Lymph Node | −11.59 | 1124875 | 18166 | 212975_at | KIAA0870 |
| Lymph Node | −11.47 | 1103497 | 50115 | 232231_at | |
| Lymph Node | −10.31 | 1099358 | 93135 | 227300_at | |
| Lymph Node | −10.27 | 1121129 | 285401 | 205159_at | CSF2RB |
| Lymph Node | −10.23 | 1100249 | 388674 | 228367_at | HAK |
| Lymph Node | −10.05 | 1132345 | 109225 | 203868_s_at | VCAM1 |
| Lymph Node | −9.93 | 1123401 | 50130 | 209550_at | NDN |
| Lymph Node | −9.75 | 1120500 | 82568 | 203979_at | CYP27A1 |
| Lymph Node | −9.57 | 1124318 | 21858 | 212190_at | SERPINE2 |
| Lymph Node | −9.48 | 1120288 | 17483 | 203547_at | CD4 |
| Lymph Node | −9.45 | 1123372 | 195825 | 209487_at | RBPMS |
| Lymph Node | −9.39 | 1123376 | 37682 | 209496_at | RARRES2 |
| Lymph Node | −9.29 | 1123213 | 12956 | 209154_at | TIP-1 |
| Lymph Node | −9.23 | 1098412 | 409515 | 226225_at | MCC |
| Lymph Node | −9.23 | 1125593 | 8910 | 214180_at | MAN1C1 |
| Lymph Node | −9.17 | 1131786 | 375957 | 202803_s_at | ITGB2 |
| Lymph Node | −9.04 | 1097683 | 132569 | 225373_at | PP2135 |
| Lymph Node | −8.91 | 1097255 | 380144 | 224861_at | |
| Lymph Node | −8.76 | 1131068 | 118400 | 201564_s_at | FSCN1 |
| Lymph Node | −8.7 | 1119074 | 54457 | 200675_at | CD81 |
| Lymph Node | −8.68 | 1125130 | 35861 | 213338_at | RIS1 |
| Lymph Node | −8.59 | 1139661 | 416456 | 219806_s_at | FN5 |

TABLE 2407-continued

FH vs. SLL

|  | Standard | Lymph Node |  |  |
|---|---|---|---|---|
| Mean FH | 1144.02 | −2223.71 | Cut 1 | 0.20 |
| Mean SLL | 1592.27 | −1798.11 | Cut 2 | 0.80 |
| Covariance FH | 902.56 | 442.69 |  |  |
|  | 442.69 | 809.90 |  |  |
| Covariance SLL | 2426.26 | 2938.58 |  |  |
|  | 2938.58 | 9435.72 |  |  |

TABLE 2408

FL vs. DLBCL-BL

| Signature | Scale | UNIQID | Unigene ID Build 167 http://www.ncbi.nlm.nih.gov/UniGene | Probe set | Gene Symbol |
|---|---|---|---|---|---|
| Standard | −23.03 | 1124833 | 356416 | 212914_at | CBX7 |
| Standard | −22.25 | 1099204 | 193784 | 227121_at |  |
| Standard | −22.2 | 1119766 | 93231 | 202423_at | MYST3 |
| Standard | −22.04 | 1099798 | 411081 | 227811_at | FGD3 |
| Standard | −22.01 | 1102898 | 145519 | 231496_at | FKSG87 |
| Standard | −21.79 | 1131197 | 269902 | 201778_s_at | KIAA0494 |
| Standard | −21.69 | 1098415 | 130900 | 226230_at | KIAA1387 |
| Standard | −21.57 | 1120834 | 57907 | 204606_at | CCL21 |
| Standard | −21.39 | 1130155 | 436657 | 222043_at | CLU |
| Standard | −20.98 | 1100904 | 426296 | 229145_at | LOC119504 |
| Standard | −20.8 | 1131531 | 153647 | 202350_s_at | MATN2 |
| Standard | −20.72 | 1137582 | 433732 | 214683_s_at | CLK1 |
| Standard | −20.66 | 1119782 | 155418 | 202478_at | TRB2 |
| Standard | −20.59 | 1122767 | 652 | 207892_at | TNFSF5 |
| Standard | −20.58 | 1125001 | 16193 | 213158_at |  |
| Standard | −20.56 | 1134921 | 413513 | 209341_s_at | IKBKB |
| Standard | −20.56 | 1132973 | 169294 | 205255_x_at | TCF7 |
| Standard | −20.53 | 1136984 | 498154 | 213364_s_at | SNX1 |
| Standard | −20.41 | 1115888 | 35096 | 225629_s_at | ZBTB4 |
| Standard | −20.37 | 1120160 | 436976 | 203288_at | KIAA0355 |
| Standard | −20.36 | 1139054 | 25726 | 218263_at | LOC58486 |
| Standard | −20.31 | 1130030 | 301872 | 221834_at | LONP |
| Standard | −20.08 | 1133024 | 436987 | 205383_s_at | ZNF288 |
| Standard | −20.05 | 1124666 | 526394 | 212672_at | ATM |
| Standard | −19.3 | 1529397 | 406557 | Lymph_Dx_127_s_at | CLK4 |
| Standard | −19.16 | 1116056 | 243678 | 226913_s_at | SOX8 |
| Standard | −19.14 | 1098433 | 202577 | 226250_at |  |
| Standard | −19.1 | 1123635 | 408614 | 210073_at | SIAT8A |
| Standard | −18.95 | 1138920 | 24395 | 218002_s_at | CXCL14 |
| Standard | −18.84 | 1133099 | 88646 | 205554_s_at | DNASE1L3 |
| Standard | −18.83 | 1098495 | 443668 | 226318_at | TBRG1 |
| Standard | −18.64 | 1100879 | 119983 | 229111_at | MASP2 |
| Standard | −18.59 | 1120695 | 385685 | 204352_at | TRAF5 |
| Standard | −18.55 | 1119983 | 409783 | 202920_at | ANK2 |
| Standard | −18.5 | 1101276 | 1098 | 229588_at | ERdj5 |
| Standard | −18.47 | 1099140 | 500350 | 227052_at |  |
| Standard | −18.46 | 1529331 | 374126 | Lymph_Dx_051_s_at |  |
| Standard | −18.45 | 1131752 | 170133 | 202724_s_at | FOXO1A |
| Standard | −18.45 | 1099265 | 375762 | 227193_at |  |
| Standard | −18.32 | 1098179 | 163725 | 225956_at | LOC153222 |
| Standard | −18.29 | 1119566 | 269777 | 201957_at | PPP1R12B |
| Standard | −18.19 | 1099900 | 444508 | 227934_at |  |
| Standard | −18.17 | 1119361 | 391858 | 201448_at | TIA1 |
| Standard | −18.02 | 1121650 | 421137 | 206002_at | GPR64 |
| Standard | −17.91 | 1100911 | 320147 | 229152_at | C4orf7 |
| Standard | −17.86 | 1529285 | 348929 | Lymph_Dx_002_at | KIAA1219 |
| Standard | −17.47 | 1529357 | 444651 | Lymph_Dx_081_at |  |
| Standard | −17.42 | 1131883 | 2316 | 202936_s_at | SOX9 |
| Standard | −17.16 | 1129943 | 512828 | 221626_at | ZNF506 |
| Standard | −17.12 | 1121301 | 449971 | 205437_at | ZNF134 |
| Standard | −17.11 | 1131340 | 437457 | 202018_s_at | LTF |
| Standard | −17.1 | 1124606 | 444324 | 212588_at | PTPRC |
| Standard | −17.08 | 1131407 | 154248 | 202125_s_at | ALS2CR3 |
| Standard | −16.97 | 1118939 | 198161 | 60528_at | PLA2G4B |
| Standard | −16.91 | 1134738 | 75842 | 209033_s_at | DYRK1A |
| Standard | −16.9 | 1134083 | 285091 | 207996_s_at | C18orf1 |
| Standard | −16.89 | 1120925 | 204891 | 204773_at | IL11RA |
| Standard | −16.86 | 1110070 | −101 | 239803_at |  |
| Standard | −16.83 | 1100042 | 351413 | 228113_at | RAB37 |

TABLE 2408-continued

| FL vs. DLBCL-BL | | | | | |
|---|---|---|---|---|---|
| Standard | −16.82 | 1120134 | 75545 | 203233_at | IL4R |
| Standard | −16.75 | 1124283 | 406612 | 212144_at | UNC84B |
| Standard | −16.72 | 1109603 | −100 | 239292_at | |
| Standard | −16.71 | 1120509 | 155090 | 204000_at | GNB5 |
| Standard | −16.65 | 1133538 | 1416 | 206780_s_at | FCER2 |
| Standard | −16.64 | 1130735 | 179526 | 201009_s_at | TXNIP |
| Standard | −16.59 | 1100150 | 9343 | 228248_at | MGC39830 |
| Standard | −16.54 | 1124237 | 258855 | 212080_at | MLL |
| Standard | −16.51 | 1124416 | 283604 | 212331_at | RBL2 |
| Standard | −16.48 | 1133091 | 73792 | 205544_s_at | CR2 |
| Standard | −16.46 | 1131263 | 249955 | 201877_s_at | PPP2R5C |
| Standard | −16.44 | 1118347 | 528404 | 243366_s_at | ITGA4 |
| Standard | −16.43 | 1529343 | 521948 | Lymph_Dx_064_at | |
| Standard | −16.43 | 1099549 | 446665 | 227533_at | |
| Standard | 17.05 | 1529453 | 372679 | Lymph_Dx_085_at | FCGR3A |
| Standard | 17.41 | 1097540 | 388087 | 225195_at | |
| Standard | 18.47 | 1140473 | 17377 | 221676_s_at | CORO1C |
| Standard | 18.55 | 1121100 | 301921 | 205098_at | CCR1 |
| Standard | 20.07 | 1124254 | 301743 | 212110_at | SLC39A14 |
| Standard | 20.2 | 1130771 | 61153 | 201068_s_at | PSMC2 |
| Standard | 21.46 | 1137583 | 273415 | 214687_x_at | ALDOA |
| Standard | 21.55 | 1098168 | 22151 | 225943_at | NLN |
| Standard | 24.07 | 1123055 | 185726 | 208691_at | TFRC |
| Standard | 24.09 | 1123052 | 180909 | 208680_at | PRDX1 |
| Lymph Node | −20.5 | 1137597 | 3903 | 214721_x_at | CDC42EP4 |
| Lymph Node | −18.52 | 1124318 | 21858 | 212190_at | SERPINE2 |
| Lymph Node | −18.5 | 1136762 | 380138 | 212624_s_at | CHN1 |
| Lymph Node | −18.07 | 1101305 | 112742 | 229623_at | |
| Lymph Node | −17.75 | 1100249 | 388674 | 228367_at | HAK |
| Lymph Node | −16.1 | 1098412 | 409515 | 226225_at | MCC |
| Lymph Node | −15.61 | 1140464 | 111676 | 221667_s_at | HSPB8 |
| Lymph Node | −15.43 | 1136832 | 434959 | 212842_x_at | RANBP2L1 |
| Lymph Node | −15.37 | 1119684 | 439586 | 202242_at | TM4SF2 |
| Lymph Node | −15.02 | 1097448 | 250607 | 225093_at | UTRN |
| Lymph Node | −14.83 | 1136844 | 16007 | 212875_s_at | C21orf25 |
| Lymph Node | −14.73 | 1135056 | 169946 | 209604_s_at | GATA3 |
| Lymph Node | −14.48 | 1097202 | 386779 | 224796_at | DDEF1 |
| Lymph Node | −14.44 | 1121278 | 21355 | 205399_at | DCAMKL1 |
| Lymph Node | −14.22 | 1125009 | 27621 | 213169_at | |
| Lymph Node | −13.97 | 1100288 | 26981 | 228411_at | ALS2CR19 |
| Lymph Node | −13.51 | 1132462 | 14845 | 204131_s_at | FOXO3A |
| Lymph Node | −13.37 | 1135322 | 450230 | 210095_s_at | IGFBP3 |
| Lymph Node | −13.35 | 1097280 | 423523 | 224891_at | |
| Lymph Node | −12.86 | 1137097 | 20107 | 213658_at | KNS2 |
| Lymph Node | −12.85 | 1098809 | 359394 | 226682_at | |
| Lymph Node | −12.28 | 1124875 | 18166 | 212975_at | KIAA0870 |
| Lymph Node | −12.18 | 1132345 | 109225 | 203868_s_at | VCAM1 |
| Lymph Node | −12 | 1097561 | 19221 | 225224_at | DKFZP566G1424 |
| Lymph Node | −11.71 | 1123401 | 50130 | 209550_at | NDN |
| Lymph Node | −11.04 | 1136996 | 283749 | 213397_x_at | RNASE4 |
| Lymph Node | −10.77 | 1136788 | 355455 | 212698_s_at | 36778 |
| Lymph Node | −10.71 | 1098822 | 443452 | 226695_at | PRRX1 |
| Lymph Node | −10.63 | 1134200 | 90786 | 208161_s_at | ABCC3 |
| Lymph Node | −10.47 | 1136427 | 276506 | 211795_s_at | FYB |
| Lymph Node | −10.46 | 1121186 | 100431 | 205242_at | CXCL13 |
| Lymph Node | −10.39 | 1099332 | 32433 | 227272_at | |
| Lymph Node | −10.39 | 1098978 | 124863 | 226869_at | |
| Lymph Node | −10.22 | 1103303 | 49605 | 232000_at | C9orf52 |
| Lymph Node | −10.16 | 1131325 | 13313 | 201990_s_at | CREBL2 |
| Lymph Node | −10.16 | 1098174 | 274401 | 225949_at | LOC340371 |
| Lymph Node | −9.93 | 1124733 | 66762 | 212771_at | LOC221061 |
| Lymph Node | −9.42 | 1123372 | 195825 | 209487_at | RBPMS |
| Lymph Node | −9.36 | 1132220 | 448805 | 203632_s_at | GPRC5B |
| Lymph Node | −9.29 | 1120703 | 83974 | 204368_at | SLCO2A1 |
| Lymph Node | −9.26 | 1132013 | 434961 | 203232_s_at | SCA1 |
| Lymph Node | −9.25 | 1097307 | 379754 | 224929_at | LOC340061 |
| Lymph Node | −9.18 | 1119251 | 433941 | 201194_at | SEPW1 |
| Lymph Node | −9.08 | 1097609 | 6093 | 225283_at | ARRDC4 |
| Lymph Node | −9.07 | 1136459 | 252550 | 211828_s_at | KIAA0551 |
| Lymph Node | −8.86 | 1132775 | 1027 | 204803_s_at | RRAD |
| Lymph Node | −8.78 | 1098946 | 135121 | 226834_at | ASAM |
| Lymph Node | −8.68 | 1140589 | 433488 | 221942_s_at | GUCY1A3 |
| Lymph Node | −8.44 | 1116966 | 301124 | 232744_x_at | |
| Lymph Node | −8.39 | 1100130 | 76494 | 228224_at | PRELP |
| Lymph Node | −8.36 | 1110019 | −94 | 239744_at | |
| Lymph Node | −8.3 | 1134647 | 298654 | 208892_s_at | DUSP6 |
| Lymph Node | −8.28 | 1125593 | 8910 | 214180_at | MAN1C1 |
| Lymph Node | 7.97 | 1134370 | 1422 | 208438_s_at | FGR |

TABLE 2408-continued

FL vs. DLBCL-BL

| | | | | | |
|---|---|---|---|---|---|
| Lymph Node | 8.05 | 1123566 | 155935 | 209906_at | C3AR1 |
| Lymph Node | 8.09 | 1131119 | 349656 | 201647_s_at | SCARB2 |
| Lymph Node | 8.11 | 1123586 | 93841 | 209948_at | KCNMB1 |
| Lymph Node | 8.13 | 1128615 | 104800 | 219410_at | FLJ10134 |
| Lymph Node | 8.21 | 1097297 | 166254 | 224917_at | VMP1 |
| Lymph Node | 8.23 | 1120299 | 79334 | 203574_at | NFIL3 |
| Lymph Node | 8.37 | 1128157 | 23918 | 218631_at | VIP32 |
| Lymph Node | 8.4 | 1130054 | 82547 | 221872_at | RARRES1 |
| Lymph Node | 8.41 | 1098152 | 377588 | 225922_at | KIAA1450 |
| Lymph Node | 8.53 | 1101566 | 98558 | 229947_at | |
| Lymph Node | 8.59 | 1135251 | 21486 | 209969_s_at | STAT1 |
| Lymph Node | 8.84 | 1099167 | 381105 | 227080_at | MGC45731 |
| Lymph Node | 9.01 | 1132920 | 753 | 205119_s_at | FPR1 |
| Lymph Node | 9.26 | 1097253 | 77873 | 224859_at | B7H3 |
| Lymph Node | 9.29 | 1120500 | 82568 | 203979_at | CYP27A1 |
| Lymph Node | 9.36 | 1131507 | 172928 | 202311_s_at | COL1A1 |
| Lymph Node | 9.38 | 1096456 | 82407 | 223454_at | CXCL16 |
| Lymph Node | 9.49 | 1136172 | 38084 | 211470_s_at | SULT1C1 |
| Lymph Node | 10.03 | 1138244 | 418138 | 216442_x_at | FN1 |
| Lymph Node | 10.34 | 1134424 | -17 | 208540_x_at | S100A14 |
| Lymph Node | 10.48 | 1136152 | 458436 | 211434_s_at | CCRL2 |
| Lymph Node | 10.51 | 1118708 | 7835 | 37408_at | MRC2 |
| Lymph Node | 10.6 | 1136540 | 179657 | 211924_s_at | PLAUR |
| Lymph Node | 10.63 | 1098278 | 166017 | 226066_at | MITF |
| Lymph Node | 10.76 | 1119477 | 163867 | 201743_at | CD14 |
| Lymph Node | 10.81 | 1096429 | 64896 | 223405_at | NPL |
| Lymph Node | 11.58 | 1123672 | 67846 | 210152_at | LILRB4 |
| Lymph Node | 12 | 1096364 | 29444 | 223276_at | NID67 |
| Lymph Node | 12.16 | 1119070 | 446570 | 200663_at | CD63 |
| Lymph Node | 12.3 | 1133065 | 77274 | 205479_s_at | PLAU |
| Lymph Node | 12.5 | 1135240 | 436852 | 209955_s_at | FAP |
| Lymph Node | 13.09 | 1116826 | 26204 | 231823_at | KIAA1295 |
| Lymph Node | 13.32 | 1119068 | 417004 | 200660_at | S100A11 |
| Lymph Node | 13.45 | 1120266 | 246381 | 203507_at | CD68 |
| Lymph Node | 13.63 | 1133216 | 502577 | 205872_x_at | PDE4DIP |
| Lymph Node | 13.67 | 1131815 | 386678 | 202856_s_at | SLC16A3 |
| Lymph Node | 14.38 | 1132132 | 279910 | 203454_s_at | ATOX1 |
| Lymph Node | 15.25 | 1134682 | 411701 | 208949_s_at | LGALS3 |
| Lymph Node | 15.46 | 1119237 | 389964 | 201141_at | GPNMB |
| Lymph Node | 15.89 | 1137698 | 442669 | 215001_s_at | GLUL |
| Lymph Node | 17.8 | 1137782 | 384944 | 215223_s_at | SOD2 |
| Lymph Node | 20.11 | 1130629 | 135226 | 200839_s_at | CTSB |
| Proliferation | 21.02 | 1119375 | 381072 | 201489_at | PPIF |
| Proliferation | 21.24 | 1119488 | 154872 | 201761_at | MTHFD2 |
| Proliferation | 21.31 | 1119467 | 21635 | 201714_at | TUBG1 |
| Proliferation | 21.68 | 1130820 | 151777 | 201144_s_at | EIF2S1 |
| Proliferation | 21.69 | 1131474 | 95577 | 202246_s_at | CDK4 |
| Proliferation | 22.2 | 1125249 | 244723 | 213523_at | CCNE1 |
| Proliferation | 22.97 | 1130501 | 2795 | 200650_s_at | LDHA |
| Proliferation | 23.12 | 1136913 | 99962 | 213113_s_at | SLC43A3 |
| Proliferation | 24.05 | 1130426 | 432607 | 200039_s_at | PSMB2 |

| | Standard | Lymph Node | Proliferation | | |
|---|---|---|---|---|---|
| Mean FL | -11121.51 | -1603.39 | 1890.60 | Cut 1 | 0.34 |
| Mean DLBCL-BL | -8760.65 | -460.71 | 2101.10 | Cut 2 | 0.94 |
| Covariance FL | 246359.77 | 111505.42 | 28908.20 | | |
| | 111505.42 | 67036.17 | 13130.59 | | |
| | 28908.20 | 13130.59 | 4617.24 | | |
| Covariance DLBCL-BL | 413069.12 | 178811.32 | 30151.89 | | |
| | 178811.32 | 106324.53 | 10877.26 | | |
| | 30151.89 | 10877.26 | 5180.68 | | |

TABLE 2409

FL vs. MCL

| Signature | Scale | UNIQID | Unigene ID Build 167 http://www.ncbi.nlm.nih.gov/UniGene | Probe set | Gene Symbol |
|---|---|---|---|---|---|
| Standard | -24.56 | 1123731 | 17165 | 210258_at | RGS13 |
| Standard | -22.56 | 1133192 | 24024 | 205801_s_at | RASGRP3 |
| Standard | -21.12 | 1114543 | 156189 | 244887_at | |
| Standard | -18.49 | 1120090 | 155024 | 203140_at | BCL6 |
| Standard | -18.07 | 1124646 | 436432 | 212646_at | RAFTLIN |

TABLE 2409-continued

FL vs. MCL

| | | | | | |
|---|---|---|---|---|---|
| Standard | −17.24 | 1132122 | 307734 | 203434_s_at | MME |
| Standard | −16.63 | 1105986 | 49614 | 235310_at | GCET2 |
| Standard | −15.09 | 1120134 | 75545 | 203233_at | IL4R |
| Standard | −14.05 | 1132651 | 439767 | 204529_s_at | TOX |
| Standard | 13.8 | 1098277 | 6786 | 226065_at | PRICKLE1 |
| Standard | 13.85 | 1109560 | 207428 | 239246_at | FARP1 |
| Standard | 13.86 | 1103504 | 142517 | 232239_at | |
| Standard | 13.88 | 1132734 | 126248 | 204724_s_at | COL9A3 |
| Standard | 13.91 | 1115905 | 301478 | 226757_s_at | CLMN |
| Standard | 14.89 | 1098840 | 55098 | 226713_at | C3orf6 |
| Standard | 14.97 | 1100873 | 445884 | 229103_at | |
| Standard | 14.99 | 1139393 | 170129 | 219032_x_at | OPN3 |
| Standard | 16.13 | 1124864 | 411317 | 212960_at | KIAA0882 |
| Standard | 16.36 | 1106855 | 455101 | 236255_at | KIAA1909 |
| Standard | 16.43 | 1120858 | 410683 | 204647_at | HOMER3 |
| Standard | 17.38 | 1130926 | 508741 | 201310_s_at | C5orf13 |
| Standard | 18.3 | 1103711 | 288718 | 232478_at | |
| Standard | 18.62 | 1109505 | 8162 | 239186_at | MGC39372 |
| Standard | 20.31 | 1132834 | 432638 | 204914_s_at | SOX11 |
| Standard | 22.61 | 1096070 | 241565 | 222640_at | DNMT3A |
| Standard | 28.66 | 1529382 | 371468 | Lymph_Dx_111_at | CCND1 |
| Lymph Node | −10.77 | 1097202 | 386779 | 224796_at | DDEF1 |
| Lymph Node | −10.22 | 1119546 | 433898 | 201921_at | GNG10 |
| Lymph Node | −9.89 | 1132766 | 82359 | 204781_s_at | TNFRSF6 |
| Lymph Node | −9.4 | 1138867 | 10706 | 217892_s_at | EPLIN |
| Lymph Node | 9.65 | 1125025 | 301094 | 213196_at | |
| Lymph Node | 10.44 | 1134797 | 433394 | 209118_s_at | TUBA3 |
| Lymph Node | 22.6 | 1529456 | 371468 | Lymph_Dx_113_at | CCND1 |
| Proliferation | −7.36 | 1097948 | 69476 | 225684_at | LOC348235 |
| Proliferation | −7.31 | 1130747 | 234489 | 201030_x_at | LDHB |
| Proliferation | −6.95 | 1130923 | 459987 | 201306_s_at | ANP32B |
| Proliferation | −6.87 | 1120205 | 5198 | 203405_at | DSCR2 |
| Proliferation | −6.64 | 1132468 | 79353 | 204147_s_at | TFDP1 |
| Proliferation | −6.1 | 1119916 | 177584 | 202780_at | OXCT |
| Proliferation | −6.08 | 1119873 | 446393 | 202697_at | CPSF5 |
| Proliferation | −6.08 | 1119488 | 154672 | 201761_at | MTHFD2 |
| Proliferation | −6.04 | 1130658 | 447492 | 200886_s_at | PGAM1 |
| Proliferation | −5.82 | 1132825 | 512813 | 204900_x_at | SAP30 |
| Proliferation | −5.53 | 1115607 | 435733 | 224428_s_at | CDCA7 |
| Proliferation | −5.44 | 1120316 | 63335 | 203611_at | TERF2 |
| Proliferation | −5.34 | 1114970 | 279529 | 223032_x_at | PX19 |
| Proliferation | −5.32 | 1140843 | 169476 | AFFX-HUMGAPDH/M33197_5_at | GAPD |
| Proliferation | −5.28 | 1131081 | 180610 | 201586_s_at | SFPQ |
| Proliferation | −5.15 | 1121062 | 408658 | 205034_at | CCNE2 |
| Proliferation | 5.15 | 1120986 | 172052 | 204886_at | PLK4 |
| Proliferation | 5.16 | 1097195 | 149931 | 224785_at | MGC29814 |
| Proliferation | 5.2 | 1120011 | 3068 | 202983_at | SMARCA3 |
| Proliferation | 5.47 | 1100183 | 180582 | 228286_at | FLJ40869 |
| Proliferation | 5.67 | 1121012 | 96055 | 204947_at | E2F1 |
| Proliferation | 5.84 | 1115679 | 8345 | 224523_s_at | MGC4308 |
| Proliferation | 5.88 | 1135285 | 449501 | 210024_s_at | UBE2E3 |
| Proliferation | 5.92 | 1120520 | 35120 | 204023_at | RFC4 |
| Proliferation | 6.16 | 1529361 | 388681 | Lymph_Dx_086_s_at | HDAC3 |
| Proliferation | 6.45 | 1096054 | 21331 | 222606_at | FLJ10036 |
| Proliferation | 6.45 | 1096738 | 87968 | 223903_at | TLR9 |
| Proliferation | 6.51 | 1136781 | 120197 | 212680_x_at | PPP1R14B |
| Proliferation | 6.63 | 1119466 | 179718 | 201710_at | MYBL2 |
| Proliferation | 6.65 | 1136285 | 182490 | 211615_s_at | LRPPRC |
| Proliferation | 6.67 | 1136853 | 66170 | 212922_s_at | SMYD2 |
| Proliferation | 7.45 | 1119390 | 77254 | 201518_at | CBX1 |
| Proliferation | 8.87 | 1116122 | 42768 | 227408_s_at | DKFZp761O0113 |
| Proliferation | 10.12 | 1119515 | 3352 | 201833_at | HDAC2 |

| | Standard | Lymph Node | Proliferation | | |
|---|---|---|---|---|---|
| Mean FL | −18.82 | −33.90 | 23.53 | Cut 1 | 0.14 |
| Mean MCL | 1558.10 | 113.95 | 165.48 | Cut 2 | 0.56 |
| Covariance FL | 21302.14 | 1098.24 | 678.04 | | |
| | 1098.24 | 226.29 | 75.99 | | |
| | 678.04 | 75.99 | 315.67 | | |
| Covariance MCL | 81008.29 | 5261.37 | 9185.20 | | |
| | 5261.37 | 2047.34 | 875.56 | | |
| | 9185.20 | 875.56 | 1447.43 | | |

TABLE 2410

FL vs. SLL

| Signature | Scale | UNIQID | Unigene ID Build 167 http://www.ncbi.nlm.nih.gov/UniGene | Probe set | Gene Symbol |
|---|---|---|---|---|---|
| Standard | −21.04 | 1123731 | 17165 | 210258_at | RGS13 |
| Standard | −20.91 | 1124646 | 436432 | 212646_at | RAFTLIN |
| Standard | −18.82 | 1099651 | 120785 | 227646_at | EBF |
| Standard | −18.12 | 1114543 | 156189 | 244887_at | |
| Standard | −17.85 | 1105986 | 49614 | 235310_at | GCET2 |
| Standard | −16.73 | 1100911 | 320147 | 229152_at | C4orf7 |
| Standard | −15.77 | 1132122 | 307734 | 203434_s_at | MME |
| Standard | −15.12 | 1120090 | 155024 | 203140_at | BCL6 |
| Standard | −14.89 | 1097897 | 266175 | 225622_at | PAG |
| Standard | −14.36 | 1529343 | 521948 | Lymph_Dx_064_at | |
| Standard | −14.32 | 1529318 | 291954 | Lymph_Dx_038_at | |
| Standard | −14.06 | 1128694 | 171466 | 219517_at | ELL3 |
| Standard | −13.61 | 1101586 | 187884 | 229971_at | GPR114 |
| Standard | −13.57 | 1119752 | 511745 | 202391_at | BASP1 |
| Standard | −13.13 | 1137561 | 67397 | 214639_s_at | HOXA1 |
| Standard | −12.85 | 1097247 | 388761 | 224851_at | CDK6 |
| Standard | −12.43 | 1529344 | 317970 | Lymph_Dx_065_at | SERPINA11 |
| Standard | −12.4 | 1120765 | 343329 | 204484_at | PIK3C2B |
| Standard | −12.33 | 1130155 | 436657 | 222043_at | CLU |
| Standard | −12.07 | 1529292 | −92 | Lymph_Dx_010_at | |
| Standard | −12.01 | 1119939 | 170087 | 202820_at | AHR |
| Standard | −11.82 | 1119919 | 199263 | 202786_at | STK39 |
| Standard | −11.77 | 1099686 | 117721 | 227684_at | |
| Standard | −11.63 | 1119782 | 155418 | 202478_at | TRB2 |
| Standard | 10.97 | 1529309 | 512797 | Lymph_Dx_028_at | HSH2 |
| Standard | 10.97 | 1139393 | 170129 | 219032_x_at | OPN3 |
| Standard | 11.04 | 1131246 | 153752 | 201853_s_at | CDC25B |
| Standard | 11.07 | 1140391 | 44865 | 221558_s_at | LEF1 |
| Standard | 11.16 | 1140418 | 58831 | 221601_s_at | TOSO |
| Standard | 11.35 | 1127807 | 7236 | 217950_at | NOSIP |
| Standard | 11.67 | 1529317 | −98 | Lymph_Dx_037_at | |
| Standard | 11.81 | 1117343 | 306812 | 234643_x_at | BUCS1 |
| Standard | 11.82 | 1102081 | 506977 | 230551_at | |
| Standard | 11.82 | 1135042 | 79015 | 209582_s_at | MOX2 |
| Standard | 11.96 | 1132734 | 126248 | 204724_s_at | COL9A3 |
| Standard | 12.09 | 1137109 | 469653 | 213689_x_at | RPL5 |
| Standard | 12.14 | 1099939 | 488173 | 227983_at | MGC7036 |
| Standard | 12.19 | 1129103 | 99430 | 220118_at | TZFP |
| Standard | 12.47 | 1135592 | 758 | 210621_s_at | RASA1 |
| Standard | 12.78 | 1108970 | 140489 | 238604_at | |
| Standard | 12.92 | 1097143 | 74335 | 224716_at | HSPCB |
| Standard | 13.18 | 1136865 | 412128 | 212959_s_at | MGC4170 |
| Standard | 13.96 | 1098220 | 80720 | 226002_at | GAB1 |
| Standard | 14.06 | 1100847 | 97411 | 229070_at | C6orf105 |
| Standard | 14.39 | 1098865 | 250905 | 226741_at | LOC51234 |
| Standard | 15.57 | 1136687 | 59943 | 212345_s_at | CREB3L2 |
| Standard | 15.75 | 1107044 | 163426 | 236458_at | |
| Standard | 16.52 | 1123622 | 8578 | 210051_at | EPAC |
| Standard | 17.74 | 1136987 | 21695 | 213370_s_at | SFMBT1 |
| Standard | 19.15 | 1129026 | 135146 | 220007_at | FLJ13984 |
| Standard | 19.65 | 1131854 | 414985 | 202923_s_at | GCLC |
| Lymph Node | −14.99 | 1124875 | 18166 | 212975_at | KIAA0870 |
| Lymph Node | −14.33 | 1099358 | 93135 | 227300_at | |
| Lymph Node | −13.26 | 1121129 | 285401 | 205159_at | CSF2RB |
| Lymph Node | −12.61 | 1119074 | 54457 | 200675_at | CD81 |
| Lymph Node | −12.52 | 1121029 | 412999 | 204971_at | CSTA |
| Lymph Node | −11.48 | 1137247 | 234734 | 213975_s_at | LYZ |
| Lymph Node | −10.97 | 1128781 | 79741 | 219648_at | FLJ10116 |
| Lymph Node | 11.79 | 1119880 | 442844 | 202709_at | FMOD |
| Lymph Node | 14.4 | 1134370 | 1422 | 208438_s_at | FGR |

| | Standard | Lymph Node | | |
|---|---|---|---|---|
| Mean FL | −663.95 | −730.08 | Cut 1 | 0.20 |
| Mean SLL | 1332.84 | −484.93 | Cut 2 | 0.80 |
| Covariance FL | 37097.15 | 1710.73 | | |
| | 1710.73 | 663.78 | | |
| Covariance SLL | 85989.25 | 17661.52 | | |
| | 17661.52 | 4555.06 | | |

TABLE 2411

GCB vs. PMBL

| Signature | Scale | UNIQID | Unigene ID Build 167 http://www.ncbi.nlm.nih.gov/UniGene | Probe set | Gene Symbol |
|---|---|---|---|---|---|
| Standard | −8.39 | 1096440 | 231320 | 223423_at | GPR160 |
| Standard | −8.13 | 1096108 | 292871 | 222731_at | ZDHHC2 |
| Standard | −8.12 | 1125231 | 446375 | 213489_at | MAPRE2 |
| Standard | −8.02 | 1136759 | 188882 | 212605_s_at | |
| Standard | −7.91 | 1096499 | 293867 | 223514_at | CARD11 |
| Standard | −7.8 | 1099388 | 124024 | 227336_at | DTX1 |
| Standard | −7.71 | 1139623 | 193736 | 219687_s_at | BANK1 |
| Standard | −7.68 | 1098592 | 283707 | 226431_at | ALS2CR13 |
| Standard | −7.67 | 1107575 | 424589 | 237033_at | MGC52498 |
| Standard | −7.63 | 1116829 | 115467 | 231840_x_at | LOC90624 |
| Standard | −7.42 | 1130114 | 445084 | 221965_at | MPHOSPH9 |
| Standard | −7.27 | 1098909 | 446408 | 226789_at | |
| Standard | 7.34 | 1138759 | 396404 | 217707_x_at | SMARCA2 |
| Standard | 7.37 | 1120355 | 80420 | 203687_at | CX3CL1 |
| Standard | 7.4 | 1134270 | 352119 | 208284_x_at | GGT1 |
| Standard | 7.44 | 1115441 | 5470 | 224156_x_at | IL17RB |
| Standard | 7.78 | 1103054 | 341531 | 231690_at | |
| Standard | 7.91 | 1119765 | 81234 | 202421_at | IGSF3 |
| Standard | 7.92 | 1119438 | 118110 | 201641_at | BST2 |
| Standard | 8.09 | 1135645 | 31439 | 210715_s_at | SPINT2 |
| Standard | 8.15 | 1106015 | 96885 | 235343_at | FLJ12505 |
| Standard | 8.18 | 1121400 | 223474 | 205599_at | TRAF1 |
| Standard | 8.38 | 1139950 | 437385 | 220731_s_at | FLJ10420 |
| Standard | 8.73 | 1122112 | 1314 | 206729_at | TNFRSF8 |
| Standard | 8.77 | 1122772 | 66742 | 207900_at | CCL17 |
| Standard | 8.84 | 1132762 | 80395 | 204777_s_at | MAL |
| Standard | 9.64 | 1139774 | 15827 | 220140_s_at | SNX11 |
| Standard | 10.53 | 1133801 | 181097 | 207426_s_at | TNFSF4 |
| Standard | 11.52 | 1106415 | 169071 | 235774_at | |
| Standard | 12.09 | 1129269 | 62919 | 220358_at | SNFT |

| Standard | | | |
|---|---|---|---|
| Mean GCB | 292.76 | Cut 1 | 0.16 |
| Mean PMBL | 725.28 | Cut 2 | 0.50 |
| Covariance GCB | 8538.86 | | |
| Covariance PMBL | 11405.23 | | |

TABLE 2412

MCL vs. DLBCL-BL

| Signature | Scale | UNIQID | Unigene ID Build 167 http://www.ncbi.nlm.nih.gov/UniGene | Probe set | Gene Symbol |
|---|---|---|---|---|---|
| Standard | −26.11 | 1529382 | 371468 | Lymph_Dx_111_at | CCND1 |
| Standard | −18.35 | 1103711 | 288718 | 232478_at | |
| Standard | −17.03 | 1106855 | 455101 | 236255_at | KIAA1909 |
| Standard | −16.49 | 1098840 | 55098 | 226713_at | C3orf6 |
| Standard | −15.41 | 1109505 | 8162 | 239186_at | MGC39372 |
| Standard | −15.11 | 1098954 | 128905 | 226844_at | MOBKL2B |
| Standard | −14.96 | 1103504 | 142517 | 232239_at | |
| Standard | −14.74 | 1096070 | 241565 | 222640_at | DNMT3A |
| Standard | −13.81 | 1137663 | 247362 | 214909_s_at | DDAH2 |
| Standard | −13.8 | 1124864 | 411317 | 212960_at | KIAA0882 |
| Standard | −13.62 | 1140127 | 125300 | 221044_s_at | TRIM34 |
| Standard | −13.62 | 1119361 | 391858 | 201448_at | TIA1 |
| Standard | −13.37 | 1127849 | 76691 | 218032_at | SNN |
| Standard | 13.72 | 1133192 | 24024 | 205801_s_at | RASGRP3 |
| Standard | 13.85 | 1137583 | 273415 | 214687_x_at | ALDOA |
| Standard | 15.02 | 1123052 | 180909 | 208680_at | PRDX1 |
| Standard | 16.21 | 1097611 | 438993 | 225285_at | BCAT1 |
| Lymph Node | −19.18 | 1529456 | 371468 | Lymph_Dx_113_at | CCND1 |
| Lymph Node | −10.71 | 1098978 | 124863 | 226869_at | |
| Lymph Node | −9.17 | 1097448 | 250607 | 225093_at | UTRN |
| Lymph Node | 8.84 | 1135240 | 436852 | 209955_s_at | FAP |
| Lymph Node | 9.11 | 1119475 | 296323 | 201739_at | SGK |
| Lymph Node | 9.22 | 1119237 | 389964 | 201141-art | GPNMB |
| Lymph Node | 9.46 | 1130629 | 135226 | 200839_s_at | CTSB |
| Lymph Node | 10.1 | 1130054 | 82547 | 221872_at | RARRES1 |

TABLE 2412-continued

MCL vs. DLBCL-BL

|  | Standard | Lymph Node | | |
|---|---|---|---|---|
| Mean MCL | −1417.55 | −25.58 | Cut 1 | 0.50 |
| Mean DLBCL-BL | −756.07 | 202.29 | Cut 2 | 0.88 |
| Covariance MCL | 15347.98 | 3525.48 | | |
|  | 3525.48 | 5420.31 | | |
| Covariance DLBCL-BL | 5132.06 | 1007.64 | | |
|  | 1007.64 | 991.38 | | |

TABLE 2413

MCL vs. SLL

| Signature | Scale | UNIQID | Unigene ID Build 167 http://www.ncbi.nlm.nih.gov/UniGene | Probe set | Gene Symbol |
|---|---|---|---|---|---|
| Standard | −20.18 | 1132834 | 432638 | 204914_s_at | SOX11 |
| Standard | −15.17 | 1130926 | 508741 | 201310_s_at | C5orf13 |
| Standard | 13.44 | 1116150 | 16229 | 227606_s_at | AMSH-LP |
| Standard | 14.44 | 1120134 | 75545 | 203233_at | IL4R |
| Standard | 15.18 | 1529437 | 445162 | Lymph_Dx_175_at | BTLA |
| Standard | 15.19 | 1529317 | −98 | Lymph_Dx_037_at | |
| Standard | 16.2 | 1135042 | 79015 | 209582_s_at | MOX2 |

|  | Standard | | |
|---|---|---|---|
| Mean MCL | 181.38 | Cut 1 | 0.20 |
| Mean SLL | 564.92 | Cut 2 | 0.80 |
| Covariance MCL | 1734.42 | | |
| Covariance SLL | 910.75 | | |

TABLE 2414

SLL vs. DLBCL-BL

| Signature | Scale | UNIQID | Unigene ID Build 167 http://www.ncbi.nlm.nih.gov/UniGene | Probe set | Gene Symbol |
|---|---|---|---|---|---|
| Standard | −16.014498123622 | | 8578 | 210051_at | EPAC |
| Standard | −15.263565392081 | | 506977 | 230551_at | |
| Standard | −14.821500287044 | | 163426 | 236458_at | |
| Standard | −14.178132098865 | | 260905 | 226741_at | LOC51234 |
| Standard | −12.928447190740 | | 416810 | 240538_at | |
| Standard | −12.865207529026 | | 135146 | 220007_at | FLJ13984 |
| Standard | −12.270274835592 | | 758 | 210621_s_at | RASA1 |
| Standard | −11.873094497343 | | 306812 | 234643_x_at | BUCS1 |
| Standard | −11.817891336987 | | 21695 | 213370_s_at | SFMBT1 |
| Standard | −11.786317004830 | | 9059 | 212911_at | KIAA0962 |
| Standard | −11.394544353538 | | 1416 | 206760_s_at | FCER2 |
| Standard | −11.390503635802 | | 439343 | 210944_s_at | CAPN3 |
| Standard | 11.729286420770 | | 300825 | 204493_at | BID |
| Lymph Node | −12.215932479880 | | 442844 | 202709_at | FMOD |
| Lymph Node | 9.514704843240 | | 436852 | 209955_s_at | FAP |
| Lymph Node | 9.739298896429 | | 64896 | 223405_at | NPL |
| Lymph Node | 10.050876449475 | | 296323 | 201739_at | SGK |
| Lymph Node | 13.119859229237 | | 389964 | 201141_at | GPNMB |
| Proliferation | 10.475258128106 | | 14559 | 218542_at | C10orf3 |
| Proliferation | 10.532957832825 | | 512813 | 204900_x_at | SAP30 |
| Proliferation | 11.939188930501 | | 2795 | 200650_s_at | LDHA |
| Proliferation | 11.987387783439 | | 287472 | 209642_at | BUB1 |
| Proliferation | 11.997416445607 | | 435733 | 224428_s_at | CDCA7 |

|  | Standard | Lymph Node | Proliferation | | |
|---|---|---|---|---|---|
| Mean SLL | −1383.640809 | 177.4452398 | 467.2463569 | Cut 1 | 0.201266305 |
| Mean DLBCL-BL | −926.7275468 | 329.6795845 | 582.9070266 | Cut 2 | 0.799816116 |
| Covariance SLL | 3591.384775 | 1789.7516 | 856.0703202 | | |
|  | 1789.7516 | 1421.869535 | 663.4782048 | | |
|  | 856.0703202 | 663.4782048 | 965.6470151 | | |

TABLE 2414-continued

| | SLL vs. DLBCL-BL | | |
|---|---|---|---|
| Covariance DLBCL-BL | 2922.643347 | 473.543487 | 634.3258773 |
| | 473.543487 | 931.9845277 | −53.85584619 |
| | 634.3258773 | −53.85584619 | 767.3545404 |

Example 19: Classification of Lymphoma Samples as BL or DLBCL Based on Bayesian Analysis of Gene Expression Data from the Affymetrix U133 Plus 2.0 Microarray and the Lymphoma Microarray Tumor biopsies were obtained from 71 previously untreated, HIV-negative patients diagnosed with sporadic BL (54 cases) or Burkitt-like lymphoma (17 cases) between 1986 and 2004 at seven institutions belonging to the Leukemia Lymphoma Molecular Profiling Project (LLMPP). In addition, 232 samples were obtained from patients diagnosed with DLBCL, 223 of these were part of previously published studies (Rosenwald 2002; Rosenwald 2003b) using the Lymphochip microarray (Alizadeh 1999), while the other nine were "high-grade" DLBCL samples with K167 scores (a measure of lymphoma cell proliferation) of nearly 100%. All 303 cases were reviewed by a panel of eight hematopathologists using current WHO criteria for morphology, immunophenotype, and cytogenetics. Specifically, specimens-classified as BL were required to have a c-myc translocation, morphology consistent with BL, a K167+ proliferative fraction of greater than 90%, and immunohistochemical evidence of CD10 and/or BCL6 expression. Specimens were classified as DLBCL based on morphological criteria and a B cell immunophenotype.

Among the 232 DLBCL cases, the median age at diagnosis was 61.5 years (range, 8.9 to 92 years). Median follow up was 2.5 years (6.8 years for survivors). FISH for c-myc translocation was performed in 87 cases, with six cases testing positive.

Among the 71 BL cases, 48% were pediatric (range, 2.9 to 18 years) and the remainder were adults (range, 18 to 73 years). Median follow-up was 1.6 years (4.9 years for survivors). The regimens used to treat BL were grouped into CHOP-like regimens (CHOP (Fisher 1993), CNOP (Vose 2002)) or intensive regimens (BFM (Pees 1992), CODOX-M IVAC (Magrath 1996), and intensive chemotherapy regimens combined with autologous stem cell transplant (ASCT)). FISH for c-myc translocation was performed in 67 of the 71 cases, including all cases in which BL was not ruled out by immunohistochemistry or morphology, and 52 cases were found to be positive. FISH for BCL2 translocation was performed in 44 of the 71 cases, with seven cases testing positive.

After pathological review and reclassification, the 71 cases originally submitted as BL or Burkitt-like lymphoma were divided into classic BL (25 cases), atypical BL (20 cases), DLBCL (20 cases), and high grade lymphomas that could not be classified by current WHO criteria (six cases). This re-review diagnosis, which is summarized in Table 2419, provided the standard against which gene expression-based predictors were measured.

TABLE 2419

| Submitting diagnosis | Pathological diagnosis | Total cases | Gene expression diagnosis | Total cases |
|---|---|---|---|---|
| BL or Burkitt-like lymphoma (71 cases) | Classic BL | 25 | BL | 25 |
| | Atypical BL | 20 | BL | 19 |
| | | | DLBCL | 1 |
| | DLBCL | 20 | BL | 7 |
| | | | DLBCL | 13 |
| | High grade lymphoma (NOS) | 6 | DLBCL | 5 |
| | | | BL | 1 |
| DLBCL (223 cases) | DLBCL | 223 | ABC | 78 |
| | | | GCB | 82 |
| | | | PMBL | 33 |
| | | | Unclassified DLBCL | 30 |
| High grade DLBCL (9 cases) | DLBCL | 9 | ABC | 6 |
| | | | GCB | 2 |
| | | | BL | 1 |

RNA was extracted from each of the 303 samples as described previously (Alizadeh 2000). Gene expression profiling was performed using the custom oligonucleotide Lymphoma microarray; which contains oligonucleotides corresponding to 2,524 unique genes that are differentially expressed among the various forms of non-Hodgkin's lymphoma. The primary gene expression profiling data is available at http://llmpp.nih.gov/BL. A subset of the samples were profiled on whole-genome Affymetrix U133 plus 2.0 arrays as well.

To develop a gene expression-based diagnosis of BL, the initial focus was on those cases that were submitted as BL and confirmed as such by pathological review (45 cases). A set of genes were identified that were differentially expressed between these BL cases and each of the DLBCL subgroups (FIG. 35A). Pair-wise Bayesian compound covariance predictors were constructed between BL and ABC, BL and GCB, and BL and PMBL as described previously (Rosenwald 2003a; Rosenwald 2003b; Wright 2003). For each comparison of two lymphoma types, a linear predictor score was calculated by:

$$LPS(S) = \sum_j t_j S_j,$$

where $S_j$ is the expression of gene j in a sample S and $t_j$ is a scale factor representing the difference in expression of gene j between a first lymphoma type and a second lymphoma type (Radmacher 2002). The scale factor used was the t-statistic generated by a t-test for the difference in expression between the two subtypes being compared. Bayes' rule was then applied to the distribution of the linear predictor scores to estimate the probability that the sample was a member of either group. Each comparison between BL and a DLBCL subtype proceeded in two stages using different sets of genes to create a compound covariance predictor as described above.

Stage one utilized c-myc and its target genes, which were defined using an RNA interference experiment. For the RNA interference experiment, the OCl-Ly10 DLBCL cell line was transfected by electroporation (Amaxa Inc., Gaithersburg, Md.) with small interfering RNAs (siRNAs) targeting the c-myc gene (Smart pool; Dharmacon, Lafayette, Colo.). Gene expression in RNAi-transduced OCl-Ly10 cells was compared to that of control-transfected OCl-Ly10 cells using Lymphochip microarrays (Alizadeh 1999). Genes that were at least 40% downregulated at 16 and 18 hours post-RNAi transfection and whose mRNA expression levels were correlated with c-myc mRNA expression (r>0.4 across all lymphoma samples) were defined as c-myc target genes (FIG. 35C). The majority of these genes have been previously described as c-myc target genes (Zelfer 2003; Basso 2005). Stage two utilized the 100 genes that exhibited the largest t-statistics differentiating expression in BL from expression in each DLBCL subtype, excluding genes used in stage one.

For a sample to be classified as BL, it had to be predicted to be BL in both stages of the predictor in each of the three pairwise comparisons between BL and the various DLBCL subtypes. Leave-one-out cross-validation was used to evaluate the predictor performance and minimize bias (Hills 1966; Ransohoff 2004; Mollnaro 2005).

Among the 25 cases identified as classic BL by pathological review, the gene expression-based predictor classified 100% correctly (FIG. 35B). Atypical BL and classic; BL could not be distinguished by gene expression, and therefore the predictor also classified 19 of the 20 atypical BL cases as BL. The cases for which the gene expression-based and pathology-based diagnoses were in agreement were labeled "BL-concordant" cases. The gene expression-based predictor also exhibited 100% accuracy in the diagnosis of ABC, GCB, and PMBL, and additionally classified all but one of the unclassified DLBCLs as DLBCL (FIG. 35C).

In addition to leave-one-out cross-validation, the BL prediction algorithm was tested by dividing the cases into equally sized training and validation sets. The predictor was generated using data from the training set and applied to the validation set cases. This analysis agreed well with leave-one-out cross-validation in 99% of the validation set cases, suggesting that the predictive algorithm is highly effective in distinguishing BL from DLBCL.

Having established the accuracy of the BL predictor, it was next used to classify those 26 cases that were originally submitted as BL or Burkitt-like lymphoma but were reassigned based on pathological review as either DLBCL (n=20) or high grade lymphoma not otherwise specified (NOS) (n=6). The expression-based predictor disagreed with the pathological diagnosis in eight of these cases (31%). In addition, the expression-based predictor classified one of the nine cases submitted and verified as high-grade DLBCL as BL.

Altogether, nine cases that were diagnosed as either DLBCL or high grade lymphoma upon pathological review had gene expression profiles consistent with BL. These cases were labeled "BL-discrepant" cases (marked by an asterisk in FIG. 35D). The BL-discrepant cases could be readily distinguished from all subtypes of DLBCL by gene expression, and had an assigned probability of being. BL ranging from 98% to 100% (FIG. 36A). The diagnosis of BL in the BL-discrepant cases was supported by the presence of a c-myc translocation in all cases. Four of the nine BL-discrepant cases expressed BCL2 mRNA and protein at high levels, and three had a t(14:18) translocation involving the BCL2 gene in addition to the t(B;14) translocation. The remaining five BL-discrepant cases were BCL2-negative and completely indistinguishable from BL by gene expression. In summary, although the BL-discrepant cases did not meet the WHO criteria for a diagnosis of BL based on morphology and immunophenotype, they nonetheless harbored a c-myc translocation and were indistinguishable from classic BL by gene expression.

It was next examined whether the expression-based BL predictor could distinguish BL from DLBCL bearing a c-myc translocation. Consistent with previous studies, 7% of the cases submitted as DLBCL (six of the 87 cases tested) were found to have a c-myc translocation. The gene expression profiles of these six cases were distinct from those of BL (FIG. 36B). All six cases had profiles of DLBCL (4 GCB, 2 ABC). Five of these cases had a BL predictor probability of 0%, but one had a BL predictor probability of 66% and may represent a rare biological overlap between BL and DLBCL.

To elucidate biological mechanisms that distinguish BL from DLBCL, hierarchical clustering (Eisen 1998) was used to organize the BL predictor genes according to their expression patterns across all BL and DLBCL samples. Many of the predictor genes segregated into four gene expression signatures reflecting distinctive biological attributes of BL. For example, c-myc and its target genes constituted one gene expression signature, which was more highly expressed in BL than in DLBCL, reflecting the influence of the c-myc translocation in BL (FIG. 37A).

Another cluster of predictor genes that were more highly expressed in BL than DLBCL included genes characteristically expressed in normal GC B cells, such as MME (CD10) and MYBL1. This was unexpected given that GCB, like BL, is derived from the germinal center stage of B cell differentiation (Mann 1976; Alizadeh 2000). To define a comprehensive GC B cell gene expression signature, whole genome microarrays were used to profile gene expression in various normal B cell subsets, including GC B cells, as well as resting and nitrogen-stimulated blood B cells. GC B cell signature genes were defined as those that were overexpressed in GC B cells compared with the blood B cell populations, but were not associated with cellular proliferation. These GC B cell signature genes could be divided into three sets; 1) genes that were expressed more highly in BL than GCB ("BL-high"), 2) genes that were expressed more highly expressed in GCB than BL ("BL-low"), and 3) genes that were expressed equivalently in BL and GCB (FIG. 37B). Thus, BL and GCB retain expression of different subsets of GC B cell signature genes.

A third gene expression signature included MHC class I genes that were expressed at lower levels in BL than in DLBCL (FIG. 37C). A fourth signature included known targets of the NF-κB pathway that were expressed at relatively low levels in BL. Expression of a recently defined set of NF-κB target genes (Lam 2005) was examined, and it was found that BL expressed these genes at very low levels compared to each DLBCL subgroup, including GCB (FIG. 37D).

Expression was quantitated for each gene expression signature within the various lymphoma types. For each signature, the average expression of its component genes in a lymphoma biopsy sample was calculated to generate a gene expression signature value for that sample. FIG. 37E displays the signature values for biopsies classified according to their molecular diagnoses. BL-concordant samples had signature values that were readily distinguished from those of samples belonging to the three DLBCL subtypes ($P<1\times10^{-7}$). Notably, BL-discrepant samples had signature values that were similar to those of BL-concordant cases, again supporting classification as BL. The BL-discrepant cases that were BCL2-negative (n=5) were indistinguishable from the BL-concordant cases by gene expression. In contrast, the BL-discrepant cases that were BCL2-positive (n=4) had lower expression of the BL-high GC B cell gene expression signature. The two BL-concordant cases with a t(14;18) also had low expression of the BL-high gene expression signature. A final important observation was that DLBCL samples with a c-myc translocation were easily distinguishable from BL in the expression of all four gene expression signatures (p<0.01).

To understand the effect of treatment on overall survival in BL, clinical data was analyzed from patients with a molecular diagnosis of BL for whom complete clinical information was available. Overall survival was markedly better for patients who received intensive chemotherapy regimens than for those who received CHOP-like regimens (P=0.02; FIG. 38B). The inferior outcome of adult patients treated with CHOP-like regimens could not be accounted for by differences in age, stage, serum lactate dehydrogenase, performance status, sites of disease, or the presence of t(14;18). Among BL-discrepant cases, CHOP-like therapies were also inferior (P=0.049), although the number of cases is low (n=7; FIG. 38C). BL patients who received CHOP-like regimens had a lower survival compared to patients in each of the three DLBCL subtypes who received similar therapy (FIG. 38D). Overall, these results are consistent with previous reports (Butler 1993; Magrath 1996; Smeland 2004) indicating that BL patients have excellent-outcomes when treated with intensive chemotherapy regimens rather than CHOP-like regimens.

Example 20: Identification and Characterization of Cyclin D1-Negative MCL Cases

Lymph node biopsies from six patients with suspected cyclin D1-negative MCL were examined. Two of these cases were identified in a previous study (Rosenwald 2003a), and the other four were newly identified as cyclin D1-negative MCL based on immunohistochemistry and RT-PCR analysis. Each of these six cases exhibited the characteristic morphological characteristics of MCL as determined by a panel of expert hematopathologists.

Gene expression data was obtained using a Lymphochip microarray and Affymetrix U133A/B microarrays, and the gene expression profile of each case was compared to those of ABC (78 cases). GCB (85 cases), PMBL (33 cases), FL (193 cases), MALT (14 cases), splenic marginal zone lymphoma (SMZL) (6 cases), and SLL (14 cases) (FIG. 33). The distributions of the Bayesian predictor for each category were used to estimate the probability that any particular sample belonged to that category by applying Bayes' rule (Rosenwald 2003a; Wright 2003). Specifically, a Bayesian predictor was generated for each lymphoma category between that category and cyclin D1-positive MCL samples, based on the 50 genes with the largest t-statistics between them. Only those samples for which all pair-wise predictors agreed that there was a greater than 90% probability that the sample was MCL were classified as cyclin D1-negative MCL. This set of models was applied to the data set in a leave-one-out cross-validated fashion so that the models tested on a given sample were based on a data set that excluded that sample. Samples that exhibited less than a 90% probability of belonging to a category were deemed "unclassified." All six suspected cyclin D1-negative MCL cases were indicated as MCL in all pair-wise models with at least 99.99% confidence. None of the samples from the other categories were indicated as MCL with greater than 20% confidence in their respective pair-wise comparisons. Thus, the six samples are considered to be bona fide cases of cyclin D1-negative MCL.

Lymph node specimens from the six cyclin D1-negative MCL cases were fixed in 10% neutral buffered formalin and embedded in paraffin, and 4 μm sections were cut and stained with hematoxylin and eosin (H&E) for histologic evaluation. Immunohistochemical stains for cyclin D1 protein were performed on formalin-fixed, paraffin-embedded tissue sections. After deparaffinization in xylene and rehydration in graded alcohols, endogenous peroxidase was blocked with hydrogen peroxide. Heat-induced antigen retrieval was performed using citrate buffer, pH 6.0 (Brynes 1997). After rinsing in phosphate-buffered saline, mouse anti-cyclin D1 antibody was applied at a dilution of 1:200 and rabbit monoclonal anti-cyclin antibody (SP4) (Neomarkers, Fremont, Calif.) was applied using the suggested procedure for antigen retrieval with minor modifications (Cheuk 2004) (Table 2416). Antibodies against CD3, CD5, CD20, CD23, CD43, cyclin D2, cyclin D3, cyclin E, retinoblastoma protein (RB), and $p27^{klp1}$ were also employed for immunohistochemical stains (Table 2416).

TABLE 2416

| Antibody | Clone | Source | Dilution | Retrieval |
|---|---|---|---|---|
| CD3 | PS1 | Ventana (Tucson, AZ) | Neat | A (10 mM citrate buffer, pH 6.0, 30 min., water bath (95° C.)) |
| CD5 | 4C7 | Novocastra (Newcastle upon Tyne, UK) | 1:20 | A |
| CD20 | L26 | DAKO (Carpinteria, CA) | 1:200 | A |
| CD23 | BU38 | The Binding Site (San Diego, CA) | 1:5 | B (Protease I enzymatic digestion, 8 min.) |
| CD43 | L60 | Ventana | Neat | None |
| Cyclin D1 | DCS-6 | DAKO | 1:200 | A |
| Cyclin D1 | SP4 | Neomarkers (Fremont, CA) | 1:100 | C |

TABLE 2416-continued

| Antibody | Clone | Source | Dilution | Retrieval |
|---|---|---|---|---|
| Cyclin D2 | Polyclonal | Santa Cruz Biotech (Santa Cruz, CA) | 1:500 | (1 mM EDTA, pH 8.0, 30 min., water bath (95° C.)) D (1 mM EDTA, pH 8.0, 60 min., water bath (95° C.)) |
| Cyclin D3 | DCS-22 | Neomarkers | 1:100 | E (10 mM citrate buffer, pH 6.0, 10 min., pressure cooker (115° C.)) |
| Cyclin E | 13A3 | Novocastra | 1:10 | E |
| RB | Rb1 | DAKO | 1:10 | A |
| $p27^{kip1}$ | SX53G8 | DAKO | 1:20 | A |

Stains were performed on a Ventana ES automated immunostainer (Ventana Biotek, Tucson, Ariz.) with a streptavidin-biotin peroxidase detection system. Positivity for the cycDns, RB, and $p27^{klp1}$ was defined as a strong nuclear staining in more than 50% of the neoplastic cells. Results of histologic and immunologic studies are set forth in Table 2417.

TABLE 2417

| | | Case | | | | | |
|---|---|---|---|---|---|---|---|
| | | 1 | 2 | 3 | 4 | 5 | 6 |
| Pathologic features | Growth pattern | Nodular | Diffuse | Nodular | Diffuse | Nodular | Nodular |
| | Cytology | Typical | Typical | Typical | Typical | Typical | Typical |
| | CD20 | + | + | + | + | + | + |
| | CD3 | − | − | − | − | − | − |
| | CD5 | + | + | + | + | + | + |
| | CD23 | − | − | − | +(w) | − | − |
| | CD43 | +(w) | + | − | + | + | + |
| | Cyclin D1 | − | − | − | − | − | − |
| | Cyclin D2 | + | + | − | − | − | NA |
| | Cyclin D3 | − | − | + | + | + | NA |
| | Cyclin E | − | − | − | − | − | NA |
| | RB | + | + | + | + | + | NA |
| | $p27^{Kip1}$ | − | − | − | − | − | − |
| Genetic features | 1(11; 14)(q13; q32) | − | − | − | − | − | − |
| | 11q13 (cyclin D1) | Normal* | Normal | Normal | Normal | Normal | Normal |
| | 12p13 (cyclin D2) | Normal | Normal | Normal | Normal | Normal | Normal |
| | 6p21 (cyclin D3) | Normal | Normal | Normal | Normal | Normal | Normal |
| | 12p13 ($p27^{Kip1}$) | Normal | Normal | Normal | Normal | Normal | Normal |

NA: not available;
+: positive;
+(w): weakly positive;
−: negative;
*normal indicates no split or amplification All six cases exhibited a nodular or diffuse growth pattern and consisted of tumor cells with typical mantle cell cytology (FIG. 34A). Immunophenotypic analysis of the tumor cells revealed a B-cell phenotype in all cases. Expression of CD5 antigen was noted in all six cases, white CD43 expression was observed in five of the six cases. The tumor cells in one of the six cases were weakly positive for CD23 antigen.

All six cases were negative for cyclin D1 using the mouse monoclonal antibody DCS-6 (FIG. 34B). All four of the cases that were tested using the rabbit monoclonal antibody SP4 were negative for cyclin D1. Two cases (1 and 2) demonstrated overexpression of cyclin D2 by Immunostaining (FIG. 34C), which correlated well with the increased cyclin D2 mRNA levels detected by microarray analysis (FIG. 33, lower panel). Both of these cases were negative for cyclin D3. Three cases (3-5) exhibited overexpression of cyclin D3 by immunostaining (FIG. 34D), which correlated well with the increased cyclin D3 mRNA levels detected by microarray analysis (FIG. 33, lower panel). Case 6 also showed upregulation of cyclin D3 mRNA by microarray analysis (FIG. 33, lower panel), but the tissue block for this case was not available for immunostaining.

All six cases were negative for cyclin E, but showed positive immunostaining for RB. RB expression levels were similar in all of the cases, and were comparable to those seen in cyclin D1-positive MCL. Downregulation of $p27^{Klp1}$ expression was observed in all six cases, with the intensity of nuclear staining much weaker than that seen in reactive T-lymphocytes.

Interphase FISH analysis was performed on cells left over from prior cytogenetic analyses or on formalin-fixed, paraffin-embedded tissue sections. For detection of the t(11;14)(q13;q32), a commercially-available LSI IGH/CCND1 double-color, double-fusion probe was used (Vysls Inc., Downers Grove, Ill.).

For break-apart FISH assays for the CCND1 (11q13), CCND2 (12p13), and GDKN1B/p27KlP1 (12p13) loci, appropriate BAC clones flanking the respective genes were selected using bioinformatic resources available from the University of California at Santa Cruz. All BAC clones were derived from the RPC111 library and were obtained from Invitrogen/Research Genetics or the Sanger Center. The following clones were used: CCND1 (pooled RP11-211G23/RP11-378E8 and pooled RP11-30016/RP11-626H12), CCND2 (RP11-578L13 and RP11-388F6), and CDKN1B/p27K1P1(RP11-180M15 and RP11-59H1). For each locus, centromeric and telomeric BAC clones were differentially labeled with Spectrum Orange or Spectrum Green (Vysis Inc.) and pooled for break-apart assays. Bacterial culture, BAC DNA isolation and labeling, probe preparation, and FISH on cytogenetic suspensions were performed as previously described (Schlegelberger 1999; Martin-Subero 2002). The CCND3 locus was investigated using a recently-described break-apart assay (Sonoki 2001). Locus-specific interphase FISH was performed on paraffin-embedded tissue sections according to the manufacturer's Instructions (Vysis Inc.), or recently-described protocols (Ye 2003) with minor modifications. Whenever possible, at least 100 cells were analyzed.

None of the six cases displayed the IGH/CCND1 fusion. FISH studies with the locus-specific probe were also negative for variant translocations or amplifications involving the CCND1 locus at band 11q13 in ail six cases (Table 2417). Conventional cytogenetic analysis was also performed on case 6, and did not reveal a chromosomal alteration affecting band 11q13. FISH analysis using break-apart probes for the CCND1 (12p13), CCND2 (6p21), and CDKN1B/p27KP1 (12p13) loci did not reveal any evidence of chromosomal translocation or amplification in these cases (Table 2417).

female with a median age of 61 years (range, 54-77 years). All patients presented with stage IV disease. Lymphadenopathy was the most common presentation and extranodal sites were involved by lymphoma in all six patients. Five patients received combination-chemotherapy initially, but none of these patients achieved a complete clinical response. One patient (case 1) was not treated initially and developed gastrointestinal involvement 26 months after the initial diagnosis. At the time of last follow-up, one of the patients had died and the other five were alive with disease.

Ninety-three cases (92 cases in the original study plus the false negative case) of cyclin D1-positive MCL (Rosenwald 2003a) were used for comparison. The median follow-up for these patients was 26 months (range, 7-166 months). The clinical features including age and sex distribution, stags, presence of B symptoms, serum lactate dehydrogenase (LDH) levels, extranodal sites, IPI scores, types of treatment, and clinical responses were similar between the cyclin D1-positive and cyclin D1-negative groups. At the time of last follow-up, 65 of 93 patients with cyclin D1-positive MCL had died, with a median overall survival of 31 months. No significant difference in overall survival was identified between the cyclin D1-positive and cyclin D1-negative groups.

TABLE 2418

| | Case | | | | | |
|---|---|---|---|---|---|---|
| | 1 | 2 | 3 | 4 | 5 | 6 |
| Age (years)/sex | 54/F | 61/M | 61/M | 60/M | 54/M | 77/M |
| Ann Arbor stage | IV | IV | IV | IV | IV | IV |
| B symptoms | − | + | − | + | − | − |
| Serum LDH levels | Normal | High | Normal | High | Normal | Normal |
| Extranodal sites | BM, PB | BM | BM | BM, spleen | BM | BM, lung, GI |
| IPI score | 2 | 3 | 2 | 3 | 2 | 3 |
| Initial therapy | None | R-CHOP | CHOP | COP | CHOP | COP |
| Response | NA | PR | PR | PR | PR | PR |
| Progression | + | − | + | + | + | + |
| Follow-up (months) | 38 | 5 | 88 | 19 | 70 | 30 |
| Status | AWD | AWD | DOD | AWD | AWD | AWD |

LDH, lactate dehydrogenase;
BM, bone marrow;
PB, peripheral blood;
GI, gastrointestinal tract;
R, Rituxan;
PR, partial response;
AWD, alive with disease;
DOD, dead of disease The INK4a/ARF locus encodes the tumor suppressor proteins p16$^{INK4a}$ and p14$^{ARF}$. To detect genomic loss of the INK4a/ARF tumor suppressor locus in the specimens, quantitative real-time PCR assays were performed using genomic DNA as previously described (Rosenwald 2003a). The REL locus on chromosome 2p was chosen as the reference gene, and a cutoff ratio of INK4a/ARF locus copy number relative to REL locus copy number was used to assess tumor DNA for genomic deletions. A tumor DNA sample that yielded an INK4a/ARF to REL ratio below the cutoff ratio was considered to have a genomic deletion of the INK4a/ARF locus. The primers and probe sets for the INK4a/ARF and the REL loci have been described previously (Goff 2000; Labuhn 2001). No INK4A/ARF locus deletions ware detected in any of the six cases.

Clinical features of the six patients are summarized in Table 2418. The patients consisted of five males and one As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Alizadeh, A. A., et al. 1998. Probing lymphocyte biology by genomic-scale gene expression analysis. J Clin Immunol 18:373-79.

2. Alizadeh, A. A., et al. 1999. The Lymphochip: a specialized cDNA microarray for the genomic-scale analysis of gene expression in normal and malignant lymphocytes. Cold Spring Harbor Symp Quant Biol 64:71-78.
3. Alizadeh, A. A., et al, 2000. Distinct types of diffuse large B-cell lymphoma identified by gene expression profiling. Nature 403:503-511.
4. Alon, U., et al. 1999. Broad patterns of gene expression revealed by clustering analysis of tumor and normal colon tissues probed by oligonucleotide arrays. Proc Natl Acad Sci USA 96:6745-6750.
5. Andreasson, P., et al. 1998. Genomic amplifications of CCDN2 is rare in non-Hodgkin lymphomas. Cancer Genet Cytogenel 102:81-82.
6. Basso, K., et al. 2004. Tracking CD40 signaling during germinal center development, Blood 104:4058-4096.
7. Basso, K., et al. 2005. Reverse engineering of regulatory networks in human B cells. Nat Genet 37:382-390.
8. Bayes, T. 1763. An essay towards solving a problem in the doctrine of chances. Phil Trans Roy Soc London 53:370,
9. Bea, S., et al. 1999. Increased number of chromosomal imbalances and high-level DNA amplifications in mantle cell lymphoma are associated with blastold variants. Blood 93:4365-4374.
10. Bea, S., et al. 2004. Clinicopathologic significance and prognostic value of chromosomal imbalances in diffuse large B-cell lymphomas. J Clin Oncol 22:3498-3506.
11. Bea, S., et al. 2005. Diffuse large B-cell lymphoma subgroups have distinct genetic profiles that influence tumor biology and improve gene expression-based survival prediction. Blood 106:3183-3190.
12. Berglund, M., et al. 2002. Chromosomal imbalances in diffuse large B-cell lymphoma detected by comparative genomic hybridization. Mod Pathol 15:807-816.
13. Bergsagel, P. L., et al. 2003. Critical roles for immunoglobulin translocations and cyclin D deregulation in multiple myeloma. Immunol Rev 194:96-104.
14. Bishop, P. C., Rao, V. K., Wilson, W. H. 2000. Burkit's lymphoma: molecular pathogenesis and treatment. Cancer Invest 18:574-583.
15. Boxer, L. M., Lozanski, G., Byrd, J. C. 2001. Translocations involving c-myc and c-myc function. Oncogene 20:5595-5610.
16. Brynes, R. K., et al. 1997, Demonstration of cyclin D1 (bcl-1) in mantle cell lymphoma. Enhanced staining using heat and ultrasound epitope retrieval. Appl Immunohistochem 5:46-49.
17. Butler, R. D., Hainsworth, J. D. 1993. Optimal therapy for small noncleaved cell lymphoma. Cancer Treat Res 66:65-79.
18. Chee, M., et al. 1996. Accessing genetic information with high density DNA arrays. Science 274:610-14.
19. Cheuk, W., et al. 2004. Consistent immunostaining for cyclin D1 can be achieved on a routine basis using a newly available rabbit monoclonal antibody. Am J Surg Pathol 28:801-807.
20. Chiarle, R., et al. 2000. Increased proteasome degradation of cyclin-dependent kinase inhibitor p27 is associated with a decreased overall survival in mantle cell lymphoma. Blood 95:619-626.
21. Cho, R. J., et al. 1998. A genome-wide transcriptional analysis of the mitotic cell cycle. Mol Cell 2:65-73.
22. Chu, S., et al. 1998. The transcriptional program of sporulation in budding yeast, Science 282:699-705.
23. Ciemerych, M. A., et al. 2002. Development of mice expressing a single D-type cyclin. Genes Dev 16:3277-3289.
24. Cigudosa, J. C., et al. 1999. Cytogenetic analysis of 363 consecutively ascertained diffuse large B-cell lymphomas. Genes Chromosomes Cancer 25:123-133.
25. Copie-Bergman, C., et al. 2002. MAL expression in lymphoid cells: further evidence for MAL as a distinct molecular marker of primary mediastinal large B-cell lymphomas. Mod Pathol 15:1172-1180.
26. Copie-Bergman, C., et al. 2003. Interieukin 4-induced gene 1 is activated in primary mediastinal large B-cell lymphoma. Blood 101:2756-2761.
27. Dave, B. J., et al. 2002. Cytogenetic characterization of diffuse large cell lymphoma using multi-color fluorescence in situ hybridization. Cancer Genet Cytogenet 132:125-132.
28. Delmer, A., et al. 1995. Overexpression of cyclin D2 in chronic B-cell malignancies. Blood 85:2870-2876.
29. DeRisl, J., et al. 1996. Use of a cDNA microarray to analyze gene expression patterns in human cancer. Nat. Genet 14:457-60.
30. DeRisl, J. L., Iyer, V. R., Brown, P. O. 1997. Exploring the metabolic and genetic control of gene expression on a genomic scale. Science 278:680-86.
31. Divine, M., et al. 2005. Burkitt lymphoma in adults: a prospective study of 72 patients treated with an adapted pediatric LMB protocol. Ann Oncol 16:1928-1935.
32. Doglioni, C., et al. 1998. Cyclin D3 expression in normal, reactive and neoplastic tissues. J Pathol 185:159-166.
33. Drapner, H. 1966. Applied regression. Wiley, New York.
34. Dudolt, S., Fridlyand, J., Speed, T. P. 2002. Comparison of discrimination methods for the classification of tumors using gene expression data. J Am Stat Assoc 97:77-87.
35. Eisen, M. B., Spellman, P. T., Brown, P. O., Botstein, D. 1998. Cluster analysis and display of genome-wide expression patterns. Proc Natl Acad Sci USA 95:14863-14808.
36. Feuerhake, F., et al. 2005. NFkappaB activity, function, and target-gene signatures in primary mediastinal large B-cell lymphoma and diffuse large B-cell lymphoma subtypes. 106:1392-1399.
37. Fisher, R. I., et al. 1993. Comparison of a standard regimen (CHOP) with three intensive chemotherapy regimens for advanced non-Hodgkin's lymphoma. N Engl J Med 328:1002-1006.
38. Furey, T. S., et al. 2000. Support vector machine classification and validation of cancer tissue samples using microarray expression data. Bioinformatics 16:906-914.
39. Gerbitz, A., et al. 1999, Deregulation of the protooncogene c-myc through t(8;22) translocation in Burkitt's lymphoma. Oncogene 18:1745-1753;
40. Goff, L. K., et al. 2000. The use of real-time quantitative polymerase chain reaction and comparative genomic hybridizations to identify amplification of the REL gene in follicular lymphoma. Br J Haematol 111:618-625.
41. Golub, T. R., et al. 1999. Molecular classification of cancer, class discovery and class prediction by gene expression monitoring, Science 286:531-537.
42. Gress, T. M., et al. 1996. A pancreatic cancer-specific expression profile, Oncogene 13:1819-30.
43. Haralambieva, E., et al. 2005. Clinical, immunophenotypic, and genetic analysis of adult lymphomas with morphologic features of Burkitt lymphoma. Am J Surg Pathol 29:1086-1094.
44. Harris, N. L, et al. 1994. A revised European-American classification of lymphoid neoplasms: a proposal from the international Lymphoma Study Group. Blood 84:1361-1392.

45. Hashimoto, Y., et al. 2002. The evaluation of the biological behavior and grade among cases with mantle cell lymphoma, Leuk Lymphoma 43:523-530.
46. Hecht, J. L., et al. 2000. Molecular biology of Burkitt's lymphoma, J Clin Oncol 18:3707-3721.
47. Heller, R. A., et al, 1997. Discovery analysis of inflammatory disease-related genes using cDNA microarrays. Proc Natl Acad Sci USA 94:2150-55.
48. Hills, M. 1966. Allocation rules and error rates. J Royal Statis Soc [B] 28:1-31.
49. Holstege, F. C., et al. 1998, Dissecting the regulatory circuitry of a eukaryotic genome, Cell 95:717-726.
50. Huang, J. Z., et al. 2002. The t(14;18) defines a unique subset of diffuse large B-cell lymphoma with a germinal center B-cell gene expression profile. Blood 99:2285-2290.
51. Hyman, E., et al, 2002. Impact of DNA amplification on gene expression patterns in breast cancer. Cancer Res 62:6240-6245.
52. Iqbal, J., et al. 2004. BCL2 translocation defines a unique tumor subset within the germinal center B-cell-like diffuse large B-cell lymphoma. Am J Pathol 165:159-166.
53. Irizarry, R. A., et al. 2003. Exploration, normalization, and summaries of high density oligonucleotide array probe level data. Biostatistics 4:249-264.
54. Hills, M. 1966. Allocation rules and error rates. J Royal Statls Soc Series B 28:1-31.
55. Inaba, T., et al. 1992. Genomic organization, chromosomal localization, and independent expression of human cyclin D genes. Genomics 13:565-574.
56. Jaffe, E. S., Harris, N. L., Stein, H., Vardiman, J. W. 2001. Tumors of hematopoietic and lymphoid tissues. IARC Press, Lyon.
57. Janes, P, et al. 1996. Expression of retinoblastoma gene product (pRb) in mantle cell lymphomas. Correlation with cyclin D1 (PRAD1/CCND1) mRNA levels and proliferative activity. Am J Pathol 148:1591-1600.
58. Khourl, I. F., et al. 1998, Hyper-CVAD and high-dose methotrexate/cytarabine followed by stem-cell transplantation: an active regimen for aggressive mantle-cell lymphoma. J Clin Oncol 12:3803-3809.
59. Kohonen, T. 1997. Self-organizing maps. Springer Press, Berlin.
60. Kilmer, M. H., et al. 1998. Clinical relevance of BCL2, BCL6, and MYC rearrangements in diffuse large B-cell lymphoma. Blood 92:3152-3162.
61. Labuhn, M., et al. 2001. Quantitative real-time PCR does not show selective targeting of p14(ARF) but concomitant inactivation of both p16(INK4A) and p14(ARF) in 105 human primary gliomas. Oncogene 20:1103-1109.
62. Lam, L. T., et al. 2005. Small molecular inhibitors of IκB-kinase are selectively toxic for subgroups of diffuse large B cell lymphoma defined by gene expression profiling. Clin Cancer Res 11:28-40.
63. Lashkari, D. A., et al. 1997. Yeast microarrays for genome wide parallel genetic and gene expression analysis. Proc Natl Acad Sci USA 94:13057-62.
64. Li. C., Wong, W. H. 2001. Model-based analysis of oligonucleotide arrays: expression index computation and outlier detection. Proc Natl Acad Sci USA 98:31-36.
65. Lin, Z., et al. 2003. Growth regulation by p27Klp1 is abrogated by multiple mechanisms in aggressive malignant lymphomas. Br J Haematol 121:739-748.
66. Lipshutz, R. J., et al. 1995. Using oligonucleotide probe arrays to access genetic diversity. Biotechniques 19:442-47.
67. Lockhart, D. J., et al. 1996. Expression monitoring by hybridization to high-density oligonucleotide arrays. Nat Biotechnol 14:1675-80.
68. Macpherson, N., et al. 1999. Small noncleaved, non-Burkitt's (Burkitt-Like) lymphoma: cytogenetics predict outcome and reflect clinical presentation, J Clin Oncol 17:1558-1567.
69. Magrath, E. S., et al. 2001. Tumours of Haematopoietic and Lymphoid Tissues. Lyon: IARC Press.
70. Mann, R. B., et al. 1976. Non-endemic Burkitt's lymphoma. A B-cell tumor related to germinal centers. N Engl J Med 295:685-691.
71. Martin-Subero, J. I., et al. 2002. Multicolor-FICTION: expanding the possibilities of combined morphologic, immunophenotypic, and genetic single cell analyses. Am J Pathol 161:413-420.
72. Mead, G. M., et al, 2002. An international; evaluation of CODOX-M and CODOX-M alternating with IVAC in adult Burkitt's lymphoma: results of United Kingdom Lymphoma Group LY06 study. Ann Oncol 13:1264-1274.
73. Molinaro, A. M., Simon, R., Pfeiffer, R. M. 2005. Predictor error estimation: a comparison of resampling methods. Bioinformatics 21:3301-3307.
74. Monni, O., et al. 1996. DNA copy number changes in diffuse large B-cell lymphoma-comparative genomic hybridization study. Blood 87:5269-5278.
75. Morton, L. M., el al. 2005. Lymphoma incidence patterns by WHO subtype in the United States, 1992-2001. Blood 107:265-276.
76. Nanjangud, G., et al. 2002. Spectral karyotyping identifies new rearrangements, translocations, and clinical associations in diffuse large B-cell lymphoma. Blood 99:2554-2561.
77. Neri, A., et al. 1988, Different regions of the immunoglobulin heavy-chain locus are involved in chromosomal translocations in distinct pathogenetic forms of Burkitt lymphoma. Proc Natl Acad Scl USA 85:2748-2752.
78. Orsetti, B., et al. 2004. Genomic and expression profiting of chromosome 17 in breast cancer reveals complex patterns of alterations and novel candidate genes. Cancer Res 64:6453-6460.
79. Ott, M. M., et al. 1997; Cyclih D1 Expression in-mantle cell lymphoma is accompanied by downregulation of cyclin D3 and is not related to the proliferative activity. Blood 90:3154-3159.
80. Pease, A. C., et al. 1994. Light generated oligonucleotide arrays for rapid DNA sequence analysis. Proc Natl Acad Sci USA 91:5022-26.
81. Pees, H. W., et al. 1992. The BFM-protocol for HIV-negative Burkitt's lymphomas and L3 ALL in adult patients: a high chance for cure. Ann Hematol 65:201-205.
82. Phillips, J. L., et al. 2001. The consequences of chromosomal aneuploidy on gene expression profiles in a cell line model for prostate carcinogenesis. Cancer Res 61:8143-8149.
83. Pletu, G., et al. 1996. Novel gene transcripts preferentially expressed in human muscles revealed by quantitative hybridization of a high density cDNA array. Genome Res 6:492-503.
84. Pollack, J. R., et al. 2002. Microarray analysis reveals a major direct role of DNA copy number alteration in the transcriptional program of human breast tumors. Proc Natl Acad Sci USA 99:12963-12968.
85. Polyak, K., et al. 1994, p27Klp1, a cyclin-Cdk inhibitor, links transforming growth factor-beta and contact inhibition to cell cycle arrest. Genes Dev 8:9-22.

86. Pruneri, G., et al. 2003. Immunoreactivity for cyclin D3 is frequently detectable in high-grade primary gastric lymphomas in the absence of the t(6;14)(p21.1;q32.3) chromosomal translocation. J Pathol 200:596-601.
87: Quintanilla-Martinez, L., et al. 1998. Mantle cell lymphomas lack expression of p27Klp1, a cyclin-dependent kinase inhibitor, Am J Pathol 153:175-182.
88. Quintanilla-Martinez, L., et al, 2003. Sequestration of p27Klp1 protein by cyclin D1 in typical and blastic variants of mantle cell lymphoma (MCL): implications for pathogenesis. Blood 101:3181-3187.
89. Radmacher, M. D., McShane, L. M., Simon, R. 2002. A paradigm for class prediction using gene expression profiles. J Comput Biol 9:505-511.
90. Ramaswamy, S., et al. 2001. Multiclass cancer diagnosis using tumor gene expression signatures. Proc Natl Acad Scl USA 98:15149-15154.
91. Ransohoff, D. F. 2004. Rules of evidence for cancer molecular-marker discovery and validation. Nat Rev Cancer 4:309-314.
92. Rao, P. H., et al. 1998. Chromosomal and gene amplification in diffuse large B-cell lymphoma. Blood 92:234-240.
93. Rosenberg, C. L, et al. 1991. PRAD1, a candidate BCL1 oncogene: mapping and expression in centrocytic lymphoma. Proc Natl Acad Sci USA 88:9638-9642.
94. Rosenwald, A., et al. 2002. The use of molecular profiling to predict survival after chemotherapy for diffuse large-B-cell lymphoma. New Engl J Med 346:1937-1947.
95. Rosenwald, A., et al. 2003a. The proliferation gene expression signature is a quantitative integrator of oncogenic events that predicts survival in mantle cell lymphoma. Cancer Cell 3:185-197.
96. Rosenwald, A., et al. 2003b. Molecular diagnosis of primary mediastinal B cell lymphoma identifies a clinically favorable subgroup of diffuse large B cell lymphoma related to Hodgkin lymphoma. J Exp Med 198:851-862.
97. Savage, K. J., et al. 2003. The molecular signature of mediastinal large B-cell lymphoma differs from that of other diffuse large B-cell lymphomas and shares features with classical Hodgkin lymphoma. Blood 102:3871-3879.
98. Schena, M., Shalon, D., Davis, R. W., Brown, P. O. 1995. Quantitative monitoring of gene expression patterns with a complementary DNA microarray. Science 270:467-70.
99. Schena, M., et al. 1996, Parallel human genome analysis: microarray based expression monitoring of 1000 genes. Proc Natl Acad Sci USA 93:10614-19.
100. Schlegelberger, B., et al. 1999. Classical and molecular cytogenetics of tumor cells. In: Diagnostic Cytogenetics. Springer-Verlag, Berlin, Heidelberg; pp. 151-185.
101. Shaffer, A. L., et al. 2001. Signatures of the immune response. Immunity 15:375-385.
102. Shalon, D., Smith, S. J., Brown, P. O. 1996. A DNA microarray system for analyzing complex DNA samples using two-color fluorescent probe-hybridization. Genome Res 6:639-45.
103. Sherr, C. J., et al. 1994. D-type cyclins and their cyclin-dependent kinases: G1 phase integrators of the mitogenic response, Cold Spring Harb Symp Quant Biol 59:11-19.
104. Sherr, C. J, 1996. Cancer cell cycles. Science 274:1672-1677.
105. Sherr, C. J., McCormick, F. 2002. The RB and p53 pathways in cancer. Cancer Cell 2:103-112.
106. Shipp, M. A., et al. 2002; Diffuse large B-cell lymphoma outcome prediction by gene-expression profiling and supervised machine learning. Nat Med 8:68-74.
107. Sicinski, P., et al. 1995. Cyclin D1 provides a link between development and oncogenesis in the retina and breast. Cell 82:621-630.
108. Sicinska, E., et al. 2003. Requirement for cyclin D3 in lymphocyte development and T cell leukemias. Cancer Cell 4:451-461.
109. Sicinski, P., et al. 1996. Cyclin D2 is an FSH-responsive gene involved in gonadal cell proliferation and oncogenesis. Nature 384:470-474.
110. Simon, R. M., et al. 2003. Design and Analysis of DNA Microarray Investigations, Springer-Verlag, New York.
111. Smeland, S., et al. 2004. Treatment of Burkitt's/Burkitt-like lymphoma in adolescents and adults: a 20-year experience from the Norwegian Radium Hospital with the use of three successive regimens. Ann Oncol 15:1072-1078.
112. Sonoki, T, et al. 2001. Cyclin D3 is a target gene of t(6;14)(p21.1;q32.3) of mature B-cell malignancies. Blood 98:2837-2844.
113. Soussain; C., et al. 1995. Small noncleaved cell lymphoma and leukemia in adults, A retrospective study of 65 adults treated with the LMB pediatric protocols. Blood 85:664-674.
114. Southern, E. M., Maskos, U., Elder, J. K. 1992. Analyzing and comparing nucleic acid sequences by hybridization to arrays of oligonucleotides: evaluation using experimental models, Genomics 13:1008-17.
115. Southern, E. M., et al. 1994. Arrays of complementary oligonucleotides for analysing the hybridisation behaviour of nucleic acids. Nucl Acids Res 22:1368-73.
116. Spellman, P. T., et al. 1998. Comprehensive identification of cell cycle regulated genes of the yeast *Saccharomyces cerevisiae* by microarray hybridization. Mol Biol Cell 9:3273-3297.
117. Suzuki, R., et al. 1999. Selective usage of D-type cyclins in lymphoid malignancies. Leukemia 13:1335-1342.
118: Tamayo, P., et al. 1999. Interpreting patterns of gene expression with self-organizing maps: methods and application to hematopoietic differentiation. Proc Natl Acad Sci USA 96:2907-2912.
119. Tavazole, S., et al. 1999. Systematic determination of genetic network architecture. Nat Genet 22:281-285.
120. Teramoto, N. et al. 1999. Expression of cyclin D2 and D3 in lymphoid lesions. Int J Cancer 81:543-550.
121. Thomas, D. A., et al. 1999. Hyper-CV AD program in Burkitt's-type adult acute lymphoblastic leukemia. J Clin Oncol 17:2461-2470;
122. Tibshirani, R., Hastie, T., Narasimhan, B., Chu, G. 2002. Diagnosis of multiple cancer types by shrunken centroids of gene expression. Proc Natl Acad Sci USA 99:6567-6572.
123. Velculescu, V. E., Zhang, L., Vogelstein, B., Kinzler; K. W. 1995. Serial analysis of gene expression. Science 270:484-87.
124. Virtaneva, K., et al. 2001. Expression profiling reveals fundamental biological differences in acute myeloid leukemia with isolated trisomy 8 and normal cytogenetics. Proc Natl Acad Sci USA 98:1124-1129.
125. Voliz, R., Jilg, W., Wolf, H. 1989. Modification of HLA expression as a possible factor in the pathogenesis of Burkitt's-lymphoma, Haematol Blood Transfus 32:289-292.
126. Vose, J. M., et al. 2002. CNOP for diffuse aggressive non-Hodgkin's lymphoma: the Nebraska lymphoma study group experience. Leuk Lymphoma 43:799-804.
127. Westfall, P. H., Young, S. S. 1993. Resampling-based Multiple-Testing. Wiley, New York.

128. Wodicka, L., et al. 1997. Genome-wide expression monitoring in Saccharomyces cerevisiae. Nat Blotechnol 15:1359-6714.
129. Wright, G., et al. 2003. A gene expression-based method to diagnose clinically distinct subgroups of diffuse large B cell lymphoma. Proc Natl Acad Sci USA 100:9991-9996.
130. Yang, W. I., et al. 1994. Cyclin D1 (Bcl-1, PRAD1) protein expression in low-grade B-cell lymphomas and reactive hyperplasia. Am J Pathol 145:86-96.
131. Yatabe, Y., et al. 2000. Significance of cyclin D1 overexpression for the diagnosis of mantle cell lymphoma: a ollnicopathologic comparison of cyclin D1-positive MCL and cyclin D1-negative MCL-like B-cell lymphoma. Blood 95:2253-2261.
132. Ye, H, et al. 2003. Variable frequencies of t(11;18)(q21; q21) in MALT lymphomas of different sites: significant association with CagA strains of H pylori in gastric MALT lymphoma. Blood 102:1012-1018.
133. Yunis, J. J., et al. 1989. bcl-2 and other genomic alterations in the prognosis of large-cell lymphoma. N Engl J Med 320:1047-1054.
134. Zeller, K. I., et al. 2003. An integrated database of genes responsive to the Myc oncogenic transcription factor: identification of direct genomic targets. Genome Biol 4; R69.

What is claimed is:

1. A method for treating a diffuse large B cell lymphoma (DLBCL) in a subject comprising:
   (a) isolating gene expression product from a DLBCL biopsy sample from a subject with DLBCL;
   (b) determining an average gene expression level of genes set forth below

| Signature | UNIQID | Unigene ID Build 167 | Gene symbol |
|---|---|---|---|
| Germinal center B-cell | 1099686 | 117721 | |
| Germinal center B-cell | 1099711 | 243596 | |
| Germinal center B-cell | 1103390 | 271752 | BPNT1 |
| Germinal center B-cell | 1106025 | 49500 | KIAA0746 |
| Germinal center B-cell | 1128287 | 300063 | ASB13 |
| Germinal center B-cell | 1132520 | 283063 | LMO2 |
| Germinal center B-cell | 1138192 | 126608 | NR3C1 |
| Germinal center B-cell | 1529318 | 291954 | |
| Germinal center B-cell | 1529344 | 317970 | SERPINA11 |
| Germinal center B-cell | 1529352 | 446195 | |
| Germinal center B-cell | 1096570 | 409813 | ANUBL |
| Germinal center B-cell | 1097897 | 266175 | PAG |
| Germinal center B-cell | 1097901 | 266175 | PAG |
| Germinal center B-cell | 1098611 | 433611 | PDK1 |
| Germinal center B-cell | 1100581 | 155024 | BCL6 |
| Germinal center B-cell | 1115034 | 387222 | NEK6 |
| Germinal center B-cell | 1120090 | 155024 | BCL6 |
| Germinal center B-cell | 1120946 | 25209 | MAPK 10 |
| Germinal center B-cell | 1121248 | 54089 | BARD1 |
| Germinal center B-cell | 1123105 | 434281 | PTK2 |
| Germinal center B-cell | 1125456 | 300592 | MYBL1 |
| Germinal center B-cell | 1128694 | 171466 | ELL3 |
| Germinal center B-cell | 1128787 | 114611 | C7orf10 |
| Germinal center B-cell | 1132122 | 307734 | MME |
| Germinal center B-cell | 1136269 | 101474 | MAST2 |
| Germinal center B-cell | 1136702 | 155584 | KIAA0121 |
| Germinal center B-cell | 1139230 | 29724 | PLEKHF2 |
| Germinal center B-cell | 1529292 | NA | |
| Germinal center B-cell | 1529295 | 116441 | |
| Lymph node | 1097126 | 274520 | ANTXR1 |
| Lymph node | 1099028 | 334838 | ENDC1 |
| Lymph node | 1099358 | 93135 | |

-continued

| Signature | UNIQID | Unigene ID Build 167 | Gene symbol |
|---|---|---|---|
| Lymph node | 1101478 | 146246 | MGC45780 |
| Lymph node | 1103497 | 50115 | |
| Lymph node | 1121029 | 412999 | CSTA |
| Lymph node | 1124429 | 409602 | SULF1 |
| Lymph node | 1135068 | 71719 | PDLIM3 |
| Lymph node | 1136051 | 520937 | CSF2RA |
| Lymph node | 1136172 | 38084 | SULT1C1 |
| MHC class II | 1136777 | 387679 | HLA-DQA1 |
| MHC class II | 1136877 | 409934 | HLA-DQB1 |
| Proliferation | 1096570 | 437460 | FLJ10385 |
| Proliferation | 1120583 | 153768 | RNU3IP2 |
| Proliferation | 1123289 | 5409 | POLR1C |
| Proliferation | 1131808 | 75447 | RALBP1 |
| Proliferation | 1133102 | 360041 | FRDA |
| Proliferation | 1136595 | 404814 | VDAC1 | for the proliferation gene expression signature to obtain a proliferation gene expression signature value;
   (c) determining an average gene expression level of genes set forth in the table of (b) for the germinal center B cell gene expression signature to obtain a germinal center B cell gene expression signature value;
   (d) determining an average gene expression level of genes set forth in the table of (b) for the MHC class II gene expression signature to obtain an MHC class II gene expression signature value;
   (e) determining an average gene expression level of genes set forth in the table of (b) for the lymph node gene expression signature to obtain a lymph node gene expression signature value;
   (f) measuring the expression level of BMP6 to obtain a BMP6 expression value;
   (g) determining a survival predictor score calculated as [0.241*(proliferation gene expression signature value)]+[0.310*(BMP6 expression value)]−[0.290*(germinal center B cell gene expression signature value)]−[0.311*(MHC class II gene expression signature value)]−[0.249*(lymph node gene expression signature value)], wherein a higher survival predictor score indicates worse survival; and
   (h) administering cyclophosphamide, doxorubicine, vincristine, and prednisone to the subject to treat DLBCL in the subject, wherein the intensity of administration is directly related to the survival predictor score.

2. The method of claim 1, wherein the method further comprises performing comparative genomic hybridization on a DLBCL biopsy sample from the subject to analyze for a gain or amplification in the 3p11-p12 region of chromosome 3.

3. The method of claim 1, wherein the method further comprises performing cytogenetic analysis of bands in the 3p11-p12 region of chromosome 3 on a DLBCL biopsy sample from the subject to analyze for a gain or amplification in the 3p11-p12 region of chromosome 3.

4. The method of claim 1, wherein the method further comprises performing polymerase chain reaction (PCR) on a DLBCL biopsy sample from the subject to analyze for a gain or amplification in the 3p11-p12 region of chromosome 3.

5. The method of claim 4, wherein the PCR is real-time quantitative PCR.

* * * * *